(12) United States Patent
Minev et al.

(10) Patent No.: US 12,351,862 B2
(45) Date of Patent: Jul. 8, 2025

(54) CRISSCROSS COOPERATIVE SELF-ASSEMBLY

(71) Applicants: President and Fellows of Harvard College, Cambridge, MA (US); Dana-Farber Cancer Institute, Inc., Boston, MA (US)

(72) Inventors: Dionis Minev, Cambridge, MA (US); Christopher Wintersinger, Cambridge, MA (US); William M. Shih, Cambridge, MA (US)

(73) Assignees: President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 571 days.

(21) Appl. No.: 17/576,550

(22) Filed: Jan. 14, 2022

(65) Prior Publication Data

US 2022/0403453 A1    Dec. 22, 2022

Related U.S. Application Data

(63) Continuation of application No. 16/322,787, filed as application No. PCT/US2017/045013 on Aug. 2, 2017, now Pat. No. 11,254,972.

(60) Provisional application No. 62/370,098, filed on Aug. 2, 2016.

(51) Int. Cl.
| | |
|---|---|
| *C12Q 1/6837* | (2018.01) |
| *B82Y 30/00* | (2011.01) |
| *C07H 1/00* | (2006.01) |
| *C07H 21/00* | (2006.01) |
| *C07H 21/04* | (2006.01) |
| *C12Q 1/6811* | (2018.01) |

(52) U.S. Cl.
CPC ............ *C12Q 1/6837* (2013.01); *B82Y 30/00* (2013.01); *C07H 1/00* (2013.01); *C07H 21/00* (2013.01); *C07H 21/04* (2013.01); *C12Q 1/6811* (2013.01)

(58) Field of Classification Search
None
See application file for complete search history.

(56) References Cited

U.S. PATENT DOCUMENTS

| | | | |
|---|---|---|---|
| 5,591,601 A | 1/1997 | Wagner et al. | |
| 5,846,949 A | 12/1998 | Wagner et al. | |
| 6,355,247 B1 | 3/2002 | Selby et al. | |
| 7,842,793 B2 | 11/2010 | Rothemund | |
| 8,501,923 B2 | 8/2013 | Rothemund | |
| 11,254,972 B2 | 2/2022 | Minev et al. | |
| 11,414,694 B2 | 8/2022 | Wong et al. | |
| 2005/0112578 A1 | 5/2005 | Matsuura et al. | |
| 2007/0117109 A1 | 5/2007 | Rothemund | |
| 2011/0033706 A1 | 2/2011 | Krishnan | |
| 2011/0243910 A1 | 10/2011 | Hahn et al. | |
| 2011/0293698 A1 | 12/2011 | Primiano et al. | |
| 2012/0263783 A1 | 10/2012 | Messmer | |
| 2013/0136925 A1 | 5/2013 | Kim et al. | |
| 2013/0245102 A1 | 9/2013 | Ryan et al. | |
| 2014/0220655 A1 | 8/2014 | Sun et al. | |
| 2014/0255939 A1 | 9/2014 | Wong et al. | |
| 2016/0271268 A1 | 9/2016 | Shih et al. | |
| 2018/0363022 A1 | 12/2018 | Li et al. | |
| 2019/0083522 A1 | 3/2019 | Shih et al. | |
| 2019/0203277 A1 | 7/2019 | Minev et al. | |
| 2020/0308625 A1 | 10/2020 | Wong et al. | |
| 2025/0019750 A1 | 1/2025 | Shih et al. | |

FOREIGN PATENT DOCUMENTS

| | | |
|---|---|---|
| JP | 2002-114797 A | 4/2002 |
| JP | 2003-522524 A | 7/2003 |
| JP | 2008-504846 A | 2/2008 |
| JP | 2008-523061 A | 7/2008 |
| JP | 2009-518008 A | 5/2009 |
| JP | 2009-213390 A | 9/2009 |
| JP | 2012-509983 A | 4/2012 |
| KR | 2011-0014258 A | 2/2011 |
| WO | WO 2012/058488 A2 | 5/2012 |
| WO | WO 2012/151328 A2 | 11/2012 |
| WO | WO 2014/018675 A1 | 1/2014 |
| WO | WO 2015/070080 A2 | 5/2015 |
| WO | WO 2015/130805 A1 | 9/2015 |
| WO | WO 2015/165643 A1 | 11/2015 |
| WO | WO 2016/144755 A1 | 9/2016 |
| WO | WO 2017/156252 A1 | 9/2017 |
| WO | WO 2017/156264 A1 | 9/2017 |
| WO | WO 2018/026880 A2 | 2/2018 |

OTHER PUBLICATIONS

U.S. Appl. No. 16/083,932, filed Sep. 11, 2018, Allowed, 2020-0308625.
U.S. Appl. No. 17/858,925, filed Jul. 6, 2022, Pending.
U.S. Appl. No. 16/322,787, filed Feb. 1, 2019, Granted, U.S. Pat. No. 11,254,972.
EP 17764091, Jul. 15, 2019, Extended European Search Report.
EP 21187413.6, Feb. 11, 2022, Extended European Search Report.
PCT/US2017/021562, May 31, 2017, International Search Report and Written Opinion.
PCT/US2017/021562, Sep. 20, 2018, International Preliminary Report on Patentability.
EP 17837580.4, Mar. 20, 2020, Partial European Search Report.
PCT/US2017/040513, Dec. 8, 2017, Invitation to Pay Additional Fees.
PCT/US2017/040513, Feb. 13, 2018, International Search Report and Written Opinion.
PCT/US2017/040513, Feb. 14, 2019, International Preliminary Report on Patentability.
Extended European Search Report mailed Jul. 15, 2019 for Application No. EP 17764091.

(Continued)

*Primary Examiner* — Robert M Kelly

(74) *Attorney, Agent, or Firm* — Wolf, Greenfield & Sacks, P.C.

(57) ABSTRACT

Provided herein, in some embodiments, are methods, compositions and kits for controlling nucleation and assembly of molecular nanostructures, microstructures and macrostructures.

11 Claims, 34 Drawing Sheets

Specification includes a Sequence Listing.

(56) References Cited

OTHER PUBLICATIONS

Extended European Search Report mailed Feb. 11, 2022 for Application No. EP 21187413.6.
International Search Report and Written Opinion mailed May 31, 2017 for Application No. PCT/US2017/021562.
International Preliminary Report on Patentability mailed Sep. 20, 2018 for Application No. PCT/US2017/021562.
Partial European Search Report mailed Mar. 20, 2020, for Application No. EP 17837580.4.
Invitation to Pay Additional Fees mailed Dec. 8, 2017 for Application No. PCT/US2017/040513.
International Search Report and Written Opinion mailed Feb. 13, 2018 for Applciation No. PCT/US2017/040513.
International Preliminary Report on Patentability mailed Feb. 14, 2019 for Applciation No. PCT/US2017/040513.
No Author Listed, Biochemistry Dictionary, 1998, 3rd edition, pp. 886.
Babic et al. Poly L-lysine-modified iron oxide nanoparticle for stem cell labelling. Bioconjug Chem. 2008;19:740-50. Epub Feb. 21, 2008.
Bikram et al., Biodegradable Poly(ethylene glycol)-co-poly(l-lysine)-g-histidine Multiblock Copolymers for Nonviral Gene Delivery. Macromolecules. Feb. 11, 2004;37(5):1903-16.
Dietz et al., Folding DNA into twisted and curved nanoscale shapes. Science. Aug. 7, 2009;325(5941):725-30.
Ding et al., Gold nanoparticle self-similar chain structure organized by DNA origami. J Am Chem Soc. 2010;132(10):3248-9. Epub Feb. 17, 2010.
Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.
Douglas et al., Self-assembly of DNA into nanoscale three-dimensional shapes. Nature. May 21, 2009;459(7245):414-8. Author Manuscript, 11 pages.
Fujigaya et al., Enhanced cell uptake via non-covalent decollation of a single-walled carbon nanotube-DNA hybrid with polyethylene glycol-grafted poly(l-lysine) labeled with an Alexa-dye and its efficient uptake in a cancer cell. Nanoscale. Oct. 5, 2011;3(10):4352-8. doi: 10.1039/c1nr10635j. Epub Sep. 20, 2011.
Han et al., DNA gridiron nanostructures based on four-arm junctions. Science. Mar. 22, 2013;339(6126):1412-5. doi: 10.1126/science.1232252.
Hansen et al., Nanoswitch-linked immunosorbent assay (NLISA) for fast, sensitive, and specific protein detection. PNAS. Sep. 26, 2017;114(39):10367-10372. Supporting Information, 4 pages.
Kadlecova et al., Hyperbranched polylysine: a versatile, biodegradable transfection agent for the production of recombinant proteins by transient gene expression and the transfection of primary cells. Macromol Biosci. Jun. 2012;12(6):794-804. doi: 10.1002/mabi.201100519. Epub Apr. 11, 2012.
Koussa et al., DNA nanoswitches: A quantitative platform for gel-based biomolecular interaction analysis. Nat Methods. Feb. 2015;12(2):123-6. Epub Dec. 8, 2014.
Koussa et al., Protocol for sortase-mediated construction of DNA-protein hybrids and functional nanostructures. Methods. May 2014;67(2):134-41.
Kuzuya et al., Precisely programmed and robust 2D streptavidin nanoarrays by using periodical nanometer-scale wells embedded in DNA origami assembly. Chembiochem. Jul. 2009;10(11):1811-5.
Kuzyk et al., DNA-based self-assembly of chiral plasmonic nanostructures with tailored optical response. Nature. Mar. 15, 2012;483(7389):311-4. doi:10.1038/nature10889.
Kwoh et al., Stablilization of poly-L-lysine/DNA polyplexes for in vivo gene delivery to the liver. Biochimica et Biophysica Acta. 1999;1444:171-90.
Liu et al., Biological properties of poly-L-lysine-DNA complexes generated by cooperative binding of the polycation. J Biol Chem. Sep. 14, 2001;276(37):34379-87. Epub Jul. 3, 2001.
Lu et al., Recent advances in the synthesis and functions of reconfigurable interlocked DNA nanostructures. J Am Chem Soc. 2016;138:5172-85. Epub Mar. 28, 2016.
Maruyama et al., Characterization of interpolyelectrolyte complexes between double-stranded DNA and polylysine comb-type copolymers having hydrophilic side chains. Bioconjugate Chem. 1998;9:292-9. Epub Feb. 24, 1998.
Rajendran et al., Single-molecule analysis using DNA origami. Angew Chem Int Ed Engl. Jan. 23, 2012;51(4):874-90. doi: 10.1002/anie.201102113. Epub Nov. 25, 2011.
Santos et al., Low-cost fabrication technologies for nanostructures: state-of-the-art and potential. Nanotechnology. Jan. 30, 2015;26(4):042001(1-20). doi: 10.1088/0957-4484/26/4/042001. Epub Jan. 8, 2015.
Schlichthaerle et al., DNA nanotechnology and fluorescence applications. Curr Opin Biotechnol. Jun. 2016;39:41-47. doi: 10.1016/j.copbio.2015.12.014. Epub Jan. 13, 2016.
Shih et al., poster. DNA-Based Molecular Containers and NMR Alignment Media. 2006. 1 page.
Simmel et al., Wireframe and tensegrity DNA nanostructures. Acc Chem Res. Jun. 17, 2014;47(6):1691-9. doi: 10.1021/ar400319n. Epub Apr. 10, 2014.
Steinhauer et al., DNA origami as a nanoscopic ruler for super-resolution microscopy. Angew Chem Int Ed Engl. 2009;48(47):8870-3. doi: 10.1002/anie.200903308.
Valero et al., Interlocked DNA topologies for nanotechnology. Curr Opin Biotechnol. May 12, 2017;48:159-67.
Walsh et al., DNA cage delivery to mammalian cells. ACS Nano. 2011;5(7):5427-32. Epub Jun. 22, 2011. Supplemental information, 12 pages.
Weizmann et al., A polycatenated DNA scaffold for the one-step assembly of hierarchical nanostructures. Proc Nat Acad Sci. Apr. 8, 2008;105(14):5289-94.
Yan et al., DNA-templated self-assembly of protein arrays and highly conductive nanowires. Science. Sep. 26, 2003;301(5641):1882-4.
Yang et al., Nanostructures as Programmable Biomolecular Scaffolds. Bioconjug Chem. Aug. 19, 2015;26(8):1381-95. doi: 10.1021/acs.bioconjchem.5b00194. Epub May 11, 2015.
Zhang et al., Dynamic DNA nanotechnology using strand-displacement reactions. Nat Chem. Feb. 2011;3(2):103-13. doi: 10.1038/nchem.957.
Zhang et al., Structural DNA nanotechnology: state of the art and future perspective. J Am Chem Soc. Aug. 13, 2014;136(32):11198-211. doi:10.1021/ja505101a. Epub Jul. 16, 2014.
Zhou et al., Lipophilic polylysines mediate efficient DNA transfection in mammalian cells. Biochim Biophys Acta. May 31, 1991;1065(1):8-14.
Zhu et al. Hollow mesoporous silica poly-(l-lysine) particles for codelivery of drug and gene with enzyme-triggered release property. J Phys Chem C. Jun. 2011;115:13630-5. Epub Jun. 15, 2011.
Evans et al., Physical principles for DNA tile self-assembly. Chem Soc Rev. Jun. 19, 2017;46(12):3808-3829. doi: 10.1039/c6cs00745g.
Hong et al., 3D Framework DNA origami with layered crossovers. Angew Chem Int Ed Engl. Oct. 4, 2016;55(41):12832-5. Epub Sep. 15, 2016.
Ke et al., Three-dimensional structures self-assembled from DNA bricks. Science. Nov. 30, 2012;338(6111):1177-83. Author Manuscript, 16 pages. doi: 10.1126/science.1227268.
Mathieu et al., Six-helix bundles designed from DNA. Nano Lett. Apr. 2005;5(4):661-5.
Minev et al., 2019 Robust nucleation control via crisscross polymerization of DNA slats. bioRxiv doi: 10.1101/2019.12.11.873349, https://www.biorxiv.org/content/10.1101/2019.12.11.873349v1, 26 pages.
Minev et al., Robust nucleation control via crisscross polymerization of highly coordinated DNA slats. Nat Commun. Mar. 19, 2021;12(1):1741. doi: 10.1038/s41467-021-21755-7.
Ong et al., Programmable self-assembly of three-dimensional nanostructures from 10,000 unique components. Nature. Dec. 6, 2017;552(7683):72-77. Author Manuscript, 17 pages. doi: 10.1038/nature24648.

(56) References Cited

OTHER PUBLICATIONS

Rothemund P.W., Folding DNA to create nanoscale shapes and patterns. Nature. Mar. 16, 2006;440(7082):297-302. doi: 10.1038/nature04586.
Seeman N., DNA Nanotechnology at 40. Nano Lett. Mar. 11, 2020;20(3):1477-1478. doi: 10.1021/acs.nanolett.0c00325. Epub Feb. 3, 2020.
Wintersinger et al., 2022 Multi-micron crisscross structures from combinatorially assembled DNA-origami slats. bioRxiv doi: 10.1101/2022.01.06.475243, https://www.biorxiv.org/content/10.1101/2022.01.06.475243v1, 22 pages.
Woods et al., Diverse and robust molecular algorithms using reprogrammable DNA self-assembly. Nature. Mar. 2019;567(7748):366-372. doi: 10.1038/s41586-019-1014-9. Epub Mar. 20, 2019. Erratum in: Nature. Aug. 2019;572(7771):E21. doi: 10.1038/s41586-019-1378-x.
Zhang et al., Programming the Nucleation of DNA Brick Self-Assembly with a Seeding Strand. Angew Chem Int Ed Engl. May 25, 2020;59(22):8594-8600. doi: 10.1002/anie.201915063. Epub Mar. 17, 2020.

C1 – 1M NaCl
C2 – 15mM MgCl2
C3 – 50mM MgCl2

FIG. 23A
FIG. 23B
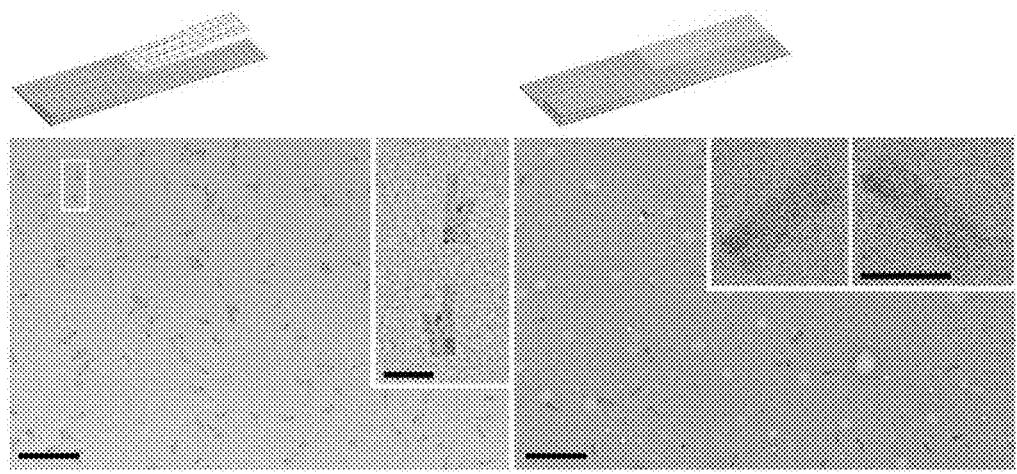
FIG. 24A
FIG. 24B
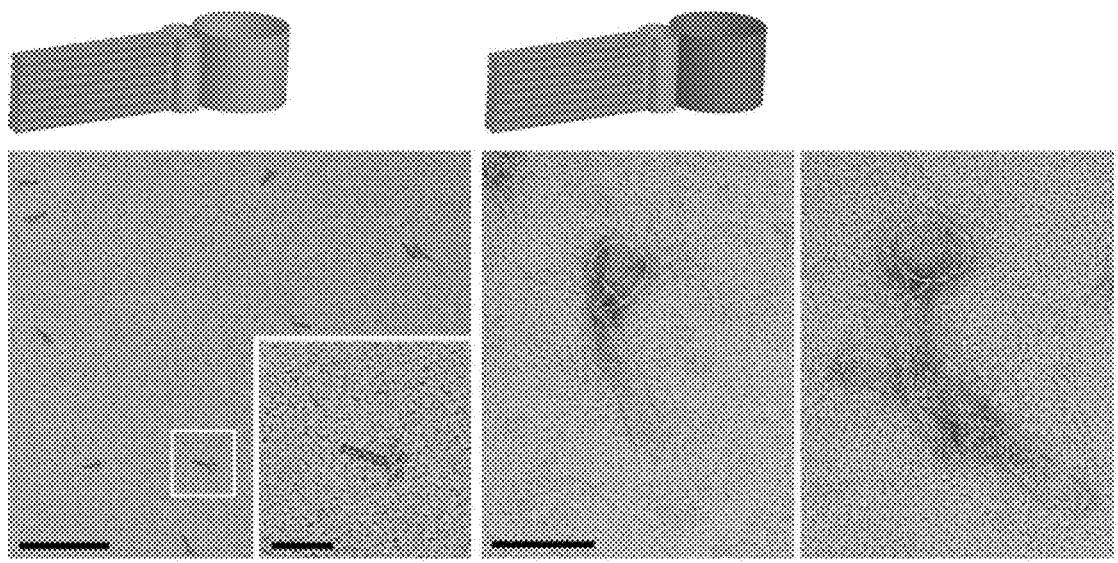

CRISSCROSS COOPERATIVE SELF-ASSEMBLY

RELATED APPLICATION

This application is a continuation of U.S. application Ser. No. 16/322,787, filed Feb. 1, 2019, which is a national stage filing under 35 U.S.C. § 371 of international application number PCT/US2017/045013, filed Aug. 2, 2017, which claims the benefit under 35 U.S.C. § 119(e) of U.S. provisional Application No. 62/370,098, filed Aug. 2, 2016, each of which is incorporated by reference herein in its entirety.

FEDERALLY SPONSORED RESEARCH

This invention was made with government support under 1435964 awarded by the Office of Naval Research. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Apr. 13, 2022, is named H049870616US02-SEQ-MSB and is 137600 bytes in size.

BACKGROUND

In nature, biomolecules assemble into hierarchical structures through intermolecular interactions. In synthetic biology, it is possible to rationally design biosynthetic building blocks, with hierarchical structures arising from built-in functionality at the molecular level controlling intermolecular interactions. Such biosynthetic self-assembling structures have useful applications in the field of nanotechnology, for example.

SUMMARY

Provided herein, in some embodiments, is a technology (including, for example, methods, compositions and kits) for controlling nucleation and hierarchical assembly (programmable self-assembly) of molecular structures, such as nucleic acid (e.g., DNA) and/or protein nanostructures, microstructures, and macrostructures. This technology, referred to herein as 'crisscross cooperative assembly' can be used to program and rapidly assemble structures that only originate from provided macromolecular 'seeds,' thus may be considered a 'zero-background' assembly method. Through the design of cooperative binding sites on individual biomolecular subunits that require simultaneous engagement with a large number of other subunits to achieve stable attachment, the system imposes an intrinsically high energetic barrier against spontaneous nucleation of structures, even in the presence of high concentrations of each individual component. Nucleation can only be triggered by providing a macromolecular 'seed' that resembles a pre-existing structural interface (presents multiple weak binding sites for stable capture of the next subunit). Addition of a seed that can stably capture individual subunits effectively bypasses the activation energy barrier against spontaneous nucleation to drive higher-order assembly of a microscale structure. Components can be continually added to the structures such that their growth in one-dimension, two-dimensions or three-dimensions is potentially as large as for other polymerization or crystallization processes.

Crisscross cooperative assembly, as provided herein, uses molecular (e.g., nucleic acid or protein) building blocks (FIG. 1A) that are programmed to self-assemble into crisscrossed layers (FIG. 1B). A building block, in some embodiments, may be a rod-shaped structure assembled from programmable nucleic acid hybridization interactions. As indicated above, this crisscross cooperative assembly technology uses a 'seed' structure from which programmable nucleic acid self-assembly begins. This seed structure is formed through irreversible interactions between a nucleating structure (FIG. 1A; 'queen') and a subset of building blocks (FIG. 1A; 'drones') that are aligned to form an initial seed layer along the nucleating structure. In the presence of a seed structure, another set of building blocks (FIG. 1A; 'workers') are added to the pre-existing seed layer (FIG. 1B). Binding between a sufficient number of building blocks (drones) and a nucleating structure (queen) to form a seed can trigger the addition of many additional layers of building blocks (workers), with each layer rotated by some degree (e.g., 90°) relative to adjacent layers (above and/or below).

The nucleating structure and the building blocks are engineered to interact with (e.g., bind to) each other based on a set of kinetic/nucleation energy parameters, as follows. An initial subset of building blocks (drones) should bind strongly (irreversibly/stably) to and form an aligned layer along the nucleating structure (queen). The building blocks (drones) of the initial subset should not interact with (bind to) each other. Likewise, building blocks (workers) of a subsequent subset should not interact with (bind to) each other. Further, in the absence of a nucleating structure (queen), any building block (drone) from the initial subset should have only one weak (reversible) interaction with any other building block (worker) from another subset. In the presence of a nucleating structure (queen), a single building block (drone) from an initial subset may interact with more than one building block (worker) from a subsequent subset, and a single building block (worker) from a subsequent subset may interact with more than one building block (drone) from the initial subset or another subset ('workers' of another subset). For example, with reference to FIG. 1B, a single building block (e.g., DNA nanorod) may bind to eight other building blocks (e.g., DNA nanorods), although the single building block binds to each of the eight building blocks only once to form two layers having a 'crisscross' pattern.

The single interaction between a building block (drone) from the initial subset and a building block from a subsequent subset (worker) should be weak enough such that there is an arbitrarily large entropy penalty against nucleation in the absence of a seed structure (a large number of individual workers would have to come together simultaneously). With these parameters, zero-background and minimal defects can be achieved, even at high concentrations of interacting building blocks, thereby enabling rapid nucleation and assembly of nucleic acid nanostructures.

Thus, provided herein are compositions, comprising (a) a nucleating nucleic acid nanostructure, (b) a first layer of parallel elongated nucleic acid nanostructures stably bound to the nucleating nanostructure of (a), and (c) a second layer of parallel elongated nucleic acid nanostructures stably bound to the elongated nanostructures of (b) and rotated at an angle relative to the parallel elongated nanostructures of (b), wherein a single elongated nanostructure of (b) binds to multiple elongated nanostructures of (c), each through a single cooperative binding site.

In some embodiments, a single elongated nanostructure of (c) binds to multiple elongated nanostructures of (b), each through a single cooperative binding site.

Also provided herein, in some aspects, are compositions comprising: (a) nucleating nanostructures; (b) a first subset of elongated nanostructures, wherein less than 10% of the nanostructures of (b) bind to each other, and wherein the nanostructures of (b) irreversibly bind to a nucleating nanostructure of (a); and (c) a second subset of elongated nanostructures, wherein less than 10% of the nanostructures of (c) bind to each other, wherein, in the absence of a nucleating nanostructure, a nanostructure of (b) can reversibly binding to a nanostructure of (a) only at a single position on the nanostructure of (a), and wherein, in the absence of a nucleating nanostructure, a nanostructure of (a) can reversibly binding to a nanostructure of (b) only at a single position on the nanostructure of (b). See, e.g., FIGS. 1A-1B.

Also provided herein, in some embodiments, are crisscross nucleic acid nanostructures, comprising a first nanorod comprising a first plug strand and a second plug strand; a second nanorod comprising a third plug strand and a fourth plug strand, wherein the second nanorod is parallel to the first nanorod; a third nanorod comprising a fifth plug strand complementary to and bound to the first plug strand and a sixth plug strand complementary to and bound to the second plug strand; a fourth nanorod comprising a seventh plug strand complementary to and bound to the third plug strand and an eighth plug strand complementary to and bound to the fourth plug strand, wherein the third nanorod is parallel to the fourth nanorod. See, e.g., FIG. 18. A crisscross nanostructure is not limited to 4 nanorods and, in many embodiments, includes at least 4 (e.g., at least 5, 10, 15, 20, 25, 50, 100 or more) nanorods arranged in a crisscross pattern as described herein.

Thus, in some embodiments, a crisscross nucleic acid nanostructure, comprises a first plurality of nanorods parallel to each other, and a second plurality of nanorods parallel to each other, wherein the nanorods of the first plurality are bound to and perpendicular to (or are non-parallel to) the nanorods of the second plurality. See, e.g., FIG. 18.

In some embodiments, each nanorod is comprised of DNA. For example, a nanorod may be comprised of a 6-helix DNA bundle (see, e.g., Douglas S M1, Chou J J, Shih W M. DNA-nanotube-induced alignment of membrane proteins for NMR structure determination. Proc Natl Acad Sci USA. 104, 6644-6648, 2007, incorporated herein by reference).

Also provided herein, in some aspects, are crisscross nucleic acid slats, comprising: a first plurality of at least four nucleic acid strands parallel to each other, each strand of the first plurality having a length of 20-100 nucleotides (e.g., 20-30, 20-40 or 20-50 nucleotides); and a second plurality of at least four nucleic acid strands parallel to each, each strand of the second plurality having a length of 20-100 nucleotides (e.g., 20-30, 20-40 or 20-50 nucleotides), wherein the at least four nucleic acid strands of the first plurality are bound to and perpendicular to the at least four nucleic acid strands of the second plurality. See, e.g., FIGS. 21A-21B.

Also provided herein, in some aspects are crisscross nucleic acid slats, comprising: a first plurality of at least four nucleic acid strands parallel to each other, each strand of the first plurality having a length of at least 21 nucleotides; and a second plurality of at least four nucleic acid strands parallel to each, each strand of the second plurality having a length of at least 21 nucleotides, wherein the at least four nucleic acid strands of the first plurality are bound to and perpendicular to the at least four nucleic acid strands of the second plurality. See, e.g., FIGS. 21A-21B.

Further provided herein, in some aspects, are nucleic acid nanostructures comprising a nucleic acid scaffold strand folded (e.g., M13 or M13-derived) into repeating loop-like shapes (e.g., 5-15 loops, or 5, 6, 7, 8, 9 or 10 loops) secured by shorter nucleic acid staple strands, wherein the repeating loop structures are bound to at least one (e.g., at least 2, 3, 4, 5, 10, 20, 25, 30, 35, 40, 45, 50, 60, 70, 80, 90, 100 or more) crisscross nucleic acid slat. See, e.g., FIGS. 22, 24A, 25 and 27B.

Further still, provided herein, in some aspects, are nucleic acid nanostructures, comprising a nucleic acid scaffold strand folded into repeating loop-like shapes secured by at least two crisscross nucleic acid slats. See, e.g., FIGS. 27B and 28B.

The present disclosure also provides, in some aspects, methods of producing a crisscross nucleic acid nanostructures, comprising: combining in a reaction mixture (a) a first nanorod comprising a first plug strand and a second plug strand, (b) a second nanorod comprising a third plug strand and a fourth plug strand, wherein the second nanorod is parallel to the first nanorod, (c) a third nanorod comprising a fifth plug strand complementary to and bound to the first plug strand and a sixth plug strand complementary to and bound to the second plug strand, and (d) a fourth nanorod comprising a seventh plug strand complementary to and bound to the third plug strand and an eighth plug strand complementary to and bound to the fourth plug strand, wherein the third nanorod is parallel to the fourth nanorod; and incubating the reaction mixture under conditions (e.g., nucleic acid hybridization conditions) that result in assembly of a crisscross nucleic acid nanostructure. See, e.g., FIG. 22.

Biomolecule (analyte) detection methods are also provided herein, in some aspects. In some embodiments, a method, comprises (a) combining in a reaction mixture (i) a sample comprising a biomolecule; (ii) a nucleic acid strand capable of self-assembling into a nanostructure that comprise vertically-stacked parallel strands; (iii) a plurality of oligonucleotides, shorter than the nucleic acid strand of (ii), wherein the oligonucleotides of (iii) bind to the strand of (ii) to assemble the vertically-stacked parallel strands; (iv) two crisscross nucleic acid slats, wherein the two slats bind to the strand of (ii), and wherein each of the slats is linked to a biomolecule binding partner that specifically binds to the biomolecule in the sample; (b) incubating the reaction mixture under conditions that permit binding of the biomolecule binding partners to the biomolecule and assembly of the nanostructure into vertically-stacked parallel strands; (c) removing the plurality of oligonucleotides of (iii) from the reaction mixture of (b); (d) incubating the reaction mixture of (c) in the presence of a plurality of crisscross nucleic acid slats described herein, wherein the crisscross nucleic acid slats bind to the vertically-stacked parallel strands to form a three-dimensional barrel structure. In some embodiments, the methods further comprise imaging the three-dimensional barrel structure. See, e.g., FIGS. 28A-28B.

In some embodiments, the methods may comprise combining in a reaction mixture (e.g., with hybridization buffer) (a) a sample comprising a biomolecule and (b) a nucleic acid nanostructure comprising (i) a nucleic acid scaffold strand capable of folding into repeating loop-like shapes (e.g., 2-15 vertically-stacked loops) and (ii) two crisscross nucleic acid slats, wherein a biomolecule binding partner (e.g., an antibody) that specifically binds to the biomolecule is linked to each of the crisscross nucleic acid slats such that in the presence of the cognate biomolecule the biomolecule binding partner binds to the biomolecule and the nucleic acid nanostructure folds into repeating loop-like shapes. See, e.g., FIGS. 28A-28B.

In some embodiments, the methods further comprise combining the reaction mixture with a plurality (e.g., 2-50 or 2-100) of crisscross nucleic acid slats to form a three-dimensional barrel-like structure. See, e.g., FIG. 24B.

It should be understood that the nucleic-acid nanostructures as described herein (e.g., nanorods, slats, barrels, etc.) and variants thereof, as provided herein, may be designed, for example, using the following publicly-available tool described by Douglas S M, Marblestone A H, Teerapittayanon S, Vazquez A, Church G M, Shih W M. Rapid prototyping of 3D DNA-origami shapes with caDNAno. *Nucleic Acids Res.* 37, 5001-5006, 2009, incorporated herein by reference. See, also, Douglas et al. *Nature,* 459(7245): 414-418, 2009, incorporated herein by reference. For example, and as described elsewhere herein, it is known in the art that custom shape (e.g., megadalton-scale) DNA nanostructures may be produced using a long 'scaffold' strand to template the assembly of hundreds of oligonucleotide 'staple' strands into a planar antiparallel array of cross-linked helices. This 'scaffolded DNA origami' method has also been adapted to produce 3D shapes formed as pleated layers of double helices constrained to a honeycomb lattice. caDNAno, an open-source software package with a graphical user interface, may be used to aid in the design of DNA sequences for folding 3D DNA (or other nucleic acid) nanostructures. The caDNAno software is available at cadnano.org, along with example designs and video tutorials demonstrating their construction.

BRIEF DESCRIPTION OF THE DRAWINGS

FIG. 1A indicates the system without a nucleation site and no self-assembly. FIG. 1B indicates the system after the addition of the nucleation site and triggered spontaneous self-assembly. Growth direction is indicated by the grey arrows and shows a 1D growth in this example. Individual components are referred to as 'queen,' 'drone' and 'worker.

FIG. 3A shows queen (Q) and drone/worker (D/W) architecture shown in cross-section (caDNAno software downloaded from cadnano.org) and in 3D representation. Each individual cylinder represents a double stranded DNA helix. FIG. 3B is a representation of 1D and 2D growth with the crisscross DNA-origami cooperative assembly. 3D growth can be achieved by creating a design that merges 1D and 2D growth. FIG. 3C shows different pathways for 2D growth.

FIG. 17A shows drone and worker subcomponents constructed from 6-helix bundle scaffolded DNA origami to form rods that are customizable in length. The 3' ends of staples contain overhanging single strand DNA sequences that act as plug binding handles to interact with other components. Similarly, the lowermost helix contains socket sequences (i.e. single strand DNA scaffold not complemented by a folding staple) that accept plug sequences from other components. The plugs and socket respectively are periodic and can be situated, for example, every 42 bp (~14 nm) along the length of the component. FIG. 17B shows TEM images of test drones folded from two different scaffold sequences. The drone in the top image is ~250 nm in length, versus the drone in the bottom image, which is ~440 nm in length.

FIG. 19A shows two 440 nm drones placed in the middle two queen cells, FIG. 19B shows one 250 nm drone placed in the middle queen cell, and FIG. 19C shows 250 nm located in every cell of the queen. The desired design is shown to the left, versus a TEM image of the assembled structure to the right. FIG. 19D shows bulk analysis of the design from FIG. 19A using agarose gel electrophoresis for one design using a 7 bp plug-socket, and another with a 10 bp plug-socket.

FIG. 21A is an abstraction of the crisscross DNA slats motif (right). Light and dark strands weave and are complementary to each other at each junction. The length of each binding site is shown on the right. Each row and column amount to 21 base pairs (bp). The matrix shows the number of base pairs (bp) per binding site at each position of the abstraction and 3D rendering. FIG. 21B is a 3D rendering of the DNA slats. On the left, the top down view shows the weaving of each strand. A cross section (A-A) is shown on the right.

FIG. 23A shows a flat DNA-origami queen without any DNA slats added. FIG. 23B shows a flat DNA-origami queen with the addition of DNA slats and the correct formation of a sheet, by tiling the ssDNA scaffold of the queen with DNA slats. DNA slat tiled region is indicated in light gray. Scale bars on images are 600 nm and on enlarged view 100 nm.

FIG. 24A shows a barrel DNA-origami queen without any DNA slats added. Scale bar on image is 400 nm and on enlarged view 100 nm. FIG. 24B shows a barrel DNA-origami queen with the addition of DNA slats and the correct formation of a barrel, by tiling the ssDNA scaffold of the queen with DNA slats. Scale bar indicates 50 nm. DNA slat tiled region is indicated in light gray.

FIG. 26A shows first generation extensions tiled with a short second generation of DNA slats, resulting in three tooth-like extensions on the queen. FIG. 26B shows first generation extensions tiled with a long second generation of DNA slats, which are terminally tiled with short third generation DNA slats. FIGS. 26C-26E show first, second, and third generations of DNA slats which are complementary to one another, resulting in extensions of linear sheet structures. FIG. 26C contains one extended first generation, FIG. 26D contains two extended first generations, and FIG. 26E contains three extended first generations. Scale bars for FIGS. 26A-26C are 100 nm and for FIGS. 26D-26E, 20 0 nm.

(FIG. 27A) Formation of eight loops with M13 scaffold through staple strands. Staple ("brown") strands fold stable DNA-Origami base and DNA slats catenate the eight loops. (FIG. 27B) 3D view of barrel queen additionally serving as multi-host-ring catenane system with high yield typical for DNA-Origami. (FIG. 27C) Abstract and 3D view of DNA slats weaving through the ssDNA M13 scaffold loops on the barrel queen. Through ligation of one side a single DNA slat catenates all eight loops. (FIG. 27D) 3D rendering of DNA slat weaving and catenating eight separate ssDNA loops. Top shows a tilted bottom view and bottom a side view. (FIG. 27E) Former technique to achieve a maximum of four-host-ring catenane system with low yield.

FIG. 28A shows that the biomolecule presence is connected to the DNA slats (black) holding the eight loops together. Without the biomolecule, the queen falls apart and no growth can occur, even with DNA slats present in solution. FIG. 28B shows that biomolecule presence in the reaction holds the DNA slats (black) together and provides the close proximity of ssDNA scaffold for the tube structure to nucleate and grow.

FIG. 30A depicts a flat DNA-origami queen without the bottom right hand sheet shown in FIG. 23A. FIG. 30B is a schematic explaining how the DNA slats (moving in a diagonal direction) assemble on the ssDNA scaffold on the flat queen.

DETAILED DESCRIPTION

Nature achieves rapid and nucleation-limited growth of cytoskeletal filaments such as actin and microtubules. This is achieved by securing each additional subunit by weak interactions to 2-3 already attached subunits at the growing end of the filament. This means that if any two monomers bind to each other in solution, they will rapidly (e.g., within milliseconds) dissociate from each other, because the single interaction is so weak. It is only after four subunits come together simultaneously—a rare event—that a stable nucleus will be formed. Therefore, untriggered spontaneous nucleation will be rare. Conversely, nucleation can be triggered by providing a macromolecular "seed" that mimics a fully formed filament end.

Rapid and nucleation-limited growth are very useful features for programmable self-assembly, however technological modification of natural filaments such as actin or microtubules has many current drawbacks: (1) there is a limited understanding of how to tune the interaction strength between subunits; (2) the level of cooperativity is relatively low (the weak interactions upon binding are spread only over 2-3 subunits), therefore the suppression of spontaneous nucleation is not as robust as it could be; and (3) growth is limited to one-dimension (filament formation).

Rapid, reversible, zero-background, triggered nucleation and growth, as provided herein, can have useful applications in nanotechnology and biotechnology, such as ultrasensitive detection, and templates for miniaturized materials.

Crisscross Cooperative Assembly

The crisscross cooperative assembly technology as provided herein is based on a concept that may apply to many self-assembling molecules, including nucleic acids and proteins. For simplicity and ease of understanding, however, reference herein primarily will address crisscross cooperative assembly in the context of nucleic acids, such as deoxyribonucleic acid (DNA). A crisscross cooperative assembly system uses three basic components: a nucleating nanostructure, an initial (first) subset of nanostructures programmed to bind to the nucleating nanostructure, and another (second) subset of nanostructures programmed to bind to the nanostructures of the initial.

Figure 1A:
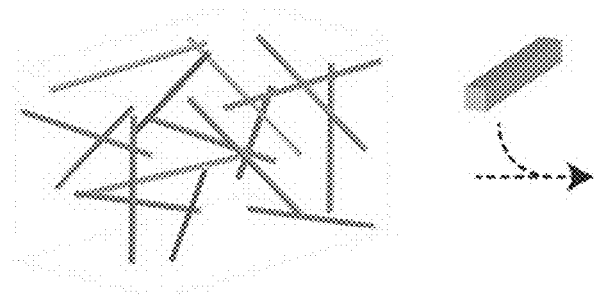
FIGS. 1A-1B show an abstraction of an example of crisscross cooperative assembly system.
Figure 1B:
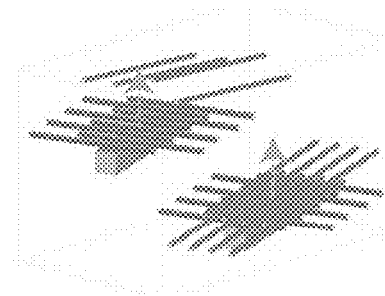
Figure 2:
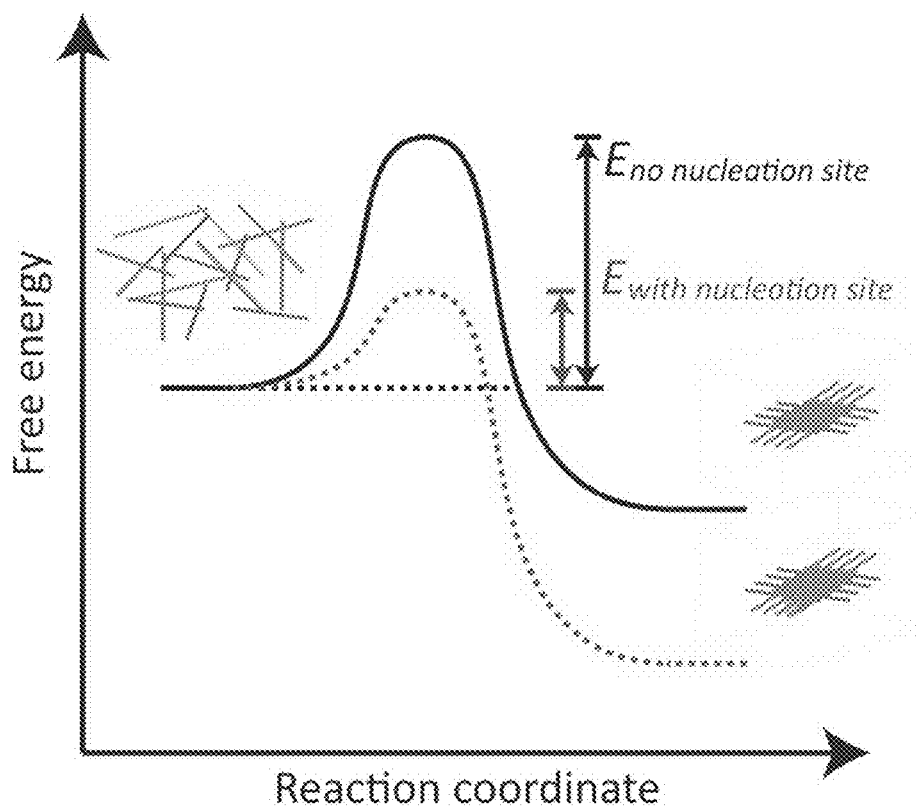
' FIG. 2 shows a graph depicting the principle by which the nucleation site (queen) structure initiates higher-order structures with drones and workers by lowering the activation energy for assembly.

An example of a crisscross cooperative assembly is provided in FIGS. 1A-1B, wherein the nucleating structure is referred to as a 'queen,' nanostructures of the first subset are referred to as 'drones,' and nanostructures of the second (and any subsequent) subset are referred to as 'workers.' The final structure, in this example, includes layers of aligned molecular rods, where each layer is rotated by some amount (e.g., 90 degrees) relative to the layer below and above. For example, one layer may be perpendicular to another adjacent (directly above or below) layer. In some embodiments, one layer is rotated 20, 30, 40, 50, 60, 70, 80 or 90 degrees relative to an adjacent layer (measured alone the length of a drone and/or worker nanorod, for example). Each intersection between rods on adjacent layers adds a small binding energy; any given rod intersects with a large number of rods below and above, and the net binding energy can be tuned (e.g., by adjusting the design of the binding interface, for example, the number of base pairs, or by adjusting subunit concentration, temperature, or salt concentration) to be large enough to achieve stable (irreversible) or slightly favorable (reversible) attachment as desired. Before assembly initiates, any spontaneous crossing between two rods in solution is short-lived, as the net energy is very low because there is only one interaction. Thus, a rod can be stably (or else slightly favorably (reversibly)) added to a pre-existing crisscross structure (many attachment points can immediately be realized), but a structure will not spontaneously assemble in the absence of a pre-existing one. There should be no growth unless a structural mimic of a pre-existing crisscross structure—a seed—is added to the solution.

An example protocol for a crisscross cooperative assembly system is as follows: (1) Design constitutive building blocks (queen, drones and workers) using DNA CAD tools. See, e.g., Douglas S M, Marblestone A H, Teerapittayanon S, Vazquez A, Church G M, Shih W M. Rapid prototyping of 3D DNA-origami shapes with caDNAno. Nucleic Acids Res. 37, 5001-5006, 2009, incorporated herein by reference in its entirety.

Cooperative binding site sequences and number of sites on queens are tailored to modulate the activation energy of nucleation as required. (2) Construct and purify constitutive building blocks using techniques in DNA synthesis and DNA origami. (3) Mix drones and workers in solution, and add queens to initiate growth of higher order DNA structures.

Nanostructures bind to each other through cooperative binding sites. A "cooperative binding site" is the location at which two nanostructures interact (hybridize/bind). For example, a nucleating nanostructure may be programmed with multiple nucleotide base sequences, each of which is complementary to a nucleotide base sequence of one of the nanostructures of the initial subset of nanostructures. A cooperative binding site may include plug and socket sites that include plug and socket strands. A plug strand is a nucleic acid strand (single-stranded nucleic acid) attached to a nucleic acid nanostructure, such as a nanorod. A plug strand contains a nucleotide sequence that is complementary to (and this binds to) a nucleotide sequence within a cognate socket strand. Thus, a pair of plug and socket strands include nucleotide sequences that are complementary to each other such that the plug and socket strand bind (hybridize) to each other to anchor, for example, a drone to a queen or a worker to a drone (see, e.g., FIG. 17B). In some embodiments, a queen includes multiple plug strands that direct and anchor a drone that includes multiple complementary (cognate) socket strands. Likewise, a drone may include multiple plug strands that direct and anchor a worker that includes multiple complementary socket strands.

Figure 22:
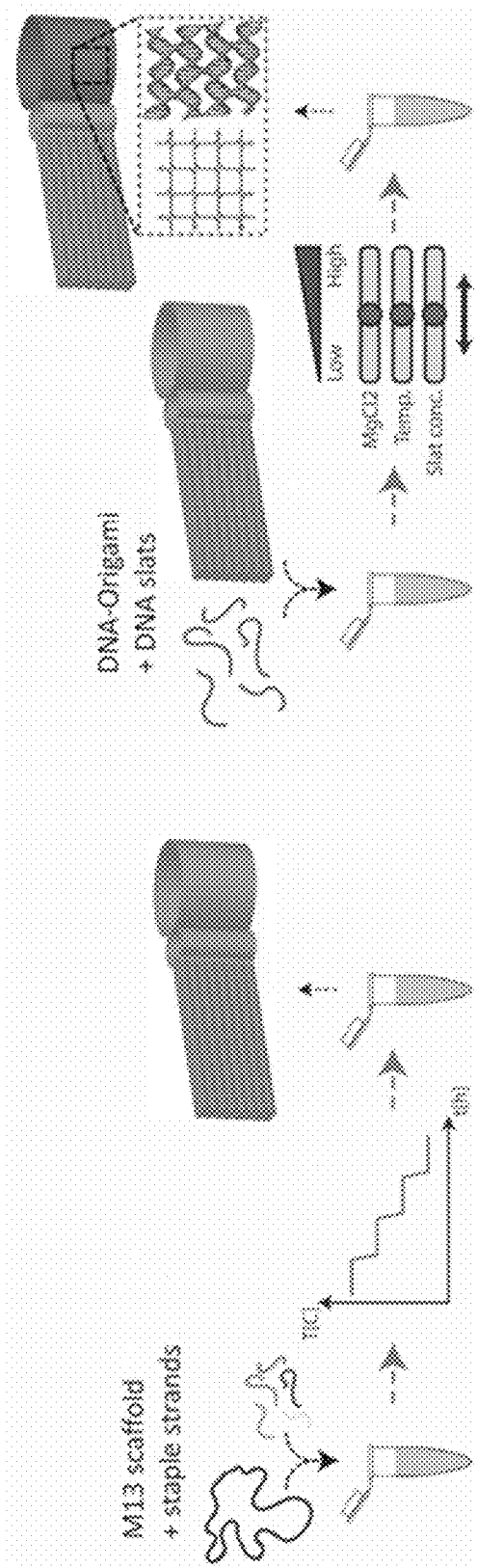
FIG. 22 shows the steps to DNA slats assembly. Step 1 shows DNA-origami folding of an arbitrary DNA-origami queen (a barrel queen shown as an example). Step 2 is the mixing of the crude DNA-origami queen reaction (from step 1) with DNA slats at various salt concentrations, temperatures, and DNA slat concentration.

Cooperative binding sites, e.g., plug and socket strands, may also be used to assemble nucleic acid (e.g., DNA) slats onto another nucleic acid scaffold structure in a similar manner. For example, as shown in FIG. 22, DNA slats may be appended to a nucleic acid scaffold (queen) to secure the two- or three-dimensional shape of the scaffold structure. In the example, shown in FIG. 22, DNA slats are used to secure (hold together) the barrel shape of a larger scaffold nanostructure. "Growth" of these slats along the scaffold through cooperative binding sites results in a barrel-like shape that may be visualized by microscopy, for example.

Cooperative binding sites (e.g., plug and socket sequences) are arranged on a nucleating nanostructure in a spatial configuration that facilitates binding and alignment of the initial e.g., scaffold) nanostructures. The length of a cooperative binding site may vary, depending in part on the desired strength (strong v. weak) of the intended interaction between two molecules having complementary sites. In some embodiments, a cooperative binding site has a length of 5-50 nucleotides. For example, a cooperative binding site may have a length of 5-40, 5-30, 5-20, 5-10, 5-15, 10-50, 10-40, 10-30, 10-20, 30-50, 30-40, or 40-50 nucleotides. In some embodiments, a cooperative binding site has a length of 5, 10, 15, 20, 25, 30, 35, 40, 45, or 50 nucleotides. A single plug strand and/or socket strand may have a length of 5-20 (e.g., 5, 6, 7, 8, 9, 10, 11, 12, 13, 14, 15, 16, 17, 18, 19 or 20) nucleotides, for example.

The number of cooperative binding sites on a nanostructure may also vary. In some embodiments, the number of cooperative binding sites on a nanostructure is 3-1000. For example, the number of cooperative binding sites on a nanostructure may be 3-900, 3-800, 3-700, 3-600, 3-500, 3-400, 3-300, 3-200, or 3-100. In some embodiments, the number of cooperative binding sites on a nanostructure is 3-10, 3-15, 3-20, 3-25, 3-30, 3-35, 3-40, 3-45 or 3-50. In some embodiments, the number of cooperative binding sites on a nanostructure is 3-15, 3-20, 3-25, 3-30, 3-35, 3-40, 3-45 or 3-50. In some embodiments, the number of cooperative binding sites on a nanostructure is 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100.

The distance between cooperative binding sites may also vary. In some embodiments, the distance between two cooperative binding sites on the same nanostructure is 20-1000 angstroms. For example, the distance between two cooperative binding sites on a nanostructures may be 20-900, 20-800, 20-700, 20-600, 20-500, 20-400, 20-300, 20-200, 20-100, 50-1000, 50-900, 50-800, 50-700, 50-600, 50-500, 50-400, 50-300, 50-200, or 50-100 angstroms. In some embodiments, the distance between two cooperative binding sites on a nanostructures is 20, 25, 30, 35, 40, 45, 50, 55, 60, 65, 70, 75, 80, 85, 90, 95, 100, 125, 150, 175, 200, 250, 300, 350, 400, 450 or 500 angstroms.

In some embodiments, the distance between cooperative binding sites, for example, the distance between plug strands (and/or between socket strands) may be 5 to 100 nucleotides (or nucleotide base pairs (bp)). In some embodiments, the distance between plug strands (and/or between socket strands) is 5-20, 5-25, 5-50 or 5-100 nucleotides. In some embodiments, the distance between plug strands (and/or between socket strands) is 5, 10, 15, 20, 25, 30, 35, 40, 45, 50, 55, 60, 65, 70, 75, 80, 85, 90, 95 or 100 nucleotides. In some embodiments, the distance between plug strands (and/or between socket strands) is 5, 6, 7, 8, 9, 10, 11, 12, 13, 14, 15, 16, 17, 18, 19, 20 or 21 nucleotides. In some embodiments, the distance between plug strands (and/or between socket strands) is 42+/−21 nucleotides. For example, the distance between plug strands (and/or between socket strands) may be 21, 42 or 63 nucleotides. In some embodiments, the distance between plug strands (and/or between socket strands) is 42 nucleotides.

One nucleotide unit measures 0.33 nm. Thus, in some embodiments, the distance between cooperative binding sites, for example, the distance between plug strands (and/or between socket strands) may be 5 to 35 nanometers (nm). In some embodiments, the distance between plug strands (and/or between socket strands) is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 nm. In some embodiments, the distance between plug strands (and/or between socket strands) is 14+/−7 nm. For example, the distance between plug strands (and/or between socket strands) may be 7, 14 or 21 nm. In some embodiments, the distance between plug strands (and/or between socket strands) is 14 nucleotides.

In some embodiments, the distance between two cooperative binding sites on a nanostructure is evenly spaced, while in other embodiments, the distances may vary. For example, the distance between a first cooperative binding site and a second cooperative binding site may be 30 angstroms, while the distance between the second cooperative binding site and a third may be 30 angstroms, 40 angstroms or 50 angstroms.

Figure 3A:
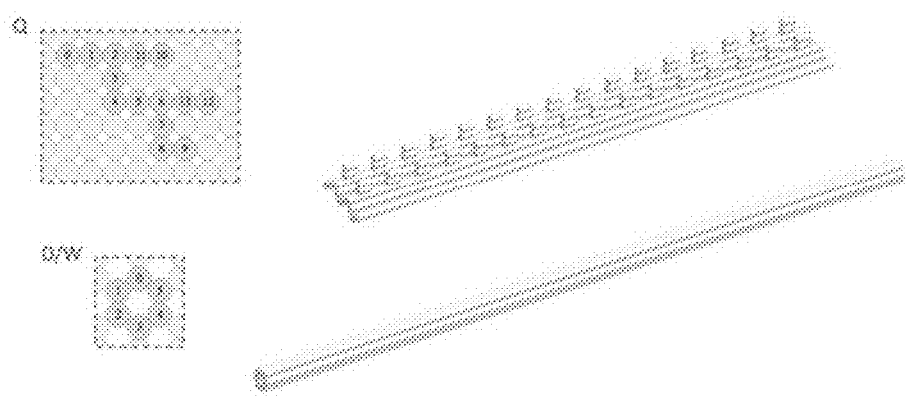
FIGS. 3A-3C show examples of DNA-origami crisscross assembly.
Figure 3B:
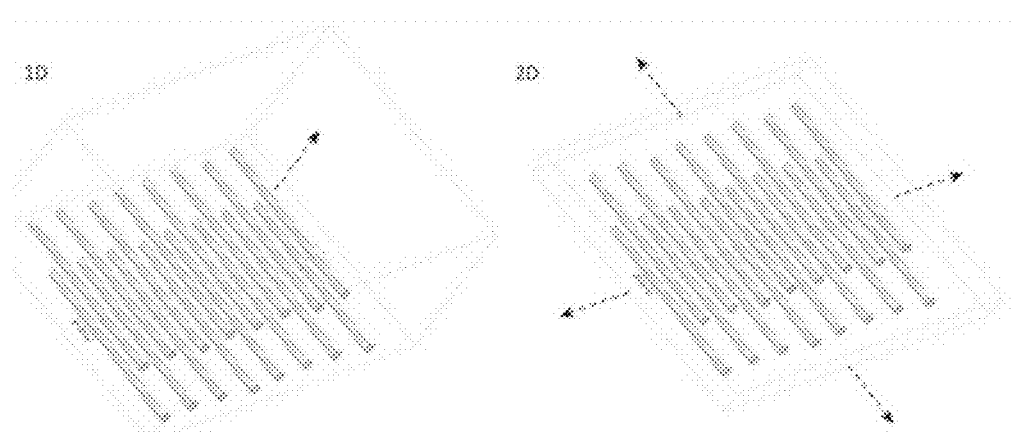
Figure 3C:
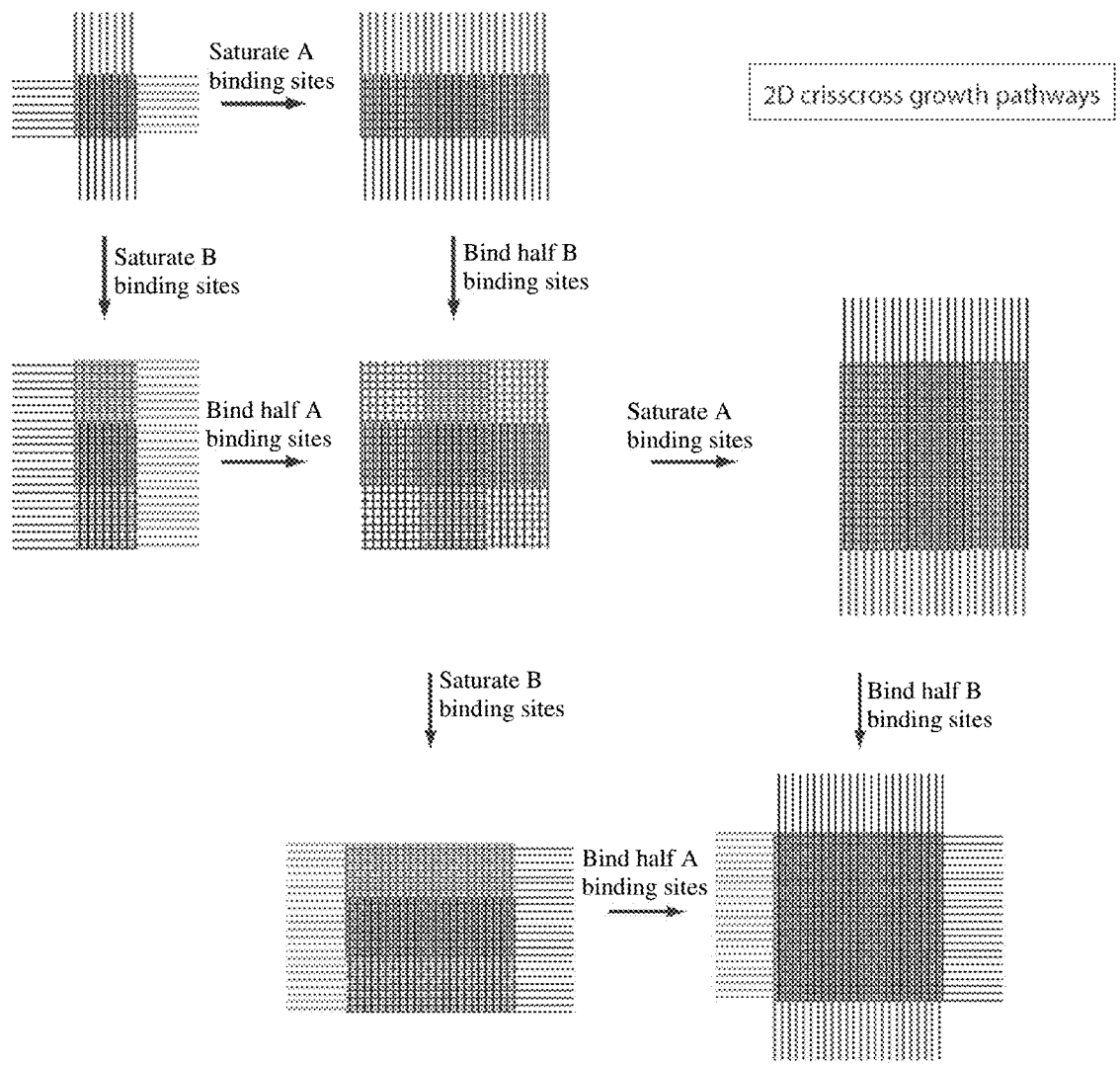

Two or more nanostructures are considered "aligned" if they are oriented in the same direction relative to one another. For example, the 5' ends (or 3' ends) of the nanostructures maybe facing the same direction along its y axis. The top layer of the structure shown in FIG. 3B shows aligned nanorods bound to a nucleating nanostructure. The nanorods, in this example, are perpendicular to the nucleating nanostructure.

A nucleating nanostructure is required to initiate assembly of the first (initial) and second (and, thus, subsequent, e.g., third, fourth, fifth, etc.) subsets of nanostructures, and binding of the nanostructures in the first subset to the nucleating structure is required to initiate assembly of the nanostructures of the second subset. A "nucleating nanostructure" is any nanostructure programmed with binding sites that interacts strongly (irreversibly) with binding sites on each member of drone nanostructures of the initial subset, and aligns them for recruitment of subsequent subsets of worker nanostructures. That is, the binding sites between a nucleating nanostructure and nanostructures of the initial subset should be strong enough that the initial nanostructures bind to and align along the nucleating nanostructures and do not dissociate from the nucleating nanostructure under reaction conditions (e.g., isothermal, physiological conditions). A nucleating nanostructure may have a two-dimensional or a three-dimensional shape, for example.

Additional subsets of nanostructures may be added to the crisscross cooperative assembly system to propagate growth of the end structure (e.g., nanostructure, microstructure or macrostructure). For example, third, fourth and fifth subsets of nanostructures may be added. Binding of the nanostructures of the second subset to the first subset is required to initiate assembly of the nanostructures of the third subset; binding of the nanostructures of the third subset to the second subset is required to initiate assembly of the nanostructures of the fourth subset; and so on. The user-defined end structure may be assembled in one dimension, two dimensions (see, e.g., FIG. 3B) or three-dimensions.

Each subset of nanostructures (e.g., nanorods) should follow a specific set of binding energy parameters. More specifically, the initial subset of nanostructures (e.g., nanorods) should bind strongly (irreversibly) to and form an aligned layer (where each nanostructure is oriented in the same direction relative to one another) along the nucleating nanostructure. The nanostructures (e.g., nanorods) of the initial subset should not interact with (bind to) each other. Likewise, nanostructures (e.g., nanorods) of a subsequent subset should not interact with (bind to) each other. Further, in the absence of a nucleating structure, any nanostructure (e.g., nanorod) from the initial subset should have only one weak (reversible) interaction with any other nanostructure (e.g., nanorod) from a subsequent subset. In the presence of a nucleating structure, a single nanostructure (e.g., nanorod) from an initial subset may interact with more than one nanostructure (e.g., nanorod) from a subsequent subset, and a single nanostructure (e.g., nanorod) from a subsequent subset may interact with more than one nanostructure (e.g., nanorod) from the initial subset. For example, with reference to FIG. 1B, a single nanostructure (e.g., nanorod) may bind to eight other nanostructure (e.g., nanorod), although the single nanostructure (e.g., nanorod) binds to each of the eight nanostructure (e.g., nanorod) only once to form two layers having a 'crisscross' pattern.

A "strong interaction" refers to binding that is engaged more than 50% (e.g., more than 60%, 70%, 80% or 90%) of the time that the binding nanostructures are in a reaction together (the dissociation constant is lower than the concentration of the species/nanostructures in excess).

A "weak interaction"—refers to binding that is engaged less than 1% of the time that the binding nanostructures are in a reaction together (the dissociation constant is at least 100 times higher than the concentration of the species/nanostructures in excess).

A nucleating nanostructure may bind to two or more other nanostructures. In some embodiments, a nucleating nanostructure binds to 5-1000 nanostructures (e.g., DNA nanorods). For example, a nucleating nanostructure may bind to 3-900, 3-800, 3-700, 3-600, 3-500, 3-400, 3-300, 3-200, or 3-100 nanostructures. In some embodiments, a nucleating nanostructure binds to 3-10, 3-15, 3-20, 3-25, 3-30, 3-35, 3-40, 3-45 or 3-50 nanostructures. In some embodiments, a nucleating nanostructure binds to 10-15, 10-20, 10-25, 10-30, 10-35, 10-40, 10-45 or 10-50 nanostructures. In some embodiments, a nucleating nanostructure binds to 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nanostructures (e.g., DNA nanorods).

Thus, a single subset of nanostructures (nanostructures programmed to interact with a single nucleating nanostructure) may comprise 3-900, 3-800, 3-700, 3-600, 3-500, 3-400, 3-300, 3-200, or 3-100 nanostructures. In some embodiments, a single subset of nanostructures comprises 3-10, 3-15, 3-20, 3-25, 3-30, 3-35, 3-40, 3-45 or 3-50 nanostructures. In some embodiments, a single subset of nanostructures comprises 10-15, 10-20, 10-25, 10-30, 10-35, 10-40, 10-45 or 10-50 nanostructures. In some embodiments, a single subset of nanostructures comprises 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nanostructures (e.g., DNA nanorods).

A "subset of nanostructures" refers to a specific group of nanostructures that are similar in size (have similar dimensions) and structure/shape and are programmed to bind to either the nucleating nanostructure (the initial subset) or to a pre-existing layer formed by alignment and binding of other nanostructures that have already aligned and bound to the nucleating structure or nanostructures of another pre-existing layer.

Nanostructures within a defined subset are programmed not bind to each other. Thus, in some embodiments, less than 10% of the nanostructures of a subset bind to another nanostructure of the same subset. In some embodiments, less than 9%, less than 8%, less than 7%, less than 6%, less than 5%, less than 4%, less than 3%, less than 2%, less than 1%, less than 0.5%, less than 0.2%, or less than 0.1% of the nanostructures of a subset bind to another nanostructure of the same subset. In some embodiments, none of the nanostructures of a subset bind to another nanostructure of the same subset.

With crisscross cooperative assembly, nanostructures are aligned to form multiple layers, each layer rotated by some degree relative to adjacent layers (above and below). An example of two layers rotated relative to one another is shown in FIG. 1B. The top layer of aligned nanorods is rotated 90 degrees relative to the bottom layer of aligned nanorods. The degree of rotation between two adjacent layers may vary. In some embodiments, one layer is rotated 10-90 degrees, 20-90 degrees, 30-90 degrees, 40-90 degrees, 50-90 degrees, 60-90 degrees, 70-90 degrees, or 80-90 degrees relative to an adjacent layer. In some embodiments, one layer is rotated 10, 15, 20, 25, 30, 35, 40, 45, 50, 55, 60, 65, 70, 75, 80, 85, or 90 degrees relative to an adjacent layer.

Nucleic Acid Nanostructures

A "nucleic acid nanostructure," including a "DNA nanostructure," refers to a nanostructure (e.g., a structure that is between 0.1 nm and 1 μm (e.g., 0.1 nm and 100 nm) in each spatial dimension, e.g., 1D, 2D or 3D) that is rationally designed to self-assemble (is programmed) into a pre-determined, defined shape that would not otherwise assemble in nature. The use of nucleic acids to build nanostructures is enabled by strict nucleotide base pairing rules (e.g., A binds to T, G binds to C, A does not bind to G or C, T does not bind to G or C), which result in portions of strands with complementary base sequences binding together to form strong, rigid structures. This allows for the rational design of nucleotide base sequences that will selectively assemble (self-assemble) to form nanostructures.

Examples of nucleic acid (e.g., DNA) nanostructures include, but are not limited to, DNA origami structures, in which a long scaffold strand (e.g., at least 500 nucleotides in length) is folded by hundreds (e.g., 100, 200, 200, 400, 500 or more) of short (e.g., less than 200, less than 100 nucleotides in length) auxiliary strands into a complex shape (Rothemund, P. W. K. *Nature* 440, 297-302 (2006); Douglas, S. M. et al. *Nature* 459, 414-418 (2009); Andersen, E. S. et al. *Nature* 459, 73-76 (2009); Dietz, H. et al. *Science* 325, 725-730 (2009); Han, D. et al. *Science* 332, 342-346 (2011); Liu, W et al. *Angew. Chem. Int. Ed.* 50, 264-267 (2011); Zhao, Z. et al. *Nano Lett.* 11, 2997-3002 (2011); Woo, S. & Rothemund, P. *Nat. Chem.* 3, 620-627 (2011); Tørring, T. et al. *Chem. Soc. Rev.* 40, 5636-5646 (2011)). Other more modular strategies have also been used to assemble DNA tiles (Fu, T. J. & Seeman, N. C. Biochemistry 32, 3211-3220 (1993); Winfree, E. et al. *Nature* 394, 539-544 (1998); Yan, H. et al. *Science* 301, 1882-1884 (2003); Rothemund, P. W. K. et al. *PLoS Biol.* 2, e424 (2004); Park, S. H. et al. *Angew. Chem. Int. Ed.* 45, 735-739 (2006); Schulman, R. & Winfree, E. *Proc. Natl Acad. Sci. USA* 104, 15236-15241 (2007); He, Y. et al. *Nature* 452, 198-201 (2008); Yin, P. et al. *Science* 321, 824-826 (2008); Sharma, J. et al. *Science* 323, 112-116 (2009); Zheng, J. P. et al. *Nature* 461, 74-77 (2009); Lin, C. et al. *ChemPhysChem* 7, 1641-1647 (2006)) or RNA tiles (Chworos, A. et al. *Science* 306, 2068-2072 (2004); Delebecque, C. J. et al. *Science* 333, 470-474 (2011)) into periodic (Winfree, E. et al., *Nature* 394, 539-544 (1998); Yan, H. et al. *Science* 301, 1882-1884 (2003); Chworos, A. et al. *Science* 306, 2068-2072 (2004); Delebecque, C. J. et al. *Science* 333, 470-474 (2011)) and algorithmic (Rothemund, P. W. K. et al. *PLoS Biol.* 2, e424 (2004)) two-dimensional lattices (Seeman, N. C. *J. Theor. Biol.* 99, 237-247 (1982); Park, S. H. et al. *Angew.* Chem. Int. Ed. 45, 735-739 (2006)), extended ribbons-(Schulman, R. & Winfree, E. *Proc. Natl Acad. Sci. USA* 104, 15236-15241 (2007); Yin, P. et al. *Science* 321, 824-826 (2008)) and tubes (Yan, H. et al. *Science* 301, 1882-1884 (2003); Yin, P. et al. *Science* 321, 824-826 (2008); Sharma, J. et al. *Science* 323, 112-116 (2009)), three-dimensional crystals (Zheng, J. P. et al. *Nature* 461, 74-77 (2009)), polyhedral (He, Y. et al. *Nature* 452, 198-201 (2008)) and simple finite two-dimensional shapes (Chworos, A. et al. *Science* 306, 2068-2072 (2004); Park, S. H. et al. *Angew. Chem. Int. Ed.* 45, 735-739 (2006)).

Thus, crisscross cooperative assembly building blocks (e.g., nucleating nanostructures and subsets of nanostructures) may be one of a number of nucleic acid nanostructure shapes, including, but not limited to, rods/tubes, sheets, ribbons, lattices, cubes, spheres, polyhedral, or another two-dimensional or three-dimensional shape. In some embodiments, a nanostructure has junction(s), branch(es); crossovers, and/or double-crossovers formed by nucleotide base pairing of two or more nucleic acid strands (see, e.g., Mao, C. *PLoS* Biology, 2(12), 2036-2038, 2004).

In some embodiments, a nucleic acid nanostructure has a handle and barrel shape, similar to that depicted in FIG. 22.

The versatile and stable nature of DNA origami enables the construction of various individual architectures that can be designed in a particular way, to facilitate to cooperative assembly of larger structures. In one example, each component is a separately folded DNA-origami structure. FIG. 3A shows an example of a DNA origami queen, drone and worker, whereby the drone and worker are of identical architecture (six helix bundle DNA nanotubes). Queen, drones and workers can then assemble in a cooperative manner to form higher order 1D, 2D and 3D structures (FIG. 3B). 3D structures are contemplated by merging 1D and 2D design principles. For example, FIG. 22 depicts a 3D queen nanostructure assembling with 2D drone/worker slats to form a barrel shape.

A nucleic acid (e.g., DNA) slat is a slat-shaped nanostructure that is composed of DNA. A slat may be an antiparallel-crossover single-stranded slat (AXSSS) comprising single strands that cross a partnering single strand only once. Also provided herein are paranemic crossover slats that include a pair of strands that cross another pair of strands.

Figure 4:
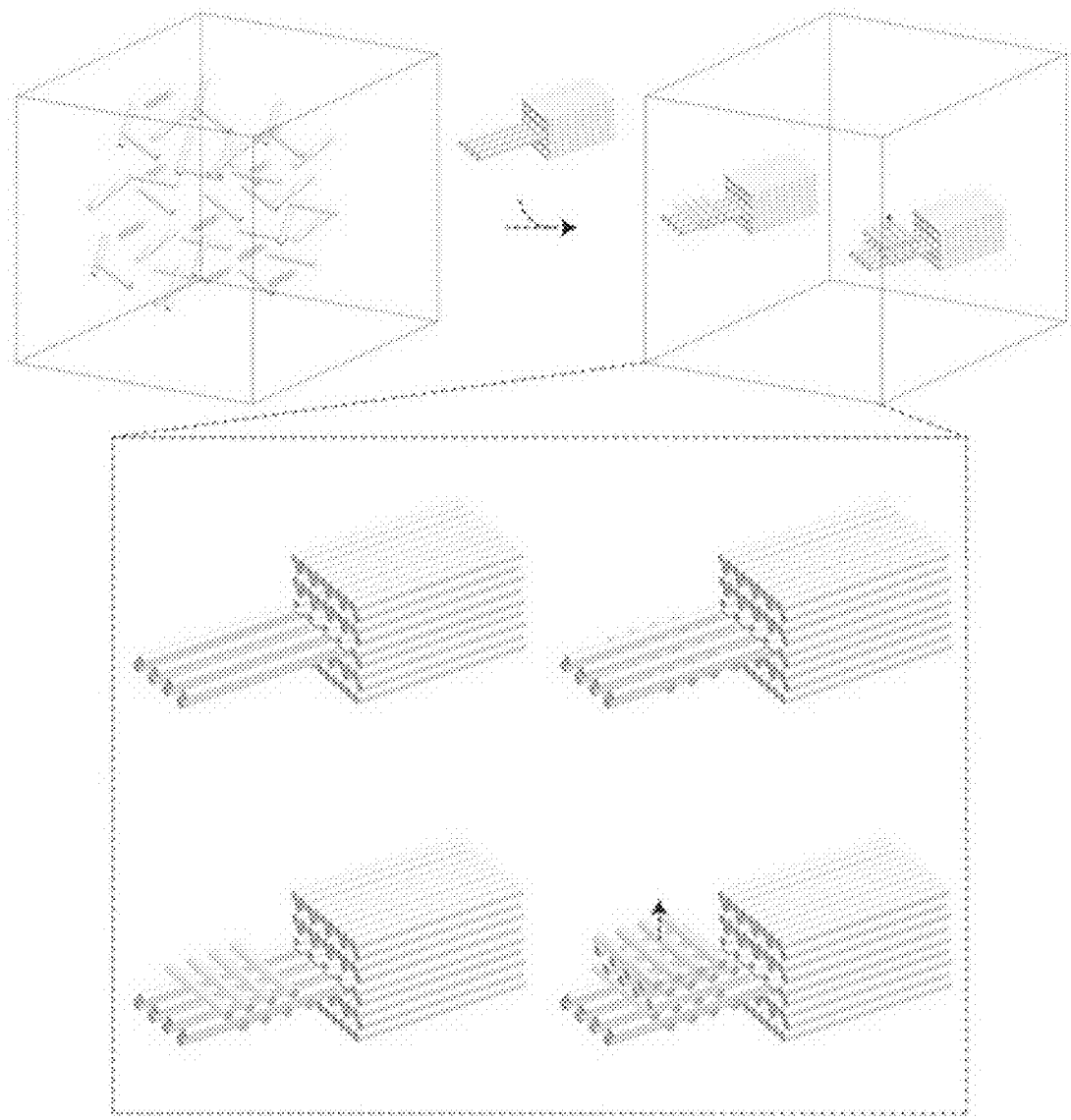
FIG. 4 shows an example of single-stranded DNA crisscross cooperative assembly. Oligonucleotides comprising the workers and drones of the system (shown as cylinders) are nucleated by the addition of a cubic DNA-Origami queen structure with a nucleation site. Stepwise assembly is shown in illustrated magnification.
Figure 5:
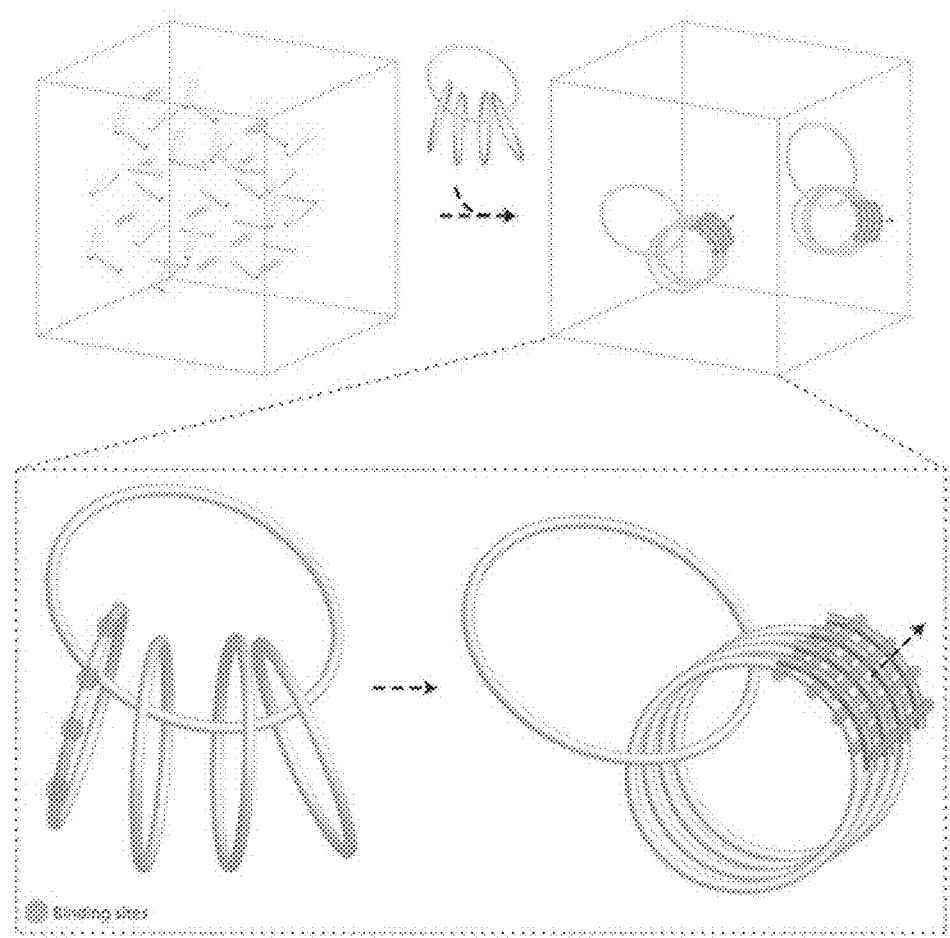
FIG. 5 shows an example of catenane crisscross cooperative assembly queen (catenane queen), useful for ultrasensitive detection. Oligonucleotides comprising the workers and drones of the system (shown as cylinders) are nucleated by the addition of a single-stranded catenane queen structure with a nucleation site. Binding sites on the structure shown to the left of the illustrated magnification indicate the nucleation for the workers/drones. Each host ring has multiple binding sites, collectively functioning as a cooperative binding site.

Similar to the larger scale DNA-origami crisscross cooperative assembly, single-stranded DNA can be used to achieve cooperative assembly of higher order structures. In order to achieve this, drones and workers are replaced with oligonucleotides of various lengths (depending on the proposed architecture) that can assemble onto a DNA-origami queen nucleation site (shown in FIG. 4) or onto a single stranded DNA catenane structure shown in FIG. 5, FIG. 22 and FIGS. 24A-24B. The ring structures depicted in FIG. 5 are comprised of single-stranded DNA that has exposed binding sites for drone and worker oligonucleotides. In another example, the components are folded into a DNA origami barrel queen (FIGS. 24A-24B). The scaffold can be tiled with extended DNA slats (slats) capable of seeding further DNA slats, leading to growth of the structure. Generally, the DNA slats work in two steps: first, folding the origami queen site (for example, mixing M13 scaffold and staple strands), and second, mixing the crude DNA origami queen reaction with DNA slats, leading to growth of the structure. Varying salt concentrations, temperatures, and DNA slat concentration can alter the binding energy of the various sub-components, leading to reversible or irreversible binding, for example.

Typically, nucleic acid nanostructures do not contain coding sequences (sequences that code for a full length mRNA or protein), thus, nucleic acid nanostructures do not contain a promoter or other genetic elements that control gene/protein expression. An individual single-stranded nucleic acid (e.g., DNA strand or RNA strand without secondary structure), or an individual double-stranded nucleic acid (e.g., without secondary structure), for example, double helices found in nature or produced synthetically or recombinantly (e.g., such as a plasmid or other expression vector), are specifically excluded from the definition of a nucleic acid nanostructure.

Nanostructures, in some embodiments, have a void volume, which is the combine volume of space between nucleic acids that form a nanostructures. It should be understood that "space" includes fluid-filled space. Thus, a nanostructure in solution, have a void volume of 25% may include 75% nucleic acids and 25% reaction buffer (filling the 25% void volume of the nanostructure). In some embodiments, a nanostructure in solution, e.g., in reaction buffer, may have a void volume of at least 10% (e.g., 10-90%, 10-80%, 10-70%, 10-60%, 10-50%, 10-40%, or 10-30%), at least 20% (e.g., 20-90%, 20-80%, 20-70%, 20-60%, 20-50%, 20-40%, or 20-30%), at least 30%, (e.g., 30-90%, 30-80%, 30-70%, 30-60%, 30-50%, or 30-40%), at least 40% (e.g., 40-90%, 40-80%, 40-70%, 40-60%, or 40-50%), at least 50% (e.g., 50-90%, 50-80%, 50-70%, or 50-60%), at least 60% (e.g., 60-90%, 60-80%, or 60-70%), at least 70% (e.g., 70-90% or 70-80%), or at least 80% (e.g., 80-90%). In some embodiments, a nanostructure has a void volume of 10%, 15%, 20%, 25%, 30%, 35%, 40%, 45%, 50%, 55%, 60%, 65%, 70%, 75%, 80%, 85%, or 90%.

A "nucleic acid nanorod," including a "DNA nanorod" is a nucleic acid (e.g., DNA) nanostructure in the shape of a rod. A nanorod is a three-dimensional cylindrical shape having a length longer than its diameter. Examples of nanorods are depicted in FIGS. 1A-1B and FIGS. 3A-3B. In some embodiments, a nucleic acid nanorod comprises six helix bundles. For example, six DNA double helices may be connected to each other at two crossover sites. DNA double helices with 10.5 nucleotide pairs per turn facilitate the programming of DNA double crossover molecules to form hexagonally symmetric arrangements when the crossover points are separated by seven or fourteen nucleotide pairs (see, e.g., Mathieu F. et al. *Nano Lett.* 5(4), 661-664 (2005)). Other methods of assembling nucleic acid nanorods (also referred to as nanotubes) may be used (see, e.g., Feldkamp, U. et al. *Angew. Chem. Int. Ed.* 45(12), 1856-1876 (2006); Hariri A. et al. *Nature Chemistry*, 7, 295-300 (2015)).

The length and diameter of a nanorod (or other nanostructure) may vary. In some embodiments, a nanorod (or other nanostructure) has a length of 10-100 nm, or 10-500 nm. For example, a nanorod may have a length of 10-500 nm, 10-400 nm, 10-300 nm, 10-200 nm, 10-100 nm, 10-90 nm, 10-80 nm, 10-70 nm, 10-60 nm, 10-50 nm, 10-30 nm, or 10-20 nm. In some embodiments, a nanorod has a length of 100-500 nm, 200-500 nm, or 300-500 nm. In some embodiments, a nanorod has a length of 100 nm, 150 nm, 200 nm, 250 nm, 300 nm, 350 nm, 400 nm, 450 nm or 500 nm. In some embodiments, a nanorod has a length of 10, 15, 20, 25, 30, 35, 40, 45, 50, 55, 60, 65, 70, 75, 80, 85, 90, 95 or 100 nm. In some embodiments, the length of a nanorod (or other nanostructure) is longer than 100 nm (e.g., 100-1000 nm), or shorter than 10 nm (e.g., 1-10 nm). In some embodiments, a nanorod (or other nanostructure) has a diameter of 5-90 nm. For example, a nanorod may have a diameter of 5-80 nm, 5-70 nm, 5-60 nm, 5-50 nm, 5-30 nm, 5-20 or 5-10 nm. In some embodiments, a nanorod has a diameter of 5, 10, 15, 20, 25, 30, 35, 40, 45, 50, 55, 60, 65, 70, 75, 80, 85 or 90 nm. In some embodiments, the diameter of a nanorod is longer than 9 nm, or shorter than 5 nm. Thus, in some embodiments, a nanorod (or other nanostructure) has a circumference of 15-300 nm (C≈3.14×d).

A nucleic acid nanostructure, such as a nanorod, is considered "elongated," if the length of the nanostructure is longer than its width/diameter (e.g., by at least 10%, 20%, 25%, 50%, 100%, or 200%).

Nucleic acid nanostructures are typically nanometer-scale structures (e.g., having lengths of 1 to 1000 nanometers). In some embodiments, however, the term "nanostructure" herein may include micrometer-scale structures (e.g., assembled from more than one nanometer-scale or micrometer-scale structure). In some embodiments, a nanostructure has a dimension (e.g., length or width/diameter) of greater than 500 nm or greater than 1000 nm. In some embodiments, a nanostructure has a dimension of 1 micrometer to 2 micrometers. In some embodiments, a nanostructure has a dimension of 10 to 500 nm, 10 to 450 nm, 10 to 400 nm, 10 to 350 nm, 10 to 300 nm, 10 to 250 nm, 10 to 200 nm, 10 to 150 nm, 10 to 100 nm, 10 to 50 nm, or 10 to 25 nm. In some embodiments, the nanostructure has a dimension of 500 to 450 nm, 500 to 400 nm, 500 to 350 nm, 500 to 300 nm, 500 to 250 nm, 500 to 200 nm, 500 to 150 nm, 500 to 100 nm, 500 to 50 nm, or 500 to 25 nm. In some embodiments, the nanostructure has a dimension of 10, 25, 50, 75, 100, 150, 200, 250, 300, 350, 400, 450, or 500 nm.

A nucleic acid nanostructure is considered to "self-assemble." Bottom up, self-assembly refers to the process by which molecules adopt a defined arrangement without guidance or management from an outside source. Although, it should be understood that with synthetic nucleic acid self-assembly, as provided herein, the nucleotide base sequences that guide assembly of nucleic acids are artificially designed, and the corresponding nucleic acids are accordingly synthesized by an outside source, such as one of skill in the art (using, for example, standard nucleic acid synthesis techniques). That is, one of ordinary skill in the art can 'program' nucleotide base sequences within a single nucleic acid strand or between two difference nucleic acid strands to selectively bind to each other in solution based on a strict set of nucleotide base pairing rules (e.g., A binds to T, G binds to C, A does not bind to G or C, T does not bind to G or C). Self-assembly may be intramolecular (folding) or intermolecular.

The nanostructures and, thus, nanostructures, microstructures and macrostructures assembled from smaller nanostructures, are "rationally designed." A nanostructure, as discussed above, does not assemble in nature. Nucleic acid strands for use in crisscross cooperative assembly are 'programmed' such that among a specific population of strands, complementary nucleotide base sequences within the same strand or between two different strands bind selectively to each other to form a complex, user-defined structure, such as a rod/tube, ribbon, lattice, sheet, polyhedral, cube, sphere, or other two-dimensional or three-dimensional shape. A nanostructure may have a regular shape (sides that are all equal and interior angles that are all equal) or an irregular shape (sides and angles of any length and degree).

Methods of Crisscross Cooperative Assembly

Self-assembly of a nucleating nanostructure and subsets of nanostructures occurs, in some embodiments, in a 'one-pot' reaction, whereby all nucleic acid nanostructures of a crisscross cooperative assembly system are combined in a reaction buffer, and then the reaction buffer is incubated under conditions that result in self-assembly of all of the nucleic acid nanostructures.

Conditions that result in self-assembly of nucleic acid nanostructures of a crisscross cooperative assembly reaction may vary depending on the size, shape, composition and number of nucleic acid nanostructures in a particular reaction. Such conditions may be determined by one of ordinary skill in the art, for example, one who rationally designs/programs the nanostructures to self-assemble.

A crisscross cooperative assembly method may be performed at a variety of temperatures. In some embodiments, a crisscross cooperative assembly method is performed at room temperature (~25° C.) or 37° C. A crisscross cooperative assembly method may be performed at a temperature lower than 25° C. or higher than 37° C.

The salt concentration of the reaction buffer in which a crisscross cooperative assembly reaction is performed may also vary. In some embodiments, the reaction buffer comprises $MgCl_2$ salt at a concentration of 1 mM-10 mM (e.g., 1 mM, 2 mM, 3 mM, 4 mM, 5 mM, 6 mM, 7 mM, 8 mM, 9 mM or 10 mM). In some embodiments, the reaction buffer comprises NaCl at a concentration of 100 mM-500 mM (e.g., 100 mM, 200 mM, 300 mM, 400 mM or 500 mM). In some embodiments, a crisscross cooperative assembly method is performed under high-salt conditions. Thus, in some embodiments, the reaction buffer comprises $MgCl_2$ salt at a concentration of at least 20 mM (e.g., 20-500 mM, or 20-200 mM). In some embodiments, the reaction buffer comprises NaCl at a concentration of at least 1 M (e.g., 1-2 M, 1-3 M, 1-4 M, or 1-5 M).

In any given reaction, the number of initial nanostructures (drones) exceeds the number of nucleating nanostructures (queens). Thus, in some embodiments, the ratio of nucleating nanostructure to non-nucleating nanostructure (e.g., a drone from an initial subset, or a worker from a subsequent subset) is $1:10-1:10^{12}$ (trillion). For example, the ratio of nucleating nanostructure to non-nucleating nanostructure may be 1:10-1:1000, 1:10-1:500, 1:10-1:100, 1:10-1:75, 1:10-1:50, or 1:10-1:25. In some embodiments, the ratio of nucleating nanostructure to non-nucleating nanostructure is 1:1000, 1:500, 1:100, 1:90, 1:80, 1:70, 1:60, 1:50, 1:40, 1:30, 1:20 or 1:10.

In some embodiments, a crisscross cooperative assembly reaction is incubated for 2-96 hours. For example, a crisscross cooperative assembly reaction may be incubated for 2-24 hours, 2-30 hours, 2-36 hours, 2-42 hours, 2-48 hours, 2-54 hours, 2-60 hours, 2-66 hours, 2-72 hours, 2-78 hours, 2-84 hours, 2-90 hours, or 2-96 hours. In some embodiments, a crisscross cooperative assembly reaction is incubated for 3, 6, 9, 12, 15, 18, 21, 24, 27, 30, 33, 36, 39, 42, 45, 48, 51, 54, 57, 60, 63, 66, 69, or 72 hours. In some embodiments, a crisscross cooperative assembly reaction is incubated for 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70 or 72 hours.

Biosensors

In some embodiments, the crisscross assembly products may be used as biosensors that are capable of detecting a selected biomolecule (analyte) using a variety of different mechanisms and the systems described herein. For example, in such systems, the presence of a biomolecule can be used to trigger crisscross assembly, which can then be detected (visualized), indicating the presence of the biomolecule.

Figure 6:
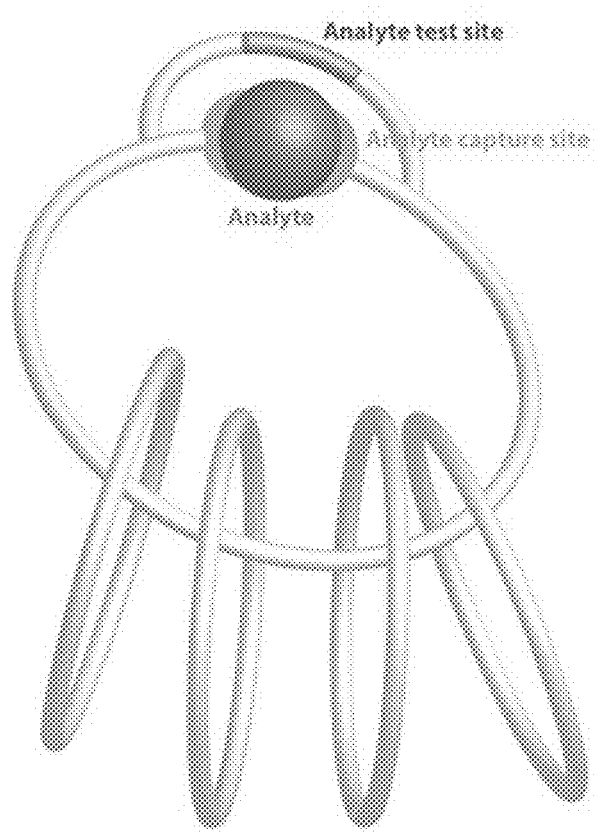
FIG. 6 shows a catenane queen from FIG. 5 that has been modified to serve as a biosensor. The large DNA ring has been split to incorporate and biomolecule capture site to bind a biomolecule (e.g., macromolecule) in biological samples. The presence of the biomolecule, in some embodiments may be detected in mixtures as follows: (1) A biological sample is mixed with a high concentration of the catenane queen and a biomolecule of interest binds the biomolecule capture site. (2) A chemical reaction is used to reversibly cleave the biomolecule capture site. (3) Catenane queens not bound to the target biomolecule fall apart more quickly compared to those held together by the target biomolecule. (4) Remaining catenane queens in the test mixture are re-ligated at the biomolecule capture site. (5) Drones and workers are added to the test mixture to amplify remaining queens using readily observable micrometer-scale DNA structures. This system is modular, as the biomolecule capture site may be customized to bind disease markers, including proteins or nucleic acid sequences.
Figure 7:
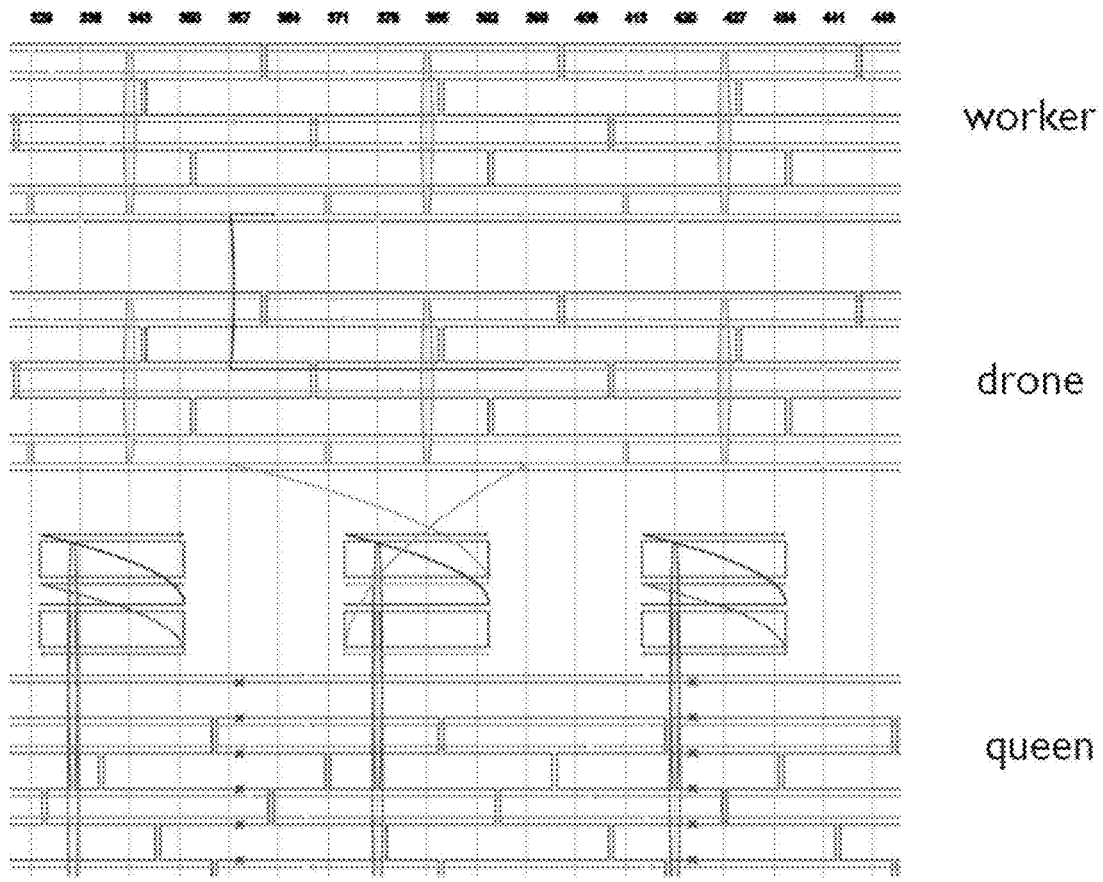
FIG. 7 shows a CAD schematic of an example of base-pairing linkages between a 6 helix bundle worker and a 6 helix bundle drone to queen. A plug socket linkage design may also be used, as shown in FIGS. 18-20. The following CAD tool was used to design the structures: Douglas S M, Marblestone A H, Teerapittayanon S, Vazquez A, Church G M, Shih W M. Rapid prototyping of 3D DNA-origami shapes with caDNAno. Nucleic Acids Res. 37, 5001-5006, 2009.
Figure 8A:
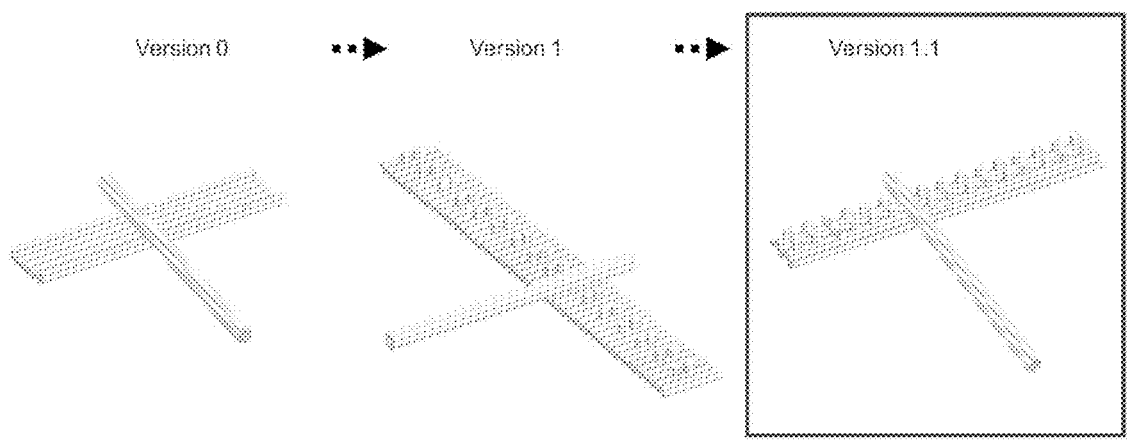
FIGS. 8A-8D are schematics depicting different example 'seed' designs (a 6-helix bundle nanorod bound to a nucleating nanostructure) with different cooperative bind site configurations. Additional example 'seed' designs are shown in FIGS. 16A-16C.
Figure 8B:
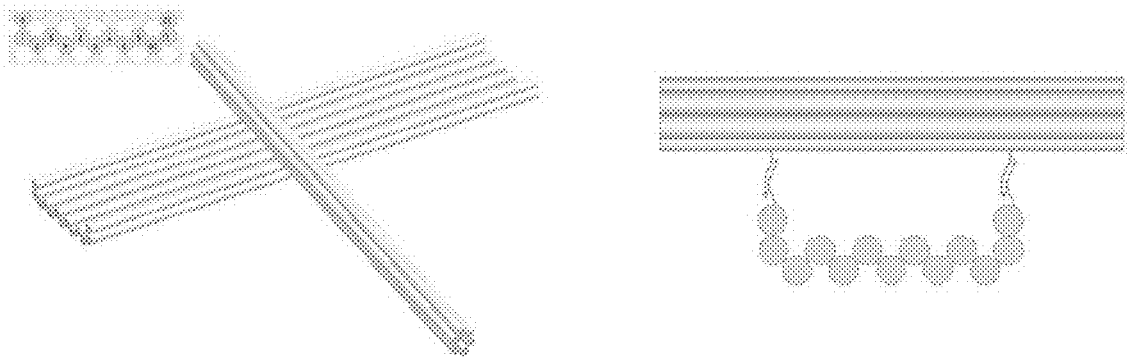
Figure 8C:
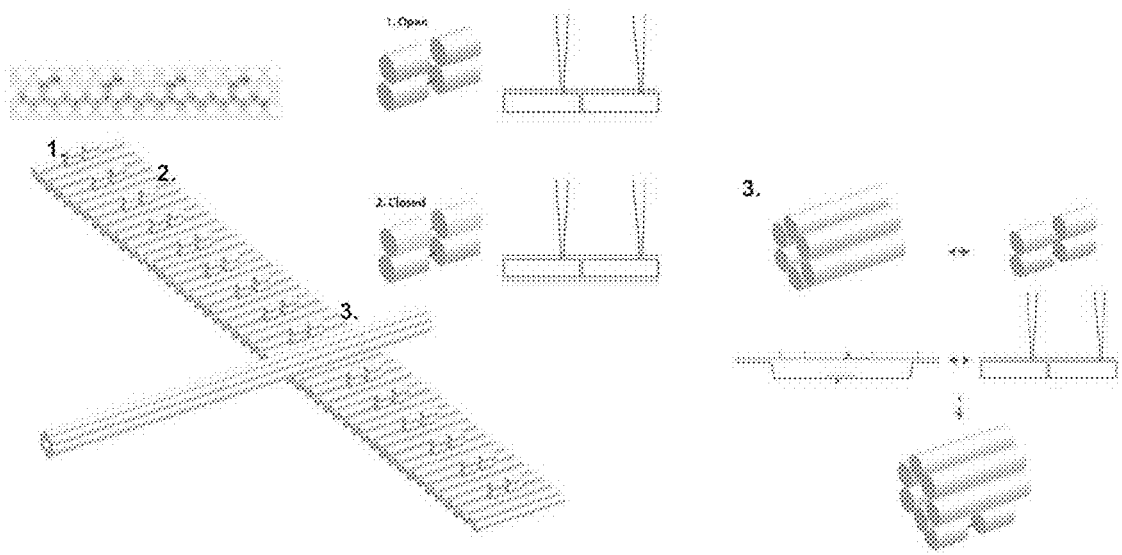
Figure 8D:
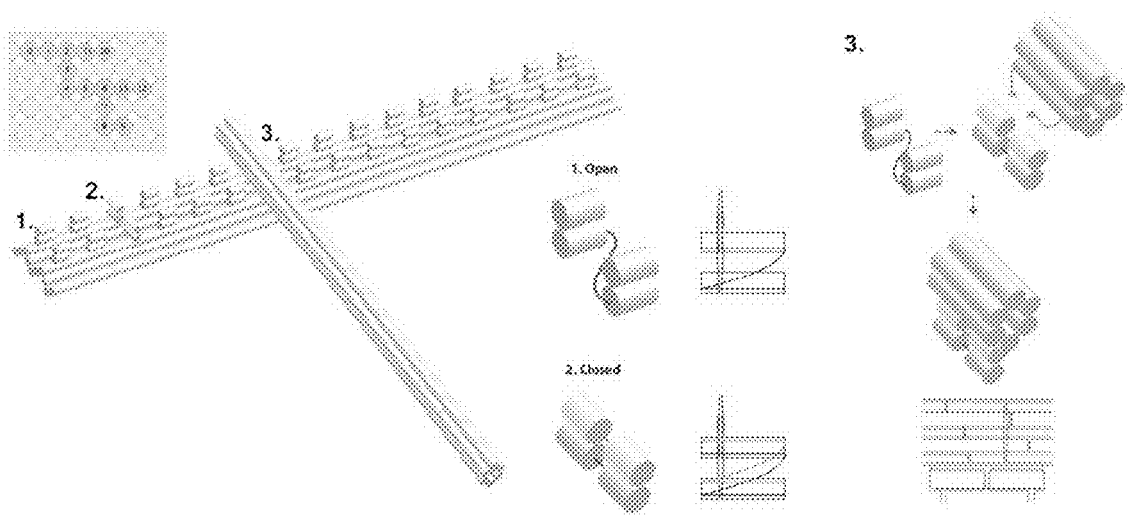

The biomolecule may be detected using a ring system. As depicted in FIG. 6, the large DNA ring ("host ring"), single-stranded DNA, may be split to incorporate a biomolecule capture site (analyte test site) to bind macromolecules in biological samples. The DNA ring loops through and encloses a number of discrete, separate "guest" rings, which are single-stranded DNA and function as catenane queens, so that the guest rings are catenated on the host ring, similar to individual beads on a bracelet. In some embodiments, the guest rings are independently formed from separate single-stranded nucleic acids (see, e.g., FIGS. 5 and 6), while in other embodiments, the guest rings are formed from a long single nucleic acid strand assembled into multiple (e.g., vertically stacked) rings (see, e.g., FIGS. 27A and 27B). The number of guest rings can be 2, 3, 4, or 5 or more. In embodiments, each guest ring (catenane queen) comprises binding sites for drone and worker oligonucleotides and is therefore capable of crisscross assembly. In embodiments, the plurality of catenated guest rings when in close proximity forms a catenane queen comprising binding sites (e.g., plug strands) for drone and worker nucleic acids and/or structures and is thus capable of crisscross assembly. The number of binding sites per guest ring can vary, and may be 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100. A biomolecule test site, located near the biomolecule capture site may also formed.

The presence of the biomolecule, in some embodiments may be detected in mixtures, such as biological samples, as follows. First, a biological sample is mixed with a high concentration of the catenane queen, allowing macromolecules of interest bind the biomolecule capture site. Then, a chemical reaction is used to reversibly cleave the biomolecule capture site. Catenane queens not bound to the target biomolecule will fall apart more quickly compared to those held together by the target biomolecule. The remaining catenane queens in the test mixture are re-ligated at the biomolecule test site. Subsequently, drones and workers are added to the test mixture to amplify remaining intact queens using readily observable micrometer-scale DNA structures. This system is modular, and the biomolecule capture site may be customized to bind disease markers, including proteins or nucleic acid sequences.

Ultraspecific biosensors can also be created by adding a biomolecule detection system to the multiple guest-ring (e.g., guest-loop) catenane systems with DNA slats, as depicted in FIGS. 27-28. In this example, a barrel-queen is used; however, other 3-dimensional shapes are also possible (e.g., sheets, blocks and dendrimers). An example of the production of a barrel queen (a rolled sheet) is described above.

Figure 21A:
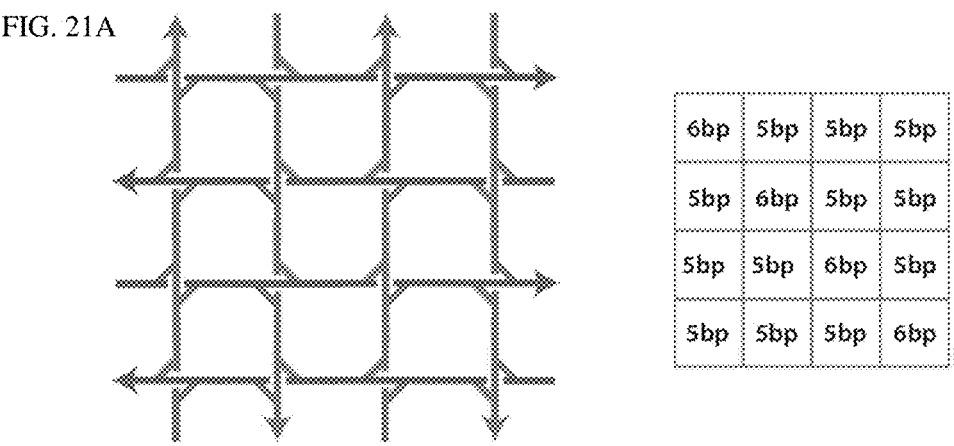
FIGS. 21A-21B show an example of a crisscross DNA slat-based architecture.
Figure 21B:
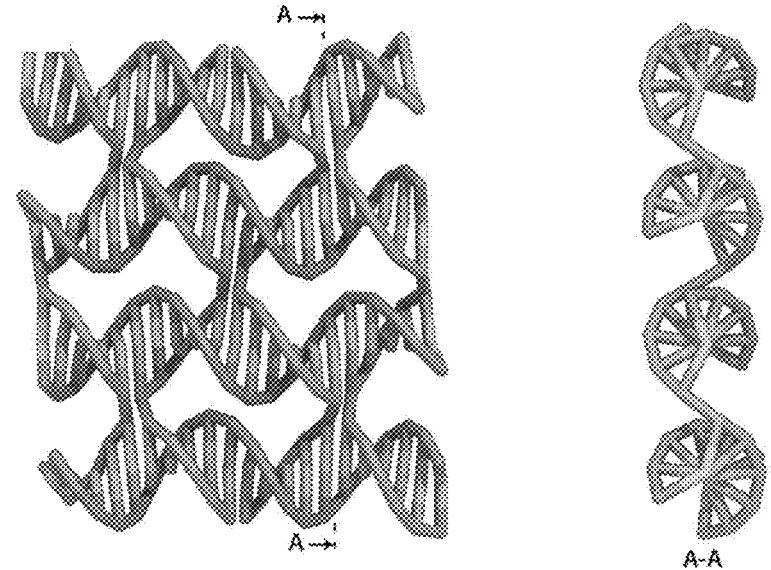

An example of a DNA slat is depicted in FIGS. 21A and 21B.

Figures 27A, 27B, 27C, 27D, 27E:
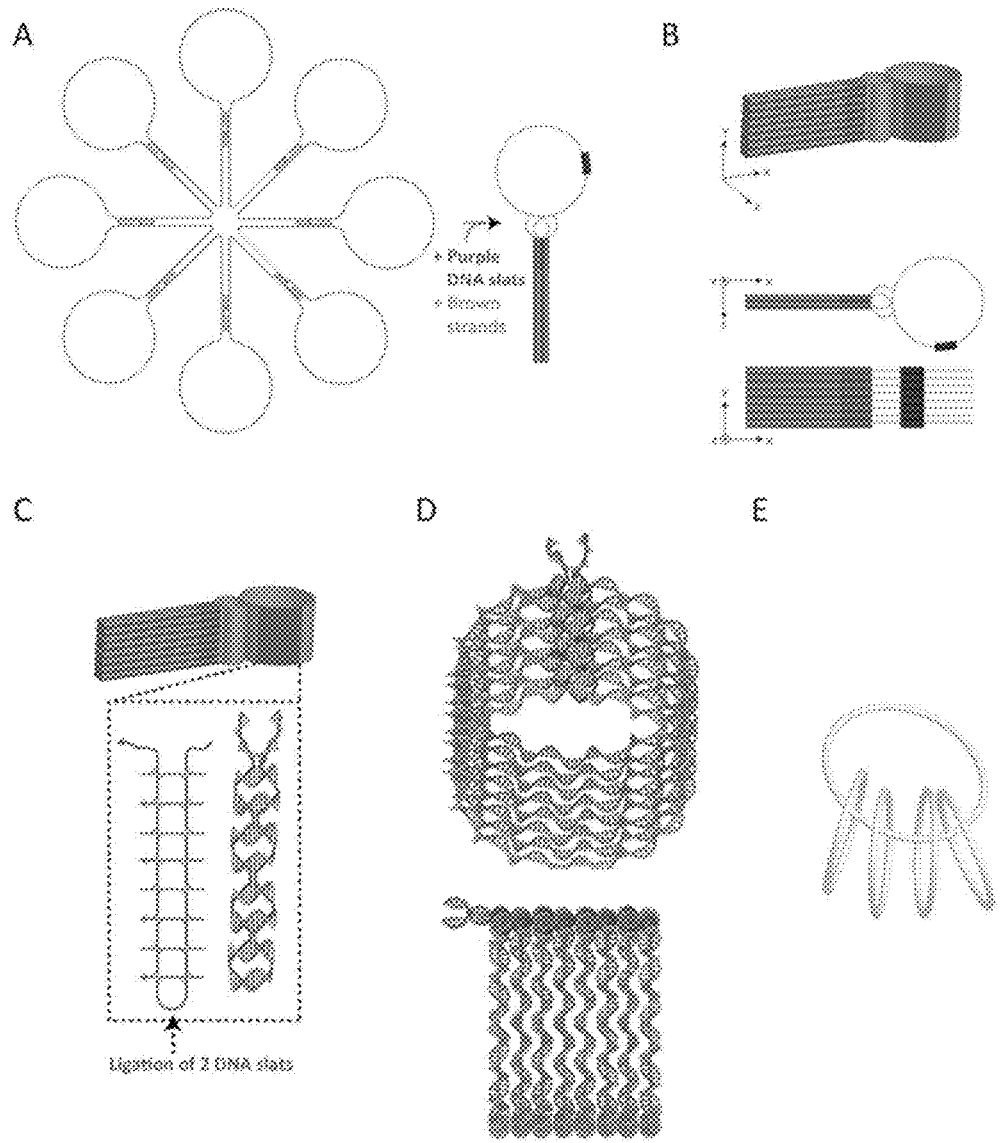
FIGS. 27A-27E show formation of multi-host-ring catenane systems with DNA slats in a one-pot reaction.
Figure 28A:
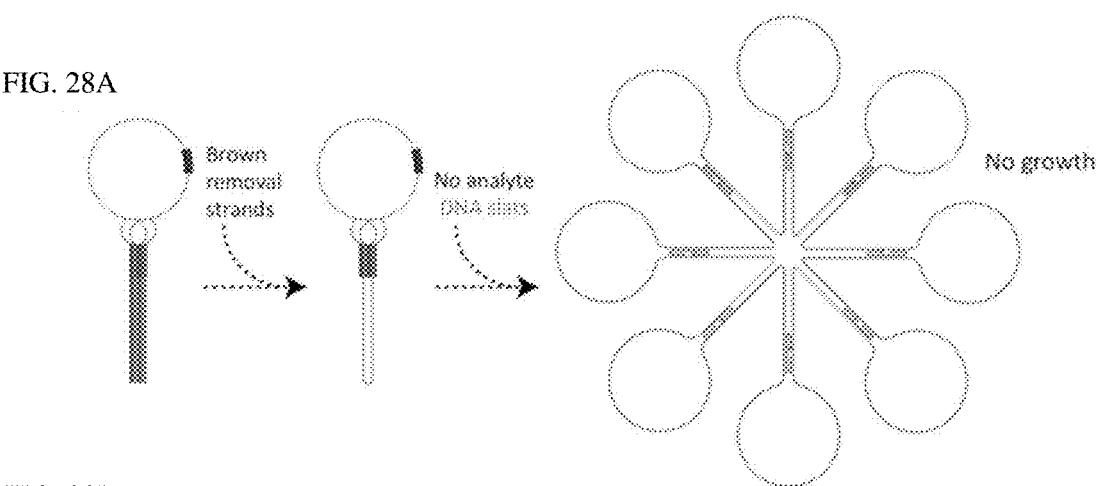
FIGS. 28A-28B show a barrel queen used for ultrasensitive detection.
Figure 28B:
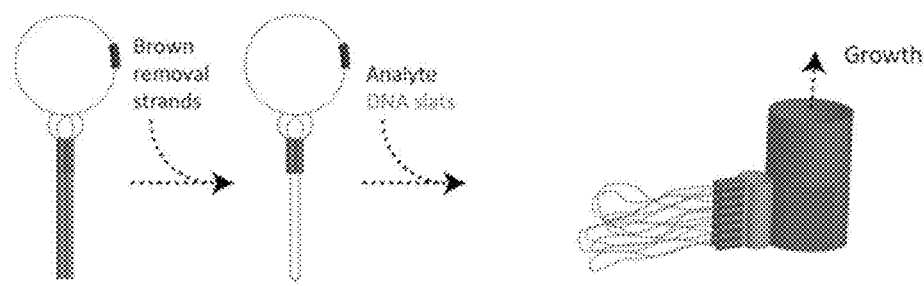
Figure 29:
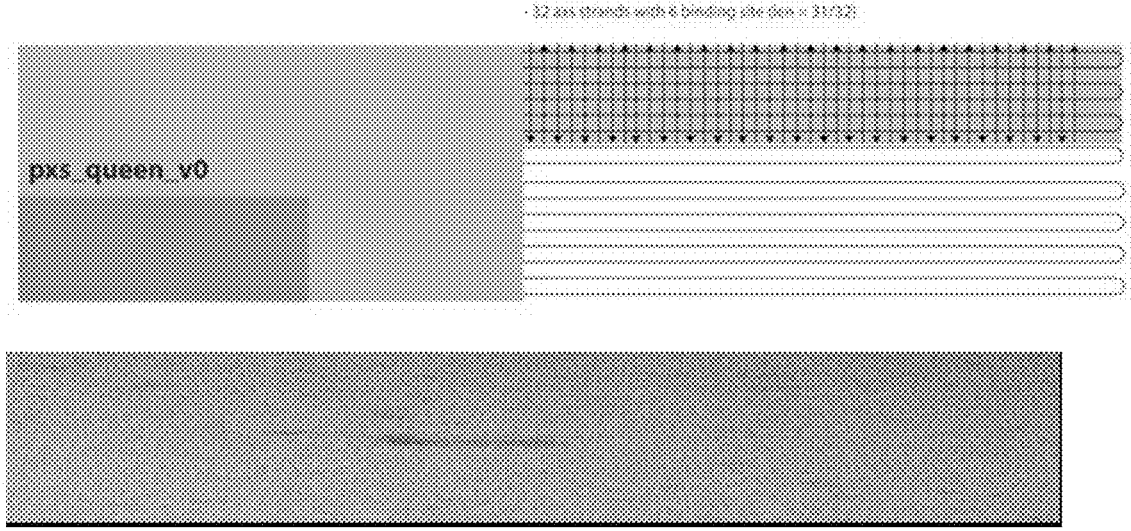
FIG. 29 shows a schematic (upper panel) of a queen with six binding sites per slat and a transmission electron microscope (TEM) image (lower panel) of the queen.

Using a scaffold for DNA origami, for example an M13 scaffold and staple strands, a multiple guest-ring catenane system can be formed. For example, in FIG. 27, an eight-loop system is formed in a one-pot reaction. The number of loops (rings) can be varied, depending on the design of the system, and may be 2, 3, 4, 5, 6, 7, 8, 9, 10, 11, 12, 13, 14, 15, 16, 17, 18, 19, or 20 loops. Additional loops may be used. Unlike the system described above, the handles (elongated structures) and loops (rings) are all part of the same single-stranded DNA (e.g., M13 DNA); the handle structures are programmed to link together by specific staple strands (slats). The system is designed around the specific staple strands/slats; in the presence of biomolecule, they hold the structure together and growth can occur from the parallel loops when drones and workers are added (FIG. 28B). In the absence of biomolecule, the staple strands/slats release the structure, and no growth can occur as the queen falls apart and the binding sites are not close enough for nucleation and growth even in the presence of drones and workers (FIG. 28A). The presence of the structures can be detected using any one of the methods described above, or with any method known in the art.

DNA slats or other nucleic acids of a biosensor may be modified with one or more switchable bridges. A "switchable bridge" is a link between functional groups that forms or breaks in the presence of a particular agent (e.g., reaction agent or dissociation agent). Examples of switchable bridges include bonds formed via a "click chemistry" reaction (e.g., a between an azide and an alkyne), protein-protein binding (e.g., one or more antibodies binding to a target protein/antigen), a disulfide bond (between two thiols).

Thus, some aspects of the present disclosure provide a biosensor comprising (i) a first DNA slat comprising a first functional group (e.g., an azide or alkyne), a first binding partner (e.g., an antibody, aptamer or nanobody), and a second functional group (e.g., a thiol or nucleic acid), and (ii) a second DNA slat comprising a third functional group (e.g., a thiol or nucleic acid), a second binding partner (e.g., an antibody, aptamer or nanobody), and a fourth functional group (e.g., an azide or alkyne), wherein the first and fourth functional groups react in the presence of a reaction agent to form a link (e.g., a covalent link), wherein the first and fourth binding partners bind specifically to a biomolecule of interest to form a link (e.g., non-covalent link), and wherein the second and third functional groups form a link (e.g., a covalent link) that breaks in the presence of a dissociation agent.

In some embodiments, a biosensor comprises a first DNA slat comprising an azide, an antibody, and a thiol group, and a second DNA slat comprising an alkyne, an antibody, and a thiol group, wherein antibody of (i) and the antibody of (ii) bind specifically to a biomolecule of interest.

A "first biomolecule binding partner" and a "second biomolecule binding partner" are any molecules that bind to the same target biomolecule to form a switchable bridge linking DNA slats to each other (via a non-covalent link). In some embodiments, the first and second biomolecule binding partners are proteins or peptides. For example, the first and second biomolecule binding partners may be antibodies that bind to different epitopes of the same antigen. Thus, in some embodiments, the first and second biomolecule binding partners are antibodies (e.g., monoclonal, polyclonal, human, humanized or chimeric). In some embodiments, the first and second biomolecule binding partners are antibody fragments (e.g., Fab, F(ab')2, Fc, scFv, or vhh). The biomolecule binding partners may also be nanobodies or aptamers. Other protein-protein binding partners may be used.

A "first functional group" and a "fourth functional group" are functional groups that react with each other to form a link (bond, such as a covalent bond or a non-covalent bond), which forms a switchable bridge linking the DNA slats to each other. In some embodiments, this bridge is formed through a click chemistry (azide-alkyne cycloaddition) reaction (e.g., V. V. Rostovtsev, et al., *Angew. Chem. Int. Ed.*, 2002, 41, 2596-2599; and F. Himo, et al. *J. Am. Chem. Soc.*, 2005, 127, 210-216, each of which is incorporated herein by reference). Thus, in some embodiments, one of the first or fourth functional group is an azide, while the other of the first or fourth functional groups is an alkyne. For example, the first functional group may be azide, and the fourth functional group may be trans-cyclooctene (TCO). Other click chemistry functional groups may be used.

A "second functional group" and a "third functional group" are functional groups that react with each other to form a link (bond, such as a covalent bond or a non-covalent bond), which forms yet another switchable bridge linking the DNA slats to each other. This bridge breaks (dissociates) in the presence of a dissociation agent. A "dissociation agent" is an agent (e.g., chemical) that breaks the bond (e.g., covalent bond) between the second and third functional groups. In some embodiments, the second and third functional groups are thiol groups that react with each other to form a disulfide bridge. Thus, in some embodiments, the dissociation agent is dithiothreitol (DTT). In some embodiments, the concentration of DTT is 50 mM-200 mM. For example, the concentration of DTT may be 100 mM. Other functional groups may be used.

ADDITIONAL EMBODIMENTS

1. A composition, comprising:
   (a) nucleating nanostructures;
   (b) a first subset of elongated nanostructures, wherein less than 10% of the nanostructures of (b) bind to each other, and wherein the nanostructures of (b) irreversibly bind to a nucleating nanostructure of (a); and
   (c) a second subset of elongated nanostructures, wherein less than 10% of the nanostructures of (c) bind to each other, wherein, in the absence of a nucleating nanostructure, a nanostructure of (b) can reversibly binding to a nanostructure of (a) only at a single position on the nanostructure of (a), and wherein, in the absence of a nucleating nanostructure, a nanostructure of (a) can reversibly binding to a nanostructure of (b) only at a single position on the nanostructure of (b).

2. The composition of embodiment 1 further comprising (d) a third subset of elongated nanostructures, wherein less than 10% of the nanostructures of (d) bind to each other.

3. The composition of embodiment 1 or 2, wherein the nanostructures of (b) are aligned in one direction and irreversibly bound to a nucleating nanostructure of (a) to form a first layer.

4. The composition of embodiment 3, wherein the nanostructures of (c) are aligned in one direction and bound to nanostructures of the first layer to form a second layer, wherein first layer is rotated by 10 degrees to 170 degrees relative to the second layer.

5. The composition of embodiment 4, wherein the first layer is rotated by 90 degrees relative to the second layer.

6. The composition of embodiment 4 or 5, wherein the nanostructures of (d) are aligned in one direction and bound to nanostructures of the second layer to form a third layer, wherein second layer is rotated by 10 degrees to 170 degrees relative to the third layer.

7. The composition of embodiment 6, wherein the first layer is rotated by 90 degrees relative to the second layer.

8. The composition of any one of embodiments 1-7, wherein the nucleating nanostructures of (a), the nanostructures of (b), the nanostructures of (c), and/or the nanostructures of (d) are nucleic acid nanostructures.

9. The composition of embodiment 8, wherein the nucleating nanostructures of (a), the nanostructures of (b), the nanostructures of (c), and/or the nanostructures of (d) are DNA nanostructures.

10. The composition of embodiment 8 or 9, wherein the nucleating nanostructures of (a), the nanostructures of (b), the nanostructures of (c), and/or the nanostructures of (d) comprise a long nucleic acid strand bound to multiple nucleic acid strands that are shorter than the long nucleic acid strand.

11. The composition of embodiment 8 or 9, wherein the nucleating nanostructures of (a), the nanostructures of (b), the nanostructures of (c), and/or the nanostructures of (d) comprise multiple nucleic acid strands, each having a length of less than 200 nm.

12. The composition of any one of embodiments 1-6, wherein the nucleating nanostructures of (a), the nanostructures of (b), the nanostructures of (c), and/or the nanostructures of (d) are protein nanostructures.

13. The composition of any one of embodiments 1-12, wherein the nucleating nanostructures of (a), the nanostructures of (b), the nanostructures of (c), and/or the nanostructures of (d) are rod-shaped.

14. A method, comprising:
   combining in reaction buffer
   (a) nucleating nanostructures,
   (b) a first subset of elongated nanostructures, wherein less than 10% of the nanostructures of (b) bind to each other, and wherein the nanostructures of (b) irreversibly bind to a nucleating nanostructure of (a), and
   (c) a second subset of elongated nanostructures, wherein less than 10% of the nanostructures of (c) bind to each other,
   wherein, in the absence of a nucleating nanostructure, a nanostructure of (b) can reversibly binding to a nanostructure of (a) only at a single position on the nanostructure of (a), and
   wherein, in the absence of a nucleating nanostructure, a nanostructure of (a) can reversibly binding to a nanostructure of (b) only at a single position on the nanostructure of (b); and
      incubating the reaction buffer comprising (a), (b) and (c) under conditions that result in binding of the nanostructures of (b) to the nucleating nanostructures of (a) and result in binding of the nanostructures of (c) to the nanostructures of (b) to form a hierarchical structure.

15. The method of embodiment 14, wherein the reaction buffer further comprises (d) a third subset of elongated nanostructures, wherein less than 10% of the nanostructures of (d) bind to each other.

16. The method of embodiment 14 or 15, wherein the nucleating nanostructures of (a), the nanostructures of (b), the nanostructures of (c), and/or the nanostructures of (d) are nucleic acid nanostructures.

17. The method of embodiment 16, wherein the nucleating nanostructures of (a), the nanostructures of (b), the nanostructures of (c), and/or the nanostructures of (d) are DNA nanostructures.

18. The method of embodiment 16 or 17, wherein the nucleating nanostructures of (a), the nanostructures of (b), the nanostructures of (c), and/or the nanostructures of (d) comprise a long nucleic acid strand bound to multiple nucleic acid strands that are shorter than the long nucleic acid strand.

19. The method of embodiment 16 or 17, wherein the nucleating nanostructures of (a), the nanostructures of (b), the nanostructures of (c), and/or the nanostructures of (d) comprise multiple nucleic acid strands, each having a length of less than 200 nm.

20. The method of any one of embodiments 14-16, wherein the nucleating nanostructures of (a), the nanostructures of (b), the nanostructures of (c), and/or the nanostructures of (d) are protein nanostructures.

21. The method of any one of embodiments 14-20, wherein the nucleating nanostructures of (a), the nanostructures of (b), the nanostructures of (c), and/or the nanostructures of (d) are rod-shaped.

22. A composition, comprising:
- (a) nucleating DNA nanostructures;
- (b) a first subset of elongated DNA nanorods, wherein less than 10% of the nanostructures of (b) bind to each other, and wherein the DNA nanorods of (b) irreversibly bind to a nucleating DNA nanostructure of (a); and
- (c) a second subset of elongated DNA nanorods, wherein less than 10% of the DNA nanorods of (c) bind to each other, wherein, in the absence of a nucleating DNA nanostructure, a DNA nanorod of (b) can reversibly binding to a DNA nanorod of (a) only at a single position on the DNA nanorod of (a), and wherein, in the absence of a nucleating DNA nanostructure, a DNA nanorod of (a) can reversibly binding to a DNA nanorod of (b) only at a single position on the DNA nanorod of (b).

EXAMPLES

Example 1

Figure 9A:
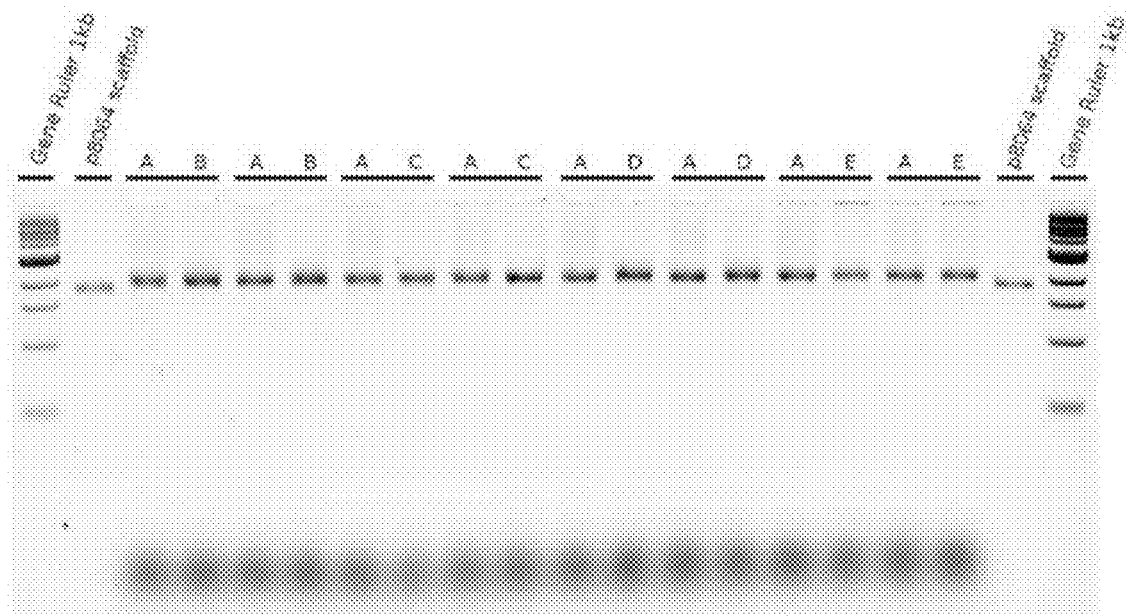
FIG. 9A-9B show results from a seesaw experiment with an example of a nucleating nanostructure (queen) folded at different temperatures (A: 65-60° C.; B: 60-55° C.; C: 65-55° C.; D: 60-50° C.) at a $MgCl_2$ concentration of 6 mM.
Figure 9B:
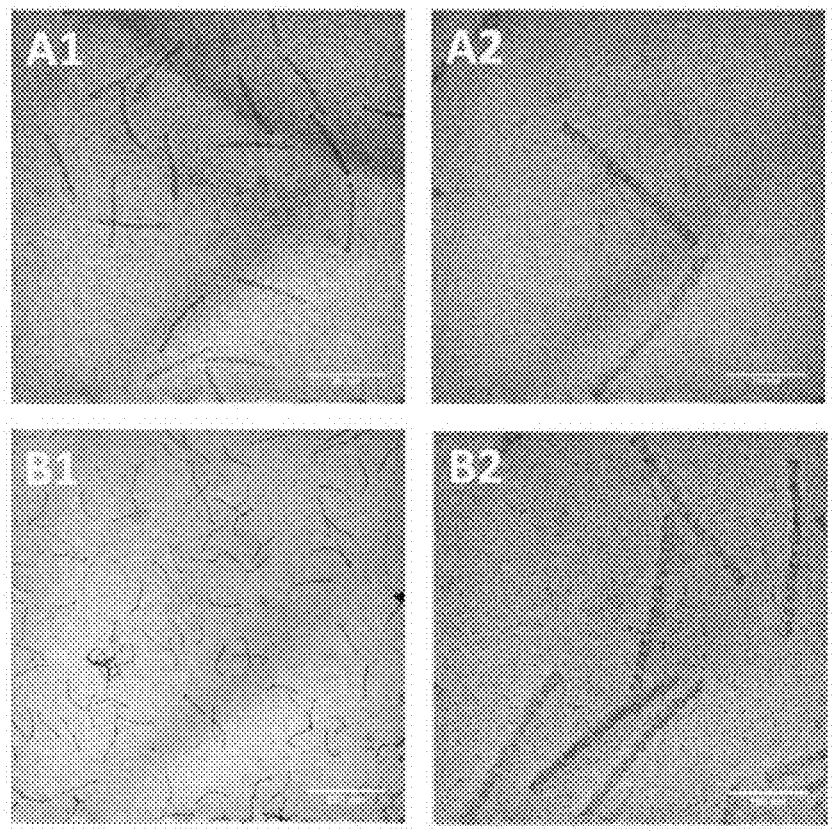

The examples demonstrates assembly of a nucleating nanostructures (queen). The sharpest bands from a screen of nucleic acid self-assembly reactions were selected and subjected to a 2 minute incubation at 90° C. for denaturing and then an 18 hour ramp. The gel (FIG. 9A) was 2% agarose (10 µL ethidium bromide, c=10 mg/mL), and run at 60V for 240 minutes in 0.5×TBE and 11 mM MgCl$_2$. A seesaw experiment was performed, whereby the temperature was varied between 65-60° C. (A), 60-55° C. (B), 65-55° C. (C), and 60-50° C. (D). The structures were purified using band excision of the gel, followed by 15 minutes at 16k×g FreezeNSqueeze and then stained with 2% UF following a 2 minute ddH$_2$O post-wash. The queen folded well, and no noticeable difference was observed between conditions A through D on the seesaw experiment (FIG. 9B).

Figure 10A:
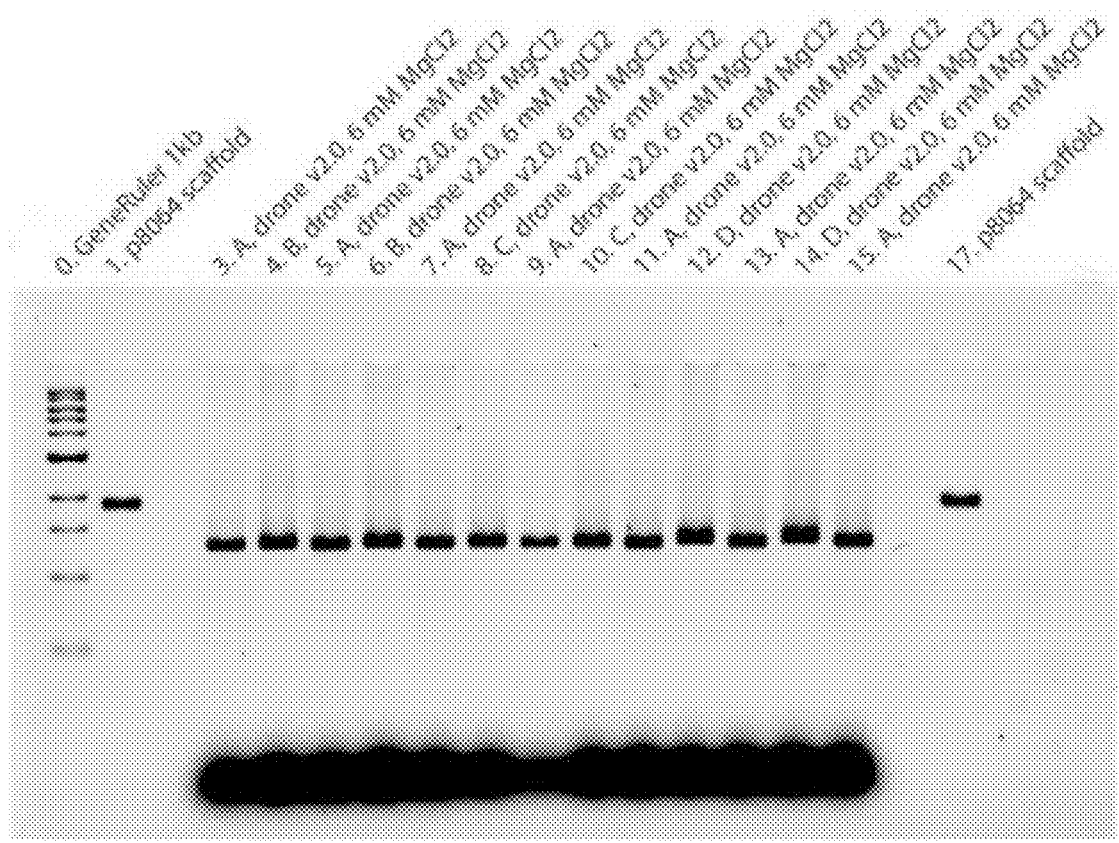
FIGS. 10A-10B show results from a seesaw experiment with an example of a nanostructure (drone) folded at different temperatures (A: 70-60° C.; B: 65-55° C.; C: 65-60° C.; D: 60-55° C.) at a $MgCl_2$ concentration of 6 mM.
Figure 10B:
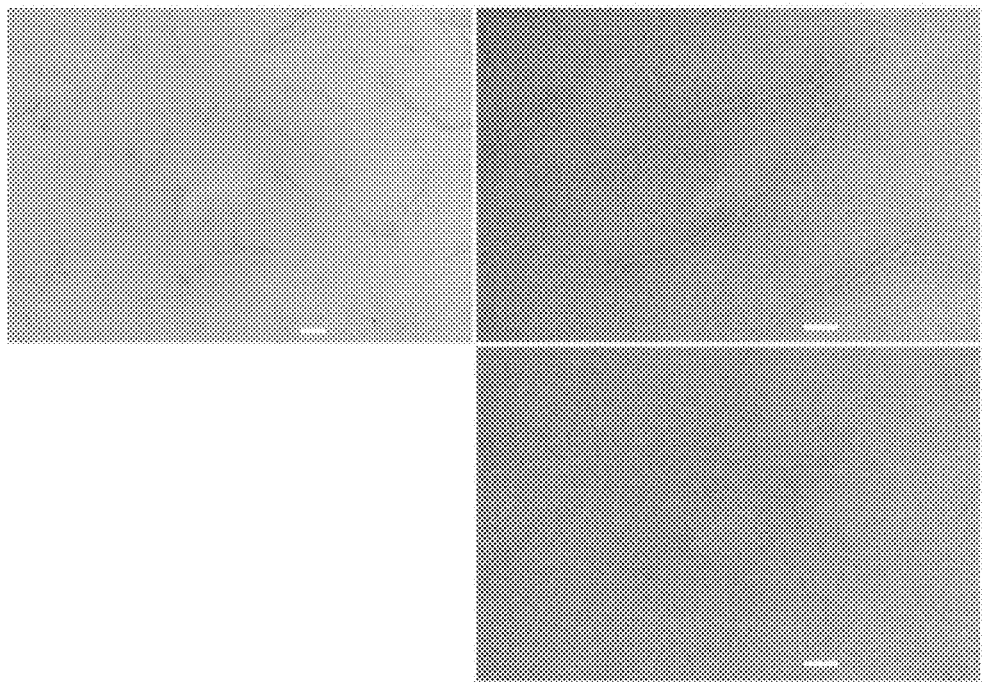

The experiment was repeated with different nanostructures that function as 'drones'. The sharpest bands from a large screen were selected and subjected to 2 minute incubation at 90° C. for denaturing and then an 18 hour ramp. The gel (FIG. 10A) was 2% agarose (10 µL ethidium bromide, c=10 mg/mL), and run at 60V for 240 minutes in 0.5×TBE and 11 mM MgCl$_2$. In this experiment, the temperature was varied between 70-60° C. (A), 65-55° C. (B), 65-60° C. (C), and 60-55° C. (D). The structures were purified using band excision of the gel, followed by 15 minutes at 16k×g FreezeNSqueeze and then stained with 1% UF. The drone folded well, and there was no noticeable difference between conditions A through D on the seesaw experiment (FIG. 10B).

Figure 11:
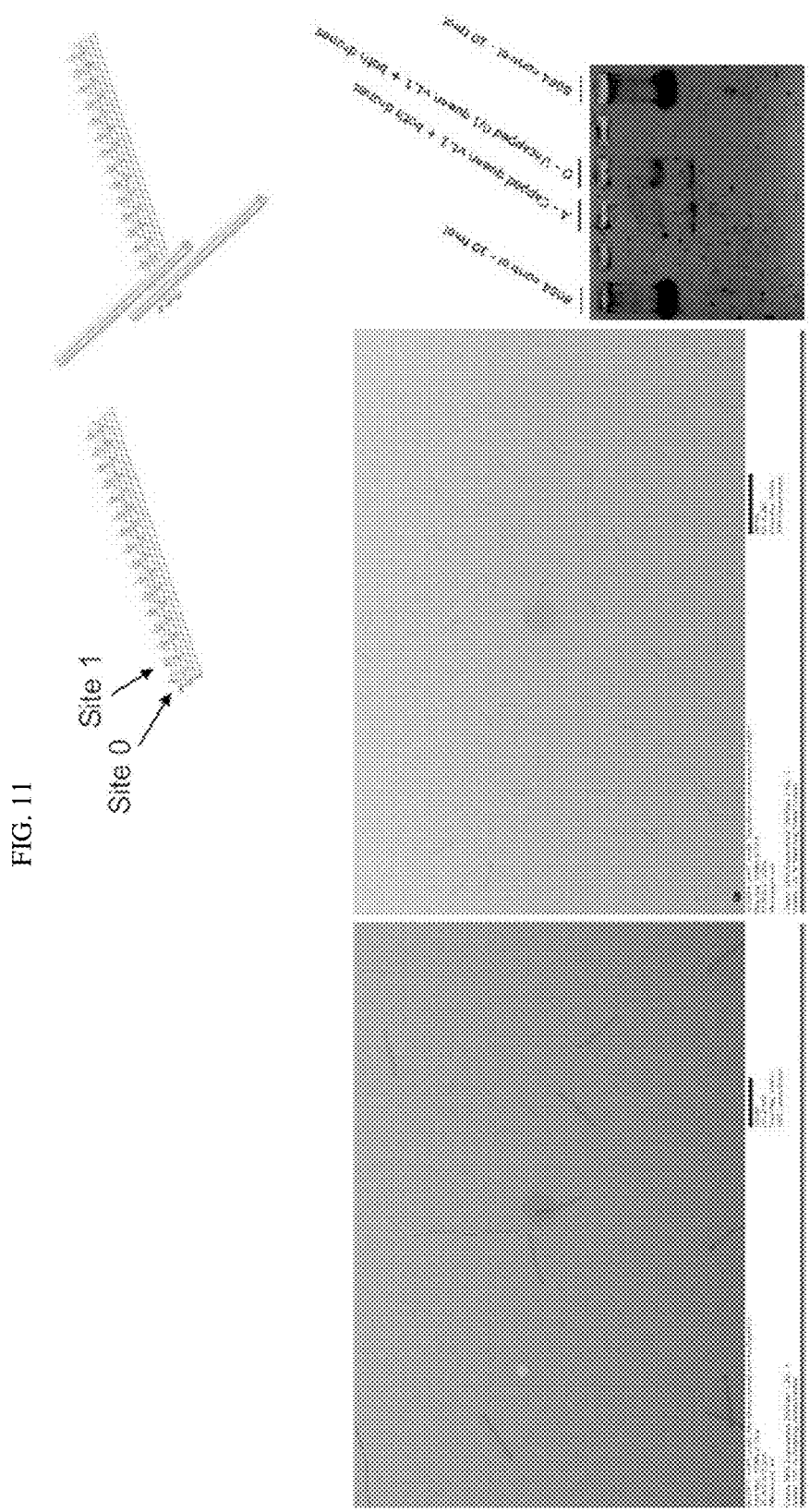
FIG. 11 shows a schematic depicting the assembly of an example seed structure (queen+drones). Images of the structures are also shown. Nanostructure assembly may also be carried out as shown in FIGS. 19A-19D.

Next, the assembly of a queen together with a drone was examined (FIG. 11). The following conditions were tested (with a 1:1:1 ratio): queen—all sites closed and both drones; queen—site 0 exposed and both drones; queen—site 1 exposed and both drones; queen—site 0/1 exposed and both drones; and queen—all sites exposed and both drones. Assembly was achieved through a 72 hour incubation period at 25° C., and the structures were purified by band excision of the gel, followed by 15 minutes at 16k×g FreezeNSqueeze followed by 2% UF staining. The samples were run on a 2% agarose gel (10 µL ethidium bromide, c=10 mg/mL), and run at 60V for 240 minutes in 0.5×TBE and 11mMM MgCl$_2$. Approximately 10-15 ng of each structure were observed.

Example 2

Figure 12A:
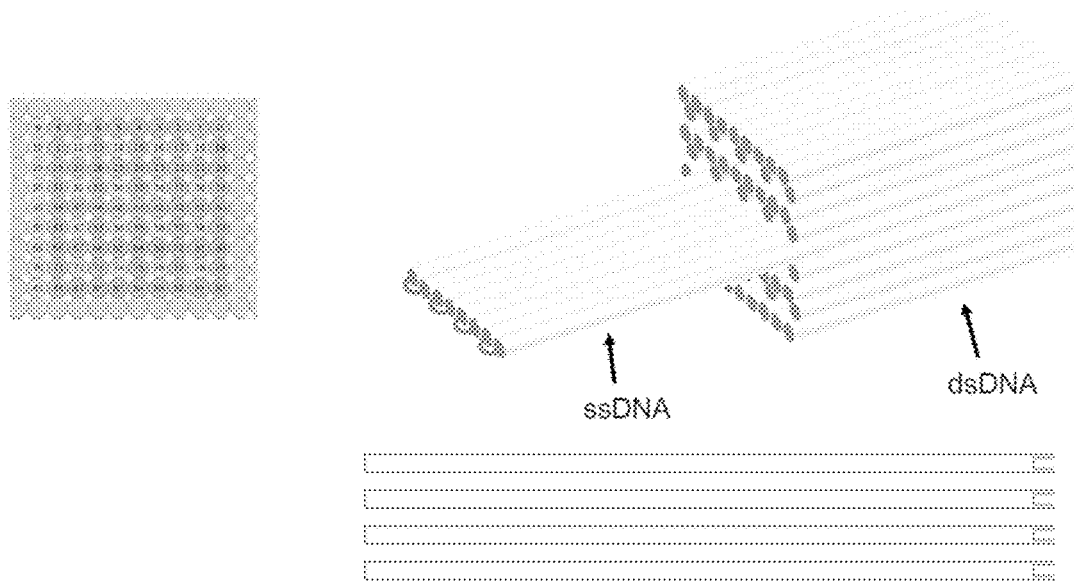
FIGS. 12A-12G show a seed structure forming from the assembly of a single-stranded DNA and additional nanostructures (drones).
Figure 12B:
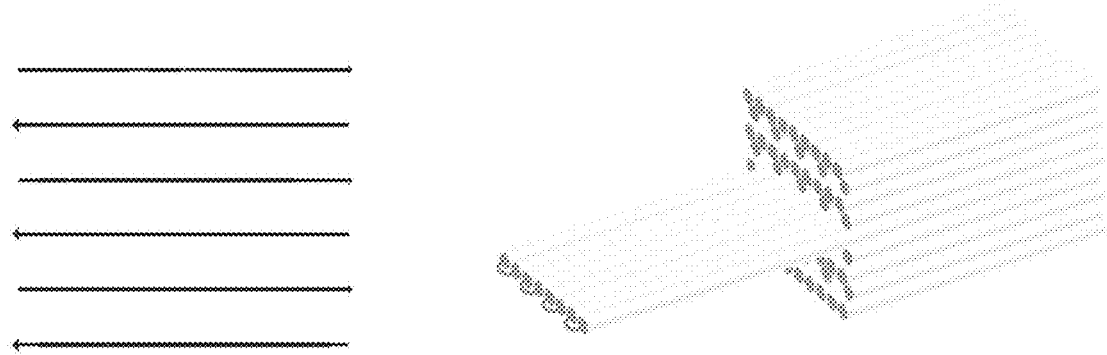
Figure 12C:
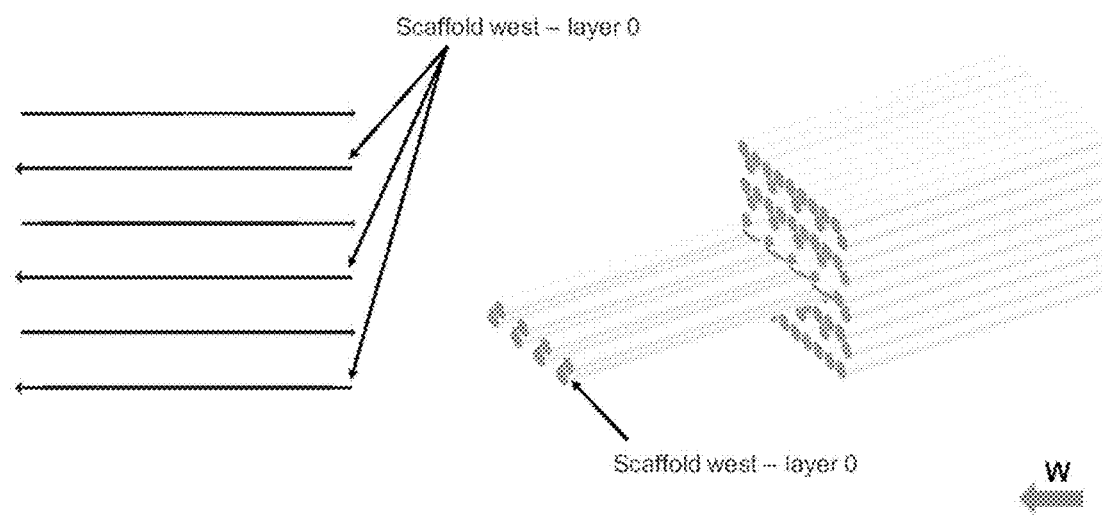
Figure 12D:
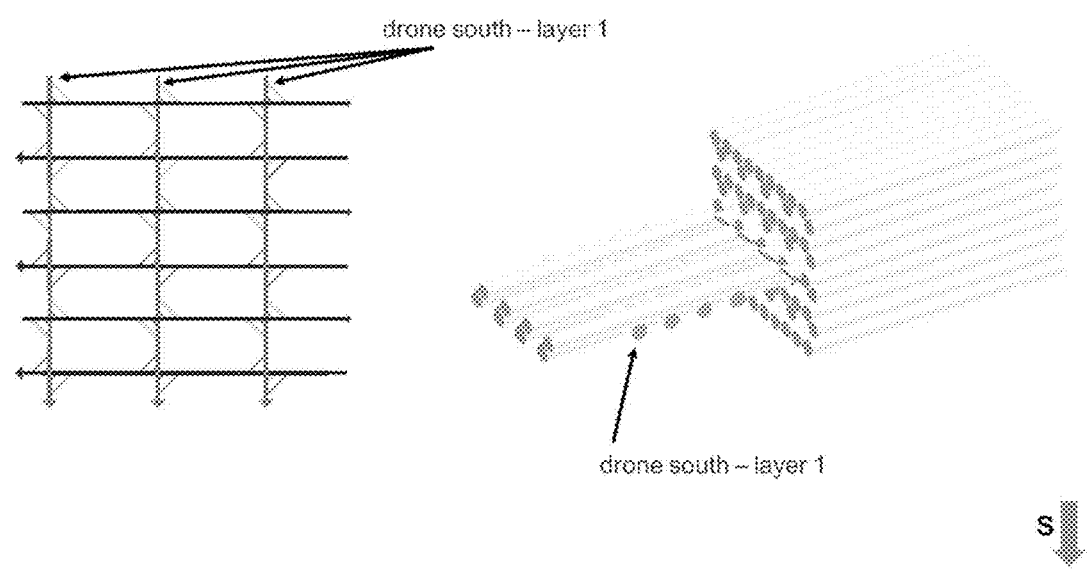
Figure 12E:
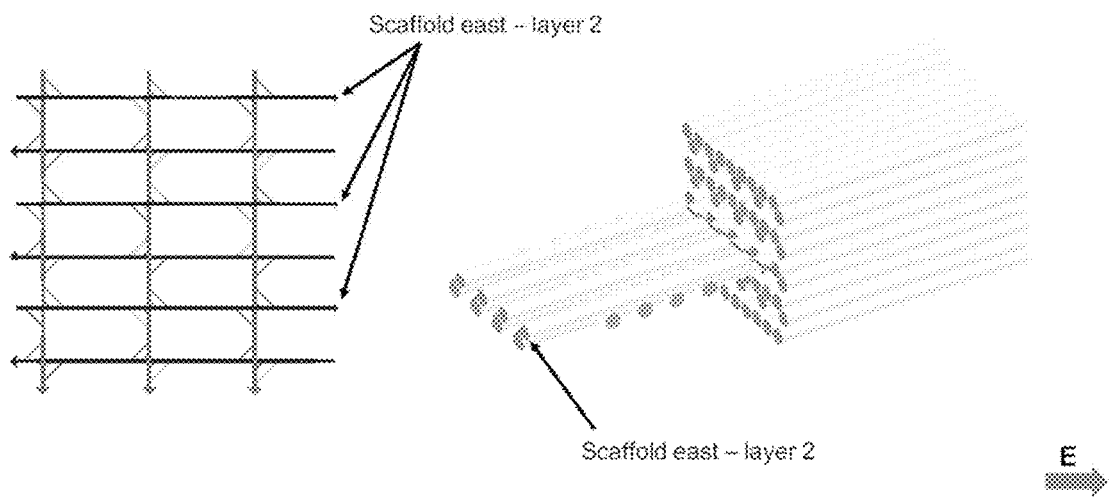
Figure 12F:
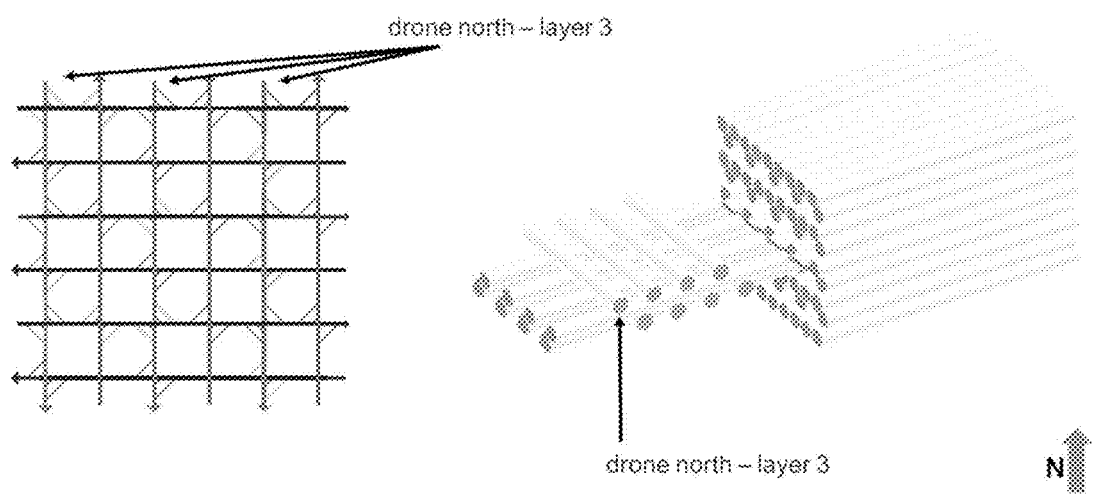
Figure 12G:
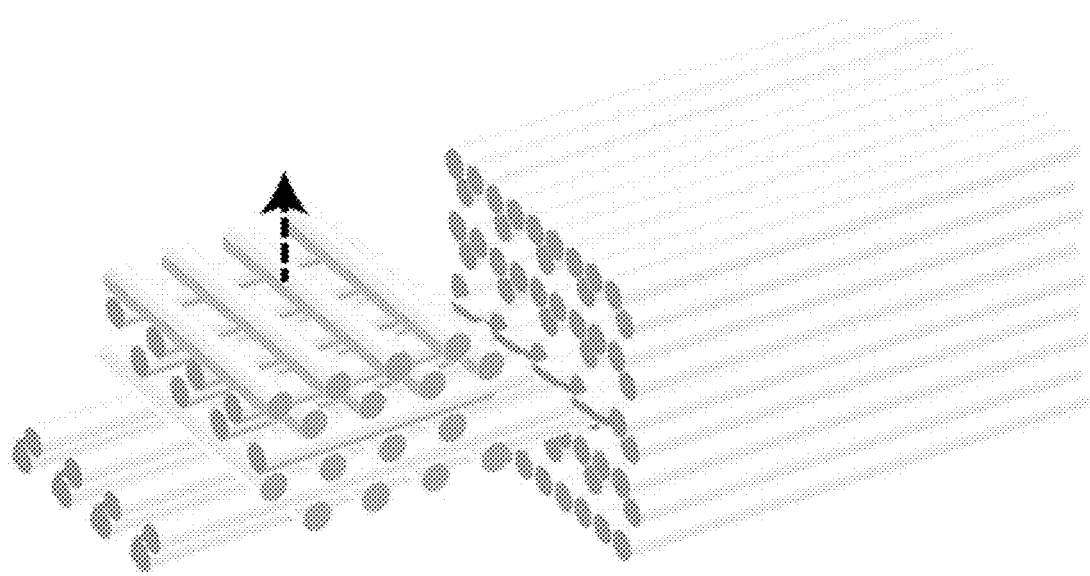

A similar system was built using single-stranded DNA instead of 6 helix bundles. A schematic of the nucleating nanostructure architecture is shown in FIG. 12A. The single strands each contain binding and linker regions, including a 5 bp binding region and 3 and 5 nucleotide linker (poly T) regions. An exemplary 5 bp, 2 nucleotide linker is shown below:

[SEQ ID NO: 683]
TGCAATTTAATTCTTTTAGCATTTCAATATTTGTAGATTTGAGAATTT
CGTTTTTTTATTCA-62 mer.

Figure 13A:
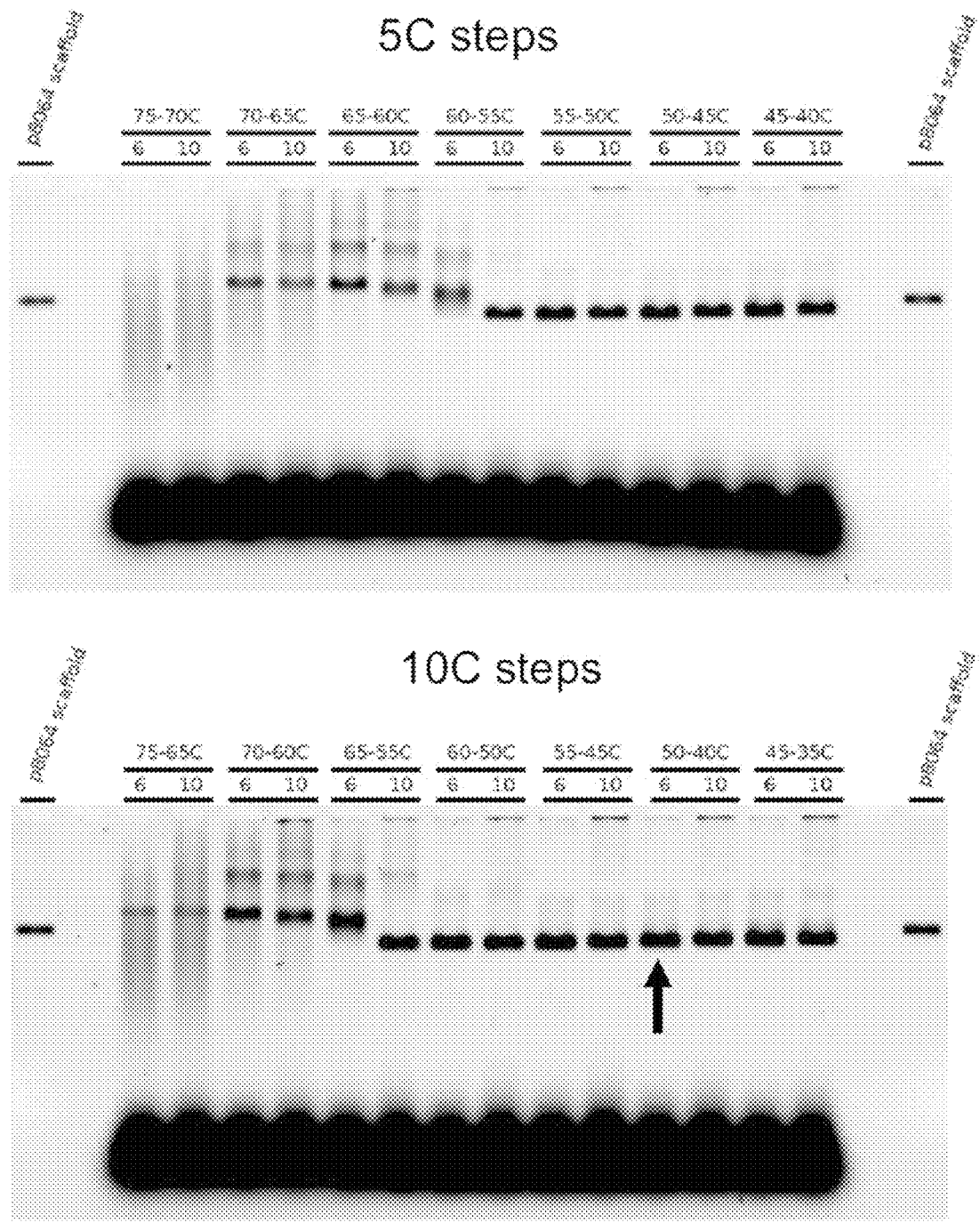
FIGS. 13A-13B show results from seesaw experiments with a single-stranded nucleating nanostructure (queen) at various temperatures and steps.
Figure 13B:
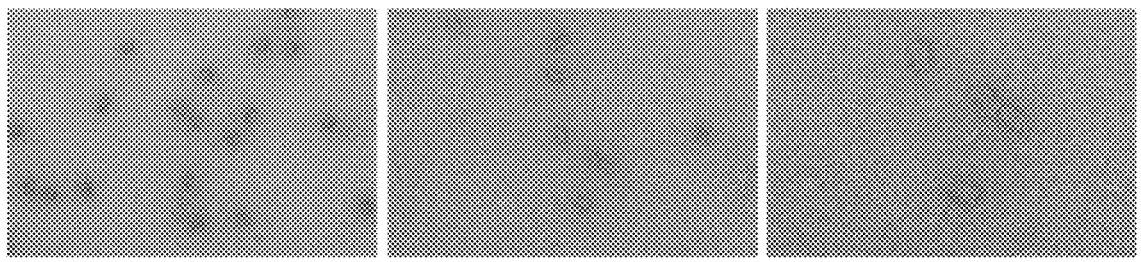

The workers stack on top of drones in layers (FIGS. 12B-12G). The queen was shown to fold in both 5C or 10C steps (FIG. 12A). Folding occurred after a 2 minute 90° C. denaturing period and then an 18 hour ramp. The samples were run on a 2% agarose gel (10 µL ethidium bromide, c=10 mg/mL), and run at 60V for 240 minutes in 0.5×TBE and 11 mM MgCl$_2$. The queen was incubated under a 50-40° C. thermal ramp, with 6 mM MgCl$_2$. The resulting structure is shown in FIG. 13B.

Example 3

Figure 14A:
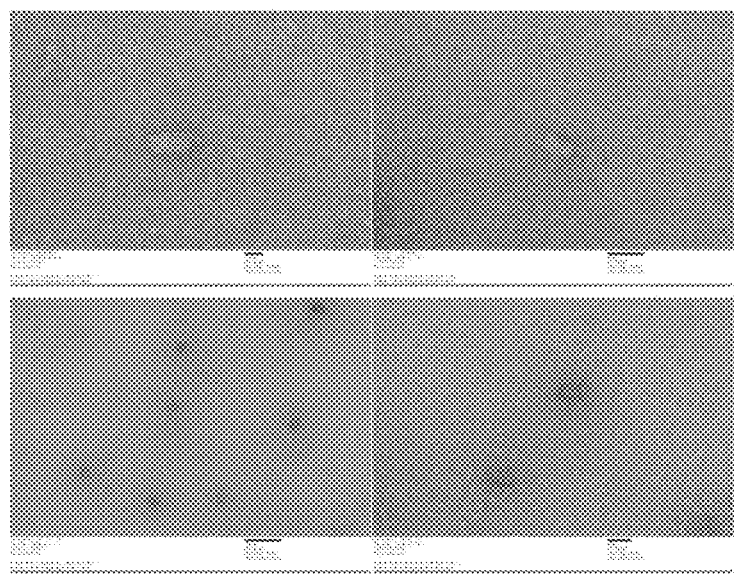
FIGS. 14A-14C show results demonstrating that nanostructures (workers) assemble in the presence of a nucleating nanostructure (queen) but not in the absence of a nucleating nanostructure.
Figure 14B:
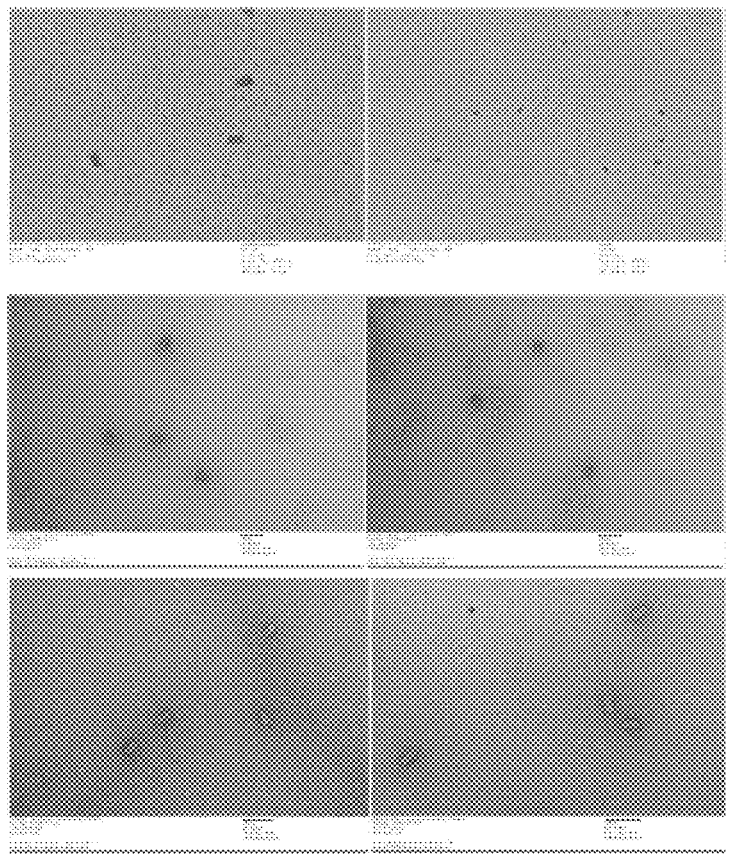
Figure 14C:
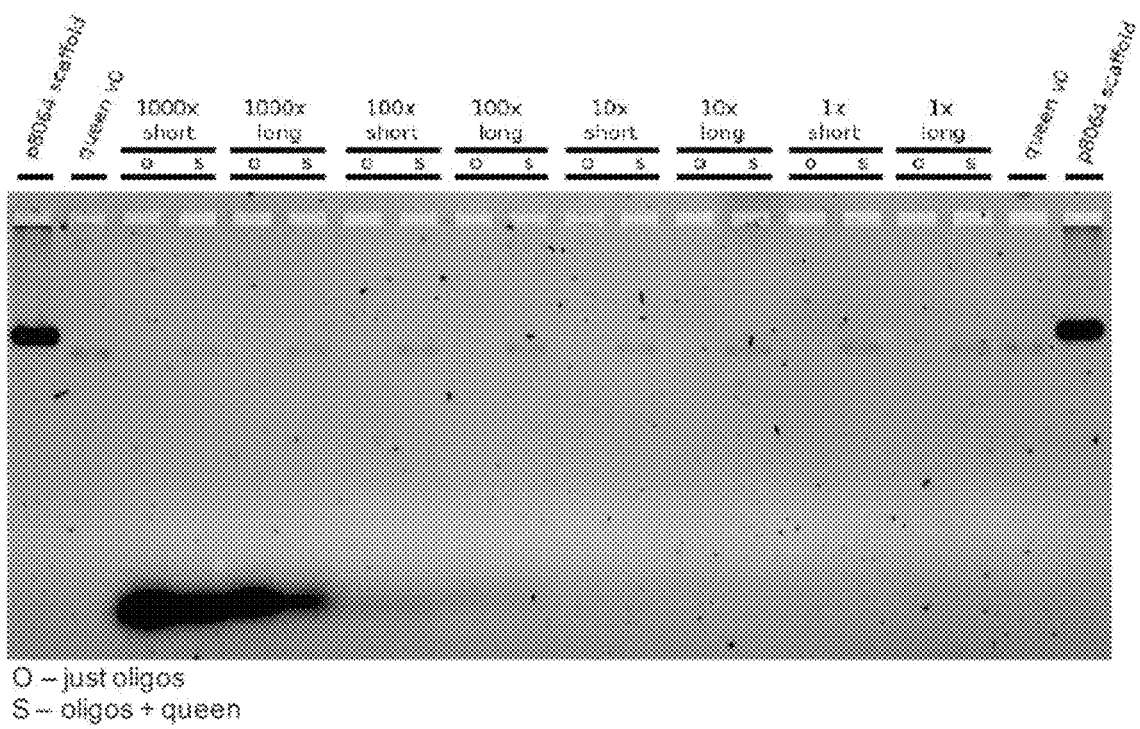

Assembly without the queen and only the workers (both short and long linkers) was examined. In this example, workers did not assemble under conditions with high salt concentration (1M NaCL, up to 15 mM MgCl$_2$), low temperature (4° C.), and a high concentration of workers (3.125 µM). Other conditions, including 10-20 mM PEG and high salt and a high concentration of oligonucleotides were also tested. No assembly occurred. FIGS. 14A-14B show drone/workers at different concentrations successfully assembling with queens. The structures were purified with band excision, 15 minutes at 16k×g FreezeNSqueeze and 2% UF staining. Without the queens, there was no sign of assembly (FIG. 14C).

Figure 15A:
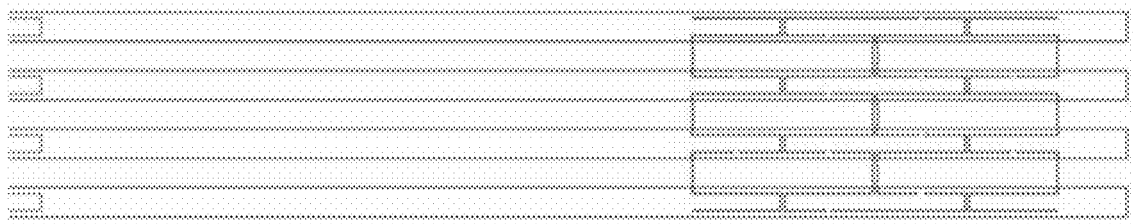
FIGS. 15A-15B show results an example of nanostructures not assembling in the absence of a nucleating nanostructure (queen).
Figure 15B:
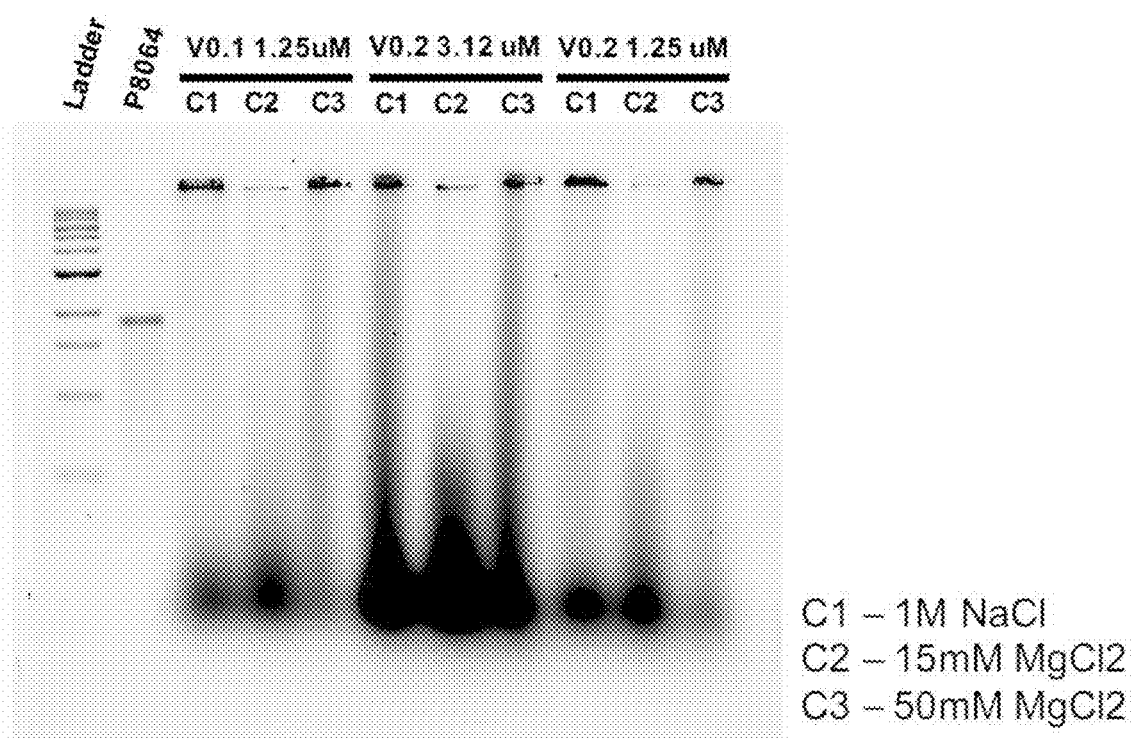

The duplex length was then increased to 8 bp and linker regions of 2 nt (v0.1) and 3 nt (v0.2) were tested. Weaving was introduced into the structure and staple strands were added to constrain the end of the scaffold loops (FIG. 15A). As seen in FIG. 16B, there was no assembly without the queen in any of the groups and under any of the salt concentration conditions.

Example 4

Figure 18:
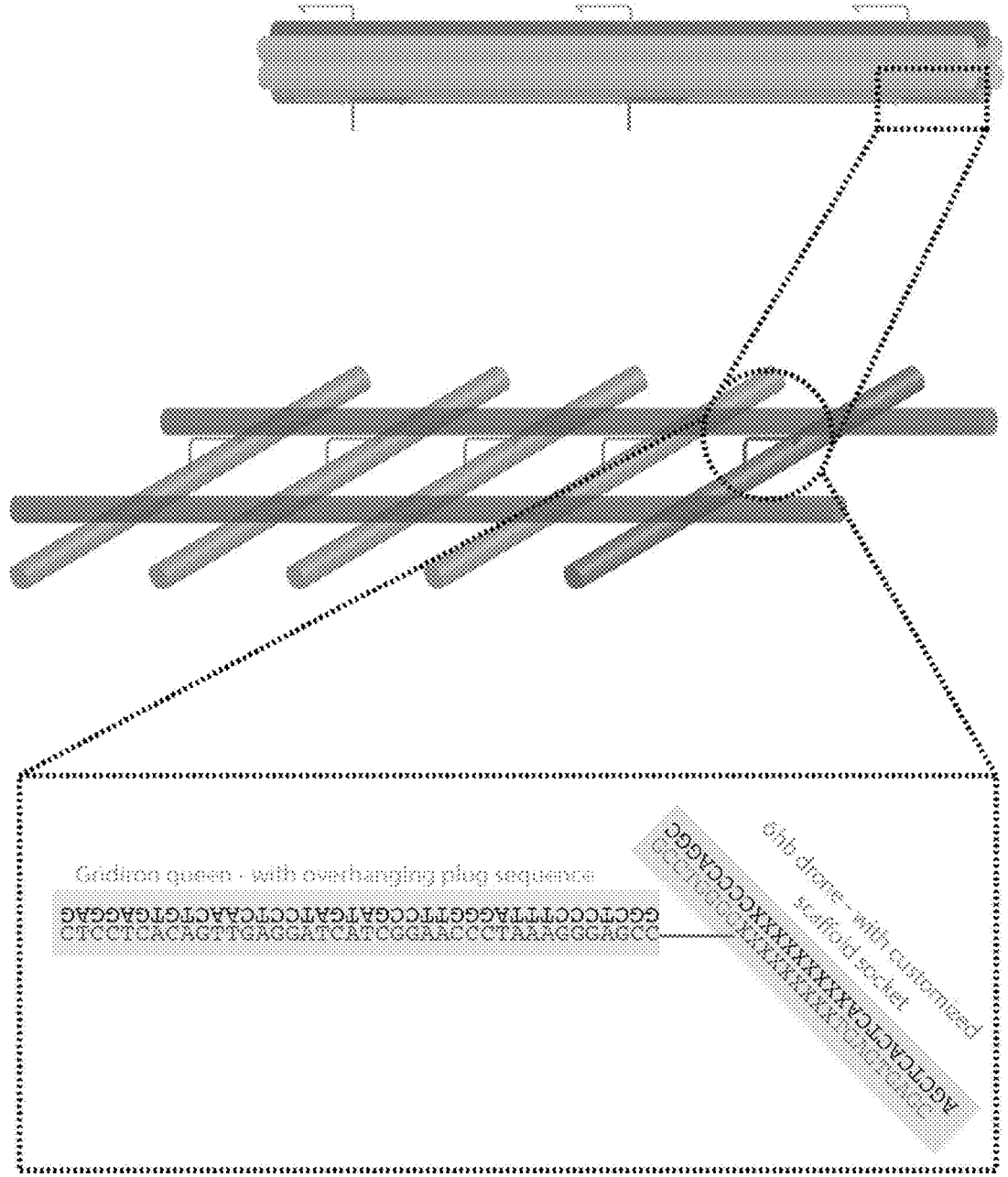
FIG. 18 shows a detailed view of the plug-socket binding system. The case shown in the upper panel shows the full set of 5 single-stranded plug sequences extending from the queen (the small arrow) with matching socket sites in a six-helix bundle drone. In the lower pane, the binding sequence is drawn as a series of 'X' to indicate that both the length and sequence of the plug and socket may be varied. The scaffold sequences are drawn in black. Note that this design (shown for a drone-queen assembly) is also used to bind drones to workers. The gridiron queen sequences, from top to bottom, correspond to SEQ ID NOs: 685 and 686. The 6 helix bundle (hb) drone sequences, from left to right, correspond to SEQ ID NOs: 687 and 688.
Figure 19A:
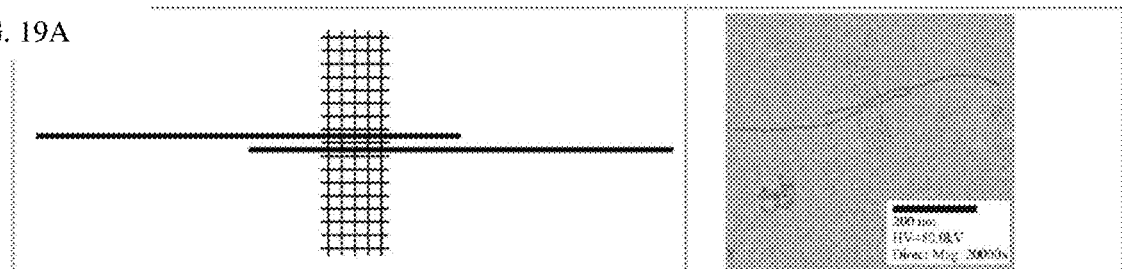
FIGS. 19A-19D shows how the plug-socket binding system can be used to program drones to bind to desired sites on the queen.
Figure 19B:
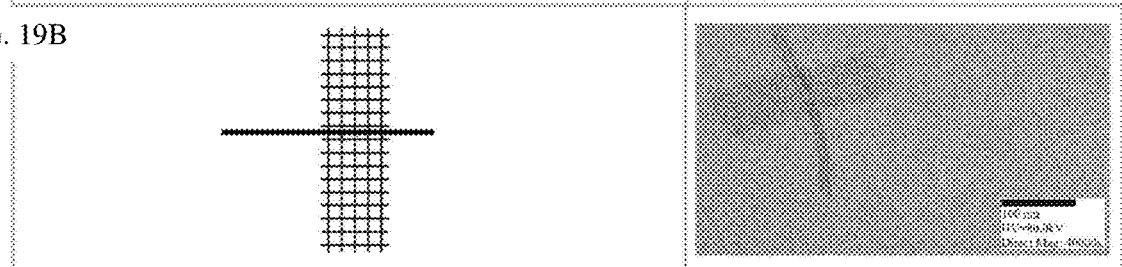
Figure 19C:
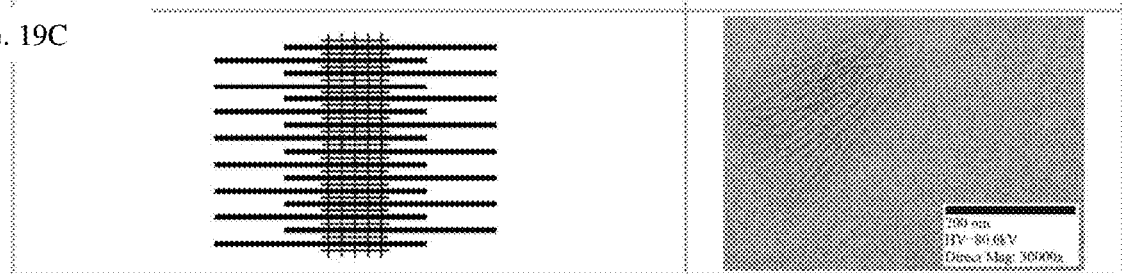
Figure 19D:
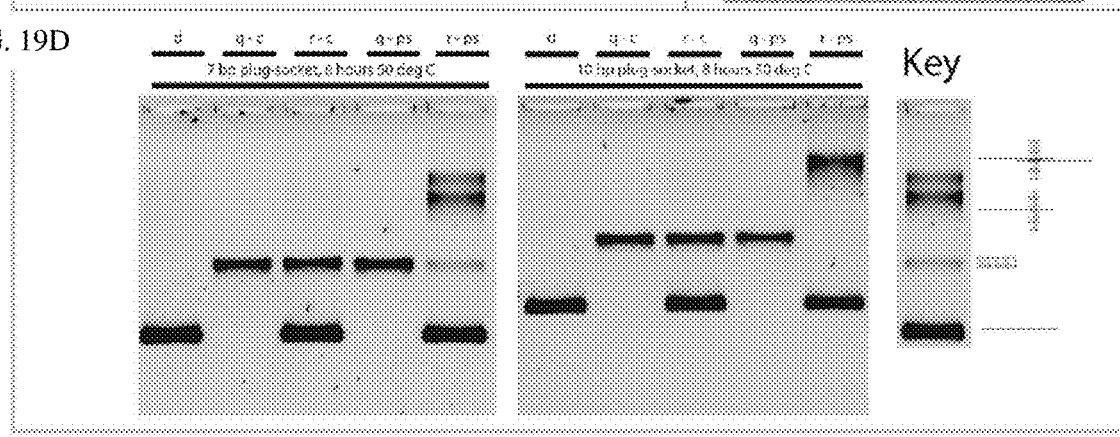

This Example demonstrates assembly of 6-helix bundle DNA nanorod drones into a crisscross structure via nucleation by a gridiron queen (FIGS. 19A-19D). The gridiron queen has 16 cells, each to which may bind a drone using 5 cooperative plug-socket binding sites. Shown here is site-specific binding of two 440 nm long drones (FIG. 19A), one 250 nm long drone (FIG. 19B), and sixteen 250 nm long drones (FIG. 19C). This example shows binding of drones to the gridiron queen using a 10 bp plug-socket. The agarose gel image in FIG. 19D shows that the queen in the reaction is completely bound by drones, when stoichiometric excess of drones is present. Additionally, functionality of the plug-socket binding system (FIG. 18) is shown with the TEM micrographs of these assemblies and kinetics data (FIGS. 19A-D and FIG. 20).

Figure 16A:
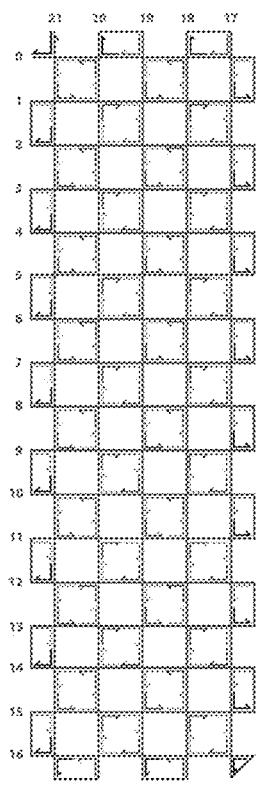
FIG. 16A shows a two-dimensional view of the gridiron queen that can bind 16 drones simultaneously in a horizontal (coordinate x in FIG. 16B) across the queen. Staples necessary to fold the scaffold into the queen are shown, and the 3' ends of the staples may be appended with overhanging single-stranded sequences to bind drones. A three-dimensional view (FIG. 16B) shows the queen with binding sites in each drone-docking cell. A transmission electron microscope (TEM) image of the queen is shown in FIG. 16C. Lateral dimensions of the structure are approximately 72 nm×240 nm.
Figure 16B:
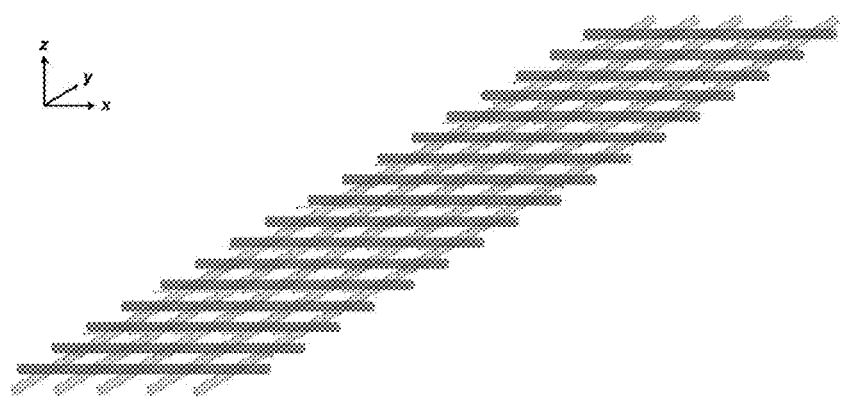
Figure 16C:
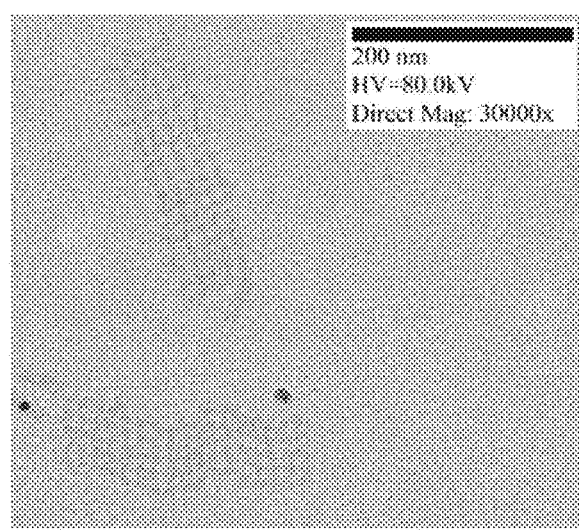
Figure 17A:
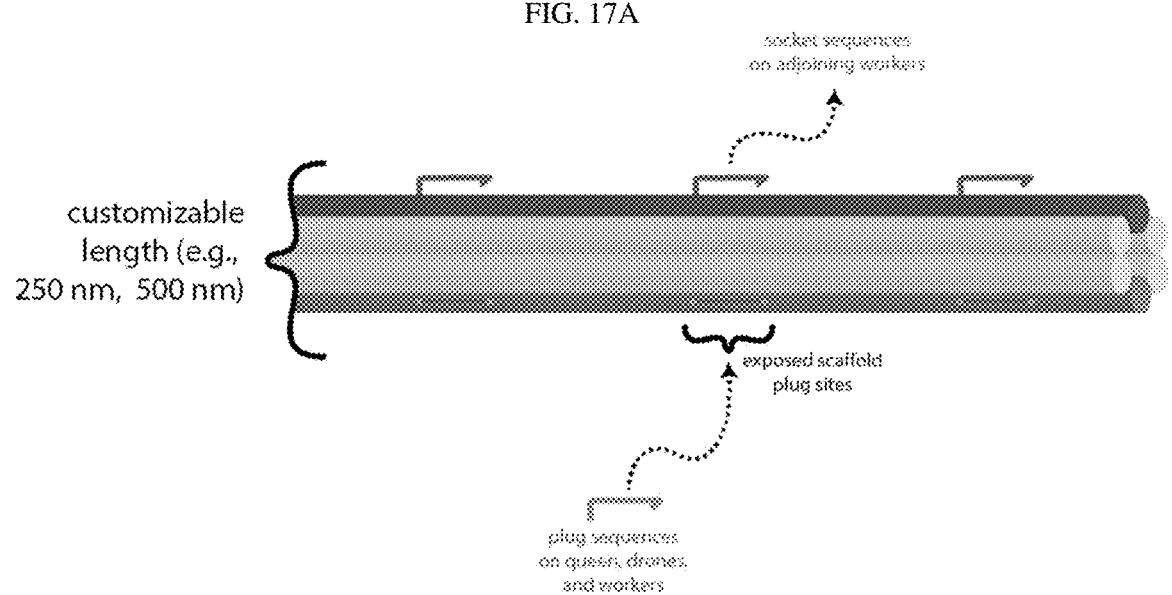
FIGS. 17A-17B depict drone and worker subcomponents.
Figure 17B:
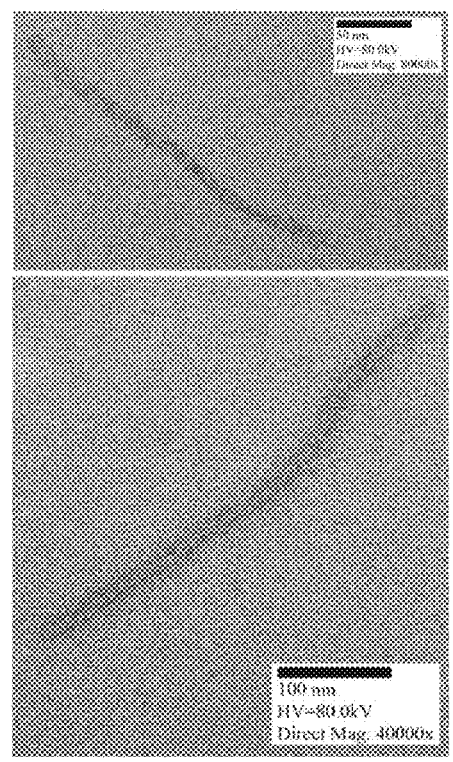

The gridiron queen and 6-helix bundle drones were conceptualized and then designed using the caDNAno design tool (see FIGS. 16A-16C (and data not shown) for the queen, FIGS. 17A-17B (and data not shown) for the drones). Staple sequences designed in caDNAno were ordered commercially and folded with M13 phage scaffold DNA over the following conditions: drones in 6 mM MgCl$_2$, (90° C./2 mins, 60-50° C./18 hrs); queen in 8 mM MgCl$_2$, ({(94° C.-86° C.) in 4° C./5 min steps}; {(85° C.-70° C.) in 1° C./5 minute steps}; {(70° C. to 40° C.) in 1° C./15 minutes steps}; {(40° C. to 25° C.) in 1° C./10 minute steps}). The scaffold for the gridiron queen was comprised of a 8634 base genome from M13 phage, and staple DNA sequences were determined by caDNAno. Binding sequences for drones were manually appended to the 3' ends of the staple DNA to bind drones in the desired orientation. The 250 nm and 440 nm 6 hb drones were also designed in caDNAno. The scaffold DNA was comprised of either the 8064 base genome from M13 phage (for the 440 nm drone), or a custom 3825 base sequence derived from M13 phage (for the 250 nm drone). Staple DNA sequences were determined by caDNAno and purchased commercially. Scaffold sections for the sockets and plug sequences were customized to determine the orientation and final location of sub-components in assembled structures. The 5' ends of a subset of the staples are truncated to free scaffold so that it could act as a socket to bind plugs. The 3' ends of another subset of staples were appended with plug DNA sequences so that they could interact with other worker subcomponents.

The folded structures were separated from excess folding staples using agarose gel electrophoresis and bands containing the structure of interest were purified from the agarose gel matrix. The purified structures were placed onto carbon grids, stained with 2% uranyl formate, and analyzed by TEM to validate assembly of the correct structure (see FIG. 16C for the queen and FIG., 17B for the drones).

Figure 20:
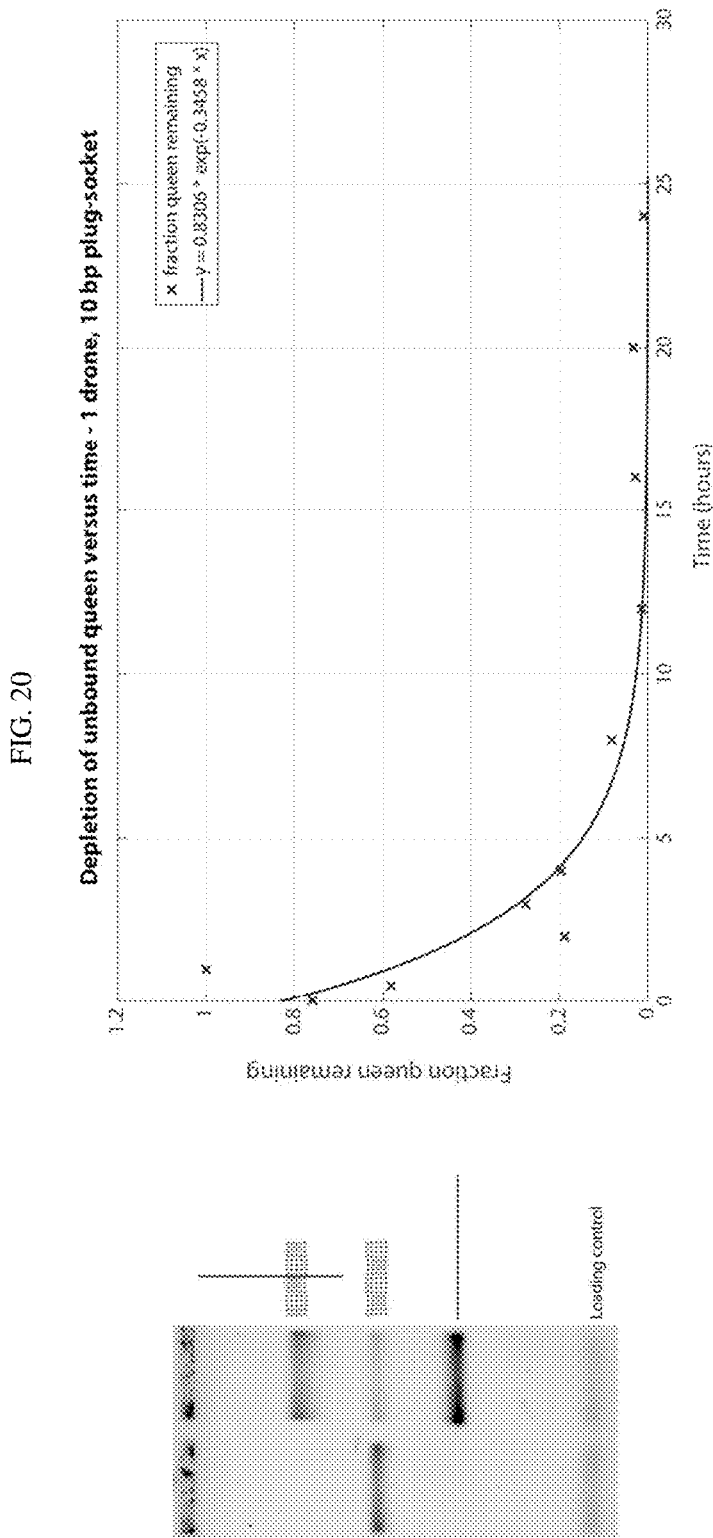
FIG. 20 shows the extent of free queen remaining over time as it becomes bound to a single 440 nm drone.

The purified sub-components were assembled into crisscross formation using the following conditions: 0.1 or 0.01 nM queen, 1 nM drones, 30 mM MgCl$_2$, 45 mM Tris-borate, 1 mM EDTA, and 0.01% Tween-20; incubation at 50° Celsius for 8-24 hours. Assembly reactions were analyzed using gel electrophoresis and TEM, as shown in FIGS. 19A-19D. Kinetics of binding between the drone and queen are shown in FIG. 20.

Example 5

A similar system was built using single-stranded DNA (ssDNA) instead of 6 helix bundles, referred to as "crisscross DNA slats" (short: "DNA slats"). A schematic of the base unit is shown in FIGS. 21A-21B. The 21 nucleotide (nt) long oligonucleotide per DNA slat shown in FIGS. 21A-21B allows the 4 by 4 DNA slats array to retains the correct 10.5 bases/turn. The length of the DNA slats can be expanded by repeats of 21 nt, for example, achieving larger structures. FIG. 21A shows an abstraction of the DNA slats architecture and a matrix with the number of base pairs (bp) per binding site at each position. The alternation of 6 bp and 5 bp is used to retain the correct helicity and approximately same binding energy per DNA slat. An exemplary DNA slat strand with 16 binding sites (84 nt) is shown below:

[SEQ ID NO: 684]
TGGTTCTGGAGTTTTACTCGGGACACTTCAGCGTAATATCGGAAGCAGG
CACTTTGAAACCTATAAGTCCTGACTATTAATAAC.

FIG. 21B shows a 3D rendering from the front and cross-section of the DNA slats architecture. The strands weave over and under each other. The DNA slats can reliably tile the ssDNA overhangs (from the M13 scaffold) of different DNA-Origami queens. FIGS. 23A-24B both show examples of ssDNA scaffold being tiled upon and the addition of DNA slats. The flat DNA-Origami queen shown in FIG. 23A is folded through a 2 minute 90° C. denaturing period following an 18-hour ramp from 55° C.-50° C. with 6 mM MgCl$_2$. The barrel DNA-Origami queen shown in FIG. 24A is folded by a 15 minute 80° C. denaturing period following an 18-hour ramp from 60° C.-25° C. with 8 mM MgCl$_2$. The assembly process of DNA slats with the queen is shown in FIG. 22. Once the queen is folded the crude reaction queen is mixed with the DNA slats, assembly conditions can be tuned by varying the concentrations of DNA slats (100 nM-1000 nM), salt (5 mM-30 mM MgCl$_2$ and 0-1 M NaCl), and the temperature of assembly (4° C.-55° C.). By altering the assembly conditions such as MgCl$_2$ and the DNA slat concentration the kinetics of the assembly process can be influenced.

Example 6

Figure 25:
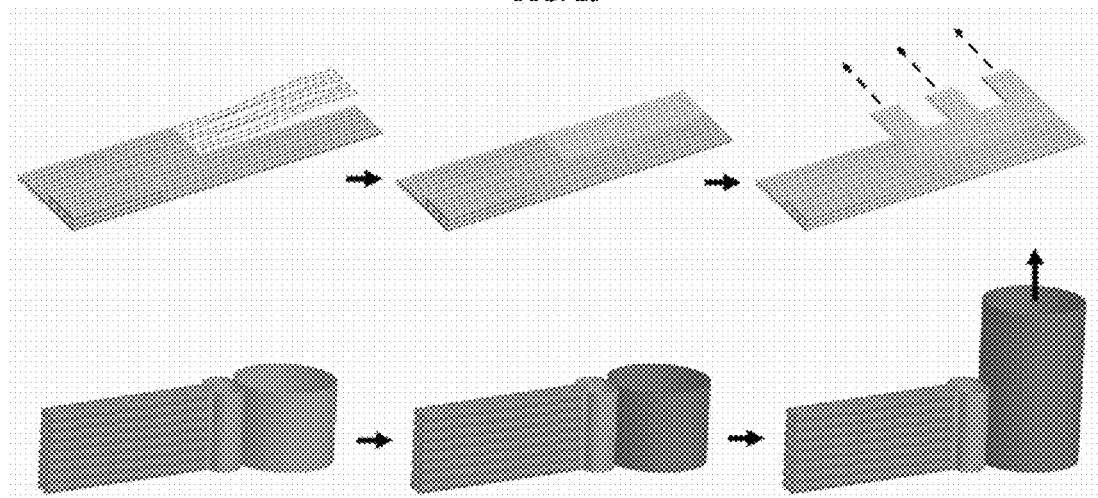
FIG. 25 depicts a growth mechanism of DNA slats seeded on a queen structure. The DNA-origami queen is mixed with DNA slats to tile the ssDNA scaffold of the queen and then later extend and polymerize the growth of micron-sized structures solely through DNA slats (DNA slats may be joined end-to-end, within the same plane, through nucleotide base pairing of adjacent slats). The upper design shows a flat DNA-origami queen with the growth of three linear sheets in the horizontal direction. The lower design shows a barrel DNA-origami queen with tubular growth in the vertical direction.
Figure 26A:
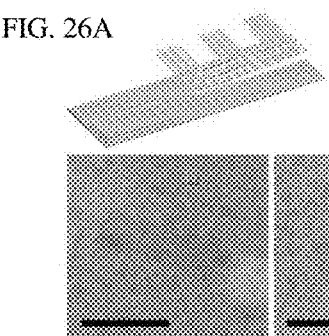
FIGS. 26A-26E show three extensions of the first generation of DNA slats binding to the flat DNA-origami queen.
Figure 26B:
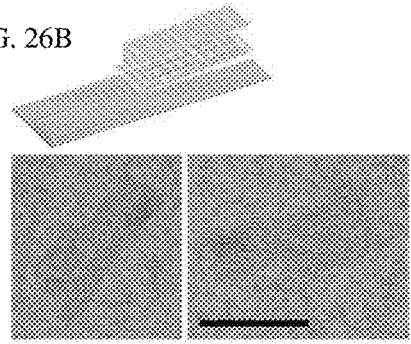
Figure 26C:
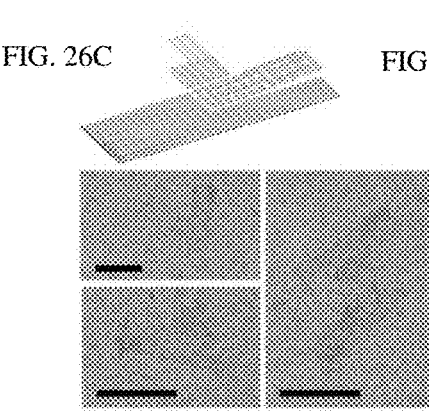
Figure 26D:
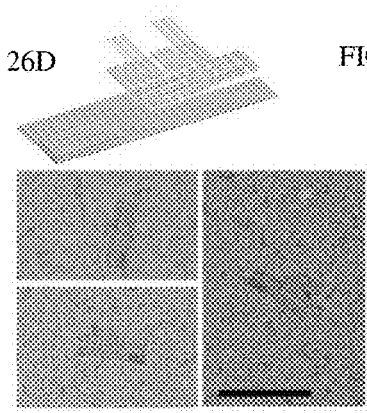
Figure 26E:
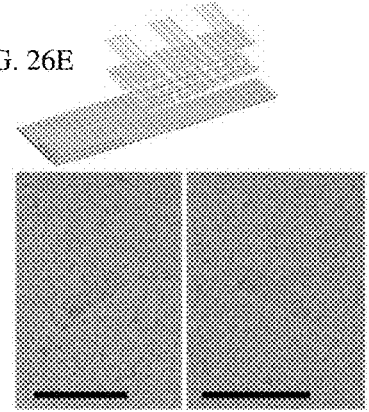
Figure 30A:
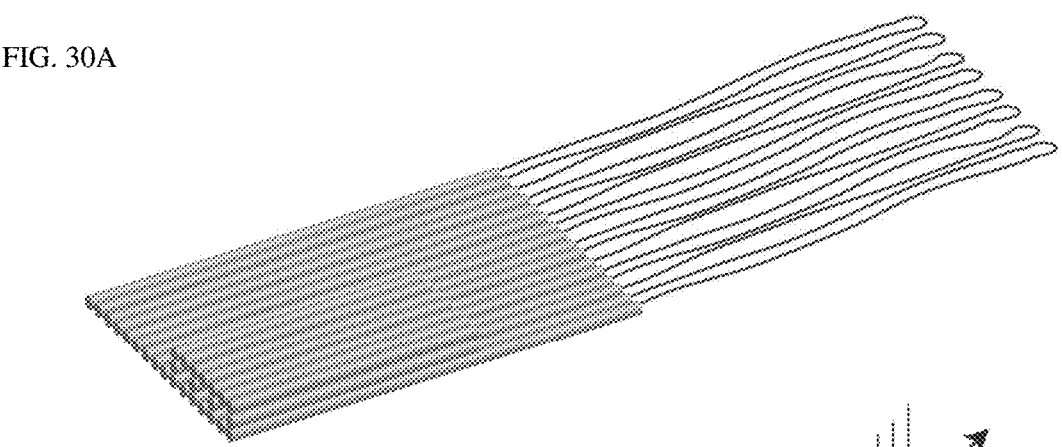
FIGS. 30A-30B show a flat DNA-origami queen nucleating a staggered DNA slats ribbon.
Figure 30B:
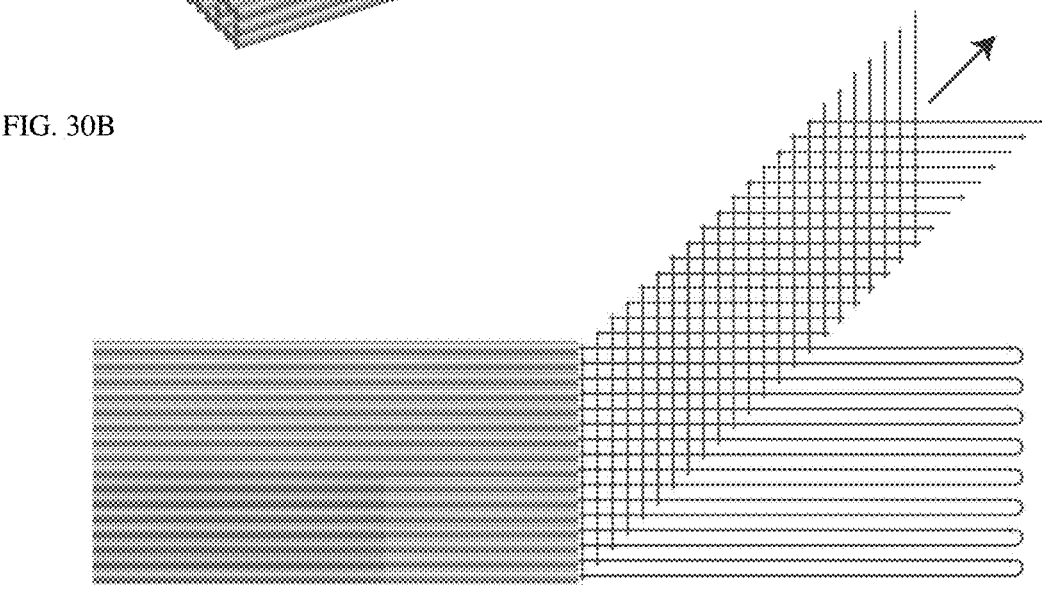
Figure 31:
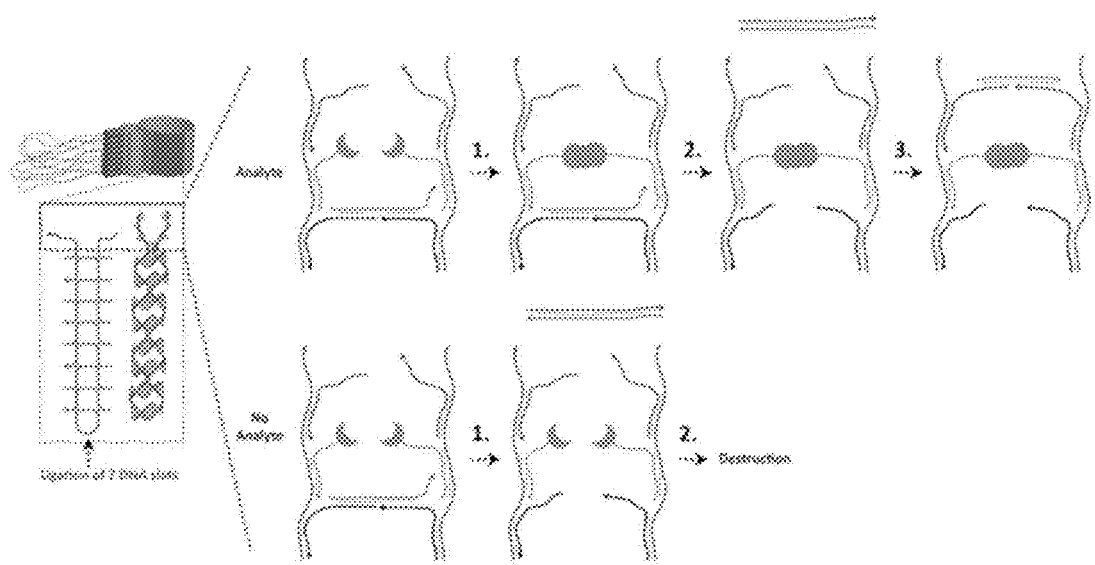
FIG. 31 shows an example of a biomolecule sensing and proofreading mechanism on DNA-Origami barrel queen. Top: Biomolecule present. (1) Biomolecule binds to antibody bridge. (2) Medium gray strand is displaced via toehold-mediated strand displacement. (3) Light gray strand binds to dark gray strands, sealing bridge. Bottom: No biomolecule present. (1) No biomolecule binds to the antibody bridge. (2) Medium gray strand is displaced via toehold-mediated strand displacement, leading to no bridge being intact and the subsequent falling apart of the barrel queen (shown in FIG. 28A).

This Example shows how extending the DNA slats to create more binding sites facilitates polymerization seeded on the queen. FIG. 25 shows both flat and barrel queen first tiled (as shown in FIGS. 23A-23B and FIGS. 24A-24B) and with extended DNA slats seeding the next generation of DNA slats to bind and eventually grow into micron sized structures. The queen nucleating site determines the shape of the subsequently grown structure. FIGS. 26A and 26B show the flat queen assembled in two types of terminal extensions. FIGS. 26C-26E show the flat queen with one, two, and three domain extensions. Samples shown in FIGS. 26A-26E were prepared using crude flat queen reaction (~1 nM), DNA slats (1000 nM/strand), and 15 mM MgCl$_2$ at 50 □ for 2 hours. FIGS. 30A-30B show a staggered design of DNA slats that bind to the flat queen, growing a ribbon like sheet. The subsequent formation of ribbons is shown in FIG. 31. Control reactions, without the flat queen, showed no assembly of the DNA slats after 18 hours of running the reaction. Samples shown in FIG. 31 were prepared using crude flat queen reaction (~9 nM), DNA slats (7500 nM/strand), and 14 mM MgCl$_2$ at 50□ for ~66 hours.

Example 7

Through the use of the barrel DNA-Origami queen multiple guest-ring catenane systems can be produced in a one-pot reaction. FIGS. 27A-27C show that by folding the barrel queen, a multiple guest-ring catenane system can be achieved through the addition of DNA slats. In order to catenate the loops two DNA slats are needed. A close up view of the DNA slats weaving and catenating the ssDNA M13 scaffold loops is shown in FIG. 27C. By ligating the two DNA slats on one end, a single DNA slat is created that captures all eight loops. A 3D rendering of the purple DNA slat capturing eight loops is shown in FIG. 27D. FIG. 24 shows the addition of 64 slats, which can simply be reduced, depending on size of the size and number of guest rings. Using the barrel queen with the DNA slats achieves a high yield in a one-pot reaction. The barrel queen can subsequently be transformed into an ultrasensitive biosensor, by coupling a biomolecule detection system to the DNA slats (see, e.g., FIG. 31). Through the integration of proofreading steps, the analyte presence can be transferred into the open or closed state of the purple DNA slat. FIGS. 28A-28B show that without a biomolecule present, the queen falls apart (open DNA slats) and no nucleation of DNA slat mediated growth can occur. The presence of a biomolecule, however, keeps the DNA slats intact and holds the queen structure together, which can then trigger the growth of micron sized tubes, for example, that can subsequently be detected using low-cost optical instruments.

TABLE 1

Exemplary Gridiron Queen Staple Sequences

| Sequence | Comment | SEQ ID NO: |
|---|---|---|
| ATCTGAACTCGCTACGGCGGGGGGAGCCCCCGATTTAGAGCT | 20170216_cc6hb_v3_queen, c0, h21, p0, control, cyan, start 0[94], end 21[94], 42 mer | 1 |
| CATTGCTGATACCGTTTAGCTAACAAACATCAAGAAAACAAA | 20170216_cc6hb_v3_queen, c0, h20, p1, control, cyan, start 1[95], end 20[95], 42 mer | 2 |
| GATACTTGCCCTCTCTGTACATAATTAATTTTCCCTTAGAAT | 20170216_cc6hb_v3_queen, c0, h19, p2, control, cyan, start 0[178], end 19[94], 42 mer | 3 |
| GATTGGGCGTTATCAATGTTGTTTTGTCACAATCAATAGAAA | 20170216_cc6hb_v3_queen, c0, h18, p3, control, cyan, start 1[179], end 18[95], 42 mer | 4 |
| TCTAATGAAGACAAATCCCCACGTCACCGACTTGAGCCATTT | 20170216_cc6hb_v3_queen, c0, h17, p4, control, cyan, start 0[262], end 17[94], 42 mer | 5 |
| AAACATCGGGTTGAGTATTATGTGGCGAGAAAGGAAGGGAAG | 20170216_cc6hb_v3_queen, c1, h21, p4, control, cyan, start 1[53], end 21[136], 42 mer | 6 |
| CGCTGGCATTCGCATCAAAGGCGAATTATTCATTTCAATTAC | 20170216_cc6hb v3_queen, c1, h20, p3, control, cyan, start 2[136], end 20[137], 42 mer | 7 |
| AGTTTATAAATGAGTATCAATTTAGATTAAGACGCTGAGAAG | 20170216_cc6hb_v3_queen, c1, h19, p2, control, cyan, start 1[137], end 19[136], 42 mer | 8 |
| TATCGACATCATTACGCATCGCAACATATAAAAGAAACGCAA | 20170216_cc6hb_v3_queen, c1, h18, p1, control, cyan, start 2[220], end 18[137], 42 mer | 9 |
| CCATGCAGACATCACGAAGGTCACCAGTAGCACCATTACCAT | 20170216_cc6hb_v3_queen, c1, h17, p0, control, cyan, start 1[221], end 17[136], 42 mer | 10 |
| AAGATAACGCTTGTGAAAATGAGGGCGCTGGCAAGTGTAGCG | 20170216_cc6hb_v3_queen, c2, h21, p0, control, cyan, start 2[94], end 21[178], 42 mer | 11 |
| GCTAACAGTAGGGAAACTGCGGCCTGATTGCTTTGAATACCA | 20170216_cc6hb_v3_queen, c2, h20, p1, control, cyan, start 3[95], end 20[179], 42 mer | 12 |
| ATGGGTTCAGGATGCAGGTGAAATCATAGGTCTGAGAGACTA | 20170216_cc6hb_v3_queen, c2, h19, p2, control, cyan, start 2[178], end 19[178], 42 mer | 13 |
| CTCGGATGGGAGTAAGCGTATGCAGTATGTTAGCAAACGTAG | 20170216_cc6hb_v3_queen, c2, h18, p3, control, cyan, start 3[179], end 18[179], 42 mer | 14 |
| AGAGTTTCTGCGGCAGTTAATCAATGAAACCATCGATAGCAG | 20170216_cc6hb_v3_queen, c2, h17, p4, control, cyan, start 2[262], end 17[178], 42 mer | 15 |
| GCAATACATCAAACGCCGCGAACACCCGCCGCGCTTAATGCG | 20170216_cc6hb_v3_queen, c3, h21, p4, control, cyan, start 3[53], end 21[220], 42 mer | 16 |
| TCAGGCACTGCGTGAAGCGGCAGTAACAGTACCTTTTACATC | 20170216_cc6hb_v3_queen, c3, h20, p3, control, cyan, start 4[136], end 20[221], 42 mer | 17 |
| ATCAAAACTCAACGAGCAGCGGTTGGGTTATATAACTATATG | 20170216_cc6hb_v3_queen, c3, h19, p2, control, cyan, start 3[137], end 19[220], 42 mer | 18 |
| AGGGTTGTCGGACTTGTGCAAGGAATACCCAAAAGAACTGGC | 20170216_cc6hb_v3_queen, c3, h18, p1, control, cyan, start 4[220], end 18[221], 42 mer | 19 |
| AGTCCGTGAAGACGGAAACCAAATCAAGTTTGCCTTTAGCGT | 20170216_cc6hb_v3_queen, c3, h17, p0, control, cyan, start 3[221], end 17[220], 42 mer | 20 |
| CTGGGGATTTGACGCAGACCTGGTTGCTTTGACGAGCACGTA | 20170216_cc6hb_v3_queen, c4, h21, p0, control, cyan, start 4[94], end 21[262], 42 mer | 21 |
| TTTTCCCAGTCACGACGTTGTGAAATTGCGTAGATTTTCAGG | 20170216_cc6hb_v3_queen, c4, h20, p1, control, cyan, start 5[95], end 20[263], 42 mer | 22 |
| TTATCAGTAAACAGAGAGGTTTCGCAAGACAAAGAACGCGAG | 20170216_cc6hb_v3_queen, c4, h19, p2, control, cyan, start 4[178], end 19[262], 42 mer | 23 |
| TCAGGGATTAATGAAAGATGGAACAAAGTTACCAGAAGGAAA | 20170216_cc6hb_v3_queen, c4, h18, p3, control, cyan, start 5[179], end 18[263], 42 mer | 24 |
| AGTGTGGCGATCCGATAGATGCGGCATTTTCGGTCATAGCCC | 20170216_cc6hb_v3_queen, c4, h17, p4, control, cyan, start 4[262], end 17[262], 42 mer | 25 |

TABLE 1-continued

Exemplary Gridiron Queen Staple Sequences

| Sequence | Comment | SEQ ID NO: |
|---|---|---|
| GGGGGATGTGCTGCAAGGCGAATCAGAGCGGGAGCTAAACAG | 20170216_cc6hb_v3_queen, c5, h21, p4, control, cyan, start 5[53], end 21[304], 42 mer | 26 |
| AGCCAGCTTTCCGGCACCGCTACCTACCATATCAAAATTATT | 20170216_cc6hb_v3_queen, c5, h20, p3, control, cyan, start 6[136], end 20[305], 42 mer | 27 |
| CTTTATTATTCGCATTCACCCTAGTTAATTTCATCTTCTGAC | 20170216_cc6hb_v3_queen, c5, h19, p2, control, cyan, start 5[137], end 19[304], 42 mer | 28 |
| TTGGTGTAGATGGGCGCATCGATCTTACCGAAGCCCTTTTTA | 20170216_cc6hb_v3_queen, c5, h18, p1, control, cyan, start 6[220], end 18[305], 42 mer | 29 |
| CAGAAATAGAAGAATTACAGCTTTCATAATCAAAATCACCGG | 20170216_cc6hb_v3_queen, c5, h17, p0, control, cyan, start 5[221], end 17[304], 42 mer | 30 |
| AAGCGCCATTCGCCATTCAGGAGACAGGAACGGTACGCCAGA | 20170216_cc6hb_v3_queen, c6, h21, p0, control, cyan, start 6[94], end 21[346], 42 mer | 31 |
| TCAGAAAAGCCCCAAAAACAGCTGATTGTTTGGATTATACTT | 20170216_cc6hb_v3_queen, c6, h20, p1, control, cyan, start 7[95], end 20[347], 42 mer | 32 |
| GAGGGGACGACGACAGTATCGACCGACCGTGTGATAAATAAG | 20170216_cc6hb_v3_queen, c6, h19, p2, control, cyan, start 6[178], end 19[346], 42 mer | 33 |
| TTTTTGTTAAATCAGCTCATTAGCCCAATAATAAGAGCAAGA | 20170216_cc6hb_v3_queen, c6, h18, p3, control, cyan, start 7[179], end 18[347], 42 mer | 34 |
| GTGGGAACAAACGGCGGATTGCGCCTCCCTCAGAGCCGCCAC | 20170216_cc6hb_v3_queen, c6, h17, p4, control, cyan, start 6[262], end 17[346], 42 mer | 35 |
| TCGTAAAACTAGCATGTCAATATCAGTGAGGCCACCGAGTAA | 20170216_cc6hb_v3_queen, c7, h21, p4, control, cyan, start 7[53], end 21[388], 42 mer | 36 |
| ATGATATTCAACCGTTCTAGCATATTCCTGATTATCAGATGA | 20170216_cc6hb_v3_queen, c7, h20, p3, control, cyan, start 8[136], end 20[389], 42 mer | 37 |
| TTAAATTGTAAACGTTAATATCGGAATCATAATTACTAGAAA | 20170216_cc6hb_v3_queen, c7, h19, p2, control, cyan, start 7[137], end 19[388], 42 mer | 38 |
| TATTTTAAATGCAATGCCTGATGAGCGCTAATATCAGAGAGA | 20170216_cc6hb_v3_queen, c7, h18, p1, control, cyan, start 8[220], end 18[389], 42 mer | 39 |
| TCAAAATAATTCGCGTCTGGAGCCACCACCCTCAGAGCCGC | 20170216_cc6hb_v3_queen, c7, h17, p0, control, cyan, start 7[221], end 17[388], 42 mer | 40 |
| GGTAGCTATTTTTGAGAGATCATTAACCGTTGTAGCAATACT | 20170216_cc6hb_v3_queen, c8, h21, p0, control, cyan, start 8[94], end 21[430], 42 mer | 41 |
| ATGGTCAATAACCTGTTTAGCTTGCGGAACAAAGAAACCACC | 20170216_cc6hb_v3_queen, c8, h20, p1, control, cyan, start 9[95], end 20[431], 42 mer | 42 |
| AAAAGGGTGAGAAAGGCCGGACGTTATACAAATTCTTACCAG | 20170216_cc6hb_v3_queen, c8, h19, p2, control, cyan, start 8[178], end 19[430], 42 mer | 43 |
| AACATCCAATAAATCATACAGGGGAGAATTAACTGAACACCC | 20170216_cc6hb_v3_queen, c8, h18, p3, control, cyan, start 9[179], end 18[431], 42 mer | 44 |
| CTTTATTTCAACGCAAGGATACGCCGCCAGCATTGACAGGAG | 20170216_cc6hb_v3_queen, c8, h17, p4, control, cyan, start 8[262], end 17[430], 42 mer | 45 |
| CGAACGAGTAGATTTAGTTTGACTTGCCTGAGTAGAAGAACT | 20170216_cc6hb_v3_queen, c9, h21, p4, control, cyan, start 9[53], end 21[472], 42 mer | 46 |
| CATTTTTGCGGATGGCTTAGACCGAACGTTATTAATTTTAAA | 20170216_cc6hb_v3_queen, c9, h20, p3, control, cyan, start 10[136], end 20[473], 42 mer | 47 |
| AGCTGAAAAGGTGGCATCAATTAGGGCTTAATTGAGAATCGC | 20170216_cc6hb_v3_queen, c9, h19, p2, control, cyan, start 9[137], end 19[472], 42 mer | 48 |
| AGCTTCAAAGCGAACCAGACCTTTACAGAGAGAATAACATAA | 20170216_cc6hb_v3_queen, c9, h18, p1, control, cyan, start 10[220], end 18[473], 42 mer | 49 |

TABLE 1-continued

Exemplary Gridiron Queen Staple Sequences

| Sequence | Comment | SEQ ID NO: |
|---|---|---|
| ATTAAGCAATAAAGCCTCAGAGGCCTTGATATTCACAAACAA | 20170216_cc6hb_v3_queen, c9, h17, p0, control, cyan, start 9[221], end 17[472], 42 mer | 50 |
| CTGTAGCTCAACATGTTTTAAAATATCCAGAACAATATTACC | 20170216_cc6hb_v3_queen, c10, h21, p0, control, cyan, start 10[94], end 21[514], 42 mer | 51 |
| GGCTTTTGCAAAAGAAGTTTTAGACTTTACAAACAATTCGAC | 20170216_cc6hb_v3_queen, c10, h20, p1, control, cyan, start 11[95], end 20[515], 42 mer | 52 |
| AGGATTAGAGAGTACCTTTAAGTAATTTAGGCAGAGGCATTT | 20170216_cc6hb_v3_queen, c10, h19, p2, control, cyan, start 10[178], end 19[514], 42 mer | 53 |
| AATATTCATTGAATCCCCCTCGAAACGATTTTTTGTTTAACG | 20170216_cc6hb_v3_queen, c10, h18, p3, control, cyan, start 11[179], end 18[515], 42 mer | 54 |
| AAGAGGAAGCCCGAAAGACTTAATGGAAAGCGCAGTCTCTGA | 20170216_cc6hb_v3_queen, c10, h17, p4, control, cyan, start 10[262], end 17[514], 42 mer | 55 |
| ACCCTCGTTTACCAGACGACGAACGCTCATGGAAATACCTAC | 20170216_cc6hb_v3_queen, c11, h21, p4, control, cyan, start 11[53], end 21[556], 42 mer | 56 |
| TAACGGAACAACATTATTACAAGAGCCGTCAATAGATAATAC | 20170216_cc6hb_v3_queen, c11, h20, p3, control, cyan, start 12[136], end 20[557], 42 mer | 57 |
| ATGTTTAGACTGGATAGCGTCATAAAGTACCGACAAAAGGTA | 20170216_cc6hb_v3_queen, c11, h19, p2, control, cyan, start 11[137], end 19[556], 42 mer | 58 |
| TGAATTACCTTATGCGATTTTTTACAAAATAAACAGCCATAT | 20170216_cc6hb_v3_queen, c11, h18, p1, control, cyan, start 12[220], end 18[557], 42 mer | 59 |
| AAACGAGAATGACCATAAATCCATACATGGCTTTTGATGATA | 20170216_cc6hb_v3_queen, c11, h17, p0, control, cyan, start 11[221], end 17[556], 42 mer | 60 |
| AGATTTAGGAATACCACATTCAAATGGATTATTTACATTGGC | 20170216_cc6hb_v3_queen, c12, h21, p0, control, cyan, start 12[94], end 21[598], 42 mer | 61 |
| CGAGGCGCAGACGGTCAATCAGTTATCTAAAATATCTTTAGG | 20170216_cc6hb_v3_queen, c12,1120, p1, control, cyan, start 13[95], end 20[599], 42 mer | 62 |
| GTCAGGACGTTGGGAAGAAAAGACAATAAACAACATGTTCAG | 20170216_cc6hb_v3_queen, c12, h19, p2, control, cyan, start 12[178], end 19[598], 42 mer | 63 |
| AGGCTGGCTGACCTTCATCAATACCAACGCTAACGAGCGTCT | 20170216_cc6hb_v3_queen, c12, h18, p3, control, cyan, start 13[179], end 18[599], 42 mer | 64 |
| TAAATTGGGCTTGAGATGGTTTTTTAACGGGGTCAGTGCCTT | 20170216_cc6hb_v3_queen, c12, h17, p4, control, cyan, start 12[262], end 17[598], 42 mer | 65 |
| TGTGTCGAAATCCGCGACCTGAGTAATAAAAGGGACATTCTG | 20170216_cc6hb_v3_queen, c13, h21, p4, control, cyan, start 13[53], end 21[640], 42 mer | 66 |
| TACGAAGGCACCAACCTAAAACTGGTCAGTTGGCAAATCAAC | 20170216_cc6hb_v3_queen, c13, h20, p3, control, cyan, start 14[136], end 20[641], 42 mer | 67 |
| CTTTGAAAGAGGACAGATGAATATCAACAATAGATAAGTCCT | 20170216_cc6hb_v3_queen, c13, h19, p2, control, cyan, start 13[137], end 19[640], 42 mer | 68 |
| GTAGCAACGGCTACAGAGGCTTAGTTGCTATTTTGCACCCAG | 20170216_cc6hb_v3_queen, c13, h18, p1, control, cyan, start 14[220], end 18[641], 42 mer | 69 |
| GATATTCATTACCCAAATCAACAGTTAATGCCCCCTGCCTAT | 20170216_cc6hb_v3_queen, c13, h17, p0, control, cyan, start 13[221], end 17[640], 42 mer | 70 |
| CTAAAACACTCATCTTTGACCCTGACCTGAAAGCGTAAGAAT | 20170216_cc6hb_v3_queen, c14, h21, p0, control, cyan, start 14[94], end 21[682], 42 mer | 71 |
| CGAATAATAATTTTTTCACGTATCACCTTGCTGAACCTCAAA | 20170216_cc6hb_v3_queen, c14, h20, p1, control, cyan, start 15[95], end 20[683], 42 mer | 72 |
| ATGAGGAAGTTTCCATTAAACATCCTAATTTACGAGCATGTA | 20170216_cc6hb_v3_queen, c14, h19, p2, control, cyan, start 14[178], end 19[682], 42 mer | 73 |

TABLE 1-continued

Exemplary Gridiron Queen Staple Sequences

| Sequence | Comment | SEQ ID NO: |
|---|---|---|
| TTCGAGGTGAATTTCTTAAACACCTCCCGAC TTGCGGGAGGT | 20170216_cc6hb_v3_queen, c14, h18, p3, control, cyan, start 15[179], end 18[683], 42 mer | 74 |
| GGATCGTCACCCTCAGCAGCGACATGAAAG TATTAAGAGGCT | 20170216_cc6hb_v3_queen, c14, h17, p4, control, cyan, start 14[262], end 17[682], 42 mer | 75 |
| TTTCAGCGGAGTGAGAATAGATGAATGGCT ATTAGTCTTTAA | 20170216_cc6hb_v3_queen, c15, h21, p4, control, cyan, start 15[53], end 21[724], 42 mer | 76 |
| CTACAACGCCTGTAGCATTCCAGTGCCACG CTGAGAGCCAGC | 20170216_cc6hb_v3_queen, c15, h20, p3, control, cyan, start 16[136], end 20[725], 42 mer | 77 |
| CTCCAAAAGGAGCCTTTAATTGTCTTTCCTT ATCATTCCAAG | 20170216_cc6hb_v3_queen, c15, h19, p2, control, cyan, start 15[137], end 19[724], 42 mer | 78 |
| CAGAGCCACCACCCTCATTTTAAGGCTTATC CGGTATTCTAA | 20170216_cc6hb_v3_queen, c15, h18, p1, contro, cyan, start 16[220], end 18[725], 42 mer | 79 |
| CCGACAATGACAACAACCATCTAGGATTAG CGGGGTTTTGCT | 20170216_cc6hb_v3_queen, c15, h17, p0, control, cyan, start 15[221], end 17[724], 42 mer | 80 |
| TCGTAAAACTAGCATGTCAATATCAGTGAG GCCACCGAGTAAGAAAAAC | 20170216_cc6hb_v3_queen, c7, h21, p4, 7 bp plug, cyan, start 7[53], end 21[388], 49 mer | 81 |
| ATGATATTCAACCGTTCTAGCATATTCCTGA TTATCAGATGAAGAGTCC | 20170216_cc6hb_v3_queen, c7, h20, p3, 7 bp plug, cyan, start 8[136], end 20[389], 49 mer | 82 |
| TTAAATTGTAAACGTTAATATCGGAATCATA ATTACTAGAAAAATAGCC | 20170216_cc6hb_v3_queen, c7, h19, p2, 7 bp plug, cyan, start 7[137], end 19[388], 49 mer | 83 |
| TATTTTAAATGCAATGCCTGATGAGCGCTAA TATCAGAGAGAATGGTGG | 20170216_cc6hb_v3_queen, c7, h18, p1, 7 bp plug, cyan, start 8[220], end 18[389], 49 mer | 84 |
| TCAAAATAATTCGCGTCTGGAGCCACCAC CCTCAGAGCCGCCGGTCCA | 20170216_cc6hb_v3_queen, c7, h17, p0, 7 bp plug, cyan, start 7[221], end 17[388], 49 mer | 85 |
| GGTAGCTATTTTTGAGAGATCATTAACCGTT GTAGCAATACTCGGTCCA | 20170216_cc6hb_v3_queen, c8, h21, p0, 7 bp plug, cyan, start 8[94], end 21[430], 49 mer | 86 |
| ATGGTCAATAACCTGTTTAGCTTGCGGAAC AAAGAAACCACCATGGTGG | 20170216_cc6hb_v3_queen, c8, h20, p1, 7 bp plug, cyan, start 9[95], end 20[431], 49 mer | 87 |
| AAAAGGGTGAGAAAGGCCGGACGTTATACA AATTCTTACCAGAATAGCC | 20170216_cc6hb_v3_queen, c8, h19, p2, 7 bp plug, cyan, start 8[178], end 19[430], 49 mer | 88 |
| AACATCCAATAAATCATACAGGGGAGAATT AACTGAACACCCAGAGTCC | 20170216_cc6hb_v3_queen, c8, h18, p3, 7 bp plug, cyan, start 9[179], end 18[431], 49 mer | 89 |
| CTTTATTTCAACGCAAGGATACGCCGCCAG CATTGACAGGAGGAAAAAC | 20170216_cc6hb_v3_queen, c8, h17, p4, 7 bp plug, cyan, start 8[262], end 17[430], 49 mer | 90 |
| TCGTAAAACTAGCATGTCAATATCAGTGAG GCCACCGAGTAAGAAAAACCGT | 20170216_cc6hb_v3_queen, c7, h21, p4, 10 bp plug, cyan, start 7[53], end 21[388], 52 mer | 91 |
| ATGATATTCAACCGTTCTAGCATATTCCTGA TTATCAGATGAAGAGTCCACT | 20170216_cc6hb_v3_queen, c7, h20, p3, 10 bp plug, cyan, start 8[136], end 20[389], 52 mer | 92 |
| TTAAATTGTAAACGTTAATATCGGAATCATA ATTACTAGAAAAATAGCCCGA | 20170216_cc6hb_v3_queen, c7, h19, p2, 10 bp plug, cyan, start 7[137], end 19[388], 52 mer | 93 |
| TATTTTAAATGCAATGCCTGATGAGCGCTAA TATCAGAGAGAATGGTGGTTC | 20170216_cc6hb_v3 queen, c7, h 18, p1, 10 bp plug, cyan, start 8[220], end 18[389], 52 mer | 94 |
| TCAAAATAATTCGCGTCTGGAGCCACCAC CCTCAGAGCCGCCGGTCCACGC | 20170216_cc6hb_v3_queen, c7, h17, p0, 10 bp plug, cyan, start 7[221], end 17[388], 52 mer | 95 |
| GGTAGCTATTTTTGAGAGATCATTAACCGTT GTAGCAATACTCGGTCCACGC | 20170216_cc6hb_v3_queen, c8, h21, p0, 10 bp plug, cyan, start 8[94], end 21[430], 52 mer | 96 |
| ATGGTCAATAACCTGTTTAGCTTGCGGAAC AAAGAAACCACCATGGTGGTTG | 20170216_cc6hb_v3_queen, c8, h20, p1, 10 bp plug, cyan, start 9[95], end 20[431], 52 mer | 97 |

TABLE 1-continued

Exemplary Gridiron Queen Staple Sequences

| Sequence | Comment | SEQ ID NO: |
|---|---|---|
| AAAAGGGTGAGAAAGGCCGGACGTTATACAAATTCTTACCAGAATAGCCCGA | 20170216_cc6hb_v3_queen, c8, h19, p2, 10 bp plug, cyan, start 8[178], end 19[430], 52 mer | 98 |
| AACATCCAATAAATCATACAGGGGAGAATTAACTGAACACCCAGAGTCCACT | 20170216_cc6hb_v3_queen, c8, h18, p3, 10 bp plug, cyan, start 9[179], end 18[431], 52 mer | 99 |
| CTTTATTTCAACGCAAGGATACGCCGCCAGCATTGACAGGAGGAAAAACCGT | 20170216_cc6hb_v3_queen, c8, h17, p4, 10 bp plug, cyan, start 8[262], end 17[430], 52 mer | 100 |
| CAATATTACATAACAATCCTCCATTTGAATTACCTTTTTAA | 20170216_cc6hb_v3_queen, edge, na, na, na, black, start 0[136], end 20[53], 42 mer | 101 |
| ACTGATACCGTGCAAAATTATCAAAGACAAAAGGGCGACATT | 20170216_cc6hb_v3_queen, edge, na, na, na, black, start 0[220], end 18[53], 42 mer | 102 |
| CGTAACGATCTAAAGTTTTGTAACATCGCCATTAAAAATACC | 20170216_cc6hb_v3_queen, edge, na, na, na, black, start 16[94], end 21[766], 42 mer | 103 |
| GAACCCATGTACCGTAACACTCGCACTCATCGAGAACAAGCA | 20170216_cc6hb_v3_queen, edge, na, na, na, black, start 16[178],end 19[766], 42 mer | 104 |
| TACCGCCACCCTCAGAACCGCCGTCGAGAGGGTTGATATAAG | 20170216_cc6hb_v3_queen, edge, na, na, na, black, start 16[262], end 17[766], 42 mer | 105 |
| TCATTAAAGGTGAATTATCACTTCTGCAATGTGCGAGAAATG | 20170216_cc6hb_v3_queen, edge, na, na, na, black, start 17[53], end 0[221], 42 mer | 106 |
| GGGAATTAGAGCCAGCAAAATGTTTATGTAGATGAAGGTATA | 20170216_cc6hb_v3_queen, edge, na, na, na, black, start 17[95], end 11262], 42 mer | 107 |
| CACCGTAATCAGTAGCGACAGGTTTCTTGTTGTTCGCCATCC | 20170216_cc6hb_v3_queen, edge, na, na, na, black, start 17[179], end 3[262], 42 mer | 108 |
| CCTTATTAGCGTTTGCCATCTGCAACACAGCAATAAAAATGC | 20170216_cc6hb_v3_queen, edge, na, na, na, black, start 17[263], end 5[262], 42 mer | 109 |
| CCTCAGAACCGCCACCCTCAGCCTTCCTGTAGCCAGCTTTCA | 20170216_cc6hb_v3_queen, edge, na, na, na, black, start 17[347], end 7[262], 42 mer | 110 |
| GTTGAGGCAGGTCAGACGATTGCATAAAGCTAAATCGGTTGT | 20170216_cc6hb_v3_queen, edge, na, na, na, black, start 17[431], end 9[262], 42 mer | 111 |
| ATTTACCGTTCCAGTAAGCGTAAAAATCAGGTCTTTACCCTG | 20170216_cc6hb_v3_queen, edge, na, na, na, black, start 17[515], end 11[262], 42 mer | 112 |
| GAGTAACAGTGCCCGTATAAACGTAACAAAGCTGCTCATTCA | 20170216_cc6hb_v3_queen, edge, na, na, na, black, start 17[599], end 13[262], 42 mer | 113 |
| GAGACTCCTCAAGAGAAGGATGCCCACGCATAACCGATATAT | 20170216_cc6hb_v3_queen, edge, na, na, na, black, start 17[683], end 15[262], 42 mer | 114 |
| TAGCAAGCAAATCAGATATAGCAGGGATAGCAAGCCCAATAG | 20170216_cc6hb_v3_queen, edge, na, na, na, black, start 18[766] end 16[179], 42 mer | 115 |
| GCTTCTGTAAATCGTCGCTATAAACATATAGATGATTAAACC | 20170216_cc6hb_v3_queen, edge, na, na, na, black, start 19[53] end 0[37], 42 mer | 116 |
| AGTATTAACACCGCCTGCAACACAGACAGCCCTCATAGTTAG | 20170216_cc6hb_v3_queen, edge, na, na, na, black, start 20[766], end 16[95], 42 mer | 117 |
| GCACTAAATCGGAACCCTAAATTTTGTTTTATGGAGATGATA | 20170216_cc6hb_v3_queen, edge, na, na, na, black, start 21[53], end 0[53], 42 mer | 118 |
| AAAGCGAAAGGAGCGGGCGCTCTGAATTTCGCGTCGTCTTCA | 20170216_cc6hb_v3_queen, edge, na, na, na, black, start 21[137], end 2[53], 42 mer | 119 |
| CCGCTACAGGGCGCGTACTATTTTCCATGAATTGGTAACACC | 20170216_cc6hb_v3_queen, edge, na, na, na, black, start 21[221], end 4[53], 42 mer | 120 |
| GAGGCCGATTAAAGGGATTTTCTGCGCAACTGTTGGGAAGGG | 20170216_cc6hb_v3_queen, edge, na, na, na, black, start 21[305], end 6[53], 42 mer | 121 |

TABLE 1-continued

Exemplary Gridiron Queen Staple Sequences

| Sequence | Comment | SEQ ID NO: |
|---|---|---|
| AAGAGTCTGTCCATCACGCAATACAAAGGCTATCAGGTCATT | 20170216_cc6hb_v3_queen, edge, na, na, na, black, start 21[389], end 8[53], 42 mer | 122 |
| CAAACTATCGGCCTTGCTGGTATATGCAACTAAAGTACGGTG | 20170216_cc6hb_v3_queen, edge, na, na, na, black, start 21[473], end 10[53], 42 mer | 123 |
| ATTTTGACGCTCAATCGTCTGAACTAATGCAGATACATAACG | 20170216_cc6hb_v3_queen, edge, na, na, na, black, start 21[557], end 12[53], 42 mer | 124 |
| GCCAACAGAGATAGAACCCTTCCCAGCGATTATACCAAGCGC | 20170216_cc6hb_v3_queen, edge, na, na, na, black, start 21[641], end 14[53], 42 mer | 125 |
| TGCGCGAACTGATAGCCCTAACGTCTTTCCAGACGTTAGTAA | 20170216_cc6hb_v3_queen, edge, na, na, na, black, start 21[725], end 16[53], 42 mer | 126 |
| CAAAGGGCGAAAAACCAACAGCTGATTGCCCTGCGCCAGG | 20170216_cc6hb_v3_queen, reference sheet, na, na, na, puke green, start 22[79], end 24[72], 40 mer | 127 |
| AGTCCACTATTAAAGAAGAGAGTTGCAGCAAGCAACGCGC | 20170216_cc6hb_v3_queen, reference sheet, na, na, na, puke green, start 22[111], end 24[104], 40 mer | 128 |
| TAGGGTTGAGTGTTGTGCCCCAGCAGGCGAAAACCTGTCG | 20170216_cc6hb_v3_queen, reference sheet, na, na, na, puke green, start 22[143], end 24[136], 40 mer | 129 |
| AATCCCTTATAAATCAGTTCCGAAATCGGCAA | 20170216_cc6hb_v3_queen, reference sheet, na, na, na, puke green, start 22[175], end 23[175], 32 mer | 130 |
| GTGAGACGGGCGTCTATCA | 20170216_cc6hb_v3_queen, reference sheet, na, na, na, puke green, start 23[53], end 22[56], 19 mer | 131 |
| GTGGTTTTTGTTTCCTGTGTGAAA | 20170216_cc6hb_v3_queen, reference sheet, na, na, na, puke green, start 24[71], end 25[79], 24 mer | 132 |
| CGTATTGGTCACCGCCTGGCCCTGACGTGGACTCCAACGT | 20170216_cc6hb_v3_queen, reference sheet, na, na, na, puke green, start 24[87], end 22[80], 40 mer | 133 |
| GGGGAGAGATTCCACACAACATAC | 20170216_cc6hb_v3_queen, reference sheet, na, na, na, puke green, start 24[103], end 25[111], 24 mer | 134 |
| GAATCGGCCGGTCCACGCTGGTTTTCCAGTTTGGAACAAG | 20170216_cc6hb_v3_queen, reference sheet, na, na, na, puke green, start 24[119], end 22[112], 40 mer | 135 |
| TGCCAGCTGTGTAAAGCCTGGGGT | 20170216_cc6hb_v3_queen, reference sheet, na, na, na, puke green, start 24[135], end 25[143], 24 mer | 136 |
| GTCGGGAAATCCTGTTTGATGGTGAAAGAATAGCCCGAGA | 20170216_cc6hb_v3_queen, reference sheet, na, na, na, puke green, start 24[151], end 22[144], 40 mer | 137 |
| GTTGCGCTCACTGCCCAACTCACATTAATTGC | 20170216_cc6hb_v3_queen, reference sheet, na, na, na, puke green, start 24[175], end 25[175], 32 mer | 138 |
| GTCATAGCTCTTTTCACCA | 20170216_cc6hb_v3_queen, reference sheet, na, na, na, puke green, start 25[56], end 24[53], 19 mer | 139 |
| TTGTTATCCGCTCACAGCGGTTTG | 20170216_cc6hb_v3_queen, reference sheet, na, na, na, puke green, start 25[80], end 24[88], 24 mer | 140 |
| GAGCCGGAAGCATAAAGCATTAAT | 20170216_cc6hb_v3_queen, reference sheet, na, na, na, puke green, start 25[112], end 24[120], 24 mer | 141 |
| GCCTAATGAGTGAGCTGCTTTCCA | 20170216_cc6hb_v3_queen, reference sheet, na, na, na, puke green, start 25[144], end 24[152], 24 mer | 142 |
| AAAATACATACATAAAGGTGGCTATTACGGGGTTGGAGGTCA | 20170216_cc6hb_v3_queen, cell not used, na, na, na, red, start 18[178], end 2[179], 42 mer | 143 |
| TAGCAAGGCCGGAAACGTCACCGAACAAGACCCGTTAGTAAC | 20170216_cc6hb_v3_queen, cell not used, na, na, na, red, start 17[137], end 2[221], 42 mer | 144 |
| CAGACTGTAGCGCGTTTTCATAACGAAGACGCCTGGTCGTTC | 20170216_cc6hb_v3_queen, cell not used, na, na, na, red, start 17[221] end 4[221] 42 mer | 145 |
| AACCAGAGCCACCACCGGAACACCGTAATGGGATAGGTCACG | 20170216_cc6hb_v3_queen, cell not used, na, na, na, red, start 17[305], end 6[221], 42 mer | 146 |

TABLE 1-continued

Exemplary Gridiron Queen Staple Sequences

| Sequence | Comment | SEQ ID NO: |
|---|---|---|
| CACCAGAACCACCACCAGAGCAAAATTTTTAGAACCCTCATA | 20170216_cc6hb_v3_queen, cell not used, na, na, na, red, start 17[389], end 8[221] 42 mer | 147 |
| ATAAATCCTCATTAAAGCCAGCAAATATCGCGTTTTAATTCG | 20170216_cc6hb_v3_queen, cell not used, na, na, na, red, start 17[473], end 10[221], 42 mer | 148 |
| CAGGAGTGTACTGGTAATAAGTAATTTCAACTTTAATCATTG | 20170216_cc6hb_v3_queen, cell not used, na, na, na, red, start 17[557], end 12[221], 42 mer | 149 |
| TTCGGAACCTATTATTCTGAAAAAGACAGCATCGGAACGAGG | 20170216_cc6hb_v3_queen, cell not used, na, na, na, red, start 17[641], end 14[221], 42 mer | 150 |
| CAGTACCAGGCGGATAAGTGCCACCCTCAGAACCGCCACCCT | 20170216_cc6hb_v3_queen, cell not used, na, na, na, red, start 17[725], end 16[221], 42 mer | 151 |
| ATTCATATGGTTTACCAGCGCTATCACGAGTACGGTGGAAAC | 20170216_cc6hb_v3_queen, cell not used, na, na, na, red, start 18[94], end 0[179], 42 mer | 152 |
| AGACACCACGGAATAAGTTTATGCAGATCCGGTGTCTTGTCT | 20170216_cc6hb_v3_queen, cell not used, na, na, na, red, start 18[136], end 1[220], 42 mer | 153 |
| ATGATTAAGACTCCTTATTACTGCTAAACTGGAAAGCAACGA | 20170216_cc6hb_v3_queen, cell not used, na, na, na, red, star[ 18 220], end 3[220], 42 mer | 154 |
| CCGAGGAAACGCAATAATAACGTTGCCAGGAGGATCTGGAAC | 20170216_cc6hb_v3_queen, cell not used, na, na, na, red, start 18[262], end 4[179], 42 mer | 155 |
| AGAAAAGTAAGCAGATAGCCGCAGACATCATTGATTCAGCAT | 20170216_cc6hb_v3_queen, cell not used, na, na, na, red, start 18[304], end 5[220], 42 mer | 156 |
| AACAATGAAATAGCAATAGCTTAACCGTGCATCTGCCAGTTT | 20170216_cc6hb_v3_queen, cell not used, na, na, na, red, start 18[346], end 6[179], 42 mer | 157 |
| TAACCCACAAGAATTGAGTTATTTTAACCAATAGGAACGCCA | 20170216_cc6hb_v3_queen, cell not used, na, na, na, red, start 18[388], end 7[220], 42 mer | 158 |
| TGAACAAAGTCAGAGGGTAATGTAATGTGTAGGTAAAGATTC | 20170216_cc6hb_v3_queen, cell not used, na, na, na, red, start 18[430], end 8[179], 42 mer | 159 |
| AAACAGGGAAGCGCATTAGACGCAAGGCAAAGAATTAGCAAA | 20170216_cc6hb_v3_queen, cell not used, na, na, na, red, start 18[472], end 9[220], 42 mer | 160 |
| TCAAAAATGAAAATAGCAGCCGGAAGCAAACTCCAACAGGTC | 20170216_cc6hb_v3_queen, cell not used, na, na, na, red, start 18[514], end 10[179], 42 mer | 161 |
| TATTTATCCCAATCCAAATAAAAATGCTTTAAACAGTTCAGA | 20170216_cc6hb_v3_queen, cell not used, na, na, na, red, start 18[556], end 11[220], 42 mer | 162 |
| TTCCAGAGCCTAATTTGCCAGAAGAACTGGCTCATTATACCA | 20170216_cc6hb_v3_queen, cell not used, na, na, na, red, start 18[598], end 12[179], 42 mer | 163 |
| CTACAATTTTATCCTGAATCTGAGTAATCTTGACAAGAACCG | 20170216_cc6hb_v3_queen, cell not used, na, na, na, red, start 18[640], end 13[220], 42 mer | 164 |
| TTTGAAGCCTTAAATCAAGATTTGAGGACTAAAGACTTTTTC | 20170216_cc6hb_v3_queen, cell not used, na, na, na, red, start 18[682], end 14[179], 42 mer | 165 |
| GAACGCGAGGCGTTTTAGCGAAGCTTGATACCGATAGTTGCG | 20170216_cc6hb_v3_queen, cell not used, na, na, na, red, start 18[724], end 15[220], 42 mer | 166 |
| CCTTGAAAACATAGCGATAGCGAGTTAGAGTCTGAGCAAAAA | 20170216_cc6hb_v3_queen, cell not used, na, na, na, red, start 19[95], end 1[178], 42 mer | 167 |
| AGTCAATAGTGAATTTATCAAGTATCTGCATATGATGTCTGA | 20170216_cc6hb_v3_queen, cell not used, na, na, na, red, start 19[137], end 2[137], 42 mer | 168 |
| CCTTTTTAACCTCCGGCTTAGTGAGTATTACGAAGGTGTTAT | 20170216_cc6hb_v3_queen, cell not used, na, na, na, red, start 19[179], end 3[178], 42 mer | 169 |
| TAAATGCTGATGCAAATCCAACGAAGTGAGCGAAATTAACTC | 20170216_cc6hb_v3_queen, cell not used, na, na, na, red, start 19[221], end 4[137], 42 mer | 170 |

TABLE 1-continued

Exemplary Gridiron Queen Staple Sequences

| Sequence | Comment | SEQ ID NO: |
|---|---|---|
| AAAACTTTTTCAAATATATTTTCATGCGTATTAACCAACAGT | 20170216_cc6hb_v3_queen, cell not used, na, na, na, red, start 19[263], end 5[178], 42 mer | 171 |
| CTAAATTTAATGGTTTGAAATGCCTCAGGAAGATCGCACTCC | 20170216_cc6hbv3_queen, cell not used, na, na, na, red, start 19[305], end 6[137], 42 mer | 172 |
| GCGTTAAATAAGAATAAACACTTTGTTAAAATTCGCATTAAA | 20170216_cc6hb_v3_queen, cell not used, na, na, na, red, start 19[347], end 7[178], 42 mer | 173 |
| AAGCCTGTTTAGTATCATATGGACAGTCAAATCACCATCAAT | 20170216_cc6hb_v3_queen, cell not used, na, na, na, red, start 19[389], end 8[137], 42 mer | 174 |
| TATAAAGCCAACGCTCAACAGTCTACTAATAGTAGTAGCATT | 20170216_cc6hb_v3_queen, cell not used, na, na, na, red, start 19[431], end 9[178], 42 mer | 175 |
| CATATTTAACAACGCCAACATTTGCTCCTTTTGATAAGAGGT | 20170216_cc6hb_v3_queen, cell not used, na, na, na, red, start 19[473], end 10[137], 42 mer | 176 |
| TCGAGCCAGTAATAAGAGAATCAATACTGCGGAATCGTCATA | 20170216_cc6hb_v3_queen, cell not used, na, na, na, red, start 19[515], end 11[178], 42 mer | 177 |
| AAGTAATTCTGTCCAGACGACATCTACGTTAATAAAACGAAC | 20170216_cc6hb_v3_queen, cell not used, na, na, na, red, start 19[557], end 12[137], 42 mer | 178 |
| CTAATGCAGAACGCGCCTGTTCGGTGTACAGACCAGGCGCAT | 20170216_cc6hb_v3_queen, cell not used, na, na, na, red, start 19[599], end 13[178], 42 mer | 179 |
| GAACAAGAAAAATAATATCCCGGGTAAAATACGTAATGCCAC | 20170216_cc6hb_v3_queen, cell not used, na, na, na, red, start 19[641], end 14[137], 42 mer | 180 |
| GAAACCAATCAATAATCGGCTGTATCGGTTTATCAGCTTGCT | 20170216_cc6hb_v3_queen, cell not used, na, na, na, red, start 19[683], end 15[178], 42 mer | 181 |
| AACGGGTATTAAACCAAGTACGAGTTTCGTCACCAGTACAAA | 20170216_cc6hb_v3_queen, cell not used, na, na, na, red, start 19[725], end 16[137], 42 mer | 182 |
| ATTAATTACATTTAACAATTTGCACTCGCGGGGATTTATTTT | 20170216_cc6hb_v3_queen, cell not used, na, na, na, red, start 20[94], end 0[95], 42 mer | 183 |
| CTGAGCAAAAGAAGATGATGAGAAACGACATACATTGCAAGG | 20170216_cc6hb_v3_queen, cell not used, na, na, na, red, start 20[136], end 1[136], 42 mer | 184 |
| AGTTACAAAATCGCGCAGAGGAGAGTGAGATCGGTTTTGTAA | 20170216_cc6hb_v3_queen, cell not used, na, na, na, red, start 20[178], end 2[95], 42 mer | 185 |
| GGGAGAAACAATAACGGATTCTGTTGAGCTTGAAACAGCAAA | 20170216_cc6hb_v3_queen, cell not used, na, na, na, red, start 20[220], end 3[136], 42 mer | 186 |
| TTTAACGTCAGATGAATATACAGAGCAGGCAATGCATGACGA | 20170216_cc6hb_v3_queen, cell not used, na, na, na, red, start 20[262], end 4[95], 42 mer | 187 |
| TGCACGTAAAACAGAAATAAAAAAACGACGGCCAGTGCCAAG | 20170216_cc6hb_v3_queen, cell not used, na, na, na, red, start 20[304], end 5[136], 42 mer | 188 |
| CTGAATAATGGAAGGGTTAGATCTGGTGCCGGAAACCAGGCA | 20170216_cc6hb_v3_queen, cell not used, na, na, na, red, start 20[346], end 6[95], 42 mer | 189 |
| TGGCAATTCATCAATATAATCGAAGATTGTATAAGCAAATAT | 20170216_cc6hb_v3_queen, cell not used, na, na, na, red, start 20[388], end 7[136], 42 mer | 190 |
| AGAAGGAGCGGAATTATCATCTGATAAATTAATGCCGGAGAG | 20170216_cc6hb_v3_queen, cell not used, na, na, na, red, start 20[430], end 8[95], 42 mer | 191 |
| AGTTTGAGTAACATTATCATTTATATTTTCATTTGGGGCGCG | 20170216_cc6hb_v3_queen, cell not used, na, na, na, red, start 20[472], end 9[136], 42 mer | 192 |
| AACTCGTATTAAATCCTTTGCGCTTAATTGCTGAATATAATG | 20170216_cc6hb_v3_queen, cell not used, na, na, na, red, start 20[514], end 10[95], 42 mer | 193 |
| ATTTGAGGATTTAGAAGTATTGCCAGAGGGGGTAATAGTAAA | 20170216_cc6hb_v3_queen, cell not used, na, na, na, red, start 20[556], end 11[136], 42 mer | 194 |
| AGCACTAACAACTAATAGATTGGTAGAAAGATTCATCAGTTG | 20170216_cc6hb_v3_queen, cell not used, na, na, na, red, start 20 598], end 12[95], 42 mer | 195 |

TABLE 1-continued

Exemplary Gridiron Queen Staple Sequences

| Sequence | Comment | SEQ ID NO: |
| --- | --- | --- |
| AGTTGAAAGGAATTGAGGAAGTAAGGGAACCGAACTGACCAA | 20170216_cc6hb_v3_queen, cell not used, na, na, na, red, start 20[640], end 13[136], 42 mer | 196 |
| TATCAAACCCTCAATCAATATCGAAAGAGGCAAAAGAATACA | 20170216_cc6hb_v3_queen, cell not used, na, na, na, red, start 20[682], end 14[95], 42 mer | 197 |
| AGCAAATGAAAAATCTAAAGCTGAAAATCTCCAAAAAAAGG | 20170216_cc6hb_v3_queen, cell not used, na, na, na, red, start 20[724], end 15[136], 42 mer | 198 |
| TGACGGGGAAAGCCGGCGAACCTTACTGTTTCTTTACATAAA | 20170216_cc6hb_v3_queen, cell not used, na, na, na, red, start 21[95], end 1[94], 42 mer | 199 |
| GTCACGCTGCGCGTAACCACCCCAGGAGAACGAGGATATTGC | 20170216_cc6hb_v3_queen, cell not used, na, na, na, red, start 21[179], end 3[94], 42 mer | 200 |
| TAACGTGCTTTCCTCGTTAGATTAAGTTGGGTAACGCCAGGG | 20170216_cc6hb_v3_queen, cell not used, na, na, na, red, start 21[263], end 5[94], 42 mer | 201 |
| ATCCTGAGAAGTGTTTTTATACATATGTACCCCGGTTGATAA | 20170216_cc6hb_v3_queen, cell not used, na, na, na, red, start 21[347], end 7[94], 42 mer | 202 |
| TCTTTGATTAGTAATAACATCACCATTAGATACATTTCGCAA | 20170216_cc6hb_v3_queen, cell not used, na, na, na, red, start 21[431], end 9[94], 42 mer | 203 |
| GCCAGCCATTGCAACAGGAAAATAAAAACCAAAATAGCGAGA | 20170216_cc6hb_v3_queen, cell not used, na, na, na, red, start 21[515], end 11[94], 42 mer | 204 |
| AGATTCACCAGTCACACGACCCTCCATGTTACTTAGCCGGAA | 20170216_cc6hb_v3_queen, cell not used, na, na, na, red, start 21[599], end 13[94], 42 mer | 205 |
| ACGTGGCACAGACAATATTTTAAGGAACAACTAAAGGAATTG | 20170216_cc6hb_v3_queen, cell not used, na, na, na, red, start 21[683], end 15[94], 42met | 206 |
| ATCTGAACTCGCTACGGCGGGGGGAGCCCCCGATTTAGAGCTCGGTCCA | 20170407_cc6hb_v3-1_queen, c0, h21, p0, 7 bp plug, cyan, start 0[94], end 21[94], 49 mer | 207 |
| CATTGCTGATACCGTTTAGCTAACAAACATCAAGAAAAGAAAATGGTGG | 20170407_cc6hb_v3-1_queen, c0, h20, p0, 7 bp plug, cyan, start 1[95], end 20195], 49 mer | 208 |
| GATACTTGCCCTCTCTGTACATAATTAATTTTCCCTTAGAATAATAGCC | 20170407_cc6hb_v3-1_queen, c0, h19, p2, 7 bp plug, cyan, start 0[178], end 19[94], 49 mer | 209 |
| GATTGGGCGTTATCAATGTTGTTTTGTCACAATCAATAGAAAAGAGTCC | 20170407_cc6hb_v3-1_queen, c0, h18, p3, 7 bp plug, cyan, start 1[179], end 18[95], 49 mer | 210 |
| TCTAATGAAGACAAATCCCCACGTCACCGACTTGAGCCATTTGAAAAAC | 2017040_cc6hb_v3-1_queen, c0, h17, p4, 7 bp plug, cyan, start 0[262], end 17[94], 49 mer | 211 |
| AAACATCGGGTTGAGTATTATGTGGCGAGAAAGGAAGGGAAGGAAAAAC | 20170407_cc6hb_v3-1_queen, c1, h21, p4, 7 bp plug, cyan, start 1[53], end 21[136], 49 mer | 212 |
| CGCTGGCATTCGCATCAAAGGCGAATTATTCATTTCAATTACAGAGTCC | 20170407_cc6hb_v3-1_queen, c1, h20, p3, 7 bp plug, cyan, start 2[136], end 20[137], 49 mer | 213 |
| AGTTTATAAATGAGTATCAATTTAGATTAAGACGCTGAGAAGAATAGCC | 20170407_cc6hb_v3-1_queen, c1, h19, p2, 7 bp plug, cyan, start 1[137], end 19[136], 49 mer | 214 |
| TATCGACATCATTACGCATCGCAACATATAAAAGAAACGCAAATGGTGG | 20170407_cc6hb_v3-1_queen, c1, h18, p1, 7 bp plug, cyan, start 2[220], end 18[137], 49 mer | 215 |
| CCATGCAGACATCACGAAGGTCACCAGTAGCACCATTACCATCGGTCCA | 20170407_cc6hb_v3-1_queen, c1, h17, p0, 7 bp plug, cyan, start 1[221], end 17[136], 49 mer | 216 |
| AAGATAACGCTTGTGAAAATGAGGGCGCTGGCAAGTGTAGCGCGGTCCA | 20170407_cc6hb_v3-1_queen, c2, h21, p0, 7 bp plug, cyan, start 2[94], end 21[178], 49 mer | 217 |
| GCTAACAGTAGGGAAACTGCGGCCTGATTGCTTTGAATACCAATGGTGG | 20170407_cc6hb_v3-1_queen, c2, h20, p1, 7 bp plug, cyan, start 3[95], end 20[179], 49 mer | 218 |
| ATGGGTTCAGGATGCAGGTGAAATCATAGGTCTGAGAGACTAAATAGCC | 20170407_cc6hb_v3-1_queen, c2, h19, p2, 7 bp plug, cyan, start 2[178], end 19[178], 49 mer | 219 |

TABLE 1-continued

Exemplary Gridiron Queen Staple Sequences

| Sequence | Comment | SEQ ID NO: |
|---|---|---|
| CTCGGATGGGAGTAAGCGTATGCAGTATGT TAGCAAACGTAGAGAGTCC | 20170407_cc6hb_v3-1_queen, c2, h18, p3, 7 bp plug, cyan, start 3[179], end 18[179], 49 mer | 220 |
| AGAGTTTCTGCGGCAGTTAATCAATGAAAC CATCGATAGCAGGAAAAAC | 20170407_cc6hb_v3-1_queen, c2, h17, p4, 7 bp plug, cyan, start 2[262], end 17[178], 49 mer | 221 |
| GCAATACATCAAACGCCGCGAACACCCGCC GCGCTTAATGCGGAAAAAC | 20170407_cc6hb_v3-1_queen, c3, h21, p4, 7 bp plug, cyan, start 3[53], end 21[220], 49 mer | 222 |
| TCAGGCACTGCGTGAAGCGGCAGTAACAGT ACCTTTTACATCAGAGTCC | 20170407_cc6hb_v3-1_queen, c3, h20, p3, 7 bp plug, cyan, start 4[136], end 20[221], 49 mer | 223 |
| ATCAAAACTCAACGAGCAGCGGTTGGGTTA TATAACTATATGAATAGCC | 20170407_cc6hb_v3-1_queen, c3, h19, p2, 7 bp plug, cyan, start 3[137], end 191220], 49 mer | 224 |
| AGGGTTGTCGGACTTGTGCAAGGAATACCC AAAAGAACTGGCATGGTGG | 20170407_cc6hb_v3-1_queen, c3, h18, p1, 7 bp plug, cyan, start 4[220], end 18[221], 49 mer | 225 |
| AGTCCGTGAAGACGGAAACCAAATCAAGTT TGCCTTTAGCGTCGGTCCA | 20170407_cc6hb_v3-1_queen, 3, h17, p0, 7 bp plug, cyan, start 3[221], end 17[220], 49 mer | 226 |
| CTGGGGATTTGACGCAGACCTGGTTGCTTTG ACGAGCACGTACGGTCCA | 20170407_cc6hb_v3-1_queen, c4, h21, p0, 7 bp plug, cyan, start 4[94], end 21[262], 49 mer | 227 |
| TTTTCCCAGTCACGACGTTGTGAAATTGCGT AGATTTTCAGGATGGTGG | 20170407_cc6hb_v3-1_queen, c4, h20, p1, 7 bp plug, cyan, start 5[95], end 20[263], 49 mer | 228 |
| TTATCAGTAAACAGAGAGGTTTCGCAAGAC AAAGAACGCGAGAATAGCC | 20170407_cc6hb_v3-1_queen, c4, h19, p2, 7 bp plug, cyan, start 4[178], end 19[262], 49 mer | 229 |
| TCAGGGATTAATGAAAGATGGAACAAAGTT ACCAGAAGGAAAAGAGTCC | 20170407_cc6hb_v3-1_queen, c4, h18, p3, 7 bp plug, cyan, start 5[179], end 18[263], 49 mer | 230 |
| AGTGTGGCGATCCGATAGATGCGGCATTTT CGGTCATAGCCCGAAAAAC | 20170407_cc6hb_v3-1_queen, c4, h17, p4, 7 bp plug, cyan, start 4[262], end 17[262], 49 mer | 231 |
| GGGGGATGTGCTGCAAGGCGAATCAGAGCG GGAGCTAAACAGGAAAAAC | 20170407_cc6hb_v3-1_queen, c5, h21, p4, 7 bp plug, cyan, start 5[53], end 21[304], 49 mer | 232 |
| AGCCAGCTTTCCGGCACCGCTACCTACCATA TCAAAATTATTAGAGTCC | 20170407_cc6hb_v3-1_queen, c5, h20, p3, 7 bp plug, cyan, start 6[136], end 20[305], 49 mer | 233 |
| CTTTATTATTCGCATTCACCCTAGTTAATTTC ATCTTCTGACAATAGCC | 20170407_cc6hb_v3-1_queen, c5, h19, p2, 7 bp plug, cyan, start 5[137], end 19[304], 49 mer | 234 |
| TTGGTGTAGATGGGCGCATCGATCTTACCG AAGCCCTTTTTAATGGTGG | 20170407_cc6hb_v3-1_queen, c5, h18, p1, 7 bp plug, cyan, start 6[220], end 18[305], 49 mer | 235 |
| CAGAAATAGAAGAATTACAGCTTTCATAAT CAAAATCACCGGCGGTCCA | 20170407_cc6hb_v3-1_queen, c5, h17, p0, 7 bp plug, cyan, start 5[221], end 17[304], 49 mer | 236 |
| AAGCGCCATTCGCCATTCAGGAGACAGGAA CGGTACGCCAGACGGTCCA | 20170407_cc6hb_v3-1_queen, c6, h21, p0, 7 bp plug, cyan, start 6[94], end 21[346], 49 mer | 237 |
| TCAGAAAAGCCCCAAAAACAGCTGATTGTT TGGATTATACTTATGGTGG | 20170407_cc6hb_v3-1_queen, c6, h20, p1, 7 bp plug, cyan, start 7[95], end 20[347], 49 mer | 238 |
| GAGGGGACGACGACAGTATCGACCGACCGT GTGATAAATAAGAATAGCC | 20170407_cc6hb_v3-1_queen, c6, h19, p2, 7 bp plug, cyan, start 6[178], end 19[346], 49 mer | 239 |
| TTTTTGTTAAATCAGCTCATTAGCCCAATAA TAAGAGCAAGAAGAGTCC | 20170407_cc6hb_v3-1_queen, c6, h18, p3, 7 bp plug, cyan, start 7[179], end 18[347], 49 mer | 240 |
| GTGGGAACAAACGGCGGATTGCGCCTCCCT CAGAGCCGCCACGAAAAAC | 20170407_cc6hb_v3-1_queen, c6, h17, p4, 7 bp plug, cyan, start 6[262], end 17[346], 49 mer | 241 |
| CGAACGAGTAGATTTAGTTTGACTTGCCTGA GTAGAAGAACTGAAAAAC | 20170407_cc6hb_v3-1_queen, c9, h21, p4, 7 bp plug, cyan, start 9[53], end 21[472], 49 mer | 242 |
| CATTTTTGCGCGATGGCTTAGACCGAACGTTA TTAATTTTAAAGAGTCC | 20170407_cc6hb_v3-1_queen, c9, h20, p3, 7 bp plug, cyan, start 10[36], end 20[473], 49 mer | 243 |

TABLE 1-continued

Exemplary Gridiron Queen Staple Sequences

| Sequence | Comment | SEQ ID NO: |
|---|---|---|
| AGCTGAAAAGGTGGCATCAATTAGGGCTTA ATTGAGAATCGCAATAGCC | 20170407_cc6hb_v3-1_queen, c9, h19, p2, 7 bp plug, cyan, start 9[137], end 19[472], 49 mer | 244 |
| AGCTTCAAAGCGAACCAGACCTTTACAGAG AGAATAACATAAATGGTGG | 20170407_cc6hb_v3-1_queen, c9, h18, p1, 7 bp plug, cyan, start 10[220], end 18[473], 49 mer | 245 |
| ATTAAGCAATAAAGCCTCAGAGGCCTTGAT ATTCACAAACAACGGTCCA | 20170407_cc6hb_v3-1_queen, c9, h17, p0, 7 bp plug, cyan, start 9[221], end 17[472], 49 mer | 246 |
| CTGTAGCTCAACATGTTTTAAAATATCCAGA ACAATATTACCCGGTCCA | 20170407_cc6hb_v3-1_queen, c10, h21, p0, 7 bp plug, cyan, start 10[94], end 21[514], 49 mer | 247 |
| GGCTTTTGCAAAAGAAGTTTTAGACTTTACA AACAATTCGACATGGTGG | 20170407_cc6hb_v3-1_queen, c10, h20, p1, 7 bp plug, cyan, start 11[95], end 20[515], 49 mer | 248 |
| AGGATTAGAGAGTACCTTTAAGTAATTTAG GCAGAGGCATTTAATAGCC | 20170407_cc6hb_v3-1_queen, c10, h19, p2, 7 bp plug, cyan, start 10[178], end 19[514], 49 mer | 249 |
| AATATTCATTGAATCCCCCTCGAAACGATTT TTTGTTTAACGAGAGTCC | 20170407_cc6hb_v3-1_queen, c10, h18, p3, 7 bp plug, cyan, start 11[179], end 18[515], 49 mer | 250 |
| AAGAGGAAGCCCGAAAGACTTAATGGAAA GCGCAGTCTCTGAGAAAAC | 20170407_cc6hb_v3-1_queen, c10, h17, p4, 7 bp plug, cyan, start 10[262], end 17[514], 49 mer | 251 |
| ACCCTCGTTTACCAGACGACGAACGCTCAT GGAAATACCTACGAAAAAC | 20170407_cc6hb_v3-1_queen, c11, h21, p4, 7 bp plug, cyan, start 11[53], end 21[556], 49 mer | 252 |
| TAACGGAACAACATTATTACAAGAGCCGTC AATAGATAATACAGAGTCC | 20170407_cc6hb_v3-1_queen, c11, h20, p3, 7 bp plug, cyan, start 12[136], end 20[557], 49 mer | 253 |
| ATGTTTAGACTGGATAGCGTCATAAAGTAC CGACAAAAGGTAAATAGCC | 20170407_cc6hb_v3-1_queen, c11, h19, p2, 7 bp plug, cyan, start 11[137], end 191556], 49 mer | 254 |
| TGAATTACCTTATGCGATTTTTTACAAAATA AACAGCCATATATGGTGG | 20170407_cc6hb_v3-1_queen, c11, h18, p1, 7 bp plug, cyan, start 12[220], end 18[557], 49 mer | 255 |
| AAACGAGAATGACCATAAATCCATACATGG CTTTTGATGATACGGTCCA | 20170407_cc6hb_v3-1_queen, c11, h17, p0, 7 bp plug, cyan, start 11[221], end 17[556], 49 mer | 256 |
| AGATTTAGGAATACCACATTCAAATGGATT ATTTACATTGGCCGGTCCA | 20170407_cc6hb_v3-1_queen, c12,h21, p0, 7 bp plug, cyan, start 12[94], end 21[598], 49 mer | 257 |
| CGAGGCGCAGACGGTCAATCAGTTATCTAA AATATCTTTAGGATGGTGG | 20170407_cc6hb_v3-1_queen, c12, h20, p1, 7 bp plug, cyan, start 13[95], end 20[599], 49 mer | 258 |
| GTCAGGACGTTGGGAAGAAAAGACAATAA ACAACATGTTCAGAATAGCC | 20170407_cc6hb_v3-1_queen, c12, h19, p2, 7 bp plug, cyan, start 12[178], end 19[598], 49 mer | 259 |
| AGGCTGGCTGACCTTCATCAATACCAACGC TAACGAGCGTCTAGAGTCC | 20170407_cc6hb_v3-1_queen, c12, h18, p3, 7 bp plug, cyan, start 13[179], end 18[599], 49 mer | 260 |
| TAAATTGGGCTTGAGATGGTTTTTTAACGGG GTCAGTGCCTTGAAAAAC | 20170407_cc6hb_v3-1_queen, c12, h17, p4, 7 bp plug, cyan, start 12[262], end 17[598], 49 mer | 261 |
| TGTGTCGAAATCCGCGACCTGAGTAATAAA AGGGACATTCTGGAAAAAC | 20170407_cc6hb_v3-1_queen, c13, h21, p4, 7 bp plug, cyan, start 13[53], end 21[640], 49 mer | 262 |
| TACGAAGGCACCAACCTAAAACTGGTCAGT TGGCAAATCAACAGAGTCC | 20170407_cc6hb_v3-1_queen, c13, h20, p3, 7 bp plug, cyan, start 14[136], end 20[641], 49 mer | 263 |
| CTTTGAAAGAGGACAGATGAATATCAACAA TAGATAAGTCCTAATAGCC | 20170407_cc6hb_v3-1_queen, c13, h19, p2, 7 bp plug, cyan, start 13[137], end 19[640], 49 mer | 264 |
| GTAGCAACGGCTACAGAGGCTTAGTTGCTA TTTTGCACCCAGATGGTGG | 20170407_cc6hb_v3-1_queen, c13, h18, p1, 7 bp plug, cyan, start 14[220], end 18[641], 49 mer | 265 |
| GATATTCATTACCCAAATCAACAGTTAATGC CCCCTGCCTATCGGTCCA | 20170407_cc6hb_v3-1_queen, c13, h17, p0, 7 bp plug, cyan, start 13[221], end 17[640], 49 mer | 266 |
| CTAAAACACTCATCTTTGACCCTGACCTGAA AGCGTAAGAATCGGTCCA | 20170407_cc6hb_v3-1_queen, c14, h21, p0, 7 bp plug, cyan, start 14[94], end 21[6821, 49 mer | 267 |

TABLE 1-continued

Exemplary Gridiron Queen Staple Sequences

| Sequence | Comment | SEQ ID NO: |
|---|---|---|
| CGAATAATAATTTTTTCACGTATCACCTTGCTGAACCTCAAAATGGTGG | 20170407_cc6hb_v3-1_queen, c14, h20, p1, 7 bp plug, cyan, start 15[95], end 20[683], 49 mer | 268 |
| ATGAGGAAGTTTCCATTAAACATCCTAATTTACGAGCATGTAAATAGCC | 20170407_cc6hb_v3-1_queen, c14, h19, p2, 7 bp plug, cyan, start 14[178], end 19[6821, 49 mer | 269 |
| TTCGAGGTGAATTTCTTAAACACCTCCCGACTTGCGGGAGGTAGAGTCC | 20170407_cc6hb_v3-1_queen, c14, h18, p3, 7 bp plug, cyan, start 15[179], end 18[6831, 49 mer | 270 |
| GGATCGTCACCCTCAGCAGCGACATGAAAGTATTAAGAGGCTGAAAAAC | 20170407_cc6hb_v3-1_queen, c14, h17, p4, 7 bp plug, cyan, start 14[262], end 17[682], 49 mer | 271 |
| TTTCAGCGGAGTGAGAATAGATGAATGGCTATTAGTCTTTAAGAAAAAC | 20170407_cc6hb_v3-1_queen, c15, h21, p4, 7 bp plug, cyan, start 15[53], end 21[724], 49 mer | 272 |
| CTACAACGCCTGTAGCATTCCAGTGCCACGCTGAGAGCCAGCAGAGTCC | 20170407_cc6hb_v3-1_queen, c15, h20, p3, 7 bp plug, cyan, start 16[136], end 20[725], 49 mer | 273 |
| CTCCAAAAGGAGCCTTTAATTGTCTTTCCTTATCATTCCAAGAATAGCC | 20170407_cc6hb_v3-1_queen, c15, h19, p2, 7 bp plug, cyan, start 15[137], end 19[724], 49 mer | 274 |
| CAGAGCCACCACCCTCATTTTAAGGCTTATCCGGTATTCTAAATGGTCG | 20170407_cc6hb_v3-1_queen, c15, h18, p1, 7 bp plug, cyan, start 16[220], end 18[725], 49 mer | 275 |
| CCGACAATGACAACAACCATCTAGGATTAGCGGGGTTTTGCTCGGTCCA | 20170407_cc6hb_v3-1_queen, c15, h17, p0, 7 bp plug, cyan, start 15[221], end 17[724], 49 mer | 276 |
| ATCTGAACTCGCTACGGCGGGGGGAGCCCCCGATTTAGAGCTCGGTCCACGC | 20170407_cc6hb_v3-1_queen, c0, h21, p0, 10 bp plug, cyan, start 0[94], end 21[94], 52 mer | 277 |
| CATTGCTGATACCGTTTAGCTAACAAACATCAAGAAAACAAAATGGTGGTTC | 20170407_cc6hb_v3-1_queen, c0, h20, p1, 10 bp plug, cyan, start 1[95], end 20[95], 52 mer | 278 |
| GATACTTGCCCTCTCTGTACATAATTAATTTTCCCTTAGAATAATAGCCCGA | 20170407_cc6hb_v3-1_queen, c0, h19, p2, 10 bp plug, cyan, start 0[178], end 19[94], 52 mer | 279 |
| GATTGGGCGTTATCAATGTTGTTTTGTCACAATCAATAGAAAAGAGTCCACT | 20170407_cc6hb_v3-1_queen, c0, h18, p3, 10 bp plug, cyan, start 1[179], end 18[95], 52 mer | 280 |
| TCTAATGAAGACAAATCCCCACGTCACCGACTTGAGCCATTTGAAAAACCGT | 20170407_cc6hb_v3-1_queen, c0, h17, p4, 10 bp plug, cyan, start 0[262], end 17[94], 52 mer | 281 |
| AAACATCGGGTTGAGTATTATGTGGCGAGAAAGGAAGGGAAGGAAAAACCGT | 20170407_cc6hb_v3-1_queen, c1, h21, p4, 10 bp plug, cyan, start 1[53], end 21[136], 52 mer | 282 |
| CGCTGGCATTCGCATCAAAGGCGAATTATTCATTTCAATTACAGAGTCCACT | 20170407_cc6hb_v3-1_queen, c1, h20, p3, 10 bp plug, cyan, start 2[136], end 20[137], 52 mer | 283 |
| AGTTTATAAATGAGTATCAATTTAGATTAAGACGCTGAGAAGAATAGCCCGA | 20170407_cc6hb_v3-1_queen, c1, h19, p2, 10 bp plug, cyan, start 1[137], end 19[136], 52 mer | 284 |
| TATCGACATCATTACGCATCGCAACATATAAAAGAAACGCAAATGGTGGTTC | 20170407_cc6hb_v3-1_queen, c1, h18, p1, 10 bp plug, cyan, start 2[220], end 18[137], 52 mer | 285 |
| CCATGCAGACATCACGAAGGTCACCAGTAGCACCATTACCATCGGTCCACGC | 20170407_cc6hb_v3-1_queen, c1, h17, p0, 10 bp plug, cyan, start 1[221], end 17[136], 52 mer | 286 |
| AAGATAACGCTTGTGAAAATGAGGGCGCTGGCAAGTGTAGCGCGGTCCACGC | 20170407_cc6hb_v3-1_queen, c2, h21, p0, 10 bp plug, cyan, start 2[94], end 21[178], 52 mer | 287 |
| GCTAACAGTAGGGAAACTGCGGCCTGATTGCTTTGAATACCAATGGTGGTTC | 20170407_cc6hb_v3-1_queen, c2, h20, p1, 10 bp plug, cyan, start 3[95], end 20[179], 52 mer | 288 |
| ATGGGTTCAGGATGCAGGTGAAATCATAGGTCTGAGAGACTAAATAGCCCGA | 20170407_cc6hb_v3-1_queen, c2, h19, p2, 10 bp plug, cyan, start 2[178], end 19[178], 52 mer | 289 |
| CTCGGATGGAGTAAGCGTATGCAGTATGTTAGCAAACGTAGAGAGTCCACT | 20170407_cc6hb_v3-1_queen, c2, h18, p3, 10 bp plug, cyan, start 3[179], end 18[179], 52 mer | 290 |
| AGAGTTTCTGCGGCAGTTAATCAATGAAACCATCGATAGCAGGAAAAACCGT | 20170407_cc6hb_v3-1_queen, c2, h17, p4, 10 bp plug, cyan, start 2[262], end 17[178], 52 mer | 291 |

TABLE 1-continued

Exemplary Gridiron Queen Staple Sequences

| Sequence | Comment | SEQ ID NO: |
|---|---|---|
| GCAATACATCAAACGCCGCGAACACCCGCCGCGCTTAATGCGGAAAAACCGT | 20170407_cc6hb_v3-1_queen, c3, h21, p4, 10 bp plug, cyan, start 3[53], end 21[220], 52 mer | 292 |
| TCAGGCACTGCGTGAAGCGGCAGTAACAGTACCTTTTACATCAGAGTCCACT | 20170407_cc6hb_v3-1_queen, c3, h20, p3, 10 bp plug, cyan, start 4[136], end 20[221], 52 mer | 293 |
| ATCAAAACTCAACGAGCAGCGGTTGGGTTATATAACTATATGAATAGCCCGA | 20170407_cc6hb_v3-1_queen, c3, h19, p2, 10 bp plug, cyan, start 3[137], end 19[220], 52 mer | 294 |
| AGGGTTGTCGGACTTGTGCAAGGAATACCCAAAAGAACTGGCATGGTGGTTC | 20170407_cc6hb_v3-1_queen, c3, h18, p1, 10 bp plug, cyan, start 4[220], end 18[2211, 52 mer | 295 |
| AGTCCGTGAAGACGGAAACCAAATCAAGTTTGCCTTTAGCGTCCGTCCACGC | 20170407_cc6hb_v3-1_queen, c3, h17, p0, 10 bp plug, cyan, start 3[221], end 17[220], 52 mer | 296 |
| CTGGGGATTTGACGCAGACCTGGTTGCTTTGACGAGCACGTACGGTCCACGC | 20170407_cc6hb_v3-1_queen, c4, h21, p0, 10 bp plug, cyan, start 4[94], end 21[262], 52 mer | 297 |
| TTTTCCCAGTCACGACGTTGTGAAATTGCGTAGATTTTCAGGATGGTGGTTC | 20170407_cc6hb_v3-1_queen, c4, h20, p1, 10 bp plug, cyan, start 5[95], end 20[263], 52 mer | 298 |
| TTATCAGTAAACAGAGAGGTTTCGCAAGACAAAGAACGCGAGAATAGCCCGA | 20170407_cc6hb_v3-1_queen, c4, h19, p2, 10 bp plug, cyan, start 4[178], end 19[262], 52 mer | 299 |
| TCAGGGATTAATGAAAGATGGAACAAAGTTACCAGAAGGAAAAGAGTCCACT | 20170407_cc6hb_v3-1_queen, c4, h18, p3, 10 bp plug, cyan, start 5[179], end 18[263], 52 mer | 300 |
| AGTGTGGCGATCCGATAGATGCGGCATTTTCGGTCATAGCCCGAAAAACCGT | 20170407_cc6hb_v3-1_queen, c4, h17, p4, 10 bp plug, cyan, start 4[262], end 17[262], 52 mer | 301 |
| GGGGGATGTGCTCCAAGGCGAATCAGAGCGGGAGCTAAACAGGAAAAACCGT | 20170407_cc6hb_v3-1_queen, c5, h21, p4, 10 bp plug, cyan, start 5[53], end 21[304], 52 mer | 302 |
| AGCCAGCTTTCCGGCACCGCTACCTACCATATCAAAATTATTAGAGTCCACT | 20170407_cc6hb_v3-1_queen, c5, h20, p3, 10 bp plug, cyan, start 6[136], end 20[305], 52 mer | 303 |
| CTTTATTATTCGCATTCACCCTAGTTAATTTCATCTTCTGACAATAGCCCGA | 20170407_cc6hb_v3-1_queen, c5, h19, p2, 10 bp plug, cyan, start 5[137], end 19[304], 52 mer | 304 |
| TTGGTGTAGATGGGCGCATCGATCTTACCGAAGCCCTTTTTAATGGTCGTTC | 20170407_cc6hb_v3-1_queen, c5, h18, p1, 10 bp plug, cyan, start 6[220], end 18[305], 52 mer | 305 |
| CAGAAATAGAAGAATTACAGCTTTCATAATCAAAATCACCGGCGGTCCACGC | 20170407_cc6hb_v3-1_queen, c5, h17, p0, 10 bp plug, cyan, start 5[221], end 17[304], 52 mer | 306 |
| AAGCGCCATTCGCCATTCAGGAGACAGGAACGGTACGCCAGACGGTCCACGC | 20170407_cc6hb_v3-1_queen, c6, h21, p0, 10 bp plug, cyan, start 6[94], end 21[346], 52 mer | 307 |
| TCAGAAAAGCCCCAAAAACAGCTGATTGTTTGGATTATACTTATGGTGGTTC | 20170407_cc6hb_v3-1_queen, c6, h20, p1, 10 bp plug, cyan, start 7[95], end 20[347], 52 mer | 308 |
| GAGGGGACGACGACAGTATCGACCGACCGTGTGATAAATAAGAATAGCCCGA | 20170407_cc6hb_v3-1_queen, c6, h19, p2, 10 bp plug, cyan, start 6[178], end 19[346], 52 mer | 309 |
| TTTTTGTTAAATCAGCTCATTAGCCCAATAATAAGAGCAAGAAGAGTCCACT | 20170407_cc6hb_v3-1_queen, c6, h18, p3, 10 bp plug, cyan, start 7[179], end 18[347], 52 mer | 310 |
| GTCKJGAACAAACGGCGGATTGCGCCTCCCTCAGAGCCGCCACGAAAAACCGT | 20170407_cc6hb_v3-1_queen, c6, h17, p4, 10 bp plug, cyan, start 6[262], end 17[346], 52 mer | 311 |
| CGAACGAGTAGATTTAGTTTGACTTGCCTGAGTAGAAGAACTGAAAAACCGT | 20170407_cc6hb_v3-1_queen, c9, h21, p4, 10 bp plug, cyan, start 9[53], end 21[472], 52 mer | 312 |
| CATTTTTGCGGATGGCTTAGACCGAACGTTATTAATTTTAAAAGAGTCCACT | 20170407_cc6hb_v3-1_queen, c9, h20, p3, 10 bp plug, cyan, start 10[136], end 20[473], 52 mer | 313 |
| AGCTGAAAAGGTGGCATCAATTAGGGCTTAATTGAGAATCGCAATAGCCCGA | 20170407_cc6hb_v3-1_queen, c9, h19, p2, 10 bp plug, cyan, start 9[137], end 19[472], 52 mer | 314 |
| AGCTTCAAAGCGAACCAGACCTTTACAGAGAGAATAACATAAATGGTGGTTC | 20170407_cc6hb_v3-1_queen, c9, h18, p1, 10 bp plug, cyan, start 10[220], end 18[473], 52 mer | 315 |

TABLE 1-continued

Exemplary Gridiron Queen Staple Sequences

| Sequence | Comment | SEQ ID NO: |
|---|---|---|
| ATTAAGCAATAAAGCCTCAGAGGCCTTGAT ATTCACAAACAACGGTCCACGC | 20170407_cc6hb_v3-1_queen, c9, h17, p0, 10 bp plug, cyan, start 9[221], end 17[472], 52 mer | 316 |
| CTGTAGCTCAACATGTTTTAAAATATCCAGA ACAATATTACCCGGTCCACGC | 20170407_cc6hb_v3-1_queen, c10, h21, p0, 10 bp plug, cyan, start 10[94], end 21[514], 52 mer | 317 |
| GGCTTTTGCAAAAGAAGTTTTAGACTTTACA AACAATTCGACATGGTGGTTC | 20170407_cc6hb_v3-1_queen, c10, h20, p1, 10 bp plug, cyan, start 11[95], end 20[515], 52 mer | 318 |
| AGGATTAGAGAGTACCTTTAAGTAATTTAG GCAGAGGCATTTAATAGCCCGA | 20170407_cc6hb_v3-1_queen, c10, h19, p2, 10 bp plug, cyan, start 10[178], end 19[514], 52 mer | 319 |
| AATATTCATTGAATCCCCCTCGAAACGATTT TTTGTTTAACGAGAGTCCACT | 20170407_cc6hb_v3-1_queen, c10, h18, p3, 10 bp plug, cyan, start 11[179], end 18[515], 52 mer | 320 |
| AAGAGGAAGCCCGAAAGACTTAATGGAAA GCGCAGTCTCTGAGAAAACCGT | 20170407_cc6hb_v3-1_queen, c10, h17, p4, 10 bp plug, cyan, start 10[262], end 17[514], 52 mer | 321 |
| ACCCTCGTTTACCAGACGACGAACGCTCAT GGAAATACCTACGAAAAACCGT | 20170407_cc6hb_v3-1_queen, c11, h21, p4, 10 bp plug, cyan, start 11[53], end 21[556], 52 mer | 322 |
| TAACGGAACAACATTATTACAAGAGCCGTC AATAGATAATACAGAGTCCACT | 20170407_cc6hb_v3-1_queen, c11, h20, p3, 10 bp plug, cyan, start 12[136], end 20[557], 52 mer | 323 |
| ATGTTTAGACTGGATAGCGTCATAAAGTAC CGACAAAAGGTAAATAGCCCGA | 20170407_cc6hb_v3-1_queen, c11, h19, p2, 10 bp plug, cyan, start 11[137], end 19[556], 52 mer | 324 |
| TGAATTACCTTATGCGATTTTTTACAAAATA AACACCCATATATGGTGGTTC | 20170407_cc6hb_v3-1_queen, c11, h18, p1, 10 bp plug, cyan, start 12[220], end 18[557], 52 mer | 325 |
| AAACGAGAATGACCATAAATCCATACATGG CTTTTGATGATACGGTCCACGC | 20170407_cc6hb_v3-1_queen, c11, h17, p0, 10 bp plug, cyan, start 11[221], end 17[556], 52 mer | 326 |
| AGATTTAGGAATACCACATTCAAATGGATT ATTTACATTGGCCGGTCCACGC | 20170407_cc6hb_v3-1_queen, c12, h21, p0, 10 bp plug, cyan, start 12[94], end 21[598], 52 mer | 327 |
| CGAGGCGCAGACGGTCAATCAGTTATCTAA AATATCTTTAGGATGGTGGTTC | 20170407_cc6hb_v3-1_queen, c12, h20, p1, 10 bp plug, cyan, start 13[95], end 20[599], 52 mer | 328 |
| GTCAGGACGTTGGGAAGAAAAGACAATAA ACAACATGTTCAGAATAGCCCGA | 20170407_cc6hb_v3-1_queen, c12, h19, p2, 10 bp plug, cyan, start 12[178], end 19[598], 52 mer | 329 |
| AGGCTGGCTGACCTTCATCAATACCAACGC TAACGAGCGTCTAGAGTCCACT | 20170407_cc6hb_v3-1_queen, c12, h18, p3, 10 bp plug, cyan, start 13[179], end 18[599], 52 mer | 330 |
| TAAATTCGGCTTGAGATGGTTTTTTAACGGG GTCAGTGCCTTGAAAAACCGT | 20170407_cc6hb_v3-1_queen, c12, h17, p4, 10 bp plug, cyan, start 12[262], end 17[598], 52 mer | 331 |
| TGTGTCGAAATCCGCGACCTGAGTAATAAA AGGGACATTCTGGAAAAACCGT | 20170407_cc6hb_v3-1_queen, c13, h21, p4, 10 bp plug, cyan, start 13[53], end 21[640], 52 mer | 332 |
| TACGAAGGCACCAACCTAAAACTGGTCAGT TGGCAAATCAACAGAGTCCACT | 20170407_cc6hb_v3-1_queen, c13, h20, p3, 10 bp plug, cyan, start 14[136], end 20[641], 52 mer | 333 |
| CTTTGAAAGAGGACAGATGAATATCAACAA TAGATAAGTCCTAATAGCCCGA | 20170407_cc6hb_v3-1_queen, c13, h19, p2, 10 bp plug, cyan, start 13[137], end 19[640], 52 mer | 334 |
| GTAGCAACGGCTACAGAGGCTTAGTTGCTA TTTTGCACCCAGATGGTGGTTC | 20170407_cc6hb_v3-1_queen, c13, h18, p1, 10 bp plug, cyan, start 14[220], end 18[641], 52 mer | 335 |
| GATATTCATTACCCAAATCAACAGTTAATGC CCCCTGCCTATCGGTCCACGC | 20170407_cc6hb_v3-1_queen, c13, h17, p0, 10 bp plug, cyan, start 13[221], end 17[640], 52 mer | 336 |
| CTAAAACACTCATCTTTGACCCTGACCTGAA AGCGTAAGAATCGGTCCACGC | 20170407_cc6hb_v3-1_queen, c14, h21, p0, 10 bp plug, cyan, start 14[94], end 21[682], 52 mer | 337 |
| CGAATAATAATTTTTTCACGTATCACCTTGC TGAACCTCAAAATGGTGGTTC | 20170407_cc6hb_v3-1_queen, c14, h20, p1, 10 bp plug, cyan, start 15[95], end 20[683], 52 mer | 338 |
| ATGAGGAAGTTTCCATTAAACATCCTAATTT ACGAGCATGTAAATAGCCCGA | 20170407_cc6hb_v3-1_queen, c14, h19, p2, 10 bp plug, cyan, start 14[178], end 19[682], 52 mer | 339 |

TABLE 1-continued

Exemplary Gridiron Queen Staple Sequences

| Sequence | Comment | SEQ ID NO: |
|---|---|---|
| TTCGAGGTGAATTTCTTAAACACCTCCCGAC TTGCGGGAGGTAGAGTCCACT | 20170407_cc6hb_v3-1_queen, c14, h18, p3, 10 bp plug, cyan, start 15[179], end 18[683], 52 mer | 340 |
| GGATCGTCACCCTCAGCAGCGACATGAAAG TATTAAGAGGCTGAAAAACCGT | 20170407_cc6hb_v3-1_queen, c14, h17, p4, 10 bp plug, cyan, start 14[262], end 17[682], 52 mer | 341 |
| TTTCAGCGGAGTGAGAATAGATGAATGGCT ATTAGTCTTTAAGAAAAACCGT | 20170407_cc6hb_v3-1_queen, c15, h21, p4, 10 bp plug, cyan, start 15[53], end 21[724], 52 mer | 342 |
| CTACAACGCCTGTAGCATTCCAGTGCCACG CTGAGAGCCAGCAGAGTCCACT | 20170407_cc6hb_v3-1_queen, c15, h20, p3, 10 bp plug, cyan, start 16[136], end 20[725], 52 mer | 343 |
| CTCCAAAAGGAGCCTTTAATTGTCTTTCCTT ATCATTCCAAGAATAGCCCGA | 20170407_cc6hb_v3-1_queen, c15, h19, p2, 10 bp plug, cyan, start 15[137], end 19[724], 52 mer | 344 |
| CAGAGCCACCACCCTCATTTTAAGGCTTATC CGGTATTCTAAATGGTGGTTC | 20170407_cc6hb_v3-1_queen, c15, h18, p1, 10 bp plug, cyan, start 16[220], end 18[725], 52 mer | 345 |
| CCGACAATGACAACAACCATCTAGGATTAG CGGGGTTTTGCTCGGTCCACGC | 20170407_cc6hb_v3-1_queen, c15, h17, p0, 10 bp plug, cyan, start 15[221], end 17[724], 52 mer | 346 |

TABLE 2

Exemplary 250 nm Six-helix Bundle Sequences

| Sequence | Comment | SEQ ID NO: |
|---|---|---|
| TCATCAACATTAAAAGAACGCGAGAAAATT GTTAAATCAGACCGTGCAT | 20170608 cc6hb v4-base 250 nm 6hb, grey standard seq, start 0[41], end 4[21], 49 mer | 347 |
| TAATCGTAAAACTAATCTTCTGACCTAAAGC TATTTTTGATA | 20170608 cc6hb v4-base 250 nm 6hb, grey standard seq, start 0[83], end 4[70], 42 mer | 348 |
| ATATATTTTAAATGGATAAATAAGGCGTAA AAACATTATGTC | 20170608 cc6hb v4-base 250 nm 6hb, grey standard seq, start 0[125], end 4[112], 42 mer | 349 |
| GCGAGCTGAAAAGGTTACTAGAAAAAGCAC GAGTAGATTTCT | 20170608 cc6hb v4-base 250 nm 6hb, grey standard seq, start 0[167], end 4[154], 42 mer | 350 |
| GGTCATTTTTGCGGTTCTTACCAGTATATTC AAAGCGAACCC | 20170608 cc6hb v4-base 250 nm 6hb, grey standard seq, start 0[209], end 4[196], 42 mer | 351 |
| AGAAAACGAGAATGTGAGAATCGCCATATT TAGACTGGATAG | 20170608 cc6hb v4-base 250 nm 6hb, grey standard seq, start 0[251], end 4[238], 42 mer | 352 |
| ACGCCAAAAGGAATAGAGGCATTTTCGACG GAACAACATTAG | 20170608 cc6hb v4-base 250 nm 6hb, grey standard seq, start 0[293], end 4[280], 42 mer | 353 |
| TAGTAAATTGGGCTACAAAAGGTAAAGTAT TCATTACCCAAG | 20170608 cc6hb v4-base 250 nm 6hb, grey standard seq, start 0[335], end 4[322], 42 mer | 354 |
| GAACGAGGCGCAGAACATGTTCAGCTAAAC AAAGTACAACCA | 20170608 cc6hb v4-base 250 nm 6hb, grey standard seq, start 0[377], end 4[364], 42 mer | 355 |
| TTCATGAGGAAGTTGATAAGTCCTGAACTC GTCACCCTCATT | 20170608 cc6hb v4-base 250 nm 6hb, grey standard seq, start 0[419], end 4[406], 42 mer | 356 |
| GCTTTCGAGGTGAACGAGCATGTAGAAAAT AATAATTTTTTG | 20170608 cc6hb v4-base 250 nm 6hb, grey standard seq, start 0[461], end 4[448], 42 mer | 357 |
| TAGCGTAACGATCTTCATTCCAAGAACGCC CATGTACCGTAA | 20170608 cc6hb v4-base 250 nm 6hb, grey standard seq, start 0[503], end 4[490], 42 mer | 358 |
| AAGTATAGCCCGGAAGAACAAGCAAGCCAC TCCTCAAGAGCA | 20170608 cc6hb v4-base 250 nm 6hb, grey standard seq, start 0[545], end 4[532], 42 mer | 359 |
| ATACAGGAGTGTACCCGCGCCCAATAGCAA TCCTCATTAATC | 20170608 cc6hb v4-base 250 nm 6hb, grey standard seq, start 0[587], end 4[574], 42 mer | 360 |

TABLE 2-continued

Exemplary 250 nm Six-helix Bundle Sequences

| Sequence | Comment | SEQ ID NO: |
| --- | --- | --- |
| CACCCTCGAGAACCGGGTATTCTAAGAACTATTAGCGTTTGAC | 20170608 cc6hb v4-base 250 nm 6hb, grey standard seq, start 0[629], end 4[616], 42 mer | 361 |
| CATTAGCAAGGCCGTGCGGGAGGTTTTGTTAAAGGTGAATTT | 20170608 cc6hb v4-base 250 nm 6hb, grey standard seq, start 0[671], end 4[658], 42 mer | 362 |
| CAAAGACACCACGGTTGCACCCAGCTACATTAAGACTCCTGG | 20170608 cc6hb v4-base 250 nm 6hb, grey standard seq, start 0[713], end 4[700], 42 mer | 363 |
| AGAAACAATGAAATACGAGCGTCTTTCCGAATTAACTGAAAA | 20170608 cc6hb v4-base 250 nm 6hb, grey standard seq, start 0[755], end 4[742], 42 mer | 364 |
| GAACAAACGGCGGATTGACAATAATTCG | 20170608 cc6hb v4-base 250 nm 6hb, grey standard seq, start 1[7], end 1[34], 28 mer | 365 |
| CGTCTGGCCTTCCTGTCCCGGTTGATAATCAGAAGAGTCTGG | 20170608 cc6hb v4-base 250 nm 6hb, grey standard seq, start 1[35], end 1[76], 42 mer | 366 |
| AGCAAACAAGAGAATCAGGTAAAGATTCAAAAGTTTCAACGC | 20170608 cc6hb 4-base 250 nm 6hb, grey standard seq, start 1[77], end 1[118], 42 mer | 367 |
| AAGGATAAAAATTTTTAGTAGTAGCATTAACATCAATAACCT | 20170608 cc6hb v4-base 250 nm 6hb, grey standard seq, start 1[119], end 1[160], 42 mer | 368 |
| GTTTAGCTATATTTTCCTGAATATAATGCTGTATAGAGAGTA | 20170608 cc6hb v4-base 250 nm 6hb, grey standard seq, start 1[161], end 1[202], 42 mer | 369 |
| CCTTTAATTGCTCCTTGTCTTTACCCTGACTATTCATTGAAT | 20170608 cc6hb v4-base 250 nm 6hb, grey standard seq, start 1[203], end 1[244], 42 mer | 370 |
| CCCCCTCAAATGCTTTAACACTATCATAACCCTTAGGAATAC | 20170608 cc6hb v4-base 250 nm 6hb, grey standard seq, start 1[245], end 1[286], 42 mer | 371 |
| CACATTCAACTAATGCCTTTAATCATTGTGAATTAAGGCTTG | 20170608 cc6hb v4-base 250 nm 6hb, grey standard seq, start 1[287], end 1[328], 42 mer | 372 |
| CCCTGACGAGAAACACCGAACTGACCAACTTTGCGAAATCCG | 20170608 cc6hb v4-base 250 nm 6hb, grey standard seq, start 1[329], end 1[370], 42 mer | 373 |
| CGACCTGCTCCATGTTACGTAATGCCACTACGAAACGGCTAC | 20170608 cc6hb v4-base 250 nm 6hb, grey standard seq, start 1[371], end 1[412] 42 mer | 374 |
| AGAGGCTTTGAGGACTCCGATAGTTGCGCCGACAAAGGAGCC | 20170608 cc6hb v4-base 250 nm 6hb, grey standard seq, start 1[413], end 1[454], 42 mer | 375 |
| TTTAATTGTATCGGTTAGACGTTAGTAAATGAAACGCCTGTA | 20170608 cc6hb v4-base 250 nm 6hb, grey standard seq, start 1[455], end 1[496], 42 mer | 376 |
| GCATTCCACAGACAGCCAGGAGGTTTAGTACCGCCAGGCGGA | 20170608 cc6hb v4-base 250 nm 6hb, grey standard seq, start 1[497], end 1[538], 42 mer | 377 |
| TAAGTGCCGTCGAGAGGGTCAGTGCCTTGAGTACCGTTCCAG | 20170608 cc6hb v4-base 250 nm 6hb, grey standard seq, start 1[539], end 1[580], 42 mer | 378 |
| TAAGCGTCATACATGGCCTCAGAGCCGCCACCAGAGCCACCA | 20170608 cc6hb v4-base 250 nm 6hb, grey standard seq, start 1[581], end 1[622], 42 mer | 379 |
| CCGGAACCGCCTCCCTCATCGATAGCAGCACCGTTAGAGCCA | 20170608 cc6hb v4-base 250 nm 6hb, grey standard seq, start 1[623], end 1[664], 42 mer | 380 |
| GCAAAATCACCAGTAGAATCAATAGAAAATTCAACATACATA | 20170608 cc6hb v4-base 250 nm 6hb, grey standard seq, start 1[665], end 1[706], 42 mer | 381 |
| AAGGTGGCAACATATAAAGCCCTTTTTAAGAAAAGAATTGAGTTAAGCC | 20170608 cc6hb v4-base 250 nm 6hb, grey standard seq, start 1[707], end 1[755], 49 mer | 382 |
| ACAGGAAGATTGAATAGGAACGCCATCAAACGTAATGGGATA | 20170608 cc6hb v4-base 250 nm 6hb, grey standard seq, start 2[55], end 2[14], 42 mer | 383 |
| AGATGGGCGCATCGTACTCATTTTTTAACCTATAA | 20170608 cc6hb v4-base 250 nm 6hb, grey standard seq, start 3[14], end 3[48], 35 mer | 384 |

TABLE 2-continued

Exemplary 250 nm Six-helix Bundle Sequences

| Sequence | Comment | SEQ ID NO: |
|---|---|---|
| GCAAATATTTAAATTGTAAACGTGAGATCT ACAAAGGAATCA | 20170608 cc6hb v4-base 250 nm 6hb, grey standard seq, start 3[49], end 3[90], 42 mer | 385 |
| CCATCAATATGATATTCAACCGTACCCTGTA ATACTTAAGAA | 20170608 cc6hb v4-base 250 nm 6hb, grey standard seq, start 3[91], end 3[132], 42 mer | 386 |
| TTAGCAAAATTAAGCAATAAAGCAGTTTGA CCATTAGCTAAA | 20170608 cc6hb v4-base 250 nm 6hb, grey standard seq, start 3[133], end 3[174], 42 mer | 387 |
| GTACGGTGTCTGGAAGTTTCATTCAGACCGG AAGCAACATCA | 20170608 cc6hb v4-base 250 nm 6hb, grey standard seq, start 3[175], end 3[216], 42 mer | 388 |
| AAAAGATTAAGAGGAAGCCCGAAAGCGTCC AATACTGCAAAA | 20170608 cc6hb v4-base 250 nm 6hb, grey standard seq, start 3[217], end 3[258], 42 mer | 389 |
| TAGCGAGAGGCTTTTGCAAAAGAATTACAG GTAGAAAGCTCA | 20170608 cc6hb v4-base 250 nm 6hb, grey standard seq, start 3[259], end 3[300], 42 mer | 390 |
| TTATACCAGTCAGGACGTTGGGAAATCAAC GTAACAAAGACC | 20170608 cc6hb v4-base 250 nm 6hb, grey standard seq, start 3[301], end 3[342], 42 mer | 391 |
| AGGCGCATAGGCTGGCTGACCTTGGAGATT TGTATCAGCAAA | 20170608 cc6hb v4-base 250 nm 6hb, grey standard seq, start 3[343], end 3[384], 42 mer | 392 |
| AGAATACACTAAAACACTCATCTGCAGCGA AAGACAGATAAC | 20170608 cc6hb v4-base 250 nm 6hb, grey standard seq, start 3[385], end 3[426], 42 mer | 393 |
| CGATAETTCGGTCGCTGAGGCTTCACGTTG AAAATCCAACT | 20170608 cc6hb v4-base 250 nm 6hb, grey standard seq, start 3[427], end 3[468], 42 mer | 394 |
| TTCAACAGTTTCAGCGGAGTGAGAACACTG AGTTTCGGAACC | 20170608 cc6hb v4-base 250 nm 6hb, grey standard seq, start 3[469], end 3[510], 42 mer | 395 |
| GCCACCCTCAGAGCCACCACCCTAAGGATT AGGATTAGCCCC | 20170608 cc6hb 4-base 250 nm 6hb, grey standard seq, start 3[551], end 3[552], 42 mer | 396 |
| CTGCCTATTTCGGAACCTATTATAGCCAGAA TGGAAAGCATT | 20170608 cc6hb v4-base 250 nm 6hb, grey standard seq, start 3[553], end 3[594], 42 mer | 397 |
| GACAGGAGGTTGAGGCAGGTCAGCCATCTT TTCATAATTGCC | 20170608 cc6hb v4-base 250 nm 6hb, grey standard seq, start 3[595], end 3[636], 42 mer | 398 |
| TTTAGCGTCAGACTGTAGCGCGTTATCACCG TCACCGAAAGG | 20170608 cc6hb v4-base 250 nm 6hb, grey standard seq, start 3[637], end 3[678], 42 mer | 399 |
| GCGACATTCAACCGATTGAGGGATATTACG CAGTATGTACCA | 20170608 cc6hb v4-base 250 nm 6hb, grey standard seq, start 3[679], end 3[720], 42 mer | 400 |
| GAAGGAAACCGAGGAAACGCAATCACCCTG AACAAAGTCAGATAATATC | 20170608 cc6hb v4-base 250 nm 6hb, grey standard seq, start 3[721], end 2[756], 49 mer | 401 |
| ATATTTGTTAAAATTCGCATTAAATTTCTTT TTCAAATATA | 20170608 cc6hb v4-base 250 nm 6hb, grey standard seq, start 4[69], end 5[55], 42 mer | 402 |
| TAGCTGATAAATTAATGCCGGAGAGGGTAT TTAATGGTTTGA | 20170608 cc6hb v4-base 250 nm 6hb, grey standard seq, start 4[111], end 5[97], 42 mer | 403 |
| CAGAGCATAAAGCTAAATCGGTTGTACCTA AATAAGAATAAA | 20170608 cc6hb v4-base 250 nm 6hb, grey standard seq, start 4[153], end 5[139], 42 mer | 404 |
| ATATAACAGTTGATTCCCAATTCTGCGACTG TTTAGTATCAT | 20170608 cc6hb v4-base 250 nm 6hb, grey standard seq, start 4[195], end 5[181], 42 mer | 405 |
| ACTTCAAATATCGCGTTTTAATTCGAGCAAG CCAACGCTCAA | 20170608 cc6hb v4-base 250 nm 6hb, grey standard seq, start 4[237], end 5[223], 42 mer | 406 |
| TTTTGCCAGAGGGGTAATAGTAAAATGTTT AACAACGCCAA | 20170608 cc6hb v4-base 250 nm 6hb, grey standard seq, start 4[279], end 5[265], 42 mer | 407 |
| AAAAATCTACGTTAATAAAACGAACTAAGC CAGTAATAAGAG | 20170608 cc6hb v4-base 250 nm 6hb, grey standard seq, start 4[321], end 5[307], 42 mer | 408 |

TABLE 2-continued

Exemplary 250 nm Six-helix Bundle Sequences

| Sequence | Comment | SEQ ID NO: |
|---|---|---|
| TCAAGAGTAATCTTGACAAGAACCGGATAATTCTGTCCAGAC | 20170608 cc6hb v4-base 250 nm 6hb, grey standard seq, start 4[363], end 5[349], 42 mer | 409 |
| GACCCCCAGCGATTATACCAAGCGCGAATGCAGAACGCGCCT | 20170608 cc6hb v4-base 250 nm 6hb, grey standard seq, start 4[405], end 5[391], 42 mer | 410 |
| CAGGGAGTTAAAGGCCGCTTTTGCGGGAAAGAAAAATAATAT | 20170608 cc6hb v4-base 250 nm 6hb, grey standard seq, start 4[447], end 5[433], 42 mer | 411 |
| TAGAAAGGAACAACTAAAGGAATTGCGACCAATCAATAATCG | 20170608 cc6hb v4-base 250 nm 6hb, grey standard seq, start 4[489], end 5[475], 42 mer | 412 |
| TTTTCAGGGATAGCAAGCCCAATAGGAAGGTATTAAACCAAG | 20170608 cc6hb v4-base 250 nm 6hb, grey standard seq, start 4[531], end 5[517], 42 mer | 413 |
| TGAAACATGAAAGTATTAAGAGGCTGAGGTTTTTATTTTCAT | 20170608 cc6hb v4-base 250 nm 6hb, grey standard seq, start 4[573], end 5[559], 42 mer | 414 |
| GATTGGCCTTGATATTCACAAACAAATAAAGCAAATCAGATA | 20170608 cc6hb v4-base 250 nm 6hb, grey standard seq, start 4[615], end 5[601], 42 mer | 415 |
| TCATCGGCATTTTCGGTCATAGCCCCCTGCGAGGCGTTTTAG | 20170608 cc6hb v4-base 250 nm 6hb, grey standard seq, start 4[657], end 5[643], 42 mer | 416 |
| GAAGGTAAATATTGACGGAAATTATTCAAAGCCTTAAATCAA | 20170608 cc6hb v4-base 250 nm 6hb, grey standard seq, start 4[699], end 5[685], 42 mer | 417 |
| TAACGGAATACCCAAAAGAACTGGCATGAATTTTATCCTGAA | 20170608 cc6hb v4-base 250 nm 6hb, grey standard seq, start 4[741], end 5[727], 42 mer | 418 |
| CGCATTAGACGGGAAGAGCCT | 20170608 cc6hb v4-base 250 nm 6hb, grey standard seq, start 4[769], end 5[762], 21 mer | 419 |
| AAGACAATGTGAGCGAGTAACAACCCGT | 20170608 cc6hb v4-base 250 nm 6hb, grey standard seq, start 5[21], end 0[7], 28 mer | 420 |
| TTTTAGTTAATTTCGCATGTCAATCATATGTACAGCCAGCTT | 20170608 cc6hb v4-base 250 nm 6hb, yellow standard seq, start 5[56], end 0[42], 42 mer | 421 |
| AATACCGACCGTGTCAATGCCTGAGTAATGTGTGATGAACGG | 20170608 cc6hb v4-base 250 nm 6hb, yellow standard seq, start 5[98], end 0[84], 42 mer | 422 |
| CACCGGAATCATAATGGCATCAATTCTACTAATAGAACCCTC | 20170608 cc6hb v4-base 250 nm 6hb, yellow standard seq, start 5[140], end 0[126], 42 mer | 423 |
| ATGCGTTATACAAAATGGCTTAGAGCTTAATTGATTTGGGGC | 20170608 cc6hb v4-base 250 nm 6hb, yellow standard seq, start 5[182], end 0[168], 42 mer | 424 |
| CAGTAGGGCTTAATACCATAAATCAAAAATCAGTTGATAAGA | 20170608 cc6hb v4-base 250 nm 6hb, yellow standard seq, start 5[224], end 0[210], 42 mer | 425 |
| CATGTAATTTAGGCTACGAGGCATAGTAAGAGCAAACAGTTC | 20170608 cc6hb v4-base 250 nm 6hb, yellow standard seq, start 5[266], end 0[252], 42 mer | 426 |
| AATATAAAGTACCGTGAGATGGTTTAATTTCAAAGATACATA | 20170608 cc6hb v4-base 250 nm 6hb, yellow standard seq, start 5[308], end 0[294], 42 mer | 427 |
| GACGACAATAAACACGGTCAATCATAAGGGAACCAGAACGAG | 20170608 cc6hb v4-base 250 nm 6hb, yellow standard seq, start 5[350], end 0[336], 42 mer | 428 |
| GTTTATCAACAATATCCATTAAACGGGTAAAATACTTAGCCG | 20170608 cc6hb v4-base 250 nm 6hb, yellow standard seq, start 5[392], end 0[378], 42 mer | 429 |
| CCCATCCTAATTTATTTCTTAAACAGCTTGATAAAAGACTTT | 20170608 cc6hb v4-base 250 nm 6hb, yellow standard seq, start 5[434], end 0[420], 42 mer | 430 |
| GCTGTCTTTCCTTAAAAGTTTTGTCGTCTTTCCTATCAGCTT | 20170608 cc6hb v4-base 250 nm 6hb, yellow standard seq, start 5[476], end 0[462], 42 mer | 431 |
| TACCGCACTCATCGATAGGTGTATCACCGTACTCCTCATAGT | 20170608 cc6hb v4-base 250 nm 6hb, yellow standard seq, start 5[518], end 0[504], 42 mer | 432 |

TABLE 2-continued

Exemplary 250 nm Six-helix Bundle Sequences

| Sequence | Comment | SEQ ID NO: |
|---|---|---|
| CGTAGGAATCATTATGGTAATAAGTTTTAACGGGGTTGATAT | 20170608 cc6hb v4-base 250 nm 6hb, yellow standard seq, start 5[560], end 0[546], 42 mer | 433 |
| TAGAAGGCTTATCCCCACCCTCAGAGCCACCACCTTTTGATG | 20170608 cc6hb v4-base 250 nm 6hb, yellow standard seq, start 5[602], end 0[588], 42 mer | 434 |
| CGAACCTCCCGACTGAAACGTCACCAATGAAACCAGAGCCGC | 20170608 cc6hb v4-base 250 nm 6hb, yellow standard seq, start 5[644], end 0[630], 42 mer | 435 |
| GATTAGTTGCTATTAATAAGTTTATTTTGTCACCACCATTAC | 20170608 cc6hb v4-base 250 nm 6hb, yellow standard seq, start 5[686], end 0[672], 42 mer | 436 |
| TCTTACCAACGCTAAGCAATAGCTATCTTACCGAAAGAAACG | 20170608 cc6hb v4-base 250 nm 6hb, yellow standard seq, start 5[728], end 0[714], 42 mer | 437 |
| CGGAGACAGTCACTATCAGGTCATTGCCTGAAAGCCCCAAAA | 20170608 cc6hb v4-base 250 nm 6hb, magenta standard seq, start 2[97], end 2[56], 42 mer | 438 |
| ACAGGCAAGGCATTGCGGGAGAAGCCTTTAGGTGAGAAAGGC | 20170608 cc6hb v4-base 250 nm 6hb, magenta standard seq, start 2[139], end 2[98], 42 mer | 439 |
| TTAAATATGCAAATACATTTCGCAAATGGTCCAATAAATCAT | 20170608 cc6hb v4-base 250 nm 6hb, magenta standard seq, start 2[181], end 2[140], 42 mer | 440 |
| CAAAGCGGATTGACTCCAACAGGTCAGGATGCTCAACATGTT | 20170608 cc6hb v4-base 250 nm 6hb, magenta standard seq, start 2[223], end 2[182], 42 mer | 441 |
| GACGATAAAAACCGGAATCGTCATAAATATTATAGTCAGAAG | 20170608 cc6hb v4-base 250 nm 6hb, magenta standard seq, start 2[265], end 2[224], 42 mer | 442 |
| TTTTAAGAACTGGATTCATCAGTTGAGATTCGTTTACCAGAC | 20170608 cc6hb v4-base 250 nm 6hb, magenta standard seq, start 2[307], end 2[266], 42 mer | 443 |
| TGAACGGTGTACAGCTGCTCATTCAGTGAATACCTTATCCGA | 20170608 cc6hb v4-base 250 nm 6hb, magenta standard seq, start 2[349], end 2[308], 42 mer | 444 |
| AAAACGAAAGAGTCGCCTGATAAATTGTGTAAAGAGGACAGA | 20170608 cc6hb v4-base 250 nm 6hb, magenta standard seq, start 2[391], end 2[350], 42 mer | 445 |
| CATCGCCCACGCCATCGGAACGAGGGTAGCAGGCACCAACCT | 20170608 cc6hb v4-base 250 nm 6hb, magenta standard seq, start 2[433], end 2[392], 42 mer | 446 |
| GATTTTGCTAAATCCAAAAAAAGGCTCCAAATGACAACAAC | 20170608 cc6hb v4-base 250 nm 6hb, magenta standard seq, start 2[475], end 2[434], 42 mer | 447 |
| CCGCCACCCTCATCACCAGTACAAACTACATTTTCTGTATGG | 2.0170608 cc6hb v4-base 250 nm 6hb, magenta standard seq, start 2[517], end 2[476], 42 mer | 448 |
| TAAACAGTTAATGCGGGGTTTTGCTCAGTACCACCCTCAGAA | 20170608 cc6hb v4-base 250 nm 6hb, magenta standard seq, start 2[559], end 2[518], 42 mer | 449 |
| GAGCCGCCGCCAGCGCAGTCTCTGAATTTAACAGTGCCCGTA | 2.0170608 cc6hb v4-base 250 nm 6hb, magenta standard seq, start 2[601], end 2[560], 42 mer | 450 |
| ACAGAATCAAGTTCAAAATCACCGGAACCAGAACCACCACCA | 20170608 cc6hb v4-base 250 nm 6hb, magenta standard seq, start 2[643], end 2|602], 42 mer | 451 |
| GCGCCAAAGACAACTTGAGCCATTTGGGAATAATCAGTAGCG | 20170608 cc6hb v4-base 250 nm 6hb, magenta standard seq, start 2[685], end 2[644], 42 mer | 452 |
| CCGAACAAAGTTTAGCAAACGTAGAAAATTATGGTTTACCA | 20170608 cc6hb v4-base 250 nm 6hb, magenta standard seq, start 2[726], end 2[686], 41 mer | 453 |
| AGAGAGATAACCCACAAGTAAGCAGATAG | 20170608 cc6hb 4-base 250 nm 6hb, magenta standard seq, start 2[755], end 2[727], 29 mer | 454 |
| AGAAGATGAAATTAACTAAAATATATTTGAAAAAGTTTTCTCGCGTTCTTTGTCTTGCGATTG | 20170608, cc6hb v4-250 nm 16 component square, default 6hb, miniseaf, node-0 | 455 |
| ATTTATCACACGGTCGGTATTTCAAACCATTAAATTTAGGTC | 20170608, cc6hb v4-250 nm 16 component square, default 6hb, miniscaf, node-1 | 456 |

TABLE 2-continued

Exemplary 250 nm Six-helix Bundle Sequences

| Sequence | Comment | SEQ ID NO: |
|---|---|---|
| CTAGTAATTATGATTCCGGTGTTTATTCTTATTTAACGCCTT | 20170608, cc6hb v4-250 nm 16 component square, default 6hb, miniscaf, node-2 | 457 |
| GTAAGAATTTGTATAACGCATATGATACTAAACAGGCTTTTT | 20170608, cc6hb v4-250 nm 16 component square, default 6hb, miniscaf, node-3 | 458 |
| ATTCTCAATTAAGCCCTACTGTTGAGCGTTGGCTTTATACTG | 20170608, cc6hb v4-250 nm 16 component square, default 6hb, miniscaf, node-4 | 459 |
| TGCCTCTGCCTAAATTACATGTTGGCGTTGTTAAATATGGCG | 20170608, cc6hb v4-250 nm 16 component square, default 6hb, miniscaf, node-5 | 460 |
| CTTTTGTCGGTACTTTATATTCTCTTATTACTGGCTCGAAAA | 20170608, cc6hb v4-250 nm 16 component square, default 6hb, miniscaf, node-6 | 461 |
| AACATGTTGTTTATTGTCGTCGTCTGGACAGAATTACTTTAC | 20170608, cc6hb v4-250 nm 16 component square, default 6hb, miniscaf, node-7 | 462 |
| ACTTATCTATTGTTGATAAACAGGCGCGTTCTGCATTAGCTG | 20170608, cc6hb v4-250 nm 16 component square, default 6hb, miniscaf, node-8 | 463 |
| ATGCTCGTAAATTAGGATGGGATATTATTTTTCTTGTTCAGG | 20170608, cc6hb v4-250 nm 16 component square, default 6hb, miniscaf, node-9 | 464 |
| GGAATGATAAGGAAAGACAGCCGATTATTGATTGGTTTCTAC | 20170608, cc6hb v4-250 nm 16 component square, default 6hb, miniscaf, node-10 | 465 |
| TTGTTCTCGATGAGTGCGGTACTTGGTTTAATACCCGTTCTT | 20170608, cc6hb v4-250 nm 16 component square, default 6hb, miniscaf, node-11 | 466 |
| GGCGCGGTAATGATTCCTACGATGAAAATAAAAACGGCTTGC | 20170608, cc6hb v4-250 nm 16 component square, default 6hb, miniscaf, node-12 | 467 |
| GAATACCGGATAAGCCTTCTATATCTGATTTGCTTGCTATTG | 20170608, cc6hb v4-250 nm 16 component square, default 6hb, miniscaf, node-13 | 468 |
| TCCCGCAAGTCGGGAGGTTCGCTAAAACGCCTCGCGTTCTTA | 20170608, cc6hb v4-250 nm 16 component square, default 6hb, miniscaf, node-14 | 469 |
| GGTGCAAAATAGCAACTAATCTTGATTTAAGGCTTCAAAACC | 20170608, cc6hb v4-250 nm 16 component square, default 6hb, miniscaf, node-15 | 470 |
| GCAAATTAGGCTCTGGAAAGACGCTCGTTAGCGTTGGTAAGATTCAGGATAAAATTGTAGCTG | 20170608, cc6hb v4-250 nm 16 component square, default 6hb, miniscaf, node-16 | 471 |
| ATTCTCAATTAGCGTGGACCGTTGAGCGTTGGCTTTATACTG | cc6hbv3_miniscaf_10s_n4 | 472 |
| TGCCTCTGCCTGAACCACCATTTGGCGTTGTTAAATATGGCG | cc6hbv3_miniscaf_10s_n5 | 473 |
| CTTTTGTCGGTTCGGGCTATTCTCTTATTACTGGCTCGAAAA | cc6hbv3_miniscaf_10s_n6 | 474 |
| AACATGTTGTTAGTGGACTCTGTCTGGACAGAATTACTTTAC | cc6hbv3_miniscaf_10s_n7 | 475 |
| ACTTATCTATTACGGTTTTTCAGGCGCGTTCTGCATTAGCTG | cc6hbv3_miniscaf_10s_n8 | 476 |
| TAATACCATAAATCAAAAATCAGTTGATAAGA | cc6hbv3_yellow_term_10s_n4 | 477 |
| AGGCTACGAGGCATAGTAAGAGCAAACAGTTC | cc6hbv3_yellow_term_10s_n5 | 478 |
| ACCGTGAGATGGTTTAATTTCAAAGATACATA | cc6hbv3_yellow_term_10s_n6 | 479 |
| AACACGGTCAATCATAAGGGAACCAGAACGAG | cc6hbv3_yellow_term_10s_n7 | 480 |

TABLE 2-continued

Exemplary 250 nm Six-helix Bundle Sequences

| Sequence | Comment | SEQ ID NO: |
|---|---|---|
| AATATCCATTAAACGGGTAAAATACTTAGCCG | cc6hbv3_yellow_term_10s_n8 | 481 |

TABLE 3

Exemplary 440 nm Six-helix Bundle

| Sequence | Comment | SEQ ID NO: |
|---|---|---|
| AACGGCATCTCCGTGAGCCTCCTCACAGAGCCTGGGGTGCCT | 6hb_440nm, start 0[76], end 5[62] | 482 |
| GGCAGCACCCATCCCTTACACTGGTGTGGTTGCGCTCACTGC | 6hb_440nm, start 0[118], end 5[104] | 483 |
| AAATCCCGTGGTCTGGTCAGCAGCAACCCCAGCTGCATTAAT | 6hb_440nm, start 0[160], end 5[146] | 484 |
| GAGCCGCCAAGCAGTTGGGCGGTTGTGTTTTGCGTATTGGGC | 6hb_440nm, start 0[202], end 5[188] | 485 |
| GGCACCGCTAAAACGACGGCCAGTGCCAAGACGGGCAACAGC | 6hb_440nm, start 0[244], end 5[230] | 486 |
| CGCGTCTGGGCCTCAGGAAGATCGCACTAGAGTTGCAGCAAG | 6hb_440nm, start 0[286], end 5[272] | 487 |
| GGAGCAAACTTTTAACCAATAGGAACGCGAAAATCCTGTTTG | 6hb_440nm, start 0[328], end 5[314] | 488 |
| GCAAGGATATACAAAGGCTATCAGGTCATTATAAATCAAAAG | 6hb_440nm, start 0[370], end 5[356] | 489 |
| CTGTTTAGCTAATACTTTTGCGGGAGAATCCAGTTTGGAACA | 6hb_440nm, start 0[412], end 5[398] | 490 |
| TACCTTTAAACCATTAGATACATTTCGCCAACGTCAAAGGGC | 6hb_440nm, start 0[454], end 5[440] | 491 |
| ATCCCCCTCGAAGCAAACTCCAACAGCACTACGTGAACCAT | 6hb_440nm, start 0[496], end 5[482] | 492 |
| ACCACATTCCAATACTGCGGAATCGTCAGTGCCGTAAAGCAC | 6hb_440nm, start 0[538], end 5[524] | 493 |
| TGCCCTGACGGTAGAAAGATTCATCAGTATTTAGAGCTTGAC | 6hb_440nm, start 0[580], end 5[566] | 494 |
| CGCGACCTGCGTAACAAAGCTGCTCATTGGAAGGGAAGAAAG | 6hb_440nm, start 0[622], end 5[608] | 495 |
| ACAGAGGCTTTGTATCATCGCCTGATAAAAGTGTAGCGGTCA | 6hb_440nm, start 0[664], end 5[650] | 496 |
| CCTTTAATTAAAGACAGCATCGGAACGAGCTTAATGCGCCGC | 6hb_440nm, start 0[706], end 5[692] | 497 |
| TAGCATTCCTGAAAATCTCCAAAAAAAACGAGCACGTATAAC | 6hb_440nm, start 0[748], end 5[734] | 498 |
| GATAAGTGCGAGTTTCGTCACCAGTACAAGCTAAACAGGAGG | 6hb_440nm, start 0[790], end 5[776] | 499 |
| AGTAAGCGTTAGGATTAGCGGGGTTTTGGTACGCCAGAATCC | 6hb_440nm, start 0[832], end 5[818] | 500 |
| CACCGGAACAATGGAAAGCGCAGTCTCTCACCGAGTAAAAGA | 6hb_440nm, start 0[874], end 5[860] | 501 |

TABLE 3-continued

Exemplary 440 nm Six-helix Bundle

| Sequence | Comment | SEQ ID NO: |
|---|---|---|
| CAGCAAAATTTTCATAATCAAAATCACCTAGCAATACTTCTT | 6hb_440nm, start 0[916], end 5[902] | 502 |
| TAAAGGTGGCGTCACCGACTTGAGCCATTAGAAGAACTCAAA | 6hb_440nm, start 0[958], end 5[944] | 503 |
| ATTGAGTTAGCAGTATGTTAGCAAACGTCAATATTACCGCCA | 6hb_440nm, start 0[1000], end 5[986] | 504 |
| ATTTGCCAGTGAGCGCTAATATCAGAGAAAATACCTACATTT | 6hb_440nm, start 0[1042], end 5[1028] | 505 |
| TTTCATCGTTACCAACGCTAACGAGCGTTTACATTGGCAGAT | 6hb_440nm, start 0[1084], end 5[1070] | 506 |
| CCAGACGACCGCACTCATCGAGAACAAGGGACATTCTGGCCA | 6hb_440nm, start 0[1126], end 5[1112] | 507 |
| AATAAACACATAAAGTACCGACAAAAGGGCGTAAGAATACGT | 6hb_440nm, start 0[1168], end 5[1154] | 508 |
| ATTTATCAAACCGACCGTGTGATAAATATAGTCTTTAATGCG | 6hb_440nm, start 0[1210], end 5[1196] | 509 |
| AGATGATGATTAGATTAAGACGCTGAGATAAAAATACCGAAC | 6hb_440nm, start 0[1252], end 5[1238] | 510 |
| AGGGTTAGACGAATTATTCATTTCAATTTGAGGCGGTCAGTA | 6hb_440nm, start 0[1294], end 5[1280] | 511 |
| AGAAGTATTCTGATTGTTTGGATTATACGAGAGCCAGCAGCA | 6hb_440nm, start 0[1336], end 5[1322] | 512 |
| TCATGGTCATAGCCGTGCCTGTTCTTCGCGAGATGCCGGGTT | 6hb_440nm, start 1[38], end 1[79] | 513 |
| ACCTGCAGCCAGCTCTTTGCTCGTCATAAAGTCGGTGGTGCC | 6hb_440nm, start 1[80], end 1[121] | 514 |
| ATCCCACGCAACCAACGTCAGCGTGGTGCTAAAAAAAGCCGC | 6hb_440nm, start 1[122], end 1[163] | 515 |
| ACAGGCGGCCTTTTCTGCTCATTTGCCGCCCGGGAACGGATA | 6hb_440nm, start 1[164], end 1[205] | 516 |
| ACCTCACCGGAAACCCAGTCACGACGTTGTTCTGGTGCCGGA | 6hb_440nm, start 1[206], end 1[247] | 517 |
| AACCAGGCAAAGCGGACGACGACAGTATCGCCTTCCTGTAGC | 6hb_440nm, start 1[248], end 1[289] | 518 |
| CAGCTTTCATCAATGTTAAATCAGCTCATTAAGAGAATCGAT | 6hb_440nm, start 1[290], end 1[331] | 519 |
| GAACGGTAATCGTGCTATTTTGAGAGATCAAAATTTTAGA | 6hb_440nm, start 1[332], end 1[373] | 520 |
| ACCCTCATATATTAAAACATTATGACCCTGTATATTTTCATT | 6hb_440nm, start 1[374], end 1[415] | 521 |
| TGGGGCGCGAGCTCGAGTAGATTTAGTTTGTTGCTCCTTTTG | 6hb_440nm, start 1[416], end 1[457] | 522 |
| ATAAGAGGTCATTTCAAAGCGAACCAGACCAAATGCTTTAAA | 6hb_440nm, start 1[458], end 1[499] | 523 |
| CAGTTCAGAAAACTTAGACTGGATAGCGTCAACTAATGCAGA | 6hb_440nm, start 1[500], end 1[541] | 524 |
| TACATAACGCCAAGGAACAACATTATTACAGAGAAACACCAG | 6hb_440nm, start 1[542], end 1[583] | 525 |

TABLE 3-continued

Exemplary 440 nm Six-helix Bundle

| Sequence | Comment | SEQ ID NO: |
|---|---|---|
| AACGAGTAGTAAATTCATTACCCAAATCAA CTCCATGTTACT | 6hb_440nm, start 1[584], end 1[625] | 526 |
| TAGCCGGAACGAGCAAAGTACAACGGAGAT TTGAGGACTAAA | 6hb_440am, start 1[626], end 1[667] | 527 |
| GACTTTTTCATGACGTCACCCTCAGCAGCGG TATCGGTTTAT | 6hb_440nm, start 1[668], end 1[709] | 528 |
| CAGCTTGCTTTCGTAATAATTTTTTCACGTA CAGACAGCCCT | 6hb_440nm, start 1[710], end 1[751] | 529 |
| CATAGTTAGCGTACCATGTACCGTAACACTC GTCGAGAGGGT | 6hb_440nm, start 1[752], end 1[793] | 530 |
| TGATATAAGTATACTCCTCAAGAGAAGGAT CATACATGGCTT | 6hb_440nm, start 1[794], end 1[835] | 531 |
| TTGATGATACAGGATCCTCATTAAAGCCAG CGCCTCCCTCAG | 6hb_440nm, start 1[836], end 1[877] | 532 |
| AGCCGCCACCCTCATTAGCGTTTGCCATCTC ACCAGTAGCAC | 6hb_440nm, start 1[878], end 1[919] | 533 |
| CATTACCATTAGCTAAAGGTGAATTATCACC AACATATAAAA | 6hb_440nm, start 1[920], end 1[961] | 534 |
| GAAACGCAAAGACTTAAGACTCCTTATTAC AGCCCAATAATA | 6hb_440nm, start 1[962], end 1[1003] | 535 |
| AGAGCAAGAAACACAAAGTCAGAGGGTAA TTTACAAAATAAA | 6hb_440nm, start 1[1004], end 1[1045] | 536 |
| CAGCCATATTATTAATTTTATCCTGAATCTA GGAATCATTAC | 6hb_440nm, start 1[1046], end 1[1087] | 537 |
| CGCGCCAATAGCGGTATTAAACCAAGTAC GACAATAAACAA | 6hb_440nm, start 1[1088], end 1[1129] | 538 |
| CATGTTCAGCTAAGCCAGTAATAAGAGAAT CGGAATCATAAT | 6hb_440nm, start 1[1130], end 1[1171] | 539 |
| TACTAGAAAAGCATTTAATGGTTTGAAAT AATCATAGGTCT | 6hb_440nm, start 1[1172], end 1[1213] | 540 |
| GAGAGACTACCTTGAAAACATAGCGATAGC AACAAACATCAA | 6hb_440nm, start 1[1214], end 1[1255] | 541 |
| GAAAACAAAATTAACAAAATCGCGCAGAG GACCTACCATATC | 6hb_440nm, start 1[1256], end 1[1297] | 542 |
| AAAATTATTTGCAAATTCATCAATATAATCA GACTTTACAAACAAT | 6hb_440nm, start 1[1298], end 1[1343] | 543 |
| TCGACAACTCTAACAACTAATCGTCAATAG ATAATGAACCTCAAATATC | 6hb_440nm, start 1[1344], end 5[1364] | 544 |
| TCTGCCAGCACGTGTTTCCTGTGTGCCGCTC AC | 6hb_440nm, start 2[62], end 3[45] | 545 |
| TGGGTAAAGGTTGGTGCCGGTGCCCCCTGC ATACCGGCGGTT | 6hb_440nm, start 2[104], end 2[63] | 546 |
| CCGGACTTGTAGAGCTTACGGCTGGAGGTG TGCGGCTCGTAA | 6hb_440nm, start 2[146], end 2[105] | 547 |
| CAAACTTAAATTAGTGATGAAGGGTAAAGT TAACGGAACGTG | 6hb_440nm, start 2[188], end 2[147] | 548 |
| CGCCAGGGTTTTCAATCGGCGAAACGTACA GAAACAGCGGAT | 6hb_440nm, start 2[230], end 2[189] | 549 |

TABLE 3-continued

Exemplary 440 nm Six-helix Bundle

| Sequence | Comment | SEQ ID NO: |
|---|---|---|
| GCCAGTTTGAGGGCCATTCGCCATTCAGGCT AAGTTGGGTAA | 6hb_440nm, start 2[272], end 2[231] | 550 |
| GCATTAAATTTTCATTAAATGTGAGCGAGTA ACCGTGCATCT | 6hb_440mn, start 2[314], end 2[273] | 551 |
| CCGGAGAGGGTAAAAACTAGCATGTCAATC TTGTTAAAATTC | 6hb_440nm, start 2[356], end 2[315] | 552 |
| TCGGTTGTACCATTAAATGCAATGCCTGAGG ATAAATTAATG | 6hb_440nm, start 2[398], end 2[357] | 553 |
| CAATTCTGCGAAGAAAAGGTGGCATCAATT CATAAAGCTAAA | 6hb_440nm, start 2[440], end 2[399] | 554 |
| TTAATTCGAGCTTTTGCGGATGGCTTAGAGA CAGTTGATTCC | 6hb_440nm, start 2[482], end 2[441] | 555 |
| ATAGTAAAATGTGAGAATGACCATAAATCA AAATATCGCGTT | 6hb_440nm, start 2[524], end 2[483] | 556 |
| AAACGAACTAACAAGGAATTACGAGGCATA CCAGAGGGGTA | 6hb_440nm, start 2[566], end 2[525] | 557 |
| AAGAACCGGATATTGGGCTTGAGATGGTTT TCTACGTTAATA | 6hb_440nm, start 2[608], end 2[567] | 558 |
| CCAAGCGCGAAAGCGCAGACGGTCAATCAT AGTAATCTTGAC | 6hb_440nm, start 2[650], end 2[609] | 559 |
| CTTTTGCGGGATGGAAGTTTCCATTAAACGC CAGCGATTATA | 6hb_440nm, start 2[692], end 2[651] | 560 |
| AGGAATTGCGAAAGGTGAATTTCTTAAACA AGTTAAAGGCCG | 6hb_440nm, start 2[734], end 2[693] | 561 |
| CCCAATAGGAACACGATCTAAAGTTTTGTC AGGAACAACTAA | 6hb_440nm, start 2[776], end 2[735] | 562 |
| AAGAGGCTGAGAGCCCGGAATAGGTGTATC AGGGATAGCAAG | 6hb_440nm, start 2[818], end 2[777] | 563 |
| ACAAACAAATAAAGTGTACTGGTAATAAGT CATGAAAGTATT | 6hb_440nm, start 2[860], end 2[819] | 564 |
| CATAGCCCCCTTAGAACCGCCACCCTCAGA GCCTTGATATTC | 6hb_440nm, start 2[902], end 2[861) | 565 |
| GAAATTATTCATAAGGCCGGAAACGTCACC GGCATTTTCGGT | 6hb_440nm, start 2[944], end 2[903] | 566 |
| GAACTGGCATGAACCACGGAATAAGTTTAT TAAATATTGACG | 6hb_440nm, start 2[986], end 2[945) | 567 |
| GAACACCCTGAAATGAAATAGCAATAGCTA GAATACCCAAAA | 6hb_440nm, start 2[1028], end 2[987] | 568 |
| GCACCCAGCTACTATCCCAATCCAAATAAG GGAGAATTAACT | 6hb_440nm, start 2[1070], end 2[1029] | 569 |
| ATTCCAAGAACGAAGCAAATCAGATATAGA AGTTGCTATTTT | 6hb_440nm, start 2[1112], end 2[1071] | 570 |
| AGGCATTTTCGATGCAGAACGCGCCTGTTTT CTTTCCTTATC | 6hb_440nm, start 2[1154], end 2[1131] | 571 |
| CTTCTGACCTAACTGTTTAGTATCATATGCT AATTTAGGCAG | 6hb_440nm, start 2[1196], end 2[1155] | 572 |
| CTTAGAATCCTTTTTAACCTCCGGCTTAGGA GTTAATTTCAT | 6hb_440nm, start 2[1238], end 2[1197] | 573 |
| GAATACCAAGTTATTACATTTAACAATTTCA ATTAATTTTCC | 6hb_440nm, start 2[1280], end 2[1239] | 574 |

TABLE 3-continued

Exemplary 440 nm Six-helix Bundle

| Sequence | Comment | SEQ ID NO: |
|---|---|---|
| TCAGATGATGGCCGTAAAACAGAAATAAAGCCTGATTGCTTT | 6hb_440nm, start 2[1322], end 2[1281] | 575 |
| TCTTTAGGAGCACGTATTAAATCCTTTGCCTATTCCTGATTA | 6hb_440nm, start 2[1364], end 2[1323] | 576 |
| AATTCCACACAAGGGCCGTTTTCACGGTCATCAGACGATCCA | 6hb_440nm, start 3[46], end 3[87] | 577 |
| GCGCAGTGTCACCCGGGTCACTGTTGCCCTCCAGCATGAGCG | 6hb_440nm, start 3[88], end 3[129] | 578 |
| GGGTCATTGCAGGCCAGAGCACATCCTCATAAACGATGCTGA | 6hb_440nm, start 3[130], end 3[171] | 579 |
| TTGCCGTTCCGGACGGAAAAAGAGACGCAGCGCCATGTTTAC | 6hb_440nm, start 3[172], end 3[213] | 580 |
| CAGTCCCGGAATATGTGCTGCAAGGCGATTGCGCAACTGTTG | 6hb_440nm, start 3[214], end 3[255] | 581 |
| GGAAGGGCGATCGTAGATGGGCGCATCGTAACAACCCGTCGG | 6hb_440nm, start 3[256], end 3[297] | 582 |
| ATTCTCCGTGGGTTGTAAACGTTAATATTATATGTACCCCGG | 6hb_440nm, start 3[298], end 3[339] | 583 |
| TTGATAATCAGAATTCAACCGTTCTAGCTTAATGTGTAGGTA | 6hb_440nm, start 3[340], end 3[381] | 584 |
| AAGATTCAAAAGGCAATAAAGCCTCAGAGCTACTAATAGTAG | 6hb_440nm, start 3[382], end 3[423] | 585 |
| TAGCATTAACATAAGTTTCATTCCATATACTTAATTGCTGAA | 6hb_440nm, start 3[424], end 3[465] | 586 |
| TATAATGCTGTAGAAGCCCGAAAGACTTCAAAATCAGGTCTT | 6hb_440um, start 3[466], end 3[507] | 587 |
| TACCCTGACTATTTGCAAAAGAAGTTTTGGTAAGAGCAACAC | 6hb_440nm, start 3[508], end 3[549] | 588 |
| TATCATAACCCTGACGTTGGGAAGAAAAAAATTTCAACTTTA | 6hb_440nm, start 3[550], end 3[591] | 589 |
| ATCATTGTGAATGGCTGACCTTCATCAAGAAGGGAACCGAAC | 6hb_440nm, start 3[592], end 3[633] | 590 |
| TGACCAACTTTGACACTCATCTTTGACCCGGTAAAATACGTA | 6hb_440nm, start 3[634], end 3[675] | 591 |
| ATGCCACTACGACGCTGAGGCTTGCAGGGGCTTGATACCGAT | 6hb_440nm, start 3[676], end 3[717] | 592 |
| AGTTGCGCCGACGCGGAGTGAGAATAGAAGTCTTTCCAGACG | 6hb_440nm, start 3[718], end 3[759] | 593 |
| TTAGTAAATGAACCACCACCCTCATTTTCACCGTACTCAGGA | 6hb_440nm, start 3[760], end 3[801] | 594 |
| GGTTTAGTACCGAACCTATTATTCTGAAATTTAACGGGGTCA | 6hb_440nm, start 3[802], end 3[843] | 595 |
| GTGCCTTGAGTAGGCAGGTCAGACGATTGGCCACCACCCTCA | 6hb_440nm, start 3[844], end 3[885] | 596 |
| GAGCCGCCACCATGTAGCGCGTTTTCATCAATGAAACCATCG | 6hb_440nm, start 3[886], end 3[927) | 597 |
| ATAGCAGCACCGGATTGAGGGAGGGAAGGTTTGTCACAATCA | 6hb_440nm, start 3[928], end 3[969] | 598 |

TABLE 3-continued

Exemplary 440 nm Six-helix Bundle

| Sequence | Comment | SEQ ID NO: |
|---|---|---|
| ATAGAAAATTCAGAAACGCAATAATAACGTCTTACCGAAGCC | 6hb_440nm, start 3[970], end 3[1011] | 599 |
| CTTTTTAAGAAAGGGAAGCGCATTAGACGAAACGATTTTTTG | 6hb_440nm, start 3[1012], end 31053] | 600 |
| TTTAACGTCAAAAGCCTTAAATCAAGATTAGGCTTATCCGGT | 6hb_440nm, start 3[1054], end 3[1095] | 601 |
| ATTCTAAGAACGCAATCAATAATCGGCTGATCAACAATAGAT | 6hb_440nm, start 3[1096], end 3[1137] | 602 |
| AAGTCCTGAACATTAACAACGCCAACATGGTTATACAAATTC | 6hb_440nm, start 3[1138], end 3[1179] | 603 |
| TTACCAGTATAATTTTTCAAATATATTTTTTGGGTTATATAA | 6hb_440nm, start 3[1180], end 3[1221] | 604 |
| CTATATGTAAATTGTAAATCGTCGCTATTATTTGAATTACCT | 6hb_440nm, start 3[1222], end 3[1263] | 605 |
| TTTTAATGGAAAAACAATAACGGATTCGAAATTGCGTAGAT | 6hb_440nm, start 3[1264], end 3[1305] | 606 |
| TTTCAGGTTTAAGAGCGGAATTATCATCACGAACGTTATTAA | 6hb_440nm, start 3[1306], end 3[1347] | 607 |
| TTTTAAAAGTTTAAAGGAATTGAGTAAAATA | 6hb_440nm, start 3[1348], end 2[1365] | 608 |
| CGGAAGCATAAAGTGTAATTGAGGATCCCCGG | 6hb_440nm, start 4[48], end 0[35] | 609 |
| GTGCACTCTGTGGTCTCACATTAATTGCTTCAGCAAATCGTT | 6hb_440nm, start 4[90], end 0[77] | 610 |
| CACTCAATCCGCCGGGAAACCTGTCGTGGCAAGAATGCCAAC | 6hb_440nm, start 4[132], end 0[119] | 611 |
| TCCGTTTTTCGTCGCGGGGAGAGGCGGACATCGACATAAAA | 6hb_440nm, start 4[174], end 0[161] | 612 |
| ATAGACTTTCTCCGTCTTTTCACCAGTGAGCTTTCAGAGGTG | 6hb_440nm, start 4[216], end 0[203] | 613 |
| CTCTTCGCTATTACCGCCTGGCCCTGAGCCAGCCAGCTTTCC | 6hb_440nm, start 4[258], end 0[245] | 614 |
| CGGATTGACCGTAATTGCCCCAGCAGGCCATCAAAAATAATT | 6hb_440nm, start 4[300], end 0[287] | 615 |
| AAAACAGGAAGATTATCGGCAAAATCCCTTGCCTGAGAGTCT | 6hb_440nm, start 4[342], end 0[329] | 616 |
| GGCCGGAGACAGTCGGGTTGAGTGTTGTGCCTTTATTTCAAC | 6hb_440nm, start 4[384], end 0[371] | 617 |
| CATACAGGCAAGGCAAGAACGTGGACTCAAATGGTCAATAAC | 6hb_440nm, start 4[426], end 0[413] | 618 |
| GTTTTAAATATGCACAGGGCGATGGCCCTCAGGATTAGAGAG | 6hb_440nm, start 4[468], end 0[455] | 619 |
| AAGCAAAGCGGATTTTTTTGGGGTCGAGTAAATATTCATTGA | 6hb_440nm, start 4[510], end 0[497] | 620 |
| GACGACGATAAAAAAAAGGGAGCCCCCGTGAGATTTAGGAAT | 6hb_440nm, start 4[552], end 0[539] | 621 |
| CGATTTTAAGAACTAACGTGGCGAGAAACAGTGAATAAGGCT | 6hb_440nm, start 4[594], end 0[581] | 622 |

TABLE 3-continued

Exemplary 440 nm Six-helix Bundle

| Sequence | Comment | SEQ ID NO: |
| --- | --- | --- |
| AGATGAACGGTGTAGCTAGGGCGCTGGCAT TGTGTCGAAATC | 6hb_440nm, start 4[636], end 0[623] | 623 |
| CCTAAAACGAAAGAACCACACCCGCCGCGG GTAGCAACGGCT | 6hb_440nm, start 4[678], end 0[665] | 624 |
| AACCATCGCCCACGTATGGTTGCTTTGAGGC TCCAAAAGGAG | 6hb_440nm, start 4[720], end 0[707] | 625 |
| TGGGATTTTGCTAAAGAATCAGAGCGGGAA CTACAACGCCTG | 6hb_440nm, start 4[762], end 0[749] | 626 |
| GAACCGCCACCCTCTTTAGACAGGAACGCT CAGTACCAGGCG | 6hb_440nm, start 4[804], end 0[791] | 627 |
| GTATAAACAGTTAAATAATCAGTGAGGCGA ATTTACCGTTCC | 6hb_440nm, start 4[846], end 0[833] | 628 |
| CCAGAGCCGCCGCCCAAATTAACCGTTGGG AACCAGAGCCAC | 6hb_440nm, start 4[888], end 0[875] | 629 |
| GCGACAGAATCAAGATCACTTGCCTGAGTT GGGAATTAGAGC | 6hb_440nm, start 4[930], end 0[917] | 630 |
| CCAGCGCCAAAGACGGTAATATCCAGAAAG AAAATACATACA | 6hb_440nm, start 4[972], end 0[959] | 631 |
| ATAGCCGAACAAAGAAAAACGCTCATGGGA TAACCCACAAGA | 6hb_440nm, start 4[1014], end 0[1001] | 632 |
| AGCAGCCTTTACAGCTGAAATGGATTATCTT TCCAGAGCCTA | 6hb_440nm, start 4[1056], end 0[1043] | 633 |
| TTAGCGAACCTCCCACCAGTAATAAAAGCA AGCCGTTTTTAT | 6hb_440nm, start 4[1098], end 0[1085] | 634 |
| ATATCCCATCCTAACTTCTGACCTGAAATAA AGTAATTCTGT | 6hb_440nm, start 4[1140], end 0[1127] | 635 |
| TCAACAGTAGGGCTTTTTGAATGGCTATAGG CGTTAAATAAG | 6hb_440nm, start 4[1182], end 0[1169] | 636 |
| AATCCAATCGCAAGTAAAACATCGCCATAG AGTCAATAGTGA | 6hb_440nm, start 4[1224], end 0[1211] | 637 |
| AAATCAATATATGTAGATAAAACAGAGGAC CTGAGCAAAAGA | 6hb_440nm, start 4[1266], end 0[1253] | 638 |
| AATATACAGTAACAAACAGTGCCACGCTTT CTGAATAATGGA | 6hb_440nm, start 4[1308], end 0[1295] | 639 |
| TATCATTTTGCGGAAGCATCACCTTGCTACA TTTGAGGATTT | 6hb_440nm, start 4[1350], end 0[1337] | 640 |
| AATGAGTGAGCTAAGCTGCGGCCAGAATGC GGCCATACGAGG | 6hb_440nm, start 5[63], end 4[49] | 641 |
| CCGCTTTCCAGTCGGGCGCGGTTGCGGTATG AGTGCCCGCCT | 6hb_440nm, start 5[105], end 4[91] | 642 |
| GAATCGGCCAACGCTCGTCGCTGGCAGCCT CCGGCGCTTTCG | 6hb_440nm, start 5[147], end 4[133] | 643 |
| GCCAGGGTGGTTTTTGGTGAAGGGATAGCT CTCCAAACGCGG | 6hb_440nm, start 5[189], end 4[175] | 644 |
| TGATTGCCCTTCACGCCAGCTGGCGAAAGG GGGTTGTGAGAG | 6hb_440nm, start 5[231], end 4[217] | 645 |
| CGGTCCACGCTGGTTGGGATAGGTCACGTT GGTGGTGCGGGC | 6hb_440nm, start 5[273], end 4[259] | 646 |

TABLE 3-continued

Exemplary 440 nm Six-helix Bundle

| Sequence | Comment | SEQ ID NO: |
|---|---|---|
| ATGGTGGTTCCGAAGTATAAGCAAATATTT AAAAACAAACGG | 6hb_440nm, start 5[315], end 4[301] | 647 |
| AATAGCCCGAGATAAAATCACCATCAATAT GATAAAGCCCCA | 6hb_440nm, start 5[357], end 4[343] | 648 |
| AGAGTCCACTATTAAAAGAATTAGCAAAT TAAGGTGAGAAA | 6hb_440nm, start 5[399], end 4[385] | 649 |
| GAAAAACCGTCTATACTAAAGTACGGTGTC TGGCCAATAAAT | 6hb_440nm, start 5[441], end 4[427] | 650 |
| CACCCAAATCAAGTGCATCAAAAAGATTAA GAGGCTAACAT | 6hb_440nm, start 5[483], end 4[469] | 651 |
| TAAATCGGAACCCTCCAAAATAGCGAGAGG CTTTATAGTCAG | 6hb_440nm, start 5[525], end 4[511] | 652 |
| GGGGAAAGCCGGCGGGCTCATTATACCAGT CAGCGTTTACCA | 6hb_440nm, start 5[567], end 4[553] | 653 |
| CGAAAGGAGCGGGCCAGACCAGGCGCATA GGCTTACCTTATG | 6hb_440nm, start 5[609], end 4[595] | 654 |
| CGCTGCGCGTAACCGGCAAAAGAATACACT AAAAAAGAGGAC | 6hb_440nm, start 5[651], end 4[637] | 655 |
| TACAGGGCGCGTACCATAACCGATATATTC GGTAGGCACCAA | 6hb_440nm, start 5[693], end 4[679] | 656 |
| GTGCTTTCCTCGTTACAACTTTCAACAGTTT CAAATGACAAC | 6hb_440nm, start 5[735], end 4[721] | 657 |
| CCGATTAAAGGGATAGAACCGCCACCCTCA GAGTTTTCTGTA | 6hb_440nm, start 5[777], end 4[763] | 658 |
| TGAGAAGTGTTTTTGCCCCCTGCCTATTTC GGCCACCCTCA | 6hb_440nm, start 5[819], end 4[805] | 659 |
| GTCTGTCCATCACGAGCATTGACAGGAGGT TGAACAGTGCCC | 6hb_440nm, start 5[861], end 4[847] | 660 |
| TGATTAGTAATAACTTTGCCTTTAGCGTCAG ACGAACCACCA | 6hb_440nm, start 5[903], end 4[889] | 661 |
| CTATCGGCCTTGCTAAAAGGGCGACATTCA ACCTAATCAGTA | 6hb_440nm, start 5[945], end 4[931] | 662 |
| GCCATTGCAACAGGTTACCAGAAGGAAACC GAGTATGGTTTA | 6hb_440nm, start 5[987], end 4[973] | 663 |
| TGACGCTCAATCGTAGAGAATAACATAAAA ACAAGTAAGCAG | 6hb_440nm, start 5[1029], end 4[1015] | 664 |
| TCACCAGTCACACGGACTTGCGGGAGGTTT TGAAATGAAAAT | 6hb_440nm, start 5[1071], end 4[1057] | 665 |
| ACAGAGATAGAACCTTTACGAGCATGTAGA AACCGAGGCGTT | 6hb_440nm, start 5[1113], end 4[1099] | 666 |
| GGCACAGACAATATTAATTGAGAATCGCCA TATAGAAAATA | 6hb_440nm, start 5[1155], end 4[1141] | 667 |
| CGAACTGATAGCCCACAAAGAACGCGAGAA AACAGCCAACGC | 6hb_440nm, start 5[1197], end 4[1183] | 668 |
| GAACCACCAGCAGAGAGTGAATAACCTTGC TTCGCTGATGCA | 6hb_440nm, start 5[1239], end 4[1225) | 669 |
| TTAACACCGCCTGCGTACCTTTTACATCGGG AGACAGTACAT | 6hb_440nm, start 5[1281], end 4[1267] | 670 |

TABLE 3-continued

Exemplary 440 nm Six-helix Bundle

| Sequence | Comment | SEQ ID NO: |
|---|---|---|
| AATGAAAAATCTAAACAAAGAAACCACCAG AAGCGTCAGATG | 6hb_440nm, start 5[1323], end 4[1309] | 671 |
| AAACCCTCAATCAAGTTGGCAAATCAACAG TTGGAGTAACAT | 6hb_440nm, start 5[1365], end 4[1351] | 672 |
| CGCTGGTTGGGATAGGTCACGTTGGTGGTG CGGGC | 6hb_440nm, 7 bp socket end distal to queen, start 5[280], end 4[259) | 673 |
| TTCCGAAGTATAAGCAAATATTTAAAAACA AACGG | 6hb_440nm, 7 bp socket end distal to queen, start 5[322], end 41301) | 674 |
| CGAGATAAAATCACCATCAATATGATAAAG CCCCA | 6hb_440nm, 7 bp socket end distal to queen, start 5[364], end 4[343] | 675 |
| ACTATTAAAAGAATTAGCAAAATTAAGGTG AGAAA | 6hb_440nm, 7 bp socket end distal to queen, start 5[406], end 4[385] | 676 |
| CGTCTATACTAAAGTACGGTGTCTGGCCAAT AAAT | 6hb_440nm, 7 bp socket end distal to queen, start 5[448],end4[427] | 677 |
| TGGTTGGGATAGGTCACGTTGGTGGTGCGG GC | 6hb_440nm, 10 bp socket end distal to queen, start 5[283], end 4[259] | 678 |
| CGAAGTATAAGCAAATATTTAAAAACAAAC GG | 6hb_440nm, 10 bp socket end distal to queen, start 5[325],end4[301] | 679 |
| GATAAAATCACCATCAATATGATAAAGCCC CA | 6hb_440nm, 10 bp socket end distal to queen, start 5[367], end 4[343] | 680 |
| ATTAAAAGAATTAGCAAAATTAAGGTGAGA AA | 6hb_440nm, 10 bp socket end distal to queen, start 5[409], end 4[385] | 681 |
| CTATACTAAAGTACGGTGTCTGGCCAATAA AT | 6hb_440nm, 10 bp socket end distal to queen, start 5[451],end 4[427] | 682 |

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A crisscross nucleic acid nanostructure, comprising:
   (a) a first plurality of deoxyribonucleic acid (DNA) nanorods aligned parallel to each other; and
   (b) a second plurality of DNA nanorods aligned parallel to each other,
   wherein the DNA nanorods of the first plurality are bound to and perpendicular to the DNA nanorods of the second plurality, a single DNA nanorod of (b) binds to multiple DNA nanorods of (a), each through a single cooperative binding site, and single DNA nanorod of (a) binds to multiple DNA nanorods of (b), each through a single cooperative binding site.

2. The crisscross nucleic acid nanostructure of claim 1, wherein the DNA nanorods of the first plurality have a length of 10-500 nm and/or the DNA nanorods of the second plurality have a length of 10-500 nm.

3. The crisscross nucleic acid nanostructure of claim 1, wherein the DNA nanorods of the first plurality comprise a 6-helix DNA bundle and/or the DNA nanorods of the second plurality comprise a 6-helix DNA bundle.

4. The crisscross nucleic acid nanostructure of claim 1, wherein the first plurality comprises at least 4 DNA nanorods and/or the second plurality comprises at least 4 DNA nanorods.

5. The crisscross nucleic acid nanostructure of claim 1, wherein the first plurality comprises at least 10 DNA nanorods and/or the second plurality comprises at least 10 DNA nanorods.

6. The crisscross nucleic acid nanostructure of claim 1, wherein the first plurality comprises at least 25 DNA nanorods and/or the second plurality comprises at least 25 DNA nanorods.

7. The crisscross nucleic acid nanostructure of claim 1, wherein the first plurality comprises at least 50 DNA nanorods and/or the second plurality comprises at least 50 DNA nanorods.

8. The crisscross nucleic acid nanostructure of claim 1, wherein the cooperative binding site has a length of 5-50 nucleotides.

9. The crisscross nucleic acid nanostructure of claim 1, wherein the nanostructure comprises 3-1000 cooperative binding sites.

10. The crisscross nucleic acid nanostructure of claim 9, wherein the distance between each of the cooperative binding sites is 20-1000 angstroms.

11. A crisscross nucleic acid slat, comprising:
a first plurality of at least four DNA strands parallel to each other, each strand of the first plurality having a length of at least 21 nucleotides; and
a second plurality of at least four DNA strands parallel to each, each strand of the second plurality having a length of at least 21 nucleotides, wherein the at least four DNA strands of the first plurality are bound to and perpendicular to the at least four DNA strands of the second plurality.

* * * * *

UNITED STATES PATENT AND TRADEMARK OFFICE
CERTIFICATE OF CORRECTION

| | |
|---|---|
| PATENT NO. | : 12,351,862 B2 |
| APPLICATION NO. | : 17/576550 |
| DATED | : July 8, 2025 |
| INVENTOR(S) | : Dionis Minev et al. |

Page 1 of 1

It is certified that error appears in the above-identified patent and that said Letters Patent is hereby corrected as shown below:

In the Specification

At Column 1, Lines 15-18, please change the paragraph:
"This invention was made with government support under 1435964 awarded by the Office of Naval Research. The government has certain rights in the invention."

To:
--This invention was made with government support under 1435964 awarded by National Science Foundation (NSF). The government has certain rights in the invention.--

Signed and Sealed this
Ninth Day of September, 2025

Coke Morgan Stewart
*Acting Director of the United States Patent and Trademark Office*

SEQUENCE LISTING

<160> NUMBER OF SEQ ID NOS: 688

<210> SEQ ID NO 1
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 1
atctgaactc gctacggcgg ggggagcccc cgatttagag ct                     42

<210> SEQ ID NO 2

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 2
cattgctgat accgtttagc taacaaacat caagaaaaca aa                          42

<210> SEQ ID NO 3
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 3
gatacttgcc ctctctgtac ataattaatt ttcccttaga at                          42

<210> SEQ ID NO 4
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 4
gattgggcgt tatcaatgtt gttttgtcac aatcaataga aa                          42

<210> SEQ ID NO 5
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 5
tctaatgaag acaaatcccc acgtcaccga cttgagccat tt                          42

<210> SEQ ID NO 6
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 6
aaacatcggg ttgagtatta tgtggcgaga aaggaaggga ag                          42

<210> SEQ ID NO 7
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 7
cgctggcatt cgcatcaaag gcgaattatt catttcaatt ac                          42

<210> SEQ ID NO 8
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 8
agtttataaa tgagtatcaa tttagattaa gacgctgaga ag                              42

<210> SEQ ID NO 9
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 9
tatcgacatc attacgcatc gcaacatata aagaaacgc aa                               42

<210> SEQ ID NO 10
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 10
ccatgcagac atcacgaagg tcaccagtag caccattacc at                              42

<210> SEQ ID NO 11
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 11
aagataacgc ttgtgaaaat gagggcgctg gcaagtgtag cg                              42

<210> SEQ ID NO 12
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 12
gctaacagta gggaaactgc ggcctgattg ctttgaatac ca                              42

<210> SEQ ID NO 13
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 13
atgggttcag gatgcaggtg aaatcatagg tctgagagac ta                              42

<210> SEQ ID NO 14
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 14
ctcggatggg agtaagcgta tgcagtatgt tagcaaacgt ag                              42

<210> SEQ ID NO 15

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 15
agagtttctg cggcagttaa tcaatgaaac catcgatagc ag                          42

<210> SEQ ID NO 16
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 16
gcaatacatc aaacgccgcg aacacccgcc gcgcttaatg cg                          42

<210> SEQ ID NO 17
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 17
tcaggcactg cgtgaagcgg cagtaacagt acctttaca tc                           42

<210> SEQ ID NO 18
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 18
atcaaaactc aacgagcagc ggttgggtta tataactata tg                          42

<210> SEQ ID NO 19
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 19
agggttgtcg gacttgtgca aggaataccc aaaagaactg gc                          42

<210> SEQ ID NO 20
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 20
agtccgtgaa gacggaaacc aaatcaagtt tgcctttagc gt                          42

<210> SEQ ID NO 21
<211> LENGTH: 42
<212> TYPE: DNA
<213> ORGANISM: Artificial Sequence
<220> FEATURE:
<223> OTHER INFORMATION: Synthetic Polynucleotide

```
<400> SEQUENCE: 21
ctggggattt gacgcagacc tggttgcttt gacgagcacg ta                    42

<210> SEQ ID NO 22
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 22
ttttcccagt cacgacgttg tgaaattgcg tagattttca gg                    42

<210> SEQ ID NO 23
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 23
ttatcagtaa acagagaggt ttcgcaagac aaagaacgcg ag                    42

<210> SEQ ID NO 24
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 24
tcagggatta atgaaagatg gaacaaagtt accagaagga aa                    42

<210> SEQ ID NO 25
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 25
agtgtggcga tccgatagat gcggcatttt cggtcatagc cc                    42

<210> SEQ ID NO 26
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 26
gggggatgtg ctgcaaggcg aatcagagcg ggagctaaac ag                    42

<210> SEQ ID NO 27
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 27
agccagcttt ccggcaccgc tacctaccat atcaaaatta tt                    42

<210> SEQ ID NO 28
```

<210> SEQ ID NO 28
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 28
ctttattatt cgcattcacc ctagttaatt tcatcttctg ac        42

<210> SEQ ID NO 29
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 29
ttggtgtaga tgggcgcatc gatcttaccg aagccctttt ta        42

<210> SEQ ID NO 30
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 30
cagaaataga agaattacag ctttcataat caaaatcacc gg        42

<210> SEQ ID NO 31
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 31
aagcgccatt cgccattcag gagacaggaa cggtacgcca ga        42

<210> SEQ ID NO 32
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 32
tcagaaaagc cccaaaaaca gctgattgtt tggattatac tt        42

<210> SEQ ID NO 33
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 33
gaggggacga cgacagtatc gaccgaccgt gtgataaata ag        42

<210> SEQ ID NO 34
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 34
tttttgttaa atcagctcat tagcccaata ataagagcaa ga                42

<210> SEQ ID NO 35
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 35
gtgggaacaa acggcggatt gcgcctccct cagagccgcc ac                42

<210> SEQ ID NO 36
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 36
tcgtaaaact agcatgtcaa tatcagtgag gccaccgagt aa                42

<210> SEQ ID NO 37
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 37
atgatattca accgttctag catattcctg attatcagat ga                42

<210> SEQ ID NO 38
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 38
ttaaattgta aacgttaata tcggaatcat aattactaga aa                42

<210> SEQ ID NO 39
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 39
tattttaaat gcaatgcctg atgagcgcta atatcagaga ga                42

<210> SEQ ID NO 40
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 40
tcaaaaataa ttcgcgtctg gagccaccac cctcagagcc gc                42

<210> SEQ ID NO 41

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 41
ggtagctatt tttgagagat cattaaccgt tgtagcaata ct                            42

<210> SEQ ID NO 42
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 42
atggtcaata acctgtttag cttgcggaac aaagaaacca cc                            42

<210> SEQ ID NO 43
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 43
aaaagggtga gaaaggccgg acgttataca aattcttacc ag                            42

<210> SEQ ID NO 44
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 44
aacatccaat aaatcataca ggggagaatt aactgaacac cc                            42

<210> SEQ ID NO 45
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 45
ctttatttca acgcaaggat acgccgccag cattgacagg ag                            42

<210> SEQ ID NO 46
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 46
cgaacgagta gatttagttt gacttgcctg agtagaagaa ct                            42

<210> SEQ ID NO 47
<211> LENGTH: 42
<212> TYPE: DNA
<213> ORGANISM: Artificial Sequence
<220> FEATURE:
<223> OTHER INFORMATION: Synthetic Polynucleotide
```

```
<400> SEQUENCE: 47 cattttttgcg gatggcttag accgaacgtt attaatttta aa                             42

<210> SEQ ID NO 48
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 48
agctgaaaag gtggcatcaa ttagggctta attgagaatc gc                             42

<210> SEQ ID NO 49
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 49
agcttcaaag cgaaccagac ctttacagag agaataacat aa                             42

<210> SEQ ID NO 50
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 50
attaagcaat aaagcctcag aggccttgat attcacaaac aa                             42

<210> SEQ ID NO 51
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 51
ctgtagctca acatgtttta aaatatccag aacaatatta cc                             42

<210> SEQ ID NO 52
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 52
ggcttttgca aagaagttt tagactttac aaacaattcg ac                              42

<210> SEQ ID NO 53
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 53
aggattagag agtacccttta agtaatttag gcagaggcat tt                            42

<210> SEQ ID NO 54
```

-continued

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 54
aatattcatt gaatccccct cgaaacgatt ttttgtttaa cg                    42

<210> SEQ ID NO 55
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 55
aagaggaagc ccgaaagact taatggaaag cgcagtctct ga                    42

<210> SEQ ID NO 56
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 56
accctcgttt accagacgac gaacgctcat ggaaatacct ac                    42

<210> SEQ ID NO 57
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 57
taacggaaca acattattac aagagccgtc aatagataat ac                    42

<210> SEQ ID NO 58
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 58
atgtttagac tggatagcgt cataaagtac cgacaaaagg ta                    42

<210> SEQ ID NO 59
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 59
tgaattacct tatgcgattt tttacaaaat aaacagccat at                    42

<210> SEQ ID NO 60
<211> LENGTH: 42
<212> TYPE: DNA
<213> ORGANISM: Artificial Sequence
<220> FEATURE:
<223> OTHER INFORMATION: Synthetic Polynucleotide
```

```
<400> SEQUENCE: 60
aaacgagaat gaccataaat ccatacatgg cttttgatga ta                      42

<210> SEQ ID NO 61
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 61
agatttagga ataccacatt caaatggatt atttacattg gc                      42

<210> SEQ ID NO 62
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 62
cgaggcgcag acggtcaatc agttatctaa aatatcttta gg                      42

<210> SEQ ID NO 63
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 63
gtcaggacgt tgggaagaaa agacaataaa caacatgttc ag                      42

<210> SEQ ID NO 64
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 64
aggctggctg accttcatca ataccaacgc taacgagcgt ct                      42

<210> SEQ ID NO 65
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 65
taaattgggc ttgagatggt tttttaacgg ggtcagtgcc tt                      42

<210> SEQ ID NO 66
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 66
tgtgtcgaaa tccgcgacct gagtaataaa agggacattc tg                      42

<210> SEQ ID NO 67
```

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 67
tacgaaggca ccaacctaaa actggtcagt tggcaaatca ac                          42

<210> SEQ ID NO 68
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 68
ctttgaaaga ggacagatga atatcaacaa tagataagtc ct                          42

<210> SEQ ID NO 69
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 69
gtagcaacgg ctacagaggc ttagttgcta ttttgcaccc ag                          42

<210> SEQ ID NO 70
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 70
gatattcatt acccaaatca acagttaatg ccccctgcct at                          42

<210> SEQ ID NO 71
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 71
ctaaaacact catctttgac cctgacctga aagcgtaaga at                          42

<210> SEQ ID NO 72
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 72
cgaataataa tttttcacg tatcaccttg ctgaacctca aa                           42

<210> SEQ ID NO 73
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 73
atgaggaagt tccattaaa catcctaatt tacgagcatg ta                              42

<210> SEQ ID NO 74
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 74
ttcgaggtga atttcttaaa cacctcccga cttgcgggag gt                              42

<210> SEQ ID NO 75
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 75
ggatcgtcac cctcagcagc gacatgaaag tattaagagg ct                              42

<210> SEQ ID NO 76
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 76
tttcagcgga gtgagaatag atgaatggct attagtcttt aa                              42

<210> SEQ ID NO 77
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 77
ctacaacgcc tgtagcattc cagtgccacg ctgagagcca gc                              42

<210> SEQ ID NO 78
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 78
ctccaaaagg agcctttaat tgtctttcct tatcattcca ag                              42

<210> SEQ ID NO 79
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 79
cagagccacc accctcattt taaggcttat ccggtattct aa                              42

<210> SEQ ID NO 80

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 80
ccgacaatga caacaaccat ctaggattag cggggttttg ct                    42

<210> SEQ ID NO 81
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 81
tcgtaaaact agcatgtcaa tatcagtgag gccaccgagt aagaaaaac             49

<210> SEQ ID NO 82
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 82
atgatattca accgttctag catattcctg attatcagat gaagagtcc             49

<210> SEQ ID NO 83
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 83
ttaaattgta aacgttaata tcggaatcat aattactaga aaaatagcc             49

<210> SEQ ID NO 84
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 84
tattttaaat gcaatgcctg atgagcgcta atatcagaga gaatggtgg             49

<210> SEQ ID NO 85
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 85
tcaaaaataa ttcgcgtctg gagccaccac cctcagagcc gccggtcca             49

<210> SEQ ID NO 86
<211> LENGTH: 49
<212> TYPE: DNA
<213> ORGANISM: Artificial Sequence
<220> FEATURE:
<223> OTHER INFORMATION: Synthetic Polynucleotide
```

<400> SEQUENCE: 86
ggtagctatt tttgagagat cattaaccgt tgtagcaata ctcggtcca                49

<210> SEQ ID NO 87
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 87
atggtcaata acctgtttag cttgcggaac aaagaaacca ccatggtgg                49

<210> SEQ ID NO 88
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 88
aaaagggtga gaaaggccgg acgttataca aattcttacc agaatagcc                49

<210> SEQ ID NO 89
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 89
aacatccaat aaatcataca ggggagaatt aactgaacac ccagagtcc                49

<210> SEQ ID NO 90
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 90
ctttatttca acgcaaggat acgccgccag cattgacagg aggaaaaac                49

<210> SEQ ID NO 91
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 91
tcgtaaaact agcatgtcaa tatcagtgag gccaccgagt aagaaaaacc gt             52

<210> SEQ ID NO 92
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 92
atgatattca accgttctag catattcctg attatcagat gaagagtcca ct             52

<210> SEQ ID NO 93

```
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 93
ttaaattgta aacgttaata tcggaatcat aattactaga aaaatagccc ga          52

<210> SEQ ID NO 94
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 94
tattttaaat gcaatgcctg atgagcgcta atatcagaga gaatggtggt tc          52

<210> SEQ ID NO 95
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 95
tcaaaaataa ttcgcgtctg gagccaccac cctcagagcc gccggtccac gc          52

<210> SEQ ID NO 96
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 96
ggtagctatt tttgagagat cattaaccgt tgtagcaata ctcggtccac gc          52

<210> SEQ ID NO 97
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 97
atggtcaata acctgtttag cttgcggaac aaagaaacca ccatggtggt tc          52

<210> SEQ ID NO 98
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 98
aaaagggtga gaaaggccgg acgttataca aattcttacc agaatagccc ga          52

<210> SEQ ID NO 99
<211> LENGTH: 52
<212> TYPE: DNA
<213> ORGANISM: Artificial Sequence
<220> FEATURE:
<223> OTHER INFORMATION: Synthetic Polynucleotide
```

<400> SEQUENCE: 99
aacatccaat aaatcataca ggggagaatt aactgaacac ccagagtcca ct                    52

<210> SEQ ID NO 100
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 100
ctttatttca acgcaaggat acgccgccag cattgacagg aggaaaaacc gt                    52

<210> SEQ ID NO 101
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 101
caatattaca taacaatcct ccatttgaat tacctttttt aa                               42

<210> SEQ ID NO 102
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 102
actgataccg tgcaaaatta tcaaagacaa aagggcgaca tt                               42

<210> SEQ ID NO 103
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 103
cgtaacgatc taaagttttg taacatcgcc attaaaaata cc                               42

<210> SEQ ID NO 104
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 104
gaacccatgt accgtaacac tcgcactcat cgagaacaag ca                               42

<210> SEQ ID NO 105
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 105
taccgccacc ctcagaaccg ccgtcgagag ggttgatata ag                               42

<210> SEQ ID NO 106

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 106
tcattaaagg tgaattatca cttctgcaat gtgcgagaaa tg                    42

<210> SEQ ID NO 107
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 107
gggaattaga gccagcaaaa tgtttatgta gatgaaggta ta                    42

<210> SEQ ID NO 108
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 108
caccgtaatc agtagcgaca ggtttcttgt tgttcgccat cc                    42

<210> SEQ ID NO 109
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 109
ccttattagc gtttgccatc tgcaacacag caataaaaat gc                    42

<210> SEQ ID NO 110
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 110
cctcagaacc gccaccctca gccttcctgt agccagcttt ca                    42

<210> SEQ ID NO 111
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 111
gttgaggcag gtcagacgat tgcataaagc taaatcggtt gt                    42

<210> SEQ ID NO 112
<211> LENGTH: 42
<212> TYPE: DNA
<213> ORGANISM: Artificial Sequence
<220> FEATURE:
<223> OTHER INFORMATION: Synthetic Polynucleotide
```

```
<400> SEQUENCE: 112
atttaccgtt ccagtaagcg taaaaatcag gtctttaccc tg                         42

<210> SEQ ID NO 113
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 113
gagtaacagt gcccgtataa acgtaacaaa gctgctcatt ca                         42

<210> SEQ ID NO 114
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 114
gagactcctc aagagaagga tgcccacgca taaccgatat at                         42

<210> SEQ ID NO 115
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 115
tagcaagcaa atcagatata gcagggatag caagcccaat ag                         42

<210> SEQ ID NO 116
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 116
gcttctgtaa atcgtcgcta taaacatata gatgattaaa cc                         42

<210> SEQ ID NO 117
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 117
agtattaaca ccgcctgcaa cacagacagc cctcatagtt ag                         42

<210> SEQ ID NO 118
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 118
gcactaaatc ggaaccctaa attttgtttt atggagatga ta                         42

<210> SEQ ID NO 119
```

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 119
aaagcgaaag gagcgggcgc tctgaatttc gcgtcgtctt ca                              42

<210> SEQ ID NO 120
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 120
ccgctacagg gcgcgtacta ttttccatga attggtaaca cc                              42

<210> SEQ ID NO 121
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 121
gaggccgatt aaagggattt tctgcgcaac tgttgggaag gg                              42

<210> SEQ ID NO 122
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 122
aagagtctgt ccatcacgca atacaaaggc tatcaggtca tt                              42

<210> SEQ ID NO 123
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 123
caaactatcg gccttgctgg tatatgcaac taaagtacgg tg                              42

<210> SEQ ID NO 124
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 124
attttgacgc tcaatcgtct gaactaatgc agatacataa cg                              42

<210> SEQ ID NO 125
<211> LENGTH: 42
<212> TYPE: DNA
<213> ORGANISM: Artificial Sequence
<220> FEATURE:
<223> OTHER INFORMATION: Synthetic Polynucleotide
```

-continued

<400> SEQUENCE: 125
gccaacagag atagaaccct tcccagcgat tataccaagc gc        42

<210> SEQ ID NO 126
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 126
tgcgcgaact gatagcccta acgtctttcc agacgttagt aa        42

<210> SEQ ID NO 127
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 127
caaagggcga aaaccaaca gctgattgcc ctgcgccagg        40

<210> SEQ ID NO 128
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 128
agtccactat taaagaagag agttgcagca agcaacgcgc        40

<210> SEQ ID NO 129
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 129
tagggttgag tgttgtgccc cagcaggcga aaacctgtcg        40

<210> SEQ ID NO 130
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 130
aatcccttat aaatcagttc cgaaatcggc aa        32

<210> SEQ ID NO 131
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 131
gtgagacggg cgtctatca        19

<210> SEQ ID NO 132

```
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 132
gtggtttttg tttcctgtgt gaaa                                         24

<210> SEQ ID NO 133
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 133
cgtattggtc accgcctggc cctgacgtgg actccaacgt                        40

<210> SEQ ID NO 134
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 134
ggggagagat tccacacaac atac                                         24

<210> SEQ ID NO 135
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 135
gaatcggccg gtccacgctg gttttccagt ttggaacaag                        40

<210> SEQ ID NO 136
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 136
tgccagctgt gtaaagcctg gggt                                         24

<210> SEQ ID NO 137
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 137
gtcgggaaat cctgtttgat ggtgaaagaa tagcccgaga                        40

<210> SEQ ID NO 138
<211> LENGTH: 32
<212> TYPE: DNA
<213> ORGANISM: Artificial Sequence
<220> FEATURE:
<223> OTHER INFORMATION: Synthetic Polynucleotide
```

```
<400> SEQUENCE: 138
gttgcgctca ctgcccaact cacattaatt gc                                32

<210> SEQ ID NO 139
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 139
gtcatagctc ttttcacca                                               19

<210> SEQ ID NO 140
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 140
ttgttatccg ctcacagcgg tttg                                         24

<210> SEQ ID NO 141
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 141
gagccggaag cataaagcat taat                                         24

<210> SEQ ID NO 142
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 142
gcctaatgag tgagctgctt tcca                                         24

<210> SEQ ID NO 143
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 143
aaaatacata cataaaggtg gctattacgg ggttggaggt ca                     42

<210> SEQ ID NO 144
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 144
tagcaaggcc ggaaacgtca ccgaacaaga cccgttagta ac                     42

<210> SEQ ID NO 145
```

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 145
cagactgtag cgcgttttca taacgaagac gcctggtcgt tc                          42

<210> SEQ ID NO 146
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 146
aaccagagcc accaccggaa caccgtaatg ggataggtca cg                          42

<210> SEQ ID NO 147
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 147
caccagaacc accaccagag caaaattttt agaaccctca ta                          42

<210> SEQ ID NO 148
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 148
ataaatcctc attaaagcca gcaaatatcg cgttttaatt cg                          42

<210> SEQ ID NO 149
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 149
caggagtgta ctggtaataa gtaatttcaa ctttaatcat tg                          42

<210> SEQ ID NO 150
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 150
ttcggaacct attattctga aaagacagc atcggaacga gg                           42

<210> SEQ ID NO 151
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 151
cagtaccagg cggataagtg ccaccctcag aaccgccacc ct      42

<210> SEQ ID NO 152
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 152
attcatatgg tttaccagcg ctatcacgag tacggtggaa ac      42

<210> SEQ ID NO 153
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 153
agacaccacg gaataagttt atgcagatcc ggtgtcttgt ct      42

<210> SEQ ID NO 154
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 154
atgattaaga ctccttatta ctgctaaact ggaaagcaac ga      42

<210> SEQ ID NO 155
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 155
ccgaggaaac gcaataataa cgttgccagg aggatctgga ac      42

<210> SEQ ID NO 156
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 156
agaaaagtaa gcagatagcc gcagacatca ttgattcagc at      42

<210> SEQ ID NO 157
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 157
aacaatgaaa tagcaatagc ttaaccgtgc atctgccagt tt      42

<210> SEQ ID NO 158

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 158
taacccacaa gaattgagtt attttaacca ataggaacgc ca                          42

<210> SEQ ID NO 159
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 159
tgaacaaagt cagagggtaa tgtaatgtgt aggtaaagat tc                          42

<210> SEQ ID NO 160
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 160
aaacagggaa gcgcattaga cgcaaggcaa agaattagca aa                          42

<210> SEQ ID NO 161
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 161
tcaaaaatga aaatagcagc cggaagcaaa ctccaacagg tc                          42

<210> SEQ ID NO 162
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 162
tatttatccc aatccaaata aaaatgcttt aaacagttca ga                          42

<210> SEQ ID NO 163
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 163
ttccagagcc taatttgcca gaagaactgg ctcattatac ca                          42

<210> SEQ ID NO 164
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 164 ctacaattt atcctgaatc tgagtaatct tgacaagaac cg          42

<210> SEQ ID NO 165
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 165
tttgaagcct taaatcaaga tttgaggact aaagactttt tc          42

<210> SEQ ID NO 166
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 166
gaacgcgagg cgttttagcg aagcttgata ccgatagttg cg          42

<210> SEQ ID NO 167
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 167
ccttgaaaac atagcgatag cgagttagag tctgagcaaa aa          42

<210> SEQ ID NO 168
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 168
agtcaatagt gaatttatca agtatctgca tatgatgtct ga          42

<210> SEQ ID NO 169
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 169 ccttttaac ctccggctta gtgagtatta cgaaggtgtt at          42

<210> SEQ ID NO 170
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 170
taaatgctga tgcaaatcca acgaagtgag cgaaattaac tc          42

<210> SEQ ID NO 171

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 171 aaaactttt caaatatatt ttcatgcgta ttaaccaaca gt                              42

<210> SEQ ID NO 172
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 172
ctaaatttaa tggtttgaaa tgcctcagga agatcgcact cc                            42

<210> SEQ ID NO 173
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 173
gcgttaaata agaataaaca ctttgttaaa attcgcatta aa                            42

<210> SEQ ID NO 174
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 174
aagcctgttt agtatcatat ggacagtcaa atcaccatca at                            42

<210> SEQ ID NO 175
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 175
tataaagcca acgctcaaca gtctactaat agtagtagca tt                            42

<210> SEQ ID NO 176
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 176
catatttaac aacgccaaca tttgctcctt ttgataagag gt                            42

<210> SEQ ID NO 177
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 177
tcgagccagt aataagagaa tcaatactgc ggaatcgtca ta                               42

<210> SEQ ID NO 178
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 178
aagtaattct gtccagacga catctacgtt aataaaacga ac                               42

<210> SEQ ID NO 179
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 179
ctaatgcaga acgcgcctgt tcggtgtaca gaccaggcgc at                               42

<210> SEQ ID NO 180
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 180
gaacaagaaa aataatatcc cgggtaaaat acgtaatgcc ac                               42

<210> SEQ ID NO 181
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 181
gaaaccaatc aataatcggc tgtatcggtt tatcagcttg ct                               42

<210> SEQ ID NO 182
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 182
aacgggtatt aaaccaagta cgagtttcgt caccagtaca aa                               42

<210> SEQ ID NO 183
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 183
attaattaca tttaacaatt tgcactcgcg gggatttatt tt                               42

<210> SEQ ID NO 184

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 184
ctgagcaaaa gaagatgatg agaaacgaca tacattgcaa gg          42

<210> SEQ ID NO 185
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 185
agttacaaaa tcgcgcagag gagagtgaga tcggttttgt aa          42

<210> SEQ ID NO 186
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 186
gggagaaaca ataacggatt ctgttgagct tgaaacagca aa          42

<210> SEQ ID NO 187
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 187
tttaacgtca gatgaatata cagagcaggc aatgcatgac ga          42

<210> SEQ ID NO 188
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 188
tgcacgtaaa acagaaataa aaaaacgacg gccagtgcca ag          42

<210> SEQ ID NO 189
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 189
ctgaataatg gaagggttag atctggtgcc ggaaaccagg ca          42

<210> SEQ ID NO 190
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 190
tggcaattca tcaatataat cgaagattgt ataagcaaat at        42

<210> SEQ ID NO 191
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 191
agaaggagcg gaattatcat ctgataaatt aatgccggag ag        42

<210> SEQ ID NO 192
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 192
agtttgagta acattatcat ttatattttc atttggggcg cg        42

<210> SEQ ID NO 193
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 193
aactcgtatt aaatcctttg cgcttaattg ctgaatataa tg        42

<210> SEQ ID NO 194
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 194
atttgaggat ttagaagtat tgccagaggg ggtaatagta aa        42

<210> SEQ ID NO 195
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 195
agcactaaca actaatagat tggtagaaag attcatcagt tg        42

<210> SEQ ID NO 196
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 196
agttgaaagg aattgaggaa gtaagggaac cgaactgacc aa        42

<210> SEQ ID NO 197

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 197
tatcaaaccc tcaatcaata tcgaaagagg caaaagaata ca                          42

<210> SEQ ID NO 198
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 198
agcaaatgaa aaatctaaag ctgaaaatct ccaaaaaaaa gg                          42

<210> SEQ ID NO 199
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 199
tgacggggaa agccggcgaa ccttactgtt tctttacata aa                          42

<210> SEQ ID NO 200
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 200
gtcacgctgc gcgtaaccac cccaggagaa cgaggatatt gc                          42

<210> SEQ ID NO 201
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 201
taacgtgctt tcctcgttag attaagttgg gtaacgccag gg                          42

<210> SEQ ID NO 202
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 202
atcctgagaa gtgttttat acatatgtac cccggttgat aa                           42

<210> SEQ ID NO 203
<211> LENGTH: 42
<212> TYPE: DNA
<213> ORGANISM: Artificial Sequence
<220> FEATURE:
<223> OTHER INFORMATION: Synthetic Polynucleotide
```

```
<400> SEQUENCE: 203
tctttgatta gtaataacat caccattaga tacatttcgc aa                              42

<210> SEQ ID NO 204
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 204
gccagccatt gcaacaggaa aataaaaacc aaaatagcga ga                              42

<210> SEQ ID NO 205
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 205
agattcacca gtcacacgac cctccatgtt acttagccgg aa                              42

<210> SEQ ID NO 206
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 206
acgtggcaca gacaatattt taaggaacaa ctaaaggaat tg                              42

<210> SEQ ID NO 207
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 207
atctgaactc gctacggcgg ggggagcccc cgatttagag ctcggtcca                       49

<210> SEQ ID NO 208
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 208
cattgctgat accgtttagc taacaaacat caagaaaaca aaatggtgg                       49

<210> SEQ ID NO 209
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 209
gatacttgcc ctctctgtac ataattaatt ttcccttaga ataatagcc                       49

<210> SEQ ID NO 210
```

```
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 210
gattgggcgt tatcaatgtt gttttgtcac aatcaataga aaagagtcc          49

<210> SEQ ID NO 211
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 211
tctaatgaag acaaatcccc acgtcaccga cttgagccat ttgaaaaac          49

<210> SEQ ID NO 212
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 212
aaacatcggg ttgagtatta tgtggcgaga aaggaaggga aggaaaaac          49

<210> SEQ ID NO 213
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 213
cgctggcatt cgcatcaaag gcgaattatt catttcaatt acagagtcc          49

<210> SEQ ID NO 214
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 214
agtttataaa tgagtatcaa tttagattaa gacgctgaga agaatagcc          49

<210> SEQ ID NO 215
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 215
tatcgacatc attacgcatc gcaacatata aagaaacgc aaatggtgg           49

<210> SEQ ID NO 216
<211> LENGTH: 49
<212> TYPE: DNA
<213> ORGANISM: Artificial Sequence
<220> FEATURE:
<223> OTHER INFORMATION: Synthetic Polynucleotide
```

<400> SEQUENCE: 216
ccatgcagac atcacgaagg tcaccagtag caccattacc atcggtcca         49

<210> SEQ ID NO 217
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 217
aagataacgc ttgtgaaaat gagggcgctg gcaagtgtag cgcggtcca         49

<210> SEQ ID NO 218
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 218
gctaacagta gggaaactgc ggcctgattg ctttgaatac caatggtgg         49

<210> SEQ ID NO 219
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 219
atgggttcag gatgcaggtg aaatcatagg tctgagagac taaatagcc         49

<210> SEQ ID NO 220
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 220
ctcggatggg agtaagcgta tgcagtatgt tagcaaacgt agagagtcc         49

<210> SEQ ID NO 221
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 221
agagtttctg cggcagttaa tcaatgaaac catcgatagc aggaaaaac         49

<210> SEQ ID NO 222
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 222
gcaatacatc aaacgccgcg aacacccgcc gcgcttaatg cggaaaaac         49

<210> SEQ ID NO 223

<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 223
tcaggcactg cgtgaagcgg cagtaacagt accttttaca tcagagtcc                49

<210> SEQ ID NO 224
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 224
atcaaaactc aacgagcagc ggttgggtta tataactata tgaatagcc                49

<210> SEQ ID NO 225
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 225
agggttgtcg gacttgtgca aggaataccc aaaagaactg gcatggtgg                49

<210> SEQ ID NO 226
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 226
agtccgtgaa gacggaaacc aaatcaagtt tgcctttagc gtcggtcca                49

<210> SEQ ID NO 227
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 227
ctggggattt gacgcagacc tggttgcttt gacgagcacg tacggtcca                49

<210> SEQ ID NO 228
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 228
ttttcccagt cacgacgttg tgaaattgcg tagattttca ggatggtgg                49

<210> SEQ ID NO 229
<211> LENGTH: 49
<212> TYPE: DNA
<213> ORGANISM: Artificial Sequence
<220> FEATURE:
<223> OTHER INFORMATION: Synthetic Polynucleotide

```
<400> SEQUENCE: 229
ttatcagtaa acagagaggt ttcgcaagac aaagaacgcg agaatagcc          49

<210> SEQ ID NO 230
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 230
tcagggatta atgaaagatg gaacaaagtt accagaagga aaagagtcc          49

<210> SEQ ID NO 231
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 231
agtgtggcga tccgatagat gcggcatttt cggtcatagc ccgaaaaac          49

<210> SEQ ID NO 232
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 232 ggggatgtg ctgcaaggcg aatcagagcg ggagctaaac aggaaaaac           49

<210> SEQ ID NO 233
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 233
agccagcttt ccggcaccgc tacctaccat atcaaaatta ttagagtcc          49

<210> SEQ ID NO 234
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 234
ctttattatt cgcattcacc ctagttaatt tcatcttctg acaatagcc          49

<210> SEQ ID NO 235
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 235
ttggtgtaga tgggcgcatc gatcttaccg aagcccttt taatggtgg           49

<210> SEQ ID NO 236
```

```
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 236
cagaaataga agaattacag ctttcataat caaaatcacc ggcggtcca            49

<210> SEQ ID NO 237
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 237
aagcgccatt cgccattcag gagacaggaa cggtacgcca gacggtcca            49

<210> SEQ ID NO 238
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 238
tcagaaaagc cccaaaaaca gctgattgtt tggattatac ttatggtgg            49

<210> SEQ ID NO 239
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 239
gaggggacga cgacagtatc gaccgaccgt gtgataaata agaatagcc            49

<210> SEQ ID NO 240
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 240
tttttgttaa atcagctcat tagcccaata ataagagcaa gaagagtcc            49

<210> SEQ ID NO 241
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 241
gtgggaacaa acggcggatt gcgcctccct cagagccgcc acgaaaaac            49

<210> SEQ ID NO 242
<211> LENGTH: 49
<212> TYPE: DNA
<213> ORGANISM: Artificial Sequence
<220> FEATURE:
<223> OTHER INFORMATION: Synthetic Polynucleotide
```

<400> SEQUENCE: 242
cgaacgagta gatttagttt gacttgcctg agtagaagaa ctgaaaaac							49

<210> SEQ ID NO 243
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 243 cattttgcg gatggcttag accgaacgtt attaatttta aaagagtcc							49

<210> SEQ ID NO 244
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 244
agctgaaaag gtggcatcaa ttagggctta attgagaatc gcaatagcc							49

<210> SEQ ID NO 245
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 245
agcttcaaag cgaaccagac ctttacagag agaataacat aaatggtgg							49

<210> SEQ ID NO 246
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 246
attaagcaat aaagcctcag aggccttgat attcacaaac aacggtcca							49

<210> SEQ ID NO 247
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 247
ctgtagctca acatgtttta aaatatccag aacaatatta cccggtcca							49

<210> SEQ ID NO 248
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 248
ggcttttgca aaagaagttt tagactttac aaacaattcg acatggtgg							49

<210> SEQ ID NO 249

```
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 249
aggattagag agtaccttta agtaatttag gcagaggcat ttaatagcc                49

<210> SEQ ID NO 250
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 250
aatattcatt gaatcccct cgaaacgatt ttttgtttaa cgagagtcc                 49

<210> SEQ ID NO 251
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 251
aagaggaagc ccgaaagact taatggaaag cgcagtctct gagaaaaac                49

<210> SEQ ID NO 252
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 252
accctcgttt accagacgac gaacgctcat ggaaatacct acgaaaaac                49

<210> SEQ ID NO 253
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 253
taacggaaca acattattac aagagccgtc aatagataat acagagtcc                49

<210> SEQ ID NO 254
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 254
atgtttagac tggatagcgt cataaagtac cgacaaaagg taaatagcc                49

<210> SEQ ID NO 255
<211> LENGTH: 49
<212> TYPE: DNA
<213> ORGANISM: Artificial Sequence
<220> FEATURE:
<223> OTHER INFORMATION: Synthetic Polynucleotide
```

```
<400> SEQUENCE: 255
tgaattacct tatgcgattt tttacaaaat aaacagccat atatggtgg                49

<210> SEQ ID NO 256
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 256
aaacgagaat gaccataaat ccatacatgg cttttgatga tacggtcca                49

<210> SEQ ID NO 257
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 257
agatttagga ataccacatt caaatggatt atttacattg gccggtcca                49

<210> SEQ ID NO 258
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 258
cgaggcgcag acggtcaatc agttatctaa aatatcttta ggatggtgg                49

<210> SEQ ID NO 259
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 259
gtcaggacgt tgggaagaaa agacaataaa caacatgttc agaatagcc                49

<210> SEQ ID NO 260
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 260
aggctggctg accttcatca ataccaacgc taacgagcgt ctagagtcc                49

<210> SEQ ID NO 261
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 261
taaattgggc ttgagatggt tttttaacgg ggtcagtgcc ttgaaaaac                49

<210> SEQ ID NO 262
```

```
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 262
tgtgtcgaaa tccgcgacct gagtaataaa agggacattc tggaaaaac          49

<210> SEQ ID NO 263
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 263
tacgaaggca ccaacctaaa actggtcagt tggcaaatca acagagtcc           49

<210> SEQ ID NO 264
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 264
ctttgaaaga ggacagatga atatcaacaa tagataagtc ctaatagcc           49

<210> SEQ ID NO 265
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 265
gtagcaacgg ctacagaggc ttagttgcta ttttgcaccc agatggtgg           49

<210> SEQ ID NO 266
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 266
gatattcatt acccaaatca acagttaatg cccctgcct atcggtcca            49

<210> SEQ ID NO 267
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 267
ctaaaacact catctttgac cctgacctga aagcgtaaga atcggtcca           49

<210> SEQ ID NO 268
<211> LENGTH: 49
<212> TYPE: DNA
<213> ORGANISM: Artificial Sequence
<220> FEATURE:
<223> OTHER INFORMATION: Synthetic Polynucleotide
```

<400> SEQUENCE: 268
cgaataataa tttttttcacg tatcaccttg ctgaacctca aaatggtgg         49

<210> SEQ ID NO 269
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 269
atgaggaagt ttccattaaa catcctaatt tacgagcatg taaatagcc          49

<210> SEQ ID NO 270
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 270
ttcgaggtga atttcttaaa cacctcccga cttgcgggag gtagagtcc          49

<210> SEQ ID NO 271
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 271
ggatcgtcac cctcagcagc gacatgaaag tattaagagg ctgaaaaac         49

<210> SEQ ID NO 272
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 272
tttcagcgga gtgagaatag atgaatggct attagtcttt aagaaaaac         49

<210> SEQ ID NO 273
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 273
ctacaacgcc tgtagcattc cagtgccacg ctgagagcca gcagagtcc          49

<210> SEQ ID NO 274
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 274
ctccaaaagg agcctttaat tgtctttcct tatcattcca agaatagcc          49

<210> SEQ ID NO 275

<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 275
cagagccacc accctcattt taaggcttat ccgtattct aaatggtgg         49

<210> SEQ ID NO 276
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 276
ccgacaatga caacaaccat ctaggattag cggggttttg ctcggtcca         49

<210> SEQ ID NO 277
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 277
atctgaactc gctacggcgg ggggagcccc cgatttagag ctcggtccac gc         52

<210> SEQ ID NO 278
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 278
cattgctgat accgtttagc taacaaacat caagaaaaca aaatggtggt tc         52

<210> SEQ ID NO 279
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 279
gatacttgcc ctctctgtac ataattaatt ttcccttaga ataatagccc ga         52

<210> SEQ ID NO 280
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 280
gattgggcgt tatcaatgtt gttttgtcac aatcaataga aaagagtcca ct         52

<210> SEQ ID NO 281
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 281
tctaatgaag acaaatcccc acgtcaccga cttgagccat tgaaaaacc gt    52

<210> SEQ ID NO 282
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 282
aaacatcggg ttgagtatta tgtggcgaga aggaaggga aggaaaaacc gt    52

<210> SEQ ID NO 283
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 283
cgctggcatt cgcatcaaag gcgaattatt catttcaatt acagagtcca ct    52

<210> SEQ ID NO 284
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 284
agtttataaa tgagtatcaa tttagattaa gacgctgaga agaatagccc ga    52

<210> SEQ ID NO 285
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 285
tatcgacatc attacgcatc gcaacatata aagaaacgc aaatggtggt tc    52

<210> SEQ ID NO 286
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 286
ccatgcagac atcacgaagg tcaccagtag caccattacc atcggtccac gc    52

<210> SEQ ID NO 287
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 287
aagataacgc ttgtgaaaat gagggcgctg gcaagtgtag cgcggtccac gc    52

<210> SEQ ID NO 288

```
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 288
gctaacagta gggaaactgc ggcctgattg ctttgaatac caatggtggt tc            52

<210> SEQ ID NO 289
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 289
atgggttcag gatgcaggtg aaatcatagg tctgagagac taaatagccc ga            52

<210> SEQ ID NO 290
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 290
ctcggatggg agtaagcgta tgcagtatgt tagcaaacgt agagagtcca ct            52

<210> SEQ ID NO 291
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 291
agagtttctg cggcagttaa tcaatgaaac catcgatagc aggaaaaacc gt            52

<210> SEQ ID NO 292
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 292
gcaatacatc aaacgccgcg aacacccgcc gcgcttaatg cggaaaaacc gt            52

<210> SEQ ID NO 293
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 293
tcaggcactg cgtgaagcgg cagtaacagt accttttaca tcagagtcca ct            52

<210> SEQ ID NO 294
<211> LENGTH: 52
<212> TYPE: DNA
<213> ORGANISM: Artificial Sequence
<220> FEATURE:
<223> OTHER INFORMATION: Synthetic Polynucleotide
```

<400> SEQUENCE: 294
atcaaaactc aacgagcagc ggttgggtta tataactata tgaatagccc ga    52

<210> SEQ ID NO 295
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 295
agggttgtcg gacttgtgca aggaataccc aaaagaactg gcatggtggt tc    52

<210> SEQ ID NO 296
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 296
agtccgtgaa gacggaaacc aaatcaagtt tgcctttagc gtcggtccac gc    52

<210> SEQ ID NO 297
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 297
ctggggattt gacgcagacc tggttgcttt gacgagcacg tacggtccac gc    52

<210> SEQ ID NO 298
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 298
ttttcccagt cacgacgttg tgaaattgcg tagattttca ggatggtggt tc    52

<210> SEQ ID NO 299
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 299
ttatcagtaa acagagaggt ttcgcaagac aaagaacgcg agaatagccc ga    52

<210> SEQ ID NO 300
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 300
tcagggatta atgaaagatg gaacaaagtt accagaagga aaagagtcca ct    52

<210> SEQ ID NO 301

```
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 301
agtgtggcga tccgatagat gcggcatttt cggtcatagc cgaaaaaacc gt          52

<210> SEQ ID NO 302
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 302
gggggatgtg ctgcaaggcg aatcagagcg ggagctaaac aggaaaaacc gt          52

<210> SEQ ID NO 303
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 303
agccagcttt ccggcaccgc tacctaccat atcaaaatta ttagagtcca ct          52

<210> SEQ ID NO 304
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 304
ctttattatt cgcattcacc ctagttaatt tcatcttctg acaatagccc ga          52

<210> SEQ ID NO 305
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 305
ttggtgtaga tgggcgcatc gatcttaccg aagccctttt taatggtggt tc          52

<210> SEQ ID NO 306
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 306
cagaaataga agaattacag ctttcataat caaaatcacc ggcggtccac gc          52

<210> SEQ ID NO 307
<211> LENGTH: 52
<212> TYPE: DNA
<213> ORGANISM: Artificial Sequence
<220> FEATURE:
<223> OTHER INFORMATION: Synthetic Polynucleotide
```

<400> SEQUENCE: 307
aagcgccatt cgccattcag gagacaggaa cggtacgcca gacggtccac gc    52

<210> SEQ ID NO 308
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 308
tcagaaaagc cccaaaaaca gctgattgtt tggattatac ttatggtggt tc    52

<210> SEQ ID NO 309
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 309
gaggggacga cgacagtatc gaccgaccgt gtgataaata agaatagccc ga    52

<210> SEQ ID NO 310
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 310
tttttgttaa atcagctcat tagcccaata ataagagcaa gaagagtcca ct    52

<210> SEQ ID NO 311
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 311
gtgggaacaa acggcggatt gcgcctccct cagagccgcc acgaaaaacc gt    52

<210> SEQ ID NO 312
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 312
cgaacgagta gatttagttt gacttgcctg agtagaagaa ctgaaaaacc gt    52

<210> SEQ ID NO 313
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 313
catttttgcg gatggcttag accgaacgtt attaatttta aaagagtcca ct    52

<210> SEQ ID NO 314

<210> SEQ ID NO 314
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 314
agctgaaaag gtggcatcaa ttagggctta attgagaatc gcaatagccc ga    52

<210> SEQ ID NO 315
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 315
agcttcaaag cgaaccagac ctttacagag agaataacat aaatggtggt tc    52

<210> SEQ ID NO 316
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 316
attaagcaat aaagcctcag aggccttgat attcacaaac aacggtccac gc    52

<210> SEQ ID NO 317
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 317
ctgtagctca acatgtttta aaatatccag aacaatatta cccggtccac gc    52

<210> SEQ ID NO 318
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 318
ggcttttgca aaagaagttt tagactttac aaacaattcg acatggtggt tc    52

<210> SEQ ID NO 319
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 319
aggattagag agtacctttta agtaatttag gcagaggcat ttaatagccc ga    52

<210> SEQ ID NO 320
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 320
aatattcatt gaatcccct cgaaacgatt ttttgtttaa cgagagtcca ct    52

<210> SEQ ID NO 321
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 321
aagaggaagc ccgaaagact taatggaaag cgcagtctct gagaaaaacc gt    52

<210> SEQ ID NO 322
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 322
accctcgttt accagacgac gaacgctcat ggaaatacct acgaaaaacc gt    52

<210> SEQ ID NO 323
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 323
taacggaaca acattattac aagagccgtc aatagataat acagagtcca ct    52

<210> SEQ ID NO 324
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 324
atgtttagac tggatagcgt cataaagtac cgacaaaagg taaatagccc ga    52

<210> SEQ ID NO 325
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 325
tgaattacct tatgcgattt tttacaaaat aaacagccat atatggtggt tc    52

<210> SEQ ID NO 326
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 326
aaacgagaat gaccataaat ccatacatgg cttttgatga tacggtccac gc    52

<210> SEQ ID NO 327

```
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 327
agatttagga ataccacatt caaatggatt atttacattg gccggtccac gc            52

<210> SEQ ID NO 328
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 328
cgaggcgcag acggtcaatc agttatctaa aatatcttta ggatggtggt tc            52

<210> SEQ ID NO 329
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 329
gtcaggacgt tgggaagaaa agacaataaa caacatgttc agaatagccc ga            52

<210> SEQ ID NO 330
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 330
aggctggctg accttcatca ataccaacgc taacgagcgt ctagagtcca ct            52

<210> SEQ ID NO 331
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 331
taaattgggc ttgagatggt tttttaacgg ggtcagtgcc ttgaaaaacc gt            52

<210> SEQ ID NO 332
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 332
tgtgtcgaaa tccgcgacct gagtaataaa agggacattc tggaaaaacc gt            52

<210> SEQ ID NO 333
<211> LENGTH: 52
<212> TYPE: DNA
<213> ORGANISM: Artificial Sequence
<220> FEATURE:
<223> OTHER INFORMATION: Synthetic Polynucleotide
```

<400> SEQUENCE: 333
tacgaaggca ccaacctaaa actggtcagt tggcaaatca acagagtcca ct        52

<210> SEQ ID NO 334
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 334
ctttgaaaga ggacagatga atatcaacaa tagataagtc ctaatagccc ga        52

<210> SEQ ID NO 335
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 335
gtagcaacgg ctacagaggc ttagttgcta ttttgcaccc agatggtggt tc        52

<210> SEQ ID NO 336
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 336
gatattcatt acccaaatca acagttaatg cccctgcct atcggtccac gc        52

<210> SEQ ID NO 337
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 337
ctaaaacact catctttgac cctgacctga aagcgtaaga atcggtccac gc        52

<210> SEQ ID NO 338
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 338
cgaataataa tttttcacg tatcaccttg ctgaacctca aatggtggt tc        52

<210> SEQ ID NO 339
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 339
atgaggaagt ttccattaaa catcctaatt tacgagcatg taaatagccc ga        52

<210> SEQ ID NO 340

```
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 340
ttcgaggtga atttcttaaa cacctcccga cttgcgggag gtagagtcca ct          52

<210> SEQ ID NO 341
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 341
ggatcgtcac cctcagcagc gacatgaaag tattaagagg ctgaaaaacc gt          52

<210> SEQ ID NO 342
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 342
tttcagcgga gtgagaatag atgaatggct attagtcttt aagaaaaacc gt          52

<210> SEQ ID NO 343
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 343
ctacaacgcc tgtagcattc cagtgccacg ctgagagcca gcagagtcca ct          52

<210> SEQ ID NO 344
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 344
ctccaaaagg agcctttaat tgtctttcct tatcattcca agaatagccc ga          52

<210> SEQ ID NO 345
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 345
cagagccacc accctcattt taaggcttat ccggtattct aaatggtggt tc          52

<210> SEQ ID NO 346
<211> LENGTH: 52
<212> TYPE: DNA
<213> ORGANISM: Artificial Sequence
<220> FEATURE:
<223> OTHER INFORMATION: Synthetic Polynucleotide
```

```
<400> SEQUENCE: 346
ccgacaatga caacaaccat ctaggattag cggggttttg ctcggtccac gc            52

<210> SEQ ID NO 347
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 347
tcatcaacat taaaagaacg cgagaaaatt gttaaatcag accgtgcat               49

<210> SEQ ID NO 348
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 348
taatcgtaaa actaatcttc tgacctaaag ctattttga ta                       42

<210> SEQ ID NO 349
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 349
atatatttta aatggataaa taaggcgtaa aaacattatg tc                      42

<210> SEQ ID NO 350
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 350
gcgagctgaa aaggttacta gaaaaagcac gagtagattt ct                      42

<210> SEQ ID NO 351
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 351
ggtcattttt gcggttctta ccagtatatt caaagcgaac cc                      42

<210> SEQ ID NO 352
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 352
agaaaacgag aatgtgagaa tcgccatatt tagactggat ag                      42

<210> SEQ ID NO 353
```

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 353
acgccaaaag aatagaggc attttcgacg aacaacatt ag                          42

<210> SEQ ID NO 354
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 354
tagtaaattg ggctacaaaa ggtaaagtat tcattaccca ag                         42

<210> SEQ ID NO 355
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 355
gaacgaggcg cagaacatgt tcagctaaac aaagtacaac ca                        42

<210> SEQ ID NO 356
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 356
ttcatgagga agttgataag tcctgaactc gtcaccctca tt                        42

<210> SEQ ID NO 357
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 357
gctttcgagg tgaacgagca tgtagaaaat aataattttt tg                        42

<210> SEQ ID NO 358
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 358
tagcgtaacg atcttcattc caagaacgcc catgtaccgt aa                        42

<210> SEQ ID NO 359
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 359
aagtatagcc cggaagaaca agcaagccac tcctcaagag ca        42

<210> SEQ ID NO 360
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 360
atacaggagt gtacccgcgc ccaatagcaa tcctcattaa tc        42

<210> SEQ ID NO 361
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 361
caccctcaga accgggtatt ctaagaacta ttagcgtttg ac        42

<210> SEQ ID NO 362
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 362
cattagcaag gccgtgcggg aggttttgtt aaaggtgaat tt        42

<210> SEQ ID NO 363
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 363
caaagacacc acggttgcac ccagctacat taagactcct gg        42

<210> SEQ ID NO 364
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 364
agaaacaatg aaatacgagc gtctttccga attaactgaa aa        42

<210> SEQ ID NO 365
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 365
gaacaaacgg cggattgaca ataattcg        28

<210> SEQ ID NO 366

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 366
cgtctggcct tcctgtcccg gttgataatc agaagagtct gg        42

<210> SEQ ID NO 367
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 367
agcaaacaag agaatcaggt aaagattcaa aagtttcaac gc        42

<210> SEQ ID NO 368
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 368
aaggataaaa atttttagta gtagcattaa catcaataac ct        42

<210> SEQ ID NO 369
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 369
gtttagctat attttcctga atataatgct gtatagagag ta        42

<210> SEQ ID NO 370
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 370
cctttaattg ctccttgtct ttaccctgac tattcattga at        42

<210> SEQ ID NO 371
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 371
ccccctcaaa tgctttaaca ctatcataac ccttaggaat ac        42

<210> SEQ ID NO 372
<211> LENGTH: 42
<212> TYPE: DNA
<213> ORGANISM: Artificial Sequence
<220> FEATURE:
<223> OTHER INFORMATION: Synthetic Polynucleotide

```
<400> SEQUENCE: 372
cacattcaac taatgccttt aatcattgtg aattaaggct tg          42

<210> SEQ ID NO 373
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 373
ccctgacgag aaacaccgaa ctgaccaact ttgcgaaatc cg          42

<210> SEQ ID NO 374
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 374
cgacctgctc catgttacgt aatgccacta cgaaacggct ac          42

<210> SEQ ID NO 375
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 375
agaggctttg aggactccga tagttgcgcc gacaaaggag cc          42

<210> SEQ ID NO 376
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 376
tttaattgta tcggttagac gttagtaaat gaaacgcctg ta          42

<210> SEQ ID NO 377
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 377
gcattccaca gacagccagg aggtttagta ccgccaggcg ga          42

<210> SEQ ID NO 378
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 378
taagtgccgt cgagagggtc agtgccttga gtaccgttcc ag          42

<210> SEQ ID NO 379
```

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 379
taagcgtcat acatggcctc agagccgcca ccagagccac ca                          42

<210> SEQ ID NO 380
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 380
ccggaaccgc ctccctcatc gatagcagca ccgttagagc ca                          42

<210> SEQ ID NO 381
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 381
gcaaaatcac cagtagaatc aatagaaaat tcaacataca ta                          42

<210> SEQ ID NO 382
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 382
aaggtggcaa catataaagc ccttttttaag aaaagaattg agttaagcc                  49

<210> SEQ ID NO 383
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 383
acaggaagat tgaataggaa cgccatcaaa cgtaatggga ta                          42

<210> SEQ ID NO 384
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 384
agatgggcgc atcgtactca ttttttaacc tataa                                  35

<210> SEQ ID NO 385
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 385
gcaaatattt aaattgtaaa cgtgagatct acaaaggaat ca                    42

<210> SEQ ID NO 386
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 386
ccatcaatat gatattcaac cgtaccctgt aatacttaag aa                    42

<210> SEQ ID NO 387
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 387
ttagcaaaat taagcaataa agcagtttga ccattagcta aa                    42

<210> SEQ ID NO 388
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 388
gtacggtgtc tggaagtttc attcagaccg gaagcaacat ca                    42

<210> SEQ ID NO 389
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 389
aaaagattaa gaggaagccc gaaagcgtcc aatactgcaa aa                    42

<210> SEQ ID NO 390
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 390
tagcgagagg cttttgcaaa agaattacag gtagaaagct ca                    42

<210> SEQ ID NO 391
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 391
ttataccagt caggacgttg ggaaatcaac gtaacaaaga cc                    42

<210> SEQ ID NO 392

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 392
aggcgcatag gctggctgac cttggagatt tgtatcagca aa                              42

<210> SEQ ID NO 393
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 393
agaatacact aaaacactca tctgcagcga aagacagata ac                              42

<210> SEQ ID NO 394
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 394
cgatatattc ggtcgctgag gcttcacgtt gaaaatccaa ct                              42

<210> SEQ ID NO 395
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 395
ttcaacagtt tcagcggagt gagaacactg agtttcggaa cc                              42

<210> SEQ ID NO 396
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 396
gccaccctca gagccaccac cctaaggatt aggattagcc cc                              42

<210> SEQ ID NO 397
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 397
ctgcctattt cggaacctat tatagccaga atggaaagca tt                              42

<210> SEQ ID NO 398
<211> LENGTH: 42
<212> TYPE: DNA
<213> ORGANISM: Artificial Sequence
<220> FEATURE:
<223> OTHER INFORMATION: Synthetic Polynucleotide
```

-continued

<400> SEQUENCE: 398
gacaggaggt tgaggcaggt cagccatctt ttcataattg cc                             42

<210> SEQ ID NO 399
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 399
tttagcgtca gactgtagcg cgttatcacc gtcaccgaaa gg                             42

<210> SEQ ID NO 400
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 400
gcgacattca accgattgag ggatattacg cagtatgtac ca                             42

<210> SEQ ID NO 401
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 401
gaaggaaacc gaggaaacgc aatcaccctg aacaaagtca gataatatc                      49

<210> SEQ ID NO 402
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 402
atattttgtt aaaattcgca ttaaatttct ttttcaaata ta                             42

<210> SEQ ID NO 403
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 403
tagctgataa attaatgccg gagagggtat ttaatggttt ga                             42

<210> SEQ ID NO 404
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 404
cagagcataa agctaaatcg gttgtaccta aataagaata aa                             42

<210> SEQ ID NO 405

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 405
atataacagt tgattcccaa ttctgcgact gtttagtatc at    42

<210> SEQ ID NO 406
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 406
acttcaaata tcgcgtttta attcgagcaa gccaacgctc aa    42

<210> SEQ ID NO 407
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 407
ttttgccaga gggggtaata gtaaaatgtt taacaacgcc aa    42

<210> SEQ ID NO 408
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 408
aaaaatctac gttaataaaa cgaactaagc cagtaataag ag    42

<210> SEQ ID NO 409
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 409
tcaagagtaa tcttgacaag aaccggataa ttctgtccag ac    42

<210> SEQ ID NO 410
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 410
gacccccagc gattatacca agcgcgaatg cagaacgcgc ct    42

<210> SEQ ID NO 411
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 411
cagggagtta aaggccgctt ttgcgggaaa gaaaaataat at                              42

<210> SEQ ID NO 412
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 412
tagaaaggaa caactaaagg aattgcgacc aatcaataat cg                              42

<210> SEQ ID NO 413
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 413
ttttcaggga tagcaagccc aataggaagg tattaaacca ag                              42

<210> SEQ ID NO 414
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 414
tgaaacatga aagtattaag aggctgaggt ttttattttc at                              42

<210> SEQ ID NO 415
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 415
gattggcctt gatattcaca aacaaataaa gcaaatcaga ta                              42

<210> SEQ ID NO 416
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 416
tcatcggcat tttcggtcat agcccctgc gaggcgtttt ag                               42

<210> SEQ ID NO 417
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 417
gaaggtaaat attgacggaa attattcaaa gccttaaatc aa                              42

<210> SEQ ID NO 418

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 418
taacggaata cccaaaagaa ctggcatgaa ttttatcctg aa            42

<210> SEQ ID NO 419
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 419
cgcattagac gggaagagcc t                                   21

<210> SEQ ID NO 420
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 420
aagacaatgt gagcgagtaa caacccgt                            28

<210> SEQ ID NO 421
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 421
ttttagttaa tttcgcatgt caatcatatg tacagccagc tt            42

<210> SEQ ID NO 422
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 422
aataccgacc gtgtcaatgc ctgagtaatg tgtgatgaac gg            42

<210> SEQ ID NO 423
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 423
caccggaatc ataatggcat caattctact aatagaaccc tc            42

<210> SEQ ID NO 424
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 424
atgcgttata caaaatggct tagagcttaa ttgatttggg gc                42

<210> SEQ ID NO 425
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 425
cagtagggct taataccata aatcaaaaat cagttgataa ga                42

<210> SEQ ID NO 426
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 426
catgtaattt aggctacgag gcatagtaag agcaaacagt tc                42

<210> SEQ ID NO 427
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 427
aatataaagt accgtgagat ggtttaattt caaagataca ta                42

<210> SEQ ID NO 428
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 428
gacgacaata aacacggtca atcataaggg aaccagaacg ag                42

<210> SEQ ID NO 429
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 429
gtttatcaac aatatccatt aaacgggtaa aatacttagc cg                42

<210> SEQ ID NO 430
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 430
cccatcctaa tttatttctt aaacagcttg ataaaagact tt                42

<210> SEQ ID NO 431

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 431
gctgtctttc cttaaaagtt ttgtcgtctt tcctatcagc tt                        42

<210> SEQ ID NO 432
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 432
taccgcactc atcgataggt gtatcaccgt actcctcata gt                        42

<210> SEQ ID NO 433
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 433
cgtaggaatc attatggtaa taagttttaa cggggttgat at                        42

<210> SEQ ID NO 434
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 434
tagaaggctt atccccaccc tcagagccac cacctttga tg                         42

<210> SEQ ID NO 435
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 435
cgaacctccc gactgaaacg tcaccaatga aaccagagcc gc                        42

<210> SEQ ID NO 436
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 436
gattagttgc tattaataag tttattttgt caccaccatt ac                        42

<210> SEQ ID NO 437
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 437
tcttaccaac gctaagcaat agctatctta ccgaaagaaa cg             42

<210> SEQ ID NO 438
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 438
cggagacagt cactatcagg tcattgcctg aaagccccaa aa             42

<210> SEQ ID NO 439
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 439
acaggcaagg cattgcggga gaagccttta ggtgagaaag gc             42

<210> SEQ ID NO 440
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 440
ttaaatatgc aaatacattt cgcaaatggt ccaataaatc at             42

<210> SEQ ID NO 441
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 441
caaagcggat tgactccaac aggtcaggat gctcaacatg tt             42

<210> SEQ ID NO 442
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 442
gacgataaaa accggaatcg tcataaatat tatagtcaga ag             42

<210> SEQ ID NO 443
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 443
ttttaagaac tggattcatc agttgagatt cgtttaccag ac             42

<210> SEQ ID NO 444

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 444
tgaacggtgt acagctgctc attcagtgaa taccttatgc ga                              42

<210> SEQ ID NO 445
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 445
aaaacgaaag agtcgcctga taaattgtgt aaagaggaca ga                              42

<210> SEQ ID NO 446
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 446
catcgcccac gccatcggaa cgagggtagc aggcaccaac ct                              42

<210> SEQ ID NO 447
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 447
gattttgcta aatccaaaaa aaaggctcca aatgacaaca ac                              42

<210> SEQ ID NO 448
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 448
ccgccaccct catcaccagt acaaactaca ttttctgtat gg                              42

<210> SEQ ID NO 449
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 449
taaacagtta atgcggggtt ttgctcagta ccaccctcag aa                              42

<210> SEQ ID NO 450
<211> LENGTH: 42
<212> TYPE: DNA
<213> ORGANISM: Artificial Sequence
<220> FEATURE:
<223> OTHER INFORMATION: Synthetic Polynucleotide
```

```
<400> SEQUENCE: 450
gagccgccgc cagcgcagtc tctgaattta acagtgcccg ta                              42

<210> SEQ ID NO 451
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 451
acagaatcaa gttcaaaatc accggaacca gaaccaccac ca                              42

<210> SEQ ID NO 452
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 452
gcgccaaaga caacttgagc catttgggaa taatcagtag cg                              42

<210> SEQ ID NO 453
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 453
ccgaacaaag tttagcaaac gtagaaaatt atggtttacc a                               41

<210> SEQ ID NO 454
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 454
agagagataa cccacaagta agcagatag                                             29

<210> SEQ ID NO 455
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 455
agaagatgaa attaactaaa atatatttga aaaagttttc tcgcgttctt tgtcttgcga           60
ttg                                                                         63

<210> SEQ ID NO 456
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 456
atttatcaca cggtcggtat ttcaaaccat taaatttagg tc                              42
```

```
<210> SEQ ID NO 457
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 457
ctagtaatta tgattccggt gtttattctt atttaacgcc tt                              42

<210> SEQ ID NO 458
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 458
gtaagaattt gtataacgca tatgatacta aacaggcttt tt                              42

<210> SEQ ID NO 459
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 459
attctcaatt aagccctact gttgagcgtt ggctttatac tg                              42

<210> SEQ ID NO 460
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 460
tgcctctgcc taaattacat gttggcgttg ttaaatatgg cg                              42

<210> SEQ ID NO 461
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 461
cttttgtcgg tactttatat tctcttatta ctggctcgaa aa                              42

<210> SEQ ID NO 462
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 462
aacatgttgt ttattgtcgt cgtctggaca gaattacttt ac                              42

<210> SEQ ID NO 463
<211> LENGTH: 42
<212> TYPE: DNA
<213> ORGANISM: Artificial Sequence
<220> FEATURE:
<223> OTHER INFORMATION: Synthetic Polynucleotide
```

```
<400> SEQUENCE: 463
acttatctat tgttgataaa caggcgcgtt ctgcattagc tg                             42

<210> SEQ ID NO 464
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 464
atgctcgtaa attaggatgg gatattattt ttcttgttca gg                            42

<210> SEQ ID NO 465
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 465
ggaatgataa ggaaagacag ccgattattg attggtttct ac                            42

<210> SEQ ID NO 466
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 466
ttgttctcga tgagtgcggt acttggttta atacccgttc tt                            42

<210> SEQ ID NO 467
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 467
ggcgcggtaa tgattcctac gatgaaaata aaaacggctt gc                            42

<210> SEQ ID NO 468
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 468
gaataccgga taagccttct atatctgatt tgcttgctat tg                            42

<210> SEQ ID NO 469
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 469
tcccgcaagt cgggaggttc gctaaaacgc ctcgcgttct ta                            42

<210> SEQ ID NO 470
```

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 470
ggtgcaaaat agcaactaat cttgatttaa ggcttcaaaa cc          42

<210> SEQ ID NO 471
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 471
gcaaattagg ctctggaaag acgctcgtta gcgttggtaa gattcaggat aaaattgtag    60
ctg                                                                 63

<210> SEQ ID NO 472
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 472
attctcaatt agcgtggacc gttgagcgtt ggctttatac tg          42

<210> SEQ ID NO 473
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 473
tgcctctgcc tgaaccacca tttggcgttg ttaaatatgg cg          42

<210> SEQ ID NO 474
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 474
cttttgtcgg ttcgggctat tctcttatta ctggctcgaa aa          42

<210> SEQ ID NO 475
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 475
aacatgttgt tagtggactc tgtctggaca gaattacttt ac          42

<210> SEQ ID NO 476
<211> LENGTH: 42
<212> TYPE: DNA
<213> ORGANISM: Artificial Sequence
<220> FEATURE:
<223> OTHER INFORMATION: Synthetic Polynucleotide -continued

<400> SEQUENCE: 476
acttatctat tacggttttt caggcgcgtt ctgcattagc tg                              42

<210> SEQ ID NO 477
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 477
taataccata aatcaaaaat cagttgataa ga                                        32

<210> SEQ ID NO 478
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 478
aggctacgag gcatagtaag agcaaacagt tc                                        32

<210> SEQ ID NO 479
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 479
accgtgagat ggtttaattt caaagataca ta                                        32

<210> SEQ ID NO 480
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 480
aacacggtca atcataaggg aaccagaacg ag                                        32

<210> SEQ ID NO 481
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 481
aatatccatt aaacgggtaa aatacttagc cg                                        32

<210> SEQ ID NO 482
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 482
aacggcatct ccgtgagcct cctcacagag cctggggtgc ct                             42

<210> SEQ ID NO 483

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 483
ggcagcaccc atcccttaca ctggtgtggt tgcgctcact gc          42

<210> SEQ ID NO 484
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 484
aaatcccgtg gtctggtcag cagcaacccc agctgcatta at          42

<210> SEQ ID NO 485
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 485
gagccgccaa gcagttgggc ggttgtgttt tgcgtattgg gc          42

<210> SEQ ID NO 486
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 486
ggcaccgcta aaacgacggc cagtgccaag acgggcaaca gc          42

<210> SEQ ID NO 487
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 487
cgcgtctggg cctcaggaag atcgcactag agttgcagca ag          42

<210> SEQ ID NO 488
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 488
ggagcaaact tttaaccaat aggaacgcga aaatcctgtt tg          42

<210> SEQ ID NO 489
<211> LENGTH: 42
<212> TYPE: DNA
<213> ORGANISM: Artificial Sequence
<220> FEATURE:
<223> OTHER INFORMATION: Synthetic Polynucleotide

```
<400> SEQUENCE: 489
gcaaggatat acaaaggcta tcaggtcatt ataaatcaaa ag                              42

<210> SEQ ID NO 490
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 490
ctgtttagct aatacttttg cgggagaatc cagtttggaa ca                              42

<210> SEQ ID NO 491
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 491
tacctttaaa ccattagata catttcgcca acgtcaaagg gc                              42

<210> SEQ ID NO 492
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 492 atcccctcg gaagcaaact ccaacaggac tacgtgaacc at                               42

<210> SEQ ID NO 493
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 493
accacattcc aatactgcgg aatcgtcagt gccgtaaagc ac                              42

<210> SEQ ID NO 494
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 494
tgccctgacg gtagaaagat tcatcagtat ttagagcttg ac                              42

<210> SEQ ID NO 495
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 495
cgcgacctgc gtaacaaagc tgctcattgg aagggaagaa ag                              42

<210> SEQ ID NO 496
```

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 496
acagaggctt tgtatcatcg cctgataaaa gtgtagcggt ca         42

<210> SEQ ID NO 497
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 497
cctttaatta aagacagcat cggaacgagc ttaatgcgcc gc         42

<210> SEQ ID NO 498
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 498
tagcattcct gaaaatctcc aaaaaaaacg agcacgtata ac         42

<210> SEQ ID NO 499
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 499
gataagtgcg agtttcgtca ccagtacaag ctaaacagga gg         42

<210> SEQ ID NO 500
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 500
agtaagcgtt aggattagcg gggttttggt acgccagaat cc         42

<210> SEQ ID NO 501
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 501
caccggaaca atggaaagcg cagtctctca ccgagtaaaa ga         42

<210> SEQ ID NO 502
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 502
cagcaaaatt ttcataatca aaatcaccta gcaatacttc tt                                42

<210> SEQ ID NO 503
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 503
taaaggtggc gtcaccgact tgagccatta gaagaactca aa                                42

<210> SEQ ID NO 504
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 504
attgagttag cagtatgtta gcaaacgtca atattaccgc ca                                42

<210> SEQ ID NO 505
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 505
atttgccagt gagcgctaat atcagagaaa atacctacat tt                                42

<210> SEQ ID NO 506
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 506
tttcatcgtt accaacgcta acgagcgttt acattggcag at                                42

<210> SEQ ID NO 507
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 507
ccagacgacc gcactcatcg agaacaaggg acattctggc ca                                42

<210> SEQ ID NO 508
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 508
aataaacaca taaagtaccg acaaaagggc gtaagaatac gt                                42

<210> SEQ ID NO 509

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 509
atttatcaaa ccgaccgtgt gataaatata gtctttaatg cg                              42

<210> SEQ ID NO 510
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 510
agatgatgat tagattaaga cgctgagata aaaataccga ac                              42

<210> SEQ ID NO 511
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 511
agggttagac gaattattca tttcaatttg aggcggtcag ta                              42

<210> SEQ ID NO 512
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 512
agaagtattc tgattgtttg gattatacga gagccagcag ca                              42

<210> SEQ ID NO 513
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 513
tcatggtcat agccgtgcct gttcttcgcg agatgccggg tt                              42

<210> SEQ ID NO 514
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 514
acctgcagcc agctctttgc tcgtcataaa gtcggtggtg cc                              42

<210> SEQ ID NO 515
<211> LENGTH: 42
<212> TYPE: DNA
<213> ORGANISM: Artificial Sequence
<220> FEATURE:
<223> OTHER INFORMATION: Synthetic Polynucleotide
```

```
<400> SEQUENCE: 515
atcccacgca accaacgtca gcgtggtgct aaaaaaagcc gc                42

<210> SEQ ID NO 516
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 516
acaggcggcc ttttctgctc atttgccgcc cgggaacgga ta                42

<210> SEQ ID NO 517
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 517
acctcaccgg aaacccagtc acgacgttgt tctggtgccg ga                42

<210> SEQ ID NO 518
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 518
aaccaggcaa agcggacgac gacagtatcg ccttcctgta gc                42

<210> SEQ ID NO 519
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 519
cagctttcat caatgttaaa tcagctcatt aagagaatcg at                42

<210> SEQ ID NO 520
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 520
gaacggtaat cgtgctattt ttgagagatc aaaattttta ga                42

<210> SEQ ID NO 521
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 521
accctcatat attaaaacat tatgaccctg tatattttca tt                42

<210> SEQ ID NO 522
```

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 522 tgggcgcga gctcgagtag atttagtttg ttgctccttt tg                42

<210> SEQ ID NO 523
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 523
ataagaggtc atttcaaagc gaaccagacc aaatgcttta aa                42

<210> SEQ ID NO 524
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 524
cagttcagaa aacttagact ggatagcgtc aactaatgca ga                42

<210> SEQ ID NO 525
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 525
tacataacgc caaggaacaa cattattaca gagaaacacc ag                42

<210> SEQ ID NO 526
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 526
aacgagtagt aaattcatta cccaaatcaa ctccatgtta ct                42

<210> SEQ ID NO 527
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 527
tagccggaac gagcaaagta caacggagat ttgaggacta aa                42

<210> SEQ ID NO 528
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 528 gacttttca tgacgtcacc ctcagcagcg gtatcggttt at                42

<210> SEQ ID NO 529
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 529
cagcttgctt tcgtaataat tttttcacgt acagacagcc ct                42

<210> SEQ ID NO 530
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 530
catagttagc gtaccatgta ccgtaacact cgtcgagagg gt                42

<210> SEQ ID NO 531
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 531
tgatataagt atactcctca agagaaggat catacatggc tt                42

<210> SEQ ID NO 532
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 532
ttgatgatac aggatcctca ttaaagccag cgcctccctc ag                42

<210> SEQ ID NO 533
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 533
agccgccacc ctcattagcg tttgccatct caccagtagc ac                42

<210> SEQ ID NO 534
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 534
cattaccatt agctaaaggt gaattatcac caacatataa aa                42

<210> SEQ ID NO 535

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 535
gaaacgcaaa gacttaagac tccttattac agcccaataa ta                          42

<210> SEQ ID NO 536
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 536
agagcaagaa acacaaagtc agagggtaat ttacaaaata aa                          42

<210> SEQ ID NO 537
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 537
cagccatatt attaattta tcctgaatct aggaatcatt ac                           42

<210> SEQ ID NO 538
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 538
cgcgcccaat agcggtatta aaccaagtac gacaataaac aa                          42

<210> SEQ ID NO 539
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 539
catgttcagc taagccagta ataagagaat cggaatcata at                          42

<210> SEQ ID NO 540
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 540
tactagaaaa agcatttaat ggtttgaaat aatcataggt ct                          42

<210> SEQ ID NO 541
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 541
gagagactac cttgaaaaca tagcgatagc aacaaacatc aa                    42

<210> SEQ ID NO 542
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 542
gaaaacaaaa ttaacaaaat cgcgcagagg acctaccata tc                    42

<210> SEQ ID NO 543
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 543
aaaattattt gcaaattcat caatataatc agactttaca aacaat                46

<210> SEQ ID NO 544
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 544
tcgacaactc taacaactaa tcgtcaatag ataatgaacc tcaaatatc             49

<210> SEQ ID NO 545
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 545
tctgccagca cgtgtttcct gtgtgccgct cac                              33

<210> SEQ ID NO 546
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 546
tgggtaaagg ttggtgccgg tgcccctgc ataccggggg tt                     42

<210> SEQ ID NO 547
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 547
ccggacttgt agagcttacg gctggaggtg tgcggctggt aa                    42

<210> SEQ ID NO 548

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 548
caaacttaaa ttagtgatga agggtaaagt taacggaacg tg                          42

<210> SEQ ID NO 549
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 549
cgccagggtt ttcaatcggc gaaacgtaca gaaacagcgg at                          42

<210> SEQ ID NO 550
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 550
gccagtttga gggccattcg ccattcaggc taagttgggt aa                          42

<210> SEQ ID NO 551
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 551
gcattaaatt ttcattaaat gtgagcgagt aaccgtgcat ct                          42

<210> SEQ ID NO 552
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 552
ccggagaggg taaaaactag catgtcaatc ttgttaaaat tc                          42

<210> SEQ ID NO 553
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 553
tcggttgtac cattaaatgc aatgcctgag gataaattaa tg                          42

<210> SEQ ID NO 554
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 554
caattctgcg aagaaaaggt ggcatcaatt cataaagcta aa                             42

<210> SEQ ID NO 555
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 555
ttaattcgag cttttgcgga tggcttagag acagttgatt cc                             42

<210> SEQ ID NO 556
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 556
atagtaaaat gtgagaatga ccataaatca aaatatcgcg tt                             42

<210> SEQ ID NO 557
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 557
aaacgaacta acaaggaatt acgaggcata ccagaggggg ta                             42

<210> SEQ ID NO 558
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 558
aagaaccgga tattgggctt gagatggttt tctacgttaa ta                             42

<210> SEQ ID NO 559
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 559
ccaagcgcga aagcgcagac ggtcaatcat agtaatcttg ac                             42

<210> SEQ ID NO 560
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 560
cttttgcggg atggaagttt ccattaaacg ccagcgatta ta                             42

<210> SEQ ID NO 561

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 561
aggaattgcg aaaggtgaat ttcttaaaca agttaaaggc cg                          42

<210> SEQ ID NO 562
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 562
cccaatagga acacgatcta aagttttgtc aggaacaact aa                          42

<210> SEQ ID NO 563
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 563
aagaggctga gagcccggaa taggtgtatc agggatagca ag                          42

<210> SEQ ID NO 564
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 564
acaaacaaat aaagtgtact ggtaataagt catgaaagta tt                          42

<210> SEQ ID NO 565
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 565
catagccccc ttagaaccgc caccctcaga gccttgatat tc                          42

<210> SEQ ID NO 566
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 566
gaaattattc ataaggccgg aaacgtcacc ggcattttcg gt                          42

<210> SEQ ID NO 567
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 567
gaactggcat gaaccacgga ataagtttat taaatattga cg                          42

<210> SEQ ID NO 568
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 568
gaacaccctg aaatgaaata gcaatagcta gaatacccaa aa                          42

<210> SEQ ID NO 569
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 569
gcacccagct actatcccaa tccaaataag ggagaattaa ct                          42

<210> SEQ ID NO 570
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 570
attccaagaa cgaagcaaat cagatataga agttgctatt tt                          42

<210> SEQ ID NO 571
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 571
aggcattttc gatgcagaac gcgcctgttt tctttcctta tc                          42

<210> SEQ ID NO 572
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 572
cttctgacct aactgtttag tatcatatgc taatttaggc ag                          42

<210> SEQ ID NO 573
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 573
cttagaatcc tttttaacct ccggcttagg agttaatttc at                          42

<210> SEQ ID NO 574

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 574
gaataccaag ttattacatt taacaatttc aattaatttt cc                         42

<210> SEQ ID NO 575
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 575
tcagatgatg gccgtaaaac agaaataaag cctgattgct tt                         42

<210> SEQ ID NO 576
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 576
tctttaggag cacgtattaa atcctttgcc tattcctgat ta                         42

<210> SEQ ID NO 577
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 577
aattccacac aagggccgtt ttcacggtca tcagacgatc ca                         42

<210> SEQ ID NO 578
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 578
gcgcagtgtc acccgggtca ctgttgccct ccagcatcag cg                         42

<210> SEQ ID NO 579
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 579
gggtcattgc aggccagagc acatcctcat aaacgatgct ga                         42

<210> SEQ ID NO 580
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 580
ttgccgttcc ggacggaaaa agagacgcag cgccatgttt ac                             42

<210> SEQ ID NO 581
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 581
cagtcccgga atatgtgctg caaggcgatt gcgcaactgt tg                             42

<210> SEQ ID NO 582
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 582
ggaagggcga tcgtagatgg gcgcatcgta acaacccgtc gg                             42

<210> SEQ ID NO 583
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 583
attctccgtg ggttgtaaac gttaatatta tatgtacccc gg                             42

<210> SEQ ID NO 584
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 584
ttgataatca gaattcaacc gttctagctt aatgtgtagg ta                             42

<210> SEQ ID NO 585
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 585
aagattcaaa aggcaataaa gcctcagagc tactaatagt ag                             42

<210> SEQ ID NO 586
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 586
tagcattaac ataagtttca ttccatatac ttaattgctg aa                             42

<210> SEQ ID NO 587

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 587
tataatgctg tagaagcccg aaagacttca aaatcaggtc tt    42

<210> SEQ ID NO 588
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 588
taccctgact atttgcaaaa gaagttttgg taagagcaac ac    42

<210> SEQ ID NO 589
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 589
tatcataacc ctgacgttgg gaagaaaaaa atttcaactt ta    42

<210> SEQ ID NO 590
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 590
atcattgtga atggctgacc ttcatcaaga agggaaccga ac    42

<210> SEQ ID NO 591
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 591
tgaccaactt tgacactcat ctttgacccg gtaaaatacg ta    42

<210> SEQ ID NO 592
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 592
atgccactac gacgctgagg cttgcagggg cttgataccg at    42

<210> SEQ ID NO 593
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 593
agttgcgccg acgcggagtg agaatagaag tctttccaga cg                              42

<210> SEQ ID NO 594
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 594
ttagtaaatg aaccaccacc ctcattttca ccgtactcag ga                              42

<210> SEQ ID NO 595
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 595
ggtttagtac cgaacctatt attctgaaat ttaacggggt ca                              42

<210> SEQ ID NO 596
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 596
gtgccttgag taggcaggtc agacgattgg ccaccaccct ca                              42

<210> SEQ ID NO 597
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 597
gagccgccac catgtagcgc gttttcatca atgaaaccat cg                              42

<210> SEQ ID NO 598
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 598
atagcagcac cggattgagg gagggaaggt ttgtcacaat ca                              42

<210> SEQ ID NO 599
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 599
atagaaaatt cagaaacgca ataataacgt cttaccgaag cc                              42

<210> SEQ ID NO 600

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 600 cttttaaga aagggaagcg cattagacga aacgattttt tg                    42

<210> SEQ ID NO 601
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 601
tttaacgtca aaagccttaa atcaagatta ggcttatccg gt                   42

<210> SEQ ID NO 602
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 602
attctaagaa cgcaatcaat aatcggctga tcaacaatag at                   42

<210> SEQ ID NO 603
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 603
aagtcctgaa cattaacaac gccaacatgg ttatacaaat tc                   42

<210> SEQ ID NO 604
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 604
ttaccagtat aatttttcaa atatattttt tgggttatat aa                   42

<210> SEQ ID NO 605
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 605
ctatatgtaa attgtaaatc gtcgctatta tttgaattac ct                   42

<210> SEQ ID NO 606
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 606
tttttaatgg aaaaacaata acggattcga aattgcgtag at                       42

<210> SEQ ID NO 607
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 607
tttcaggttt aagagcggaa ttatcatcac gaacgttatt aa                       42

<210> SEQ ID NO 608
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 608
ttttaaaagt ttaaaggaat tgagtaaaat a                                   31

<210> SEQ ID NO 609
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 609
cggaagcata aagtgtaatt gaggatcccc gg                                  32

<210> SEQ ID NO 610
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 610
gtgcactctg tggtctcaca ttaattgctt cagcaaatcg tt                       42

<210> SEQ ID NO 611
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 611
cactcaatcc gccgggaaac ctgtcgtggc aagaatgcca ac                       42

<210> SEQ ID NO 612
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 612 tccgttttt cgtcgcgggg agaggcggac atcgacataa aa                        42

<210> SEQ ID NO 613

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 613
atagactttc tccgtctttt caccagtgag ctttcagagg tg                          42

<210> SEQ ID NO 614
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 614
ctcttcgcta ttaccgcctg gccctgagcc agccagcttt cc                          42

<210> SEQ ID NO 615
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 615
cggattgacc gtaattgccc cagcaggcca tcaaaaataa tt                          42

<210> SEQ ID NO 616
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 616
aaaacaggaa gattatcggc aaaatcccctt gcctgagagt ct                         42

<210> SEQ ID NO 617
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 617
ggccggagac agtcgggttg agtgttgtgc ctttatttca ac                          42

<210> SEQ ID NO 618
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 618
catacaggca aggcaagaac gtggactcaa atggtcaata ac                          42

<210> SEQ ID NO 619
<211> LENGTH: 42
<212> TYPE: DNA
<213> ORGANISM: Artificial Sequence
<220> FEATURE:
<223> OTHER INFORMATION: Synthetic Polynucleotide
```

-continued

<400> SEQUENCE: 619
gttttaaata tgcacagggc gatggccctc aggattagag ag                42

<210> SEQ ID NO 620
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 620
aagcaaagcg gatttttttg gggtcgagta aatattcatt ga                42

<210> SEQ ID NO 621
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 621
gacgacgata aaaaaaggg agcccccgtg agatttagga at                 42

<210> SEQ ID NO 622
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 622
cgattttaag aactaacgtg gcgagaaaca gtgaataagg ct                42

<210> SEQ ID NO 623
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 623
agatgaacgg tgtagctagg gcgctggcat tgtgtcgaaa tc                42

<210> SEQ ID NO 624
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 624
cctaaaacga aagaaccaca cccgccgcgg gtagcaacgg ct                42

<210> SEQ ID NO 625
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 625
aaccatcgcc cacgtatggt tgctttgagg ctccaaaagg ag                42

<210> SEQ ID NO 626

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 626
tgggattttg ctaaagaatc agagcgggaa ctacaacgcc tg                          42

<210> SEQ ID NO 627
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 627
gaaccgccac cctctttaga caggaacgct cagtaccagg cg                          42

<210> SEQ ID NO 628
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 628
gtataaacag ttaaataatc agtgaggcga atttaccgtt cc                          42

<210> SEQ ID NO 629
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 629
ccagagccgc cgcccaaatt aaccgttggg aaccagagcc ac                          42

<210> SEQ ID NO 630
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 630
gcgacagaat caagatcact tgcctgagtt gggaattaga gc                          42

<210> SEQ ID NO 631
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 631
ccagcgccaa agacggtaat atccagaaag aaaatacata ca                          42

<210> SEQ ID NO 632
<211> LENGTH: 42
<212> TYPE: DNA
<213> ORGANISM: Artificial Sequence
<220> FEATURE:
<223> OTHER INFORMATION: Synthetic Polynucleotide
```

```
<400> SEQUENCE: 632
atagccgaac aaagaaaaac gctcatggga taacccacaa ga                              42

<210> SEQ ID NO 633
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 633
agcagccttt acagctgaaa tggattatct ttccagagcc ta                              42

<210> SEQ ID NO 634
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 634
ttagcgaacc tcccaccagt aataaaagca agccgttttt at                              42

<210> SEQ ID NO 635
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 635
atatcccatc ctaacttctg acctgaaata aagtaattct gt                              42

<210> SEQ ID NO 636
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 636
tcaacagtag ggcttttga atggctatag gcgttaaata ag                               42

<210> SEQ ID NO 637
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 637
aatccaatcg caagtaaaac atcgccatag agtcaatagt ga                              42

<210> SEQ ID NO 638
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 638
aaatcaatat atgtagataa aacagaggac ctgagcaaaa ga                              42

<210> SEQ ID NO 639
```

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 639
aatatacagt aacaaacagt gccacgcttt ctgaataatg ga         42

<210> SEQ ID NO 640
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 640
tatcattttg cggaagcatc accttgctac atttgaggat tt         42

<210> SEQ ID NO 641
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 641
aatgagtgag ctaagctgcg gccagaatgc ggccatacga gc         42

<210> SEQ ID NO 642
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 642
ccgctttcca gtcgggcgcg gttgcggtat gagtgcgcgc ct         42

<210> SEQ ID NO 643
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 643
gaatcggcca acgctcgtcg ctggcagcct ccggcgcttt cg         42

<210> SEQ ID NO 644
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 644
gccagggtgg tttttggtga agggatagct ctccaaacgc gg         42

<210> SEQ ID NO 645
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 645
tgattgccct tcacgccagc tggcgaaagg gggttgtgag ag                              42

<210> SEQ ID NO 646
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 646
cggtccacgc tggttgggat aggtcacgtt ggtggtgcgg gc                              42

<210> SEQ ID NO 647
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 647
atggtggttc cgaagtataa gcaaatattt aaaaacaaac gg                              42

<210> SEQ ID NO 648
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 648
aatagcccga gataaaatca ccatcaatat gataaagccc ca                              42

<210> SEQ ID NO 649
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 649
agagtccact attaaaagaa ttagcaaaat taaggtgaga aa                              42

<210> SEQ ID NO 650
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 650
gaaaaaccgt ctatactaaa gtacggtgtc tggccaataa at                              42

<210> SEQ ID NO 651
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 651
cacccaaatc aagtgcatca aaaagattaa gaggctcaac at                              42

<210> SEQ ID NO 652

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 652
taaatcggaa ccctccaaaa tagcgagagg ctttatagtc ag                              42

<210> SEQ ID NO 653
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 653
ggggaaagcc ggcgggctca ttataccagt cagcgtttac ca                              42

<210> SEQ ID NO 654
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 654
cgaaaggagc gggccagacc aggcgcatag gcttacctta tg                              42

<210> SEQ ID NO 655
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 655
cgctgcgcgt aaccggcaaa agaatacact aaaaaagagg ac                              42

<210> SEQ ID NO 656
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 656
tacagggcgc gtaccataac cgatatattc ggtaggcacc aa                              42

<210> SEQ ID NO 657
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 657
gtgctttcct cgttacaact ttcaacagtt tcaaatgaca ac                              42

<210> SEQ ID NO 658
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 658
ccgattaaag ggatagaacc gccaccctca gagttttctg ta                              42

<210> SEQ ID NO 659
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 659
tgagaagtgt tttttgcccc ctgcctattt cggccaccct ca                              42

<210> SEQ ID NO 660
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 660
gtctgtccat cacgagcatt gacaggaggt tgaacagtgc cc                              42

<210> SEQ ID NO 661
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 661
tgattagtaa taactttgcc tttagcgtca gacgaaccac ca                              42

<210> SEQ ID NO 662
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 662
ctatcggcct tgctaaaagg gcgacattca acctaatcag ta                              42

<210> SEQ ID NO 663
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 663
gccattgcaa caggttacca gaaggaaacc gagtatggtt ta                              42

<210> SEQ ID NO 664
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 664
tgacgctcaa tcgtagagaa taacataaaa acaagtaagc ag                              42

<210> SEQ ID NO 665

```
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 665
tcaccagtca cacggacttg cgggaggttt tgaaatgaaa at                42

<210> SEQ ID NO 666
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 666
acagagatag aacctttacg agcatgtaga aaccgaggcg tt                42

<210> SEQ ID NO 667
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 667
ggcacagaca atattaattg agaatcgcca tatagaaaaa ta                42

<210> SEQ ID NO 668
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 668
cgaactgata gcccacaaag aacgcgagaa aacagccaac gc                42

<210> SEQ ID NO 669
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 669
gaaccaccag cagagagtga ataaccttgc ttcgctgatg ca                42

<210> SEQ ID NO 670
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 670
ttaacaccgc ctgcgtacct tttacatcgg gagacagtac at                42

<210> SEQ ID NO 671
<211> LENGTH: 42
<212> TYPE: DNA
<213> ORGANISM: Artificial Sequence
<220> FEATURE:
<223> OTHER INFORMATION: Synthetic Polynucleotide
```

<400> SEQUENCE: 671
aatgaaaaat ctaaacaaag aaaccaccag aagcgtcaga tg            42

<210> SEQ ID NO 672
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 672
aaaccctcaa tcaagttggc aaatcaacag ttggagtaac at            42

<210> SEQ ID NO 673
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 673
cgctggttgg gataggtcac gttggtggtg cgggc                    35

<210> SEQ ID NO 674
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 674
ttccgaagta taagcaaata tttaaaaaca aacgg                    35

<210> SEQ ID NO 675
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 675
cgagataaaa tcaccatcaa tatgataaag cccca                    35

<210> SEQ ID NO 676
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 676
actattaaaa gaattagcaa aattaaggtg agaaa                    35

<210> SEQ ID NO 677
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 677
cgtctatact aaagtacggt gtctggccaa taaat                    35

<210> SEQ ID NO 678

```
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 678
tggttgggat aggtcacgtt ggtggtgcgg gc                           32

<210> SEQ ID NO 679
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 679
cgaagtataa gcaaatattt aaaaacaaac gg                           32

<210> SEQ ID NO 680
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 680
gataaaatca ccatcaatat gataaagccc ca                           32

<210> SEQ ID NO 681
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 681
attaaaagaa ttagcaaaat taaggtgaga aa                           32

<210> SEQ ID NO 682
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 682
ctatactaaa gtacggtgtc tggccaataa at                           32

<210> SEQ ID NO 683
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 683
tgcaatttaa ttcttttagc atttcaatat ttgtagattt gagaatttcg tttttttatt    60
ca                                                                  62

<210> SEQ ID NO 684
<211> LENGTH: 84
<212> TYPE: DNA
<213> ORGANISM: Artificial Sequence
<220> FEATURE:
<223> OTHER INFORMATION: Synthetic Polynucleotide
```

```
<400> SEQUENCE: 684
tggttctgga gttttactcg ggacacttca gcgtaatatc ggaagcaggc actttgaaac      60
ctataagtcc tgactattaa taac                                            84

<210> SEQ ID NO 685
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 685
ggctcccttt agggttccga tgatcctcaa ctgtgaggag                           40

<210> SEQ ID NO 686
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 686
ctcctcacag ttgaggatca tcggaaccct aaagggagcc                           40

<210> SEQ ID NO 687
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(17)
<223> OTHER INFORMATION: n is a, c, g, or t

<400> SEQUENCE: 687
gcctggggnn nnnnnnntga gtgagc                                          26

<210> SEQ ID NO 688
<211> LENGTH: 27
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(19)
<223> OTHER INFORMATION: n is a, c, g, or t

<400> SEQUENCE: 688
agctcactca nnnnnnnnnc cccaggc                                         27
```